(12) United States Patent
Spence et al.

(10) Patent No.: US 12,295,840 B2
(45) Date of Patent: *May 13, 2025

(54) VALVE DOCKING DEVICES, SYSTEMS AND METHODS

(71) Applicant: Mitral Valve Technologies Sarl, Nyon (CH)

(72) Inventors: Paul A. Spence, Louisville, KY (US); Landon H. Tompkins, Peachtree Corners, GA (US)

(73) Assignee: Mitral Valve Technologies Sarl, Nyon (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/410,698

(22) Filed: Jan. 11, 2024

(65) Prior Publication Data

US 2024/0148499 A1 May 9, 2024

Related U.S. Application Data

(60) Continuation of application No. 17/453,961, filed on Nov. 8, 2021, now Pat. No. 11,925,553, which is a
(Continued)

(51) Int. Cl.
*A61F 2/24* (2006.01)
*A61B 17/00* (2006.01)
(Continued)

(52) U.S. Cl.
CPC .......... *A61F 2/2427* (2013.01); *A61F 2/2409* (2013.01); *A61F 2/2418* (2013.01);
(Continued)

(58) Field of Classification Search
CPC A61B 2017/00234; A61B 2017/00358; A61B 2017/0649; A61B 2017/3425;
(Continued)

(56) References Cited

U.S. PATENT DOCUMENTS 3,564,617 A 2/1971 Sauvage et al.
4,035,849 A 7/1977 Angell et al.
(Continued)

FOREIGN PATENT DOCUMENTS

CA 2702615 A1 4/2009
CN 1684644 A 10/2005
(Continued)

OTHER PUBLICATIONS

Bonhoeffer et at., "Percutaneous Replacement of Pulmonary valve in a Right-Ventricle to Pulmonary-Artery Prosthetic Conduit with Valve Dysfunction," Early Report, The Lancet, vol. 356, Oct. 21, 2000.
(Continued)

*Primary Examiner* — Jocelin C Tanner
(74) *Attorney, Agent, or Firm* — Klarquist Sparkman, LLP; Linda Allyson Nassif

(57) ABSTRACT

Various systems, devices and methods associated with the placement of a dock or anchor for a prosthetic valve. The anchor can comprise a plurality of coils adapted to support a valve prosthesis, the plurality of coils including an upper coil, one or more middle coils, and a lower coil. The upper coil can have a larger diameter than the one or more middle coils and the lower coil, and the upper coil is configured to engage a wall of an atrium of the heart at a position superior to and spaced axially from the mitral valve annulus after the plurality of coils have been fully delivered from the coil guide catheter.

18 Claims, 79 Drawing Sheets

Related U.S. Application Data continuation of application No. 16/292,161, filed on Mar. 4, 2019, now Pat. No. 11,166,812, which is a division of application No. 14/372,953, filed as application No. PCT/IB2013/000593 on Jan. 31, 2013, now Pat. No. 10,226,339.

(60) Provisional application No. 61/796,964, filed on Nov. 26, 2012, provisional application No. 61/744,468, filed on Sep. 27, 2012, provisional application No. 61/687,898, filed on May 3, 2012, provisional application No. 61/592,796, filed on Jan. 31, 2012.

(51) Int. Cl.
  *A61B 17/064* (2006.01)
  *A61B 17/34* (2006.01)
  *A61M 25/01* (2006.01)

(52) U.S. Cl.
  CPC .......... *A61F 2/2436* (2013.01); *A61F 2/2466* (2013.01); *A61B 2017/00243* (2013.01); *A61B 2017/00358* (2013.01); *A61B 2017/0649* (2013.01); *A61B 2017/3425* (2013.01); *A61F 2220/0008* (2013.01); *A61F 2230/0054* (2013.01); *A61F 2230/0078* (2013.01); *A61F 2230/0091* (2013.01); *A61F 2250/006* (2013.01); *A61M 25/0133* (2013.01)

(58) Field of Classification Search
  CPC .... A61F 2/2409; A61F 2/2418; A61F 2/2427; A61F 2/2436; A61F 2/2466; A61F 2220/0008; A61F 2230/0054; A61F 2230/0078; A61F 2230/0091; A61F 2250/006; A61M 25/0133
  See application file for complete search history.

(56) References Cited

U.S. PATENT DOCUMENTS

| | | | |
|---|---|---|---|
| 4,490,859 A | 1/1985 | Black et al. | |
| 4,512,338 A | 4/1985 | Balko et al. | |
| 4,790,843 A | 12/1988 | Carpentier et al. | |
| 5,059,177 A | 10/1991 | Towne et al. | |
| 5,403,305 A | 4/1995 | Sauter et al. | |
| 5,411,552 A | 5/1995 | Andersen et al. | |
| 5,443,500 A | 8/1995 | Sigwart | |
| 5,554,185 A | 9/1996 | Block et al. | |
| 5,840,081 A | 11/1998 | Andersen et al. | |
| 5,957,949 A | 9/1999 | Leonhardt et al. | |
| 6,120,534 A | 9/2000 | Ruiz | |
| 6,168,614 B1 | 1/2001 | Andersen et al. | |
| 6,235,042 B1 | 5/2001 | Katzman | |
| 6,306,141 B1 | 10/2001 | Jervis | |
| 6,406,492 B1 | 6/2002 | Lytle | |
| 6,409,758 B2 | 6/2002 | Stobie et al. | |
| 6,419,696 B1 | 7/2002 | Ortiz et al. | |
| 6,425,916 B1 | 7/2002 | Garrison et al. | |
| 6,432,134 B1 | 8/2002 | Anson et al. | |
| 6,458,153 B1 | 10/2002 | Bailey et al. | |
| 6,527,979 B2 | 3/2003 | Constantz | |
| 6,582,462 B1 | 6/2003 | Andersen et al. | |
| 6,625,578 B2 | 9/2003 | Spaur et al. | |
| 6,652,578 B2 | 11/2003 | Bailey et al. | |
| 6,730,121 B2 | 5/2004 | Ortiz et al. | |
| 6,797,002 B2 | 9/2004 | Spence et al. | |
| 6,908,481 B2 | 6/2005 | Cribier | |
| 6,971,998 B2 | 12/2005 | Rosenman et al. | |
| 7,018,408 B2 | 3/2006 | Bailey et al. | |
| 7,037,334 B1 | 5/2006 | Hlavka et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,166,126 B2 | 1/2007 | Spence et al. | |
| 7,166,127 B2 | 1/2007 | Spence et al. | |
| 7,404,824 B1 | 7/2008 | Webler et al. | |
| 7,431,726 B2 | 10/2008 | Spence et al. | |
| 7,445,632 B2 | 11/2008 | McGuckin, Jr. et al. | |
| 7,527,646 B2 | 5/2009 | Rahdert et al. | |
| 7,585,321 B2 | 9/2009 | Cribier | |
| 7,618,446 B2 | 11/2009 | Andersen et al. | |
| 7,618,449 B2 | 11/2009 | Tremulis et al. | |
| 7,637,946 B2 | 12/2009 | Solem et al. | |
| 7,708,775 B2 | 5/2010 | Rowe et al. | |
| 7,737,060 B2 | 6/2010 | Strickler et al. | |
| 7,758,639 B2 | 7/2010 | Mathis | |
| 7,780,726 B2 | 8/2010 | Seguin | |
| 7,785,366 B2 | 8/2010 | Maurer et al. | |
| 7,942,927 B2 | 5/2011 | Kaye et al. | |
| 7,951,195 B2 | 5/2011 | Antonsson et al. | |
| 7,955,385 B2 * | 6/2011 | Crittenden | A61F 2/2466 |
| | | | 623/2.11 |
| 8,016,882 B2 | 9/2011 | Macoviak et al. | |
| 8,052,750 B2 | 11/2011 | Tuval et al. | |
| 8,092,520 B2 | 1/2012 | Quadri | |
| 8,128,691 B2 | 3/2012 | Keranen | |
| 8,142,492 B2 | 3/2012 | Forster et al. | |
| 8,236,049 B2 | 8/2012 | Rowe et al. | |
| 8,323,335 B2 | 12/2012 | Rowe et al. | |
| 8,377,115 B2 | 2/2013 | Thompson | |
| 8,398,708 B2 | 3/2013 | Meiri et al. | |
| 8,449,599 B2 | 5/2013 | Chau et al. | |
| 8,449,605 B2 | 5/2013 | Lichtenstein et al. | |
| 8,449,606 B2 | 5/2013 | Eliasen et al. | |
| 8,657,872 B2 | 2/2014 | Seguin | |
| 8,663,322 B2 | 3/2014 | Keranen | |
| 8,672,998 B2 | 3/2014 | Lichtenstein et al. | |
| 8,685,086 B2 | 4/2014 | Navia et al. | |
| 8,734,507 B2 | 5/2014 | Keranen | |
| 8,795,352 B2 | 8/2014 | O'Beirne et al. | |
| 8,801,776 B2 | 8/2014 | House et al. | |
| 8,840,664 B2 | 9/2014 | Karapetian et al. | |
| 8,986,373 B2 | 3/2015 | Chau et al. | |
| 9,078,747 B2 | 7/2015 | Conklin | |
| 9,095,434 B2 | 8/2015 | Rowe | |
| 9,119,718 B2 | 9/2015 | Keranen | |
| 9,192,471 B2 | 11/2015 | Bolling | |
| 9,237,886 B2 | 1/2016 | Seguin et al. | |
| 9,314,335 B2 | 4/2016 | Konno | |
| 9,326,853 B2 | 5/2016 | Olson et al. | |
| 9,364,326 B2 | 6/2016 | Yaron | |
| 9,463,268 B2 | 10/2016 | Spence | |
| 9,474,599 B2 | 10/2016 | Keranen | |
| 9,526,572 B2 | 12/2016 | Kunis | |
| 9,597,205 B2 | 3/2017 | Tuval | |
| 9,622,863 B2 | 4/2017 | Karapetian et al. | |
| 9,867,702 B2 | 1/2018 | Keränen et al. | |
| 10,016,272 B2 | 7/2018 | Spence et al. | |
| 10,016,276 B2 | 7/2018 | Brunnett et al. | |
| 10,034,749 B2 | 7/2018 | Spence et al. | |
| 10,039,637 B2 | 8/2018 | Maimon et al. | |
| 10,052,198 B2 | 8/2018 | Chau et al. | |
| 10,195,028 B2 | 2/2019 | Hosmer et al. | |
| 10,195,033 B2 | 2/2019 | Tuval et al. | |
| 10,226,339 B2 | 3/2019 | Spence et al. | |
| 10,357,361 B2 | 7/2019 | Rafi et al. | |
| 10,463,479 B2 | 11/2019 | Manash et al. | |
| 10,828,150 B2 | 11/2020 | Tamir | |
| 11,020,225 B2 | 6/2021 | Keränen et al. | |
| 11,039,924 B2 | 6/2021 | Yaron | |
| 11,065,111 B2 | 7/2021 | Manash et al. | |
| 11,141,273 B2 | 10/2021 | Dakin et al. | |
| 11,185,406 B2 | 11/2021 | Haivatov et al. | |
| 11,364,114 B2 | 6/2022 | Gorman, III et al. | |
| 11,382,748 B2 | 7/2022 | Keränen et al. | |
| 11,471,282 B2 | 10/2022 | Argento et al. | |
| 11,547,563 B2 | 1/2023 | Keränen et al. | |
| 11,654,025 B2 | 5/2023 | O'Carroll et al. | |
| 11,666,441 B2 | 6/2023 | McDaniel et al. | |
| 2002/0032481 A1 | 3/2002 | Gabbay | |
| 2002/0045936 A1 | 4/2002 | Moe | |
| 2002/0107535 A1 | 8/2002 | Wei et al. | |
| 2002/0151970 A1 | 10/2002 | Garrison et al. | |

(56) References Cited

U.S. PATENT DOCUMENTS

| | | |
|---|---|---|
| 2002/0173841 A1 | 11/2002 | Ortiz et al. |
| 2003/0167089 A1 | 9/2003 | Lane |
| 2003/0225420 A1 | 12/2003 | Wardle |
| 2004/0111006 A1 | 6/2004 | Alferness et al. |
| 2004/0167620 A1 | 8/2004 | Ortiz et al. |
| 2004/0260389 A1 | 12/2004 | Case et al. |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137691 A1 | 6/2005 | Salahieh et al. |
| 2005/0182486 A1 | 8/2005 | Gabbay |
| 2005/0203614 A1 | 9/2005 | Forster et al. |
| 2005/0203617 A1 | 9/2005 | Forster et al. |
| 2006/0025857 A1 | 2/2006 | Bergheim et al. |
| 2006/0195134 A1 | 8/2006 | Crittenden |
| 2006/0265056 A1 | 11/2006 | Nguyen et al. |
| 2006/0271172 A1 | 11/2006 | Tehrani |
| 2007/0185572 A1 | 8/2007 | Solem et al. |
| 2007/0203575 A1 | 8/2007 | Forster et al. |
| 2007/0213813 A1 | 9/2007 | Von Segesser et al. |
| 2007/0232898 A1 | 10/2007 | Huynh et al. |
| 2007/0244553 A1 | 10/2007 | Rafiee et al. |
| 2007/0265700 A1 | 11/2007 | Eliasen et al. |
| 2007/0293808 A1 | 12/2007 | Williams et al. |
| 2008/0004697 A1 | 1/2008 | Lichtenstein et al. |
| 2008/0033542 A1 | 2/2008 | Antonsson et al. |
| 2008/0077235 A1 | 3/2008 | Kirson |
| 2008/0125853 A1 | 5/2008 | Bailey et al. |
| 2008/0140190 A1 | 6/2008 | Macoviak et al. |
| 2008/0208327 A1 | 8/2008 | Rowe |
| 2008/0208330 A1* | 8/2008 | Keranen .............. A61F 2/2448 623/2.36 |
| 2008/0228265 A1 | 9/2008 | Spence et al. |
| 2008/0243245 A1 | 10/2008 | Thambar et al. |
| 2008/0275503 A1 | 11/2008 | Spence et al. |
| 2009/0177278 A1 | 7/2009 | Spence |
| 2009/0192601 A1 | 7/2009 | Rafiee et al. |
| 2009/0234318 A1 | 9/2009 | Loulmet et al. |
| 2009/0259307 A1 | 10/2009 | Gross et al. |
| 2009/0276038 A1 | 11/2009 | Tremulis et al. |
| 2009/0276040 A1 | 11/2009 | Rowe et al. |
| 2009/0299471 A1 | 12/2009 | Keranen |
| 2009/0319037 A1 | 12/2009 | Rowe et al. |
| 2010/0036484 A1 | 2/2010 | Hariton et al. |
| 2010/0076549 A1 | 3/2010 | Keidar et al. |
| 2010/0145440 A1* | 6/2010 | Keranen .............. A61F 2/2448 623/2.37 |
| 2010/0152839 A1 | 6/2010 | Shandas et al. |
| 2010/0161047 A1 | 6/2010 | Cabiri |
| 2010/0217382 A1 | 8/2010 | Chau et al. |
| 2010/0312333 A1 | 12/2010 | Navia et al. |
| 2010/0318183 A1 | 12/2010 | Keranen |
| 2010/0318184 A1 | 12/2010 | Spence |
| 2010/0331971 A1* | 12/2010 | Keranen .............. A61F 2/2466 623/2.11 |
| 2010/0331973 A1 | 12/2010 | Keranen |
| 2011/0098802 A1 | 4/2011 | Braido et al. |
| 2011/0106247 A1 | 5/2011 | Miller et al. |
| 2011/0137397 A1 | 6/2011 | Chau et al. |
| 2011/0178597 A9 | 7/2011 | Navia et al. |
| 2011/0208298 A1 | 8/2011 | Tuval et al. |
| 2011/0218621 A1 | 9/2011 | Antonsson et al. |
| 2011/0224785 A1 | 9/2011 | Hacohen |
| 2011/0245911 A1 | 10/2011 | Quill et al. |
| 2011/0288634 A1 | 11/2011 | Tuval et al. |
| 2011/0295361 A1 | 12/2011 | Claiborne, III et al. |
| 2011/0319989 A1 | 12/2011 | Lane et al. |
| 2011/0319990 A1 | 12/2011 | Macoviak et al. |
| 2012/0016464 A1* | 1/2012 | Seguin ................ A61F 2/2436 623/1.26 |
| 2012/0053680 A1 | 3/2012 | Bolling et al. |
| 2012/0059458 A1 | 3/2012 | Buchbinder et al. |
| 2012/0123529 A1 | 5/2012 | Levi et al. |
| 2012/0130468 A1* | 5/2012 | Khosravi ............ A61M 25/104 623/1.11 |
| 2012/0150287 A1 | 6/2012 | Forster et al. |
| 2012/0283820 A1 | 11/2012 | Tseng et al. |
| 2012/0310328 A1 | 12/2012 | Olson et al. |
| 2012/0316643 A1 | 12/2012 | Keranen |
| 2013/0006352 A1 | 1/2013 | Yaron |
| 2013/0190865 A1 | 7/2013 | Anderson |
| 2013/0204311 A1 | 8/2013 | Kunis |
| 2013/0310917 A1 | 11/2013 | Richter et al. |
| 2013/0310928 A1 | 11/2013 | Morriss et al. |
| 2014/0074299 A1 | 3/2014 | Endou et al. |
| 2014/0081394 A1 | 3/2014 | Keranen et al. |
| 2014/0163669 A1 | 6/2014 | Ben-Zvi et al. |
| 2014/0172070 A1 | 6/2014 | Seguin |
| 2014/0236287 A1 | 8/2014 | Clague et al. |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0190227 A1 | 7/2015 | Johnson et al. |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0374493 A1 | 12/2015 | Yaron et al. |
| 2016/0015514 A1 | 1/2016 | Lashinski et al. |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0217385 A1 | 8/2017 | Rinkleff et al. |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2017/0360426 A1 | 12/2017 | Hacohen et al. |
| 2018/0000580 A1 | 1/2018 | Wallace et al. |
| 2018/0085217 A1 | 3/2018 | Lashinski et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |
| 2020/0054453 A1 | 2/2020 | Zerkowski et al. |
| 2020/0360143 A1 | 11/2020 | O'Carroll et al. |
| 2021/0212826 A1 | 7/2021 | Zerkowski et al. |
| 2021/0361426 A1 | 11/2021 | Hacohen |
| 2023/0086853 A1 | 3/2023 | Zerkowski et al. |

FOREIGN PATENT DOCUMENTS

| | | |
|---|---|---|
| CN | 1714766 A | 1/2006 |
| CN | 101588771 A | 11/2009 |
| CN | 102131479 A | 7/2011 |
| DE | 19532846 A1 | 3/1997 |
| DE | 19907646 A1 | 8/2000 |
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1296618 B1 | 1/2008 |
| EP | 2072027 A1 | 6/2009 |
| EP | 1827314 B1 | 12/2010 |
| EP | 2620125 A1 | 7/2013 |
| EP | 2726018 A2 | 5/2014 |
| EP | 2806829 A2 | 12/2014 |
| EP | 3395296 B1 | 12/2019 |
| EP | 2747708 B1 | 1/2022 |
| WO | 9117720 A1 | 11/1991 |
| WO | 0149213 A2 | 7/2001 |
| WO | 0154625 A1 | 8/2001 |
| WO | 0247575 A2 | 6/2002 |
| WO | 03028558 A2 | 4/2003 |

(56) References Cited

FOREIGN PATENT DOCUMENTS

| WO | 2005084595 A1 | 9/2005 |
|---|---|---|
| WO | 2006011127 A2 | 2/2006 |
| WO | 2005102015 A3 | 4/2007 |
| WO | 2007067942 A1 | 6/2007 |
| WO | 2009080801 A1 | 7/2009 |
| WO | 2009134701 A2 | 11/2009 |
| WO | 2010057262 A1 | 5/2010 |
| WO | 2010121076 A2 | 10/2010 |
| WO | 2012063228 A1 | 5/2012 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |
| WO | 2017103833 A1 | 6/2017 |

OTHER PUBLICATIONS

Casselman et al., "Reducing Operative Morality in Valvular Reoperations: The "valve in ring" Procedure," Brief Technique Reports, The Journal of Thoracic and Cardiovascular Surgery, vol. 141, No. 5. May 2011.

Cheung et al, Live Case Transmissions, NYHA III CHF, Case Summary, Sep. 23, 2010, St. Paul's Hospital/University of British Columbia.

Cheung et al,"Transapical Transcatheter Mitral Valve-in-Valve Implantation in a Human," The Society of Thoracic Surgeons, 2009.

Descoutures et al., "Transcatheter Valve-in-Ring Implantation After Failure of Surgical Mitral Repair," European Journal of Cardio-Thoracic Surgery 44, e8-e15, 2013.

Himbert et al., "Transseptal Implantation of a Transcatheter Heart Valve in a Mitral Annuloplasty Ring to Treat Mitral Repair Failure," Circulation Cardiovascular Interventions, American Heart Association, 2011.

Himbert, Dominique, "Transvenous Mitral Valve Repair Replacement After Failure of Surgical Ring Annuloplasty," Research Correspondence, Journal of the American College of Cardiology, 2012.

Kempfert et al., "Minimally invasive off-pump valve-in-a-ring implantation: the atrial transcatheter approach for re-operative mitral valve replacement after failed repair," European Journal of Cardiothoracic Surgery, 2009, 35:965-969.

Ma et al., "Double-Crowned Valved Stents for Off-Pump Mitral Valve Replacement," European Journal of Cardio-Thoracic Surgery, 28, 194-199, 2005.

Shuto et al., "Percutaneous Transvenous Melody Valve-in-Ring Procedure for Mitral Valve Replacement," J AM Coll Cardiol, 58(24): 2475-2480, 2011.

Walther et al., "Human Minimally Invasive Off-Pump Valve-in-a-Valve Implantation," Case Reports, The Society of Thoracic Surgeons, 2008.

Walther et al., "Valve-in-a-Valve Concept for Transcatheter Minimally Invasive Repeat Xenograph Implantation," Preclinical Studies, Journal of the American College of Cardiology, 2007.

Webb et al., "Mitral Valve in Valve," TCT Sep. 2009, Live Case: 30 Minutes, St. Paul's Hospital/University of British Columbia.

Webb et al., "Transcatheter Valve-in-Valve Implantation for Failed Bioprosthetic Heart Valves," Journal of the American Heart Association, 11, Apr. 27, 2010.

Weger et al., "First-in-Man Implantation of a Trans-Catheter Aortic Valve in a Mitral Annuloplasty Ring: Novel Treatment Modality for Failed Mitral Valve Repair," European Journal of Cardio-Thoracic Surgery 39, 1054-1056, 2011.

Wenaweser et al., "Percutaneous Aortic Valve Replacement for Severe Aortic Regurgitation in Degenerated Bioprosthesis: The First Valve Procedure Using Corevalve Revalving System," Catheterization and Cardiovascular Interventions, 70:760-764, 2007.

\* cited by examiner

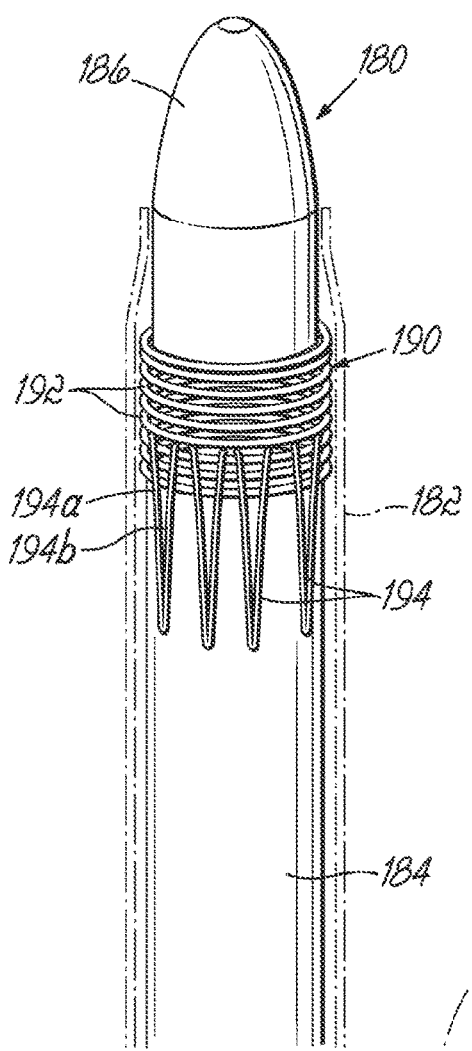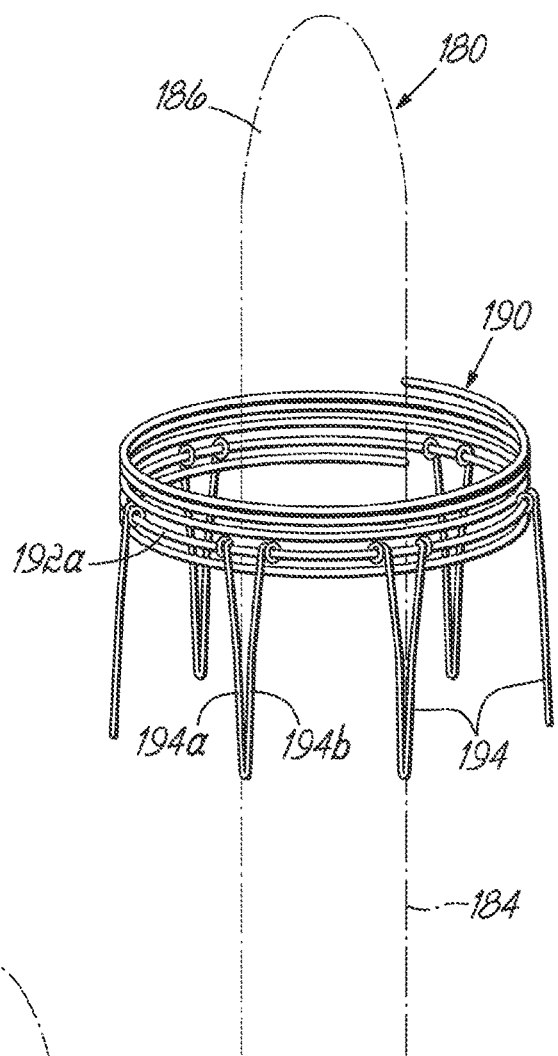
FIG. 9A
FIG. 9B
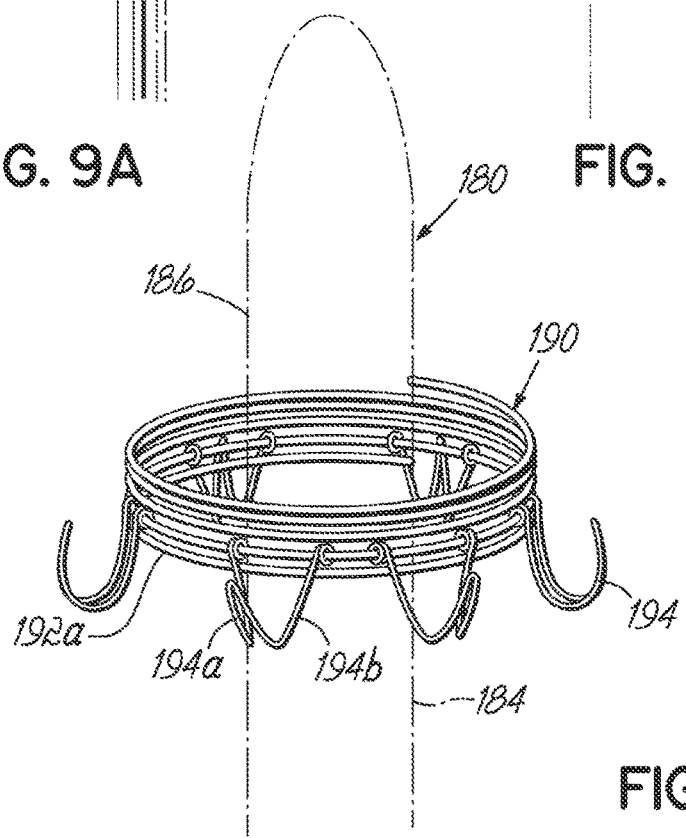
FIG. 9C

VALVE DOCKING DEVICES, SYSTEMS AND METHODS

CROSS-REFERENCE TO RELATED APPLICATIONS

This application is a continuation of U.S. patent application Ser. No. 17/453,961, filed Nov. 8, 2021, which is a continuation of Ser. No. 16/292,161, filed Mar. 4, 2019, now U.S. Pat. No. 11,166,812, which is a divisional of U.S. patent application Ser. No. 14/372,953, filed Jul. 17, 2014, now U.S. Pat. No. 10,226,339, which is the U.S. national stage of International Patent Application No. PCT/IB2013/000593, filed Jan. 31, 2013, which claims the benefit of U.S. Provisional Application Nos. 61/796,964, filed Nov. 26, 2012, 61/744,468, filed Sep. 27, 2012, 61/687,898, filed May 3, 2012, and 61/592,796, filed Jan. 31, 2012. The disclosure of each related application is incorporated by reference herein.

TECHNICAL FIELD

The present invention generally relates to medical procedures and devices pertaining to heart valves such as replacement techniques and apparatus. More specifically, the invention relates to the replacement of heart valves having various malformations and dysfunctions.

BACKGROUND

Complications of the mitral valve, which controls the flow of blood from the left atrium into the left ventricle of the human heart, have been known to cause fatal heart failure. In the developed world, one of the most common forms of valvular heart disease is mitral valve leak, also known as mitral regurgitation, which is characterized by the abnormal leaking of blood from the left ventricle through the mitral valve and back into the left atrium. This occurs most commonly due to ischemic heart disease when the leaflets of the mitral valve no longer meet or close properly after multiple infarctions, idiopathic and hypertensive cardiomyopathies where the left ventricle enlarges, and with leaflet and chordal abnormalities, such as those caused by a degenerative disease.

In addition to mitral regurgitation, mitral narrowing or stenosis is most frequently the result of rheumatic disease. While this has been virtually eliminated in developed countries, it is still common where living standards are not as high.

Similar to complications of the mitral valve are complications of the aortic valve, which controls the flow of blood from the left ventricle into the aorta. For example, many older patients develop aortic valve stenosis. Historically, the traditional treatment had been valve replacement by a large open heart procedure. The procedure takes a considerable amount of time for recovery since it is so highly invasive. Fortunately, in the last decade great advances have been made in replacing this open heart surgery procedure with a catheter procedure that can be performed quickly without surgical incisions or the need for a heart-lung machine to support the circulation while the heart is stopped. Using catheters, valves are mounted on stents or stent-like structures, which are compressed and delivered through blood vessels to the heart. The stents are then expanded and the valves begin to function. The diseased valve is not removed, but instead it is crushed or deformed by the stent which contains the new valve. The deformed tissue serves to help anchor the new prosthetic valve.

Delivery of the valves can be accomplished from arteries which can be easily accessed in a patient. Most commonly this is done from the groin where the femoral and iliac arteries can be cannulated. The shoulder region is also used, where the subclavian and axillary arteries can also be accessed. Recovery from this procedure is remarkably quick.

Not all patients can be served with a pure catheter procedure. In some cases the arteries are too small to allow passage of catheters to the heart, or the arteries are too diseased or tortuous. In these cases, surgeons can make a small chest incision (thoractomy) and then place these catheter-based devices directly into the heart. Typically, a purse string suture is made in the apex of the left ventricle and the delivery system is place through the apex of the heart. The valve is then delivered into its final position. These delivery systems can also be used to access the aortic valve from the aorta itself. Some surgeons introduce the aortic valve delivery system directly in the aorta at the time of open surgery. The valves vary considerably. There is a mounting structure that is often a form of stent. Prosthetic leaflets are carried inside the stent on mounting and retention structure. Typically, these leaflets are made from biologic material that is used in traditional surgical valves. The valve can be actual heart valve tissue from an animal or more often the leaflets are made from pericardial tissue from cows, pigs or horses. These leaflets are treated to reduce their immunogenicity and improve their durability. Many tissue processing techniques have been developed for this purpose. In the future biologically engineered tissue may be used or polymers or other non-biologic materials may be used for valve leaflets. All of these can be incorporated into the inventions described in this disclosure.

There are in fact more patients with mitral valve disease than aortic valve disease. In the course of the last decade many companies have been successful in creating catheter or minimally invasive implantable aortic valves, but implantation of a mitral valve is more difficult and to date there has been no good solution. Patients would be benefited by implanting a device by a surgical procedure employing a small incision or by a catheter implantation such as from the groin. From the patient's point of view, the catheter procedure is very attractive. At this time there is no commercially available way to replace the mitral valve with a catheter procedure. Many patients who require mitral valve replacement are elderly and an open heart procedure is painful, risky and takes time for recovery. Some patients are not even candidates for surgery due to advanced age and frailty. Therefore, there exists a particular need for a remotely placed mitral valve replacement device.

While previously it was thought that mitral valve replacement rather than valve repair was associated with a more negative long term prognosis for patients with mitral valve disease, this belief has come into question. It is now believed that the outcome for patients with mitral valve leak or regurgitation is almost equal whether the valve is repaired or replaced. Furthermore, the durability of a mitral valve surgical repair is now under question. Many patients, who have undergone repair, redevelop a leak over several years. As many of these are elderly, a repeat intervention in an older patient is not welcomed by the patient or the physicians.

The most prominent obstacle for catheter mitral valve replacement is retaining the valve in position. The mitral valve is subject to a large cyclic load. The pressure in the left ventricle is close to zero before contraction and then rises to the systolic pressure (or higher if there is aortic stenosis) and this can be very high if the patient has systolic hypertension. Often the load on the valve is 150 mmHg or more. Since the heart is moving as it beats, the movement and the load can combine to dislodge a valve. Also the movement and rhythmic load can fatigue materials leading to fractures of the materials. Thus, there is a major problem associated with anchoring a valve.

Another problem with creating a catheter delivered mitral valve replacement is size. The implant must have strong retention and leak avoidance features and it must contain a valve. Separate prostheses may contribute to solving this problem, by placing an anchor or dock first and then implanting the valve second. However, in this situation the patient must remain stable between implantation of the anchor or dock and implantation of the valve. If the patient's native mitral valve is rendered non-functional by the anchor or dock, then the patient may quickly become unstable and the operator may be forced to hastily implant the new valve or possibly stabilize the patient by removing the anchor or dock and abandoning the procedure.

Another problem with mitral replacement is leak around the valve, or paravalvular leak. If a good seal is not established around the valve, blood can leak back into the left atrium. This places extra load on the heart and can damage the blood as it travels in jets through sites of leaks. Hemolysis or breakdown of red blood cells is a frequent complication if this occurs. Paravalvular leak was one of the common problems encountered when the aortic valve was first implanted on a catheter. During surgical replacement, a surgeon has a major advantage when replacing the valve as he or she can see a gap outside the valve suture line and prevent or repair it. With catheter insertion, this is not possible. Furthermore, large leaks may reduce a patient's survival and may cause symptoms that restrict mobility and make the patient uncomfortable (e.g. short of breathe, edematous, fatigued). Therefore, devices, systems, and methods which relate to mitral valve replacement should also incorporate means to prevent and repair leaks around the replacement valve.

A patient's mitral valve annulus can also be quite large. When companies develop surgical replacement valves, this problem is solved by restricting the number of sizes of the actual valve produced and then adding more fabric cuff around the margin of the valve to increase the valve size. For example, a patient may have a 45 mm valve annulus. In this case, the actual prosthetic valve diameter may be 30 mm and the difference is made up by adding a larger band of fabric cuff material around the prosthetic valve. However, in catheter procedures, adding more material to a prosthetic valve is problematic since the material must be condensed and retained by small delivery systems. Often this method is very difficult and impractical, so alternative solutions are necessary.

Since numerous valves have been developed for the aortic position, it is desirable to avoid repeating valve development and to take advantage of existing valves. These valves have been very expensive to develop and bring to market, so extending their application can save considerable amounts of time and money. It would be useful then to create a mitral anchor or docking station for such a valve. An existing valve developed for the aortic position, perhaps with some modification, could then be implanted in the docking station. Some previously developed valves may fit well with no modification, such as the Edwards Sapien™ valve. Others, such as the Corevalve™ may be implantable but require some modification for an optimal engagement with the anchor and fit inside the heart.

A number of further complications may arise from a poorly retained or poorly positioned mitral valve replacement prosthesis. Namely, a valve can be dislodged into the atrium or ventricle, which could be fatal for a patient. Prior prosthetic anchors have reduced the risk of dislodgement by puncturing tissue to retain the prosthesis. However, this is a risky maneuver since the penetration must be accomplished by a sharp object at a long distance, leading to a risk of perforation of the heart and patient injury.

Orientation of the mitral prosthesis is also important. The valve must allow blood to flow easily from the atrium to the ventricle. A prosthesis that enters at an angle may lead to poor flow, obstruction of the flow by the wall of the heart or a leaflet and a poor hemodynamic result. Repeated contraction against the ventricular wall can also lead to rupture of the back wall of the heart and sudden death of the patient.

With surgical mitral valve repair or replacement, sometimes the anterior leaflet of the mitral valve leaflet is pushed into the area of the left ventricular outflow and this leads to poor left ventricular emptying. This syndrome is known as left ventricular tract outflow obstruction. The replacement valve itself can cause left ventricular outflow tract obstruction if it is situated close to the aortic valve.

Yet another obstacle faced when implanting a replacement mitral valve is the need for the patient's native mitral valve to continue to function regularly during placement of the prosthesis so that the patient can remain stable without the need for a heart-lung machine to support circulation.

In addition, it is desirable to provide devices and methods that can be utilized in a variety of implantation approaches. Depending on a particular patient's anatomy and clinical situation, a medical professional may wish to make a determination regarding the optimal method of implantation, such as inserting a replacement valve directly into the heart in an open procedure (open heart surgery or a minimally invasive surgery) or inserting a replacement valve from veins and via arteries in a closed procedure (such as a catheter-based implantation). It is preferable to allow a medical professional a plurality of implantation options to choose from. For example, a medical professional may wish to insert a replacement valve either from the ventricle or from the atrial side of the mitral valve.

Therefore, the present invention provides devices and methods that address these and other challenges in the art.

SUMMARY

The present invention provides a docking station which is stabilized and capable of retaining a mitral valve replacement prosthesis for controlling the flow of blood from the left atrium into the left ventricle. Other devices and methods are provided to improve the positioning of such a combination during a non-invasive procedure or minimally invasive procedure. Additional devices and methods are also provided to prevent further regurgitation or leaking of blood, such as leakage either through the commissures of the native mitral valve or around the outer surface of the replacement valve prosthesis.

In one aspect, the invention provides a system for docking a mitral valve prosthesis. The system comprises a coil guide catheter and a helical anchor. The coil guide catheter includes a stem portion and a distal portion connected to the stem portion at a first curved portion. The distal portion includes a second curved portion configured to generally follow the curvature of the mitral valve annulus. The helical anchor is adapted to be received in and extruded, or otherwise delivered from the coil guide catheter. The helical anchor is formed as multiple coils having a preformed, coiled configuration after being extruded from the coil guide catheter. The helical anchor may be delivered from the coil guide catheter in other manners instead, but extrusion allows the coils to gradually and accurately be placed into the proper and desired position relative to the native mitral valve. Also, if the operator is not satisfied with the positioning that is being obtained, the helical anchor may be moved back into the coil guide catheter and the placement procedure may be started again. The helical anchor is adapted to support a prosthetic mitral valve upon being fully extruded or delivered from the coil guide catheter and implanted with coil portions above and below the mitral valve annulus. The system can further comprise various components. A prosthetic valve is provided and capable of being delivered to the mitral valve position of the patient and expanded inside the multiple coils and into engagement with leaflets of the mitral valve. The prosthetic valve may include grooves configured to engage with the multiple coils for coupling the prosthetic valve with the helical anchor. The helical anchor may further comprise a shape memory material. The multiple coils may include an end coil portion, such as a tail-like extension, formed as an enlarged diameter coil relative to the next adjacent coil. The extension may take other forms as well. The coils of the helical anchor may take on many different shapes and forms, some of which are shown herein. The coils may be in separate planes such as a coil spring, or some or all coils may, at least initially before implantation, be generally in the same plane. The end coil portion is configured to engage the left atrial wall of the heart when the multiple coils have been fully delivered from the coil guide catheter with the coil portions positioned above and below the mitral valve annulus.

The system may further comprise a plurality of anchoring arms coupled with the helical anchor and configured to engage the mitral valve leaflets. The anchoring arms may have various configurations, such as hook-like members. A control element may be provided in the system and includes a connecting element configured to coupled directly or indirectly with the helical anchor for guiding the placement of the helical anchor relative to the mitral valve. The control element may take various forms, such as a snare catheter or a catheter including a grasping tool, or simply a cable or suture and the like. The helical anchor may further include an engagement element configured to allow coupling of the connecting element therewith. This engagement element may also take various forms, such as an enlarged tip or end of the helical anchor.

The system may further comprise a positioning helix configured to be extruded or otherwise delivered from the coil guide catheter for assisting with positioning of the helical anchor. An extension may be coupled with the second curved portion of the coil guide catheter and configured to assist with positioning of the second curved portion on top of the mitral valve as the helical anchor is being delivered. The extension may comprise various forms, such as including a flat membrane for engagement with the top of the mitral valve. The system may further comprise an anchor delivery catheter and an anchor. The anchor delivery catheter is, for example, coupled with the coil guide catheter and/or the helical anchor for delivering the anchor into tissue at the mitral valve position. Multiple anchors may be delivered, for example, for plicating the annulus tissue and/or closing gaps at the commissures of the native mitral valve.

The helical anchor may, for example, comprise a solid wire or a hollow wire configured to be delivered over a guidewire.

In another illustrative embodiment, the invention provides a device for docking a mitral valve prosthesis comprising an expandable stent and a plurality of anchoring arms. The expandable stent is configured to be delivered from a catheter to the mitral valve position of a patient and then expanded. The expandable stent includes an upper end and a lower end. The plurality of anchoring arms are coupled with the lower end and are configured to engage the mitral valve leaflets. The anchoring arms may comprise various configurations, such as hook-like members. In various embodiments, the hook-like members or other configurations of anchoring arms may change in dimension as the stent is expanded. The expandable stent may further comprise an expandable atrial portion and an expandable valve retaining portion. The expandable atrial portion is configured to engage the left atrial wall when expanded at the mitral position in the heart. The valve retaining portion is adapted to engage the mitral valve leaflets. The anchoring arms are coupled with the valve retaining portion.

The invention also provides various methods and additional devices, systems and components for performing such methods associated with docking a mitral valve prosthesis at the mitral position in the heart. For example, various methods and systems allow a prosthetic mitral valve anchor or docking device to be implanted without requiring the operator to turn a catheter, but rather allowing the operator to use pushing and/or pulling motions that are easier during catheter-based percutaneous procedures. The leading tip of the multiple coiled helical anchor may be directed to an opposite side of the native mitral valve from the coil guide catheter. Control elements, such as snare catheters or catheters with grasping elements may be used to assist with directing the position of the helical anchor during delivery to the mitral valve position. Another method involves the placement of the multiple coiled helical anchor such that a portion of the helical anchor is positioned beneath the native mitral valve and another portion is placed above the native mitral valve but not in contact with valve tissue, but rather engage against only atrial tissue. The lower portion of the helical anchor may be engaged and pressed against the native mitral leaflets. The helical anchor may have coils with various diameters, and one or more segments of the coils may be configured to abut or engage against the atrial wall for stabilization of the helical anchor and, ultimately, a prosthetic mitral valve.

In more specific terms, the invention, for example, provides a method of implanting a mitral valve prosthesis in the heart of a patient comprising directing a coil guide catheter to the mitral valve position within the heart of the patient. A preformed, curved portion generally in the plane of the mitral valve is placed in the left atrium with a curvature of the preformed, curved portion generally following a curve of the mitral valve annulus. This preformed, curved portion may take on its curved shape as it is extruded or extended from the coil guide catheter, or may be activated to the preformed, curved shape after or as it is inserted into position at the mitral valve position. A helical anchor is delivered in the form of multiple coils from the coil guide catheter such that a portion of the helical anchor is above the native mitral valve and a portion is below the mitral valve. A mitral valve prosthesis is implanted within the multiple coils of the helical anchor such that the mitral valve prosthesis is supported by the helical anchor.

In further aspects, for example, an introducer is directed through heart tissue and the coil guide catheter is directed through the introducer to the mitral valve position. Alternatively, the method may be performed percutaneously by directing the coil guide catheter through the venous system of the patient to the mitral valve position. A control element may be used to guide the helical anchor into a desired position relative to the native mitral valve. The control element may take any suitable form, such as any element that suitably couples (either directly or indirectly) with a portion of the helical anchor. For example, the control element may be directly coupled to the helical anchor, such as by a grasping tool or a suture, or a control element may be coupled with the coil guide catheter. The control element is used to push and/or pull the helical anchor into position relative to the native mitral valve. The tip of the helical anchor may be extruded or otherwise delivered between and above the leaflets of the native mitral valve at one of the commissures and then further directed below the mitral valve into the left ventricle of the patient. Alternatively, the tip of the helical anchor may be initially delivered within the left ventricle and subsequently delivered into the left atrium, such as by directing it between the leaflets. Fabric may be placed between the mitral valve prosthesis and a portion of the helical anchor. A guidewire may be used for reference purposes. For example, the guidewire may be placed through the aortic valve and into the aorta. The guidewire may then be used as a reference to assist with positioning the helical anchor.

In additional aspects, a tissue anchor delivering catheter may be guided to the mitral valve position using the helical anchor and/or the coil guide catheter. A first tissue anchor is delivered into tissue at the mitral valve position using the tissue anchor delivery catheter. A second tissue anchor may then be delivered into tissue at the mitral valve position and the first and second tissue anchors may then be secured together to plicate or approximate the tissue.

The mitral valve prosthesis is delivered to a location within the helical anchor and the mitral valve prosthesis is initially in an unexpanded condition during delivery through a suitable catheter. The mitral valve prosthesis is then expanded such that the mitral valve prosthesis is supported by multiple coils. When the mitral valve prosthesis is expanded, the prosthesis expands against the native mitral leaflets and the leaflets are secured between the prosthesis and the ventricular coils or other anchoring structure such that the leaflets are firmly secured. This serves to prevent obstruction of the aortic valve by the anterior leaflet in addition to providing valve prosthesis support.

In another general method, a mitral valve prosthesis is implanted in the heart of a patient by directing a stent delivery catheter to the mitral valve position within the heart of the patient. A stent dock is extended from the stent delivery catheter. An atrial portion of the stent dock is expanded in the left atrium such that the atrial portion engages the wall of the left atrium. A valve retaining portion of the stent dock is expanded against the leaflets of the native mitral valve. The mitral valve prosthesis is implanted within the valve retaining portion such that the mitral valve prosthesis is supported by the stent dock.

In further aspects, various helical anchors are provided in desirable embodiments for docking a mitral valve prosthesis. In one embodiment, the anchor comprises a plurality of coils having a preformed, coiled configuration after being delivered from the coil guide catheter and adapted to support the prosthetic mitral valve upon being fully delivered from the coil guide catheter and implanted with respective coil portions above and below the mitral valve annulus. In one aspect, the helical anchor includes a distal end portion and the distal end portion is formed to extended downward and radially outward relative to a next adjacent coil such that the distal end portion is spaced from the next adjacent coil and is configured to be delivered between the commissures of the native mitral valve.

In another aspect, the helical anchor comprises an upper, atrial coil adapted to be placed above the native mitral valve annulus and a lower, ventricular coil adapted to be placed below the mitral valve annulus. The upper coil is adjacent the lower coil and a gap is formed between the upper and lower coils creating a space that exists prior to implantation of the coils such that the upper and lower coils do not trap mitral leaflet tissue upon implantation. This, for example, can allow the native mitral valve tissue to naturally close at the commissures and prevent blood leakage at those locations. The upper coil may be of larger diameter than the lower coil so as to engage the atrial wall of the heart upon implantation.

In another aspect, the plurality of coils include an upper, atrial coil adapted to be placed above the native mitral valve annulus and a lower, ventricular coil adapted to be placed below the native mitral valve annulus. In this aspect, an extension extends out of a plane of the upper coil and is spaced from the upper coil so as to engage the wall of the atrium and provide stabilization upon implantation in the heart.

In another aspect, the plurality of coils include a plurality of upper, atrial coils and a plurality of lower, ventricular coils. The upper, atrial coils are adapted to be placed above the native mitral valve annulus and extend upwardly to adjustably position the mitral valve prosthesis at a desired height relative to the mitral valve annulus. This can allow the operator to position the mitral valve prosthesis at a height that, for example, does not obstruct the outflow of blood from the ventricle through the aortic valve. The plurality of lower, ventricle coils may be configured to contain the mitral valve leaflets therein and also prevent obstruction of the aortic valve by the anterior mitral leaflet.

Various additional advantages, methods, devices, systems and features will become more readily apparent to those of ordinary skill in the art upon review of the following detailed description of the illustrative embodiments taken in conjunction with the accompanying drawings.

BRIEF DESCRIPTION OF THE DRAWINGS

FIGS. 9A-9C illustrate in perspective an alternative helical anchor having anchoring arms and expanding from a compressed state within a sheath to a deployed state.

DETAILED DESCRIPTION OF THE ILLUSTRATIVE EMBODIMENTS

Referring first to FIGS. 1A-1F, a device, system and method for positioning a helical anchor in the mitral position of a patient's heart are shown. In this series of figures the system is delivered from the apex of the left ventricle. However, it should be appreciated that the system can also be used by direct implantation into an open heart from the atrium, ventricle or aorta, or implantation can be made from catheters delivered into the left atrium or retrograde from the aortic valve into the left ventricle. Likewise, the system could be introduced in an open chest into the atrium or percutaneously via the apex of the heart.

Figure 1A:
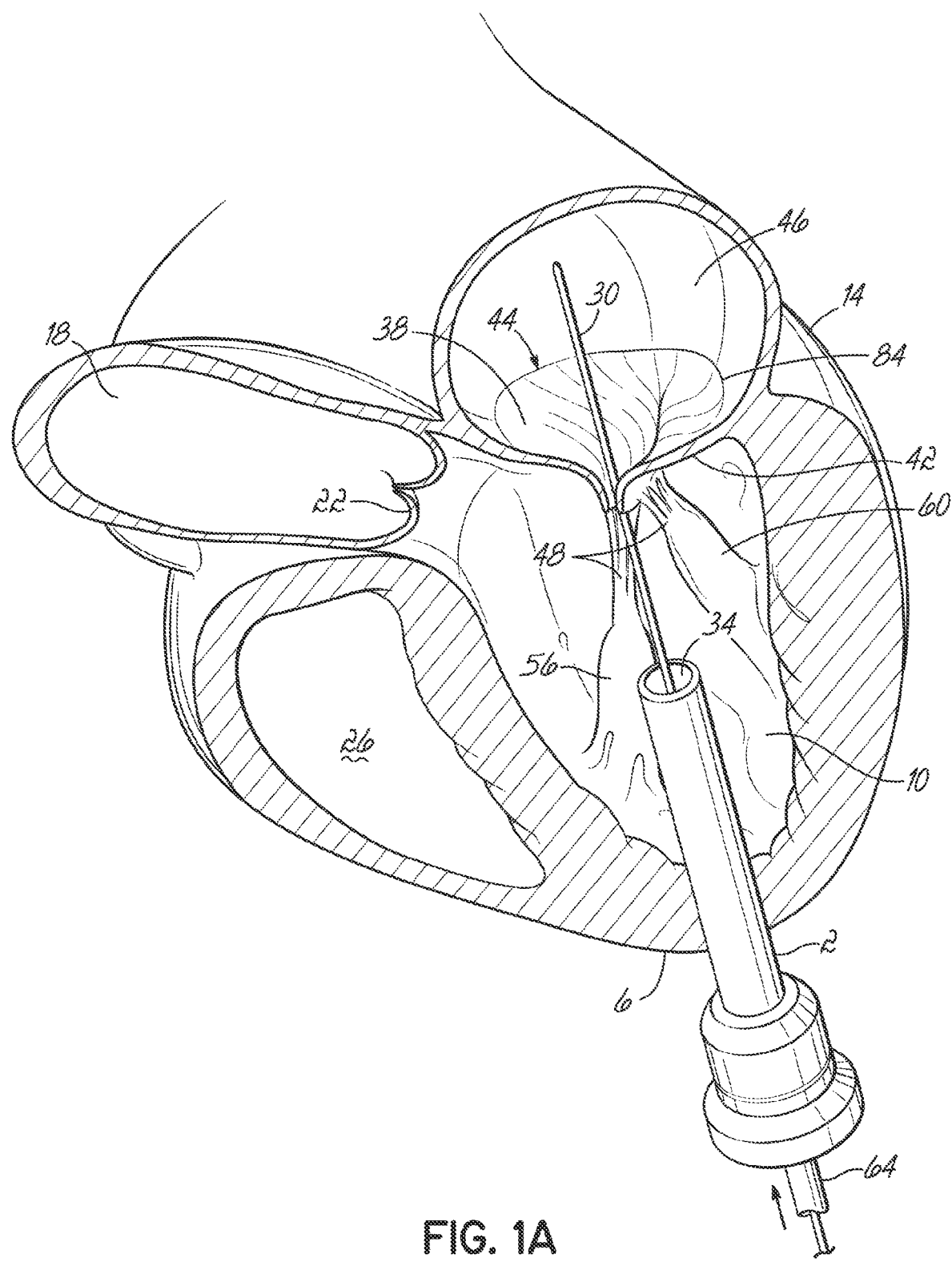
FIGS. 1A-1F illustrate in perspective the placement of one embodiment of a helical anchor in the mitral position of a heart, which is shown in partial cross section.

FIG. 1A shows an introducer 2 inserted into the apex 6 of the left ventricle 10 of a patient's heart 14 by a small thoracotomy, a sternotomy, or from below the diaphragm with an upper abdominal incision. One particularly favorable approach is to make a small incision on the patient's chest near the apex 6 of the left ventricle 10 and then through the apex 6 of the heart 14. To prevent blood leakage from the apex 6, a standard purse string suture could be used to hold the introducer 2 in place and close the defect on removal. It is also possible to use an occluder device for entry and exit. The aorta 18, aortic valve 22, and right ventricle 26 are shown for illustrative purposes. A guidewire 30 is advanced from a lumen 34 of the introducer 2 through the left ventricle 10 and between the anterior and posterior leaflets 38, 42 of the native mitral valve 44 such that a portion of the guidewire 30 is positioned in the left atrium 46. Care should be taken when advancing the guidewire 30 to avoid entanglement of the guidewire 30 with the chordae tendineae 48 or their associated papillary muscles 56, 60. A delivery catheter 64 (FIG. 1B) may then be advanced upon the guidewire 30. The lumen 34 of the introducer 2 should be sufficiently large to allow entry of the various delivery system components.

In another embodiment, the introducer 2 may incorporate a check valve (not shown) to prevent blood leakage. A large number of such devices have been described which often employ one or more duck-bill shaped valves. The guidewire 30 can be straight or feature a U-shaped tip or any convenient shape to allow entry into the left atrium 46.

Figure 1B:
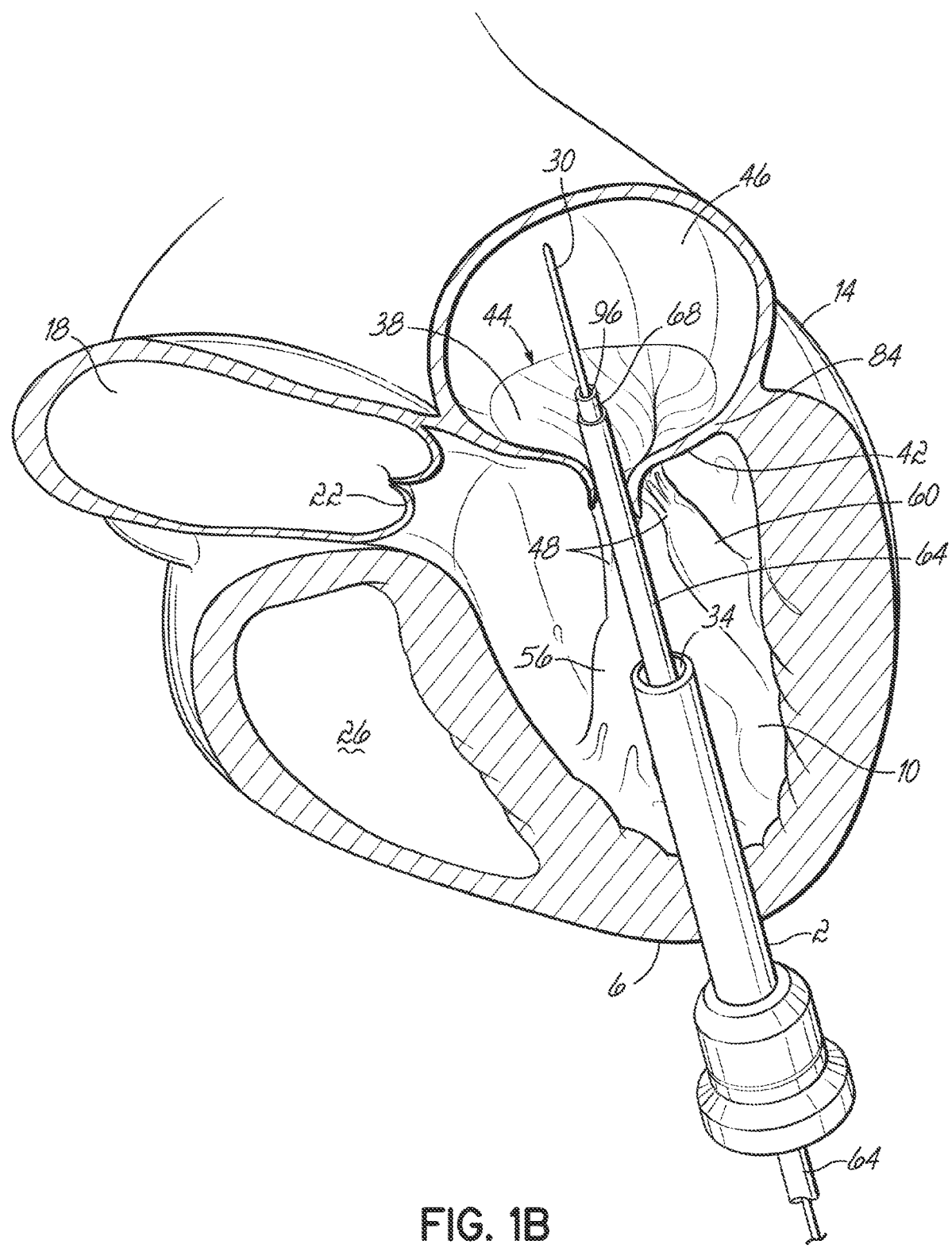

As shown in FIG. 1B, a delivery catheter 64 is introduced over the guidewire 30 into the left atrium 46. The delivery catheter 64 allows the introduction of a coil guide catheter 68. The coil guide catheter 68 has a preformed shape designed to assist in the introduction of a helical anchor 72, and can be composed of any material and/or designed in any manner that allows it to be activated during use to the preformed shape. It may, for example, be designed such that it can be straightened and retain its preformed shape upon release. For example, the coil guide catheter 68 can be formed from a shape memory material such as Nitinol (NiTi) or from a plastic that retains its shape. Also, the coil guide catheter 68 could be a composite of several layers. For example, it may comprise a Nitinol tube with a polymeric cover. It could also be composed of a mesh or weave of Nitinol with or without a cover. The interior could also be lined with a friction reducing material, such as a lubricious coating material to make it more smooth and slippery to introduce the helical anchor 72. The coil guide catheter 68 is straightened for introduction by the delivery catheter 64, which is relatively stiff compared to the coil guide catheter 68. Other options for obtaining the preformed shape may include introducing the distal end of the coil guide catheter 68 as a relatively straight element and then activating it such that it takes on the desired preformed shape, such as with one or more curves that will be discussed below and assist with proper introduction and positioning of the helical anchor 72. One such activatable design would include small coil segments with bevels that, when pulled together, assume the desired shape. It will be appreciated by those of skill in the art that the coil guide catheter 68 may be directed to the mitral valve position without the use of a delivery device, such as the delivery catheter 64. For purposes of the maneuvering the coil guide catheter 68 or other catheter devices used in the embodiments of this invention, any of the various known manners of deflecting the distal end may be utilized.

In one embodiment, the coil guide catheter 68 is positioned in the left atrium 46 or just inside the left ventricle 10 near a mitral valve commissure 80. It should be noted that commissures 80 are the points where the anterior mitral leaflet 38 and posterior mitral leaflet 42 contact each other to close the mitral valve 44 at the valve perimeter or annulus 84. This position can be confirmed visually if the heart 14 is open. However, it is preferred to conduct this procedure with a closed and beating heart 14. In this case imaging modalities such as fluoroscopy, X-ray, CT or MR imaging can be used. Echocardiography in 2D or 3D can also be used to help guide the position. It should be appreciated that the coil guide catheter 68 can also be positioned in the left ventricle 10 for placement of the helical anchor 72.

Figure 1C:
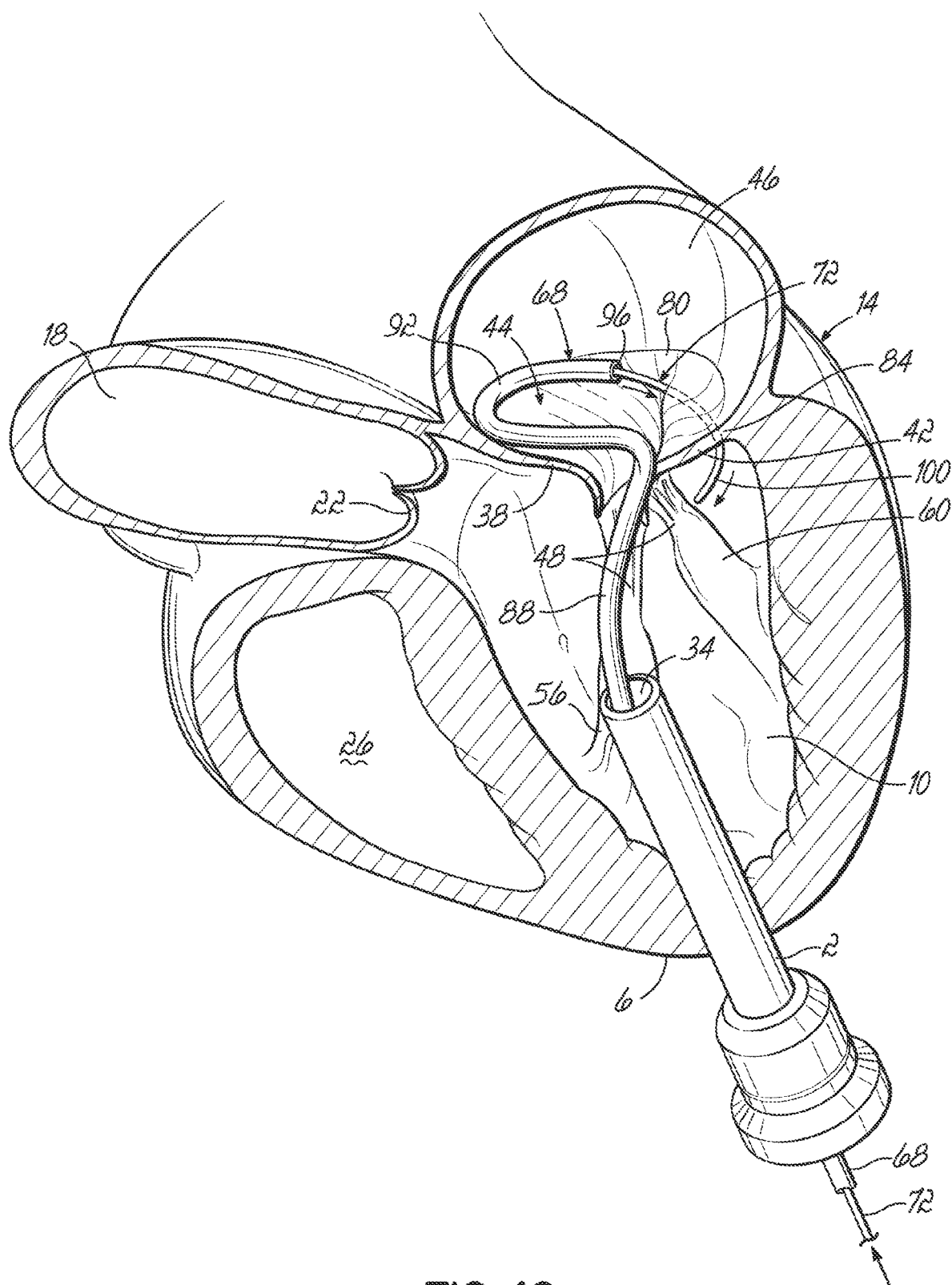

When the delivery catheter 64 is removed, the coil guide catheter 68 assumes its preformed shape to facilitate the introduction of the helical anchor 72, as shown in FIG. 1C. The coil guide catheter 68 comprises a stem 88 and a U-shaped portion 92. The coil guide catheter 68 has a lumen 96 which is roughly circular with a diameter similar to the helical anchor 72 which it delivers. The U-shaped portion 92 of the coil guide catheter 68 is oriented generally parallel to the plane of the mitral valve 44 and helps to correctly position the depth of the coil guide catheter 68 inside the heart 14 so that the helical anchor 72 is extruded into the plane of the mitral valve 44. This ensures that the helical anchor 72 will be directed closely under the leaflets 38, 42. The tip 100 of the helical anchor 72 may also have a slight outward and downward turn to allow direction of the helical anchor 72 under the valve leaflets 38, 42. The coil guide catheter 68 is shown with a slight upward turn at the stem 88 before the U-shaped portion 92 that sits parallel to the valve 46. This is not necessary but helps to make pushing the helical anchor 72 into position less difficult. It will also be appreciated that the distal portion of the coil guide catheter 68 need not be parallel to the valve 44 and annulus 84, as shown. It may instead be angled and yet the distal end of the helical anchor 72 will naturally orient itself downwardly and between the leaflets 38, 42 and then extrude and coil or spiral into the proper position. It should also be noted that in each embodiment herein, no puncturing of valve, leaflet or heart tissue needs to take place.

As shown in FIG. 1C, the helical anchor 72 has been advanced so that the end of the helical anchor 72 is starting to track under the posterior leaflet 42. The tip 100 of the coil guide catheter 68 is located above the plane of the valve 46, but it can also be located under the posterior leaflet 42. It should be noted that there is no need for penetration through any area of tissue. The helical anchor 72 is passed between leaflets 38, 42 near a commissure 80. It is appreciated that penetration through the leaflets 38, 42 could be used, but is less desirable due to the delicate nature of the leaflets 38, 42. It is also possible to pass the helical anchor 72 at any location, including a location that is distal from a commissure 80. This may result in folding or bending of one or both of the leaflets 38, 42 if the starting point is not at or near the commissure 80 once the helical anchor 72 is placed.

Figure 1D:
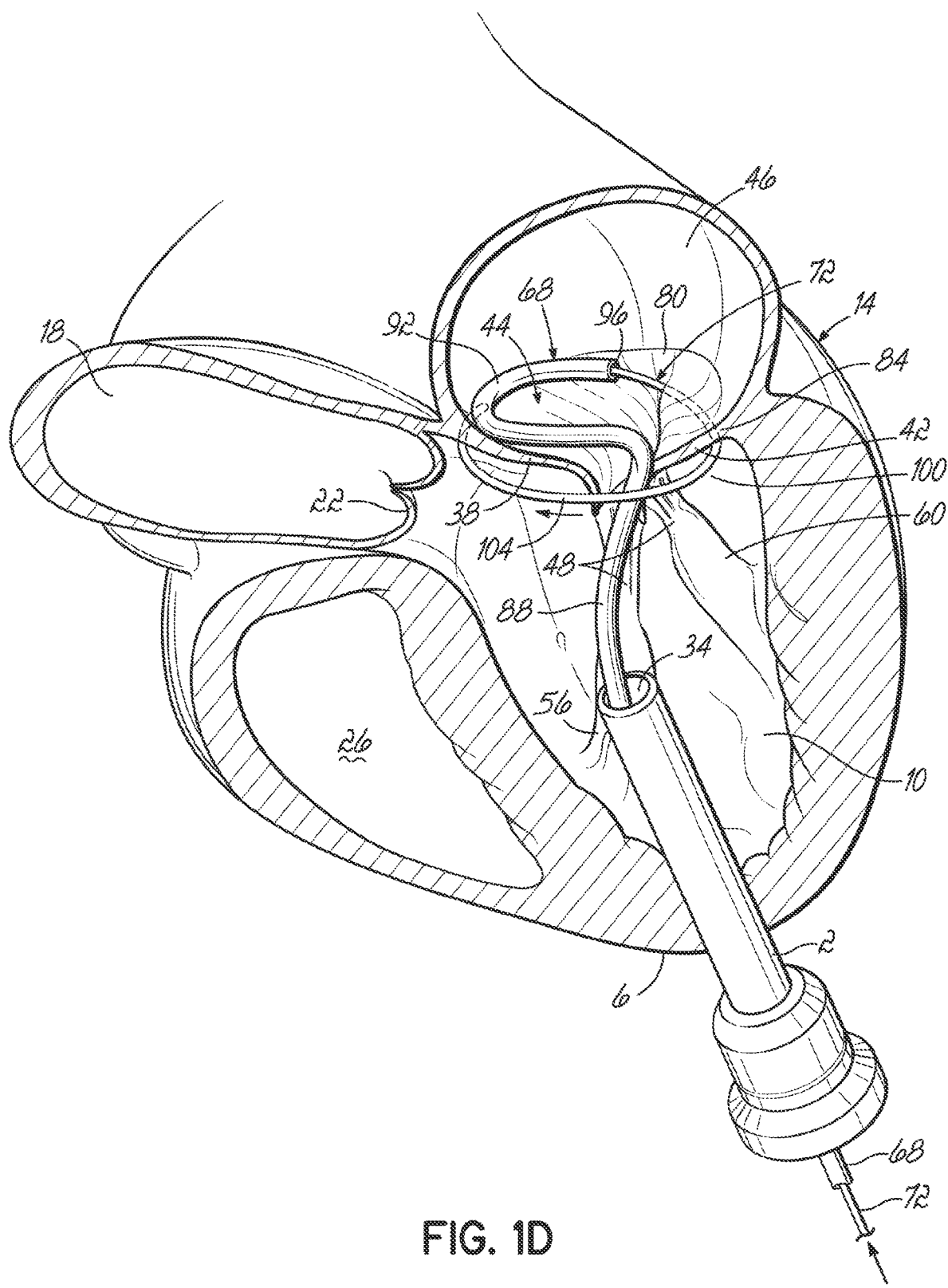
Figure 1E:
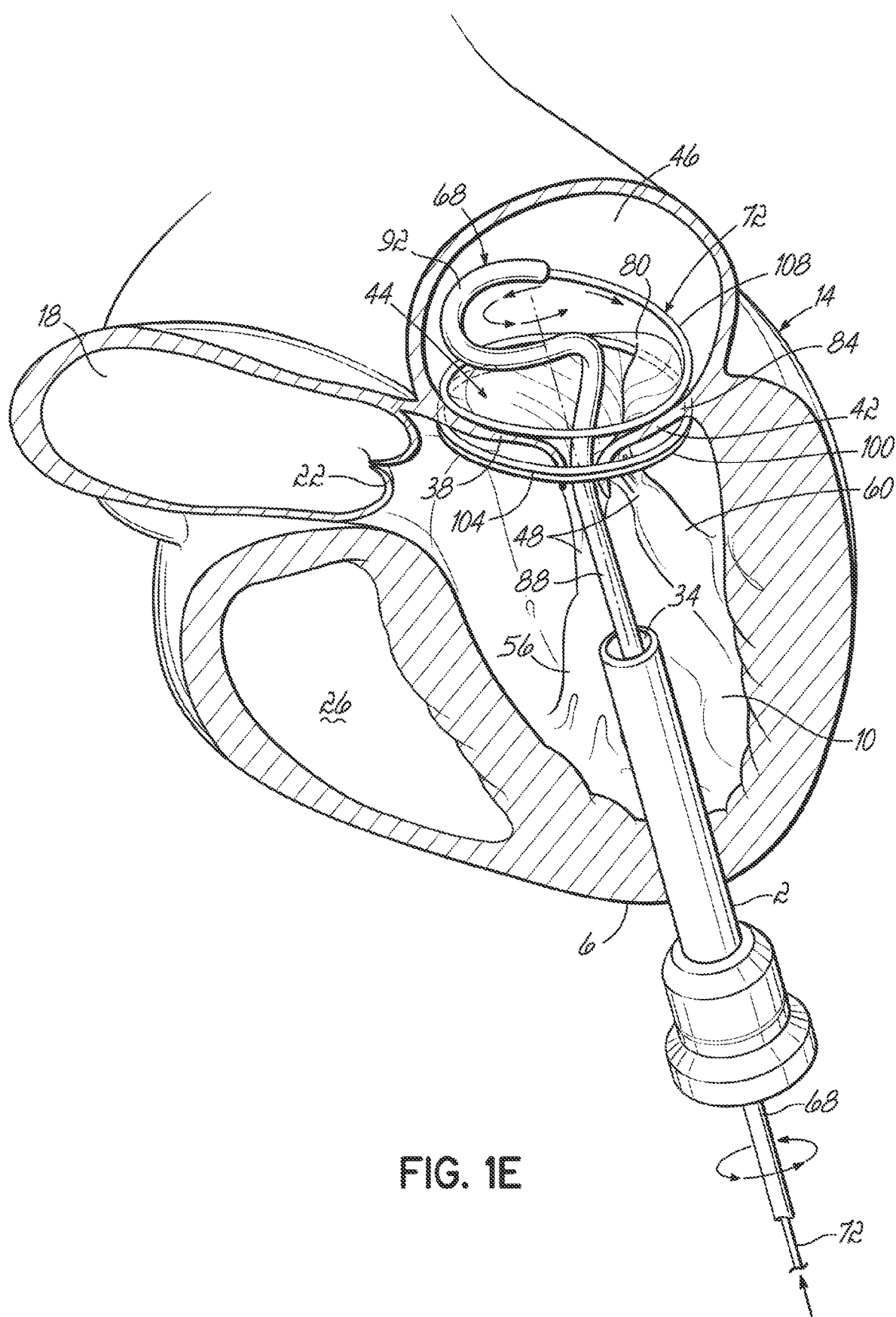

The helical anchor 72 is further advanced by being pushed through the coil guide catheter 68. FIG. 1D shows most of a complete revolution of the helical anchor 72 positioned under the mitral valve 44. The number of lower coils 104 of the helical anchor 72 can vary from less than one to as many as the operator thinks is useful. After the lower coils of the anchor 72 have been placed under the mitral valve annulus 84, upper coils 108 of the helical anchor 72 are positioned above the annulus 84 by rotating the coil guide catheter 68 as the helical anchor 72 is advanced. This is shown in FIG. 1E.

It is also possible to avoid rotation during delivery of the helical anchor 72 above the mitral valve annulus 84, since the shape memory material will assume the correct position. However, it is understood that the helical anchor 72 may jump and put force on the coil guide catheter 68 if there is no rotation. Another valuable option for inserting the helical anchor 72 without the need for rotation of the coil guide catheter 68 is to straighten the coil guide catheter 68. When the coil guide catheter 68 has been straightened, the helical anchor 72 which has a circular preformed shape will not have to compete with the preformed shape of the coil guide catheter 68 and can resume its preformed shape inside the atrium 46.

Figure 1F:
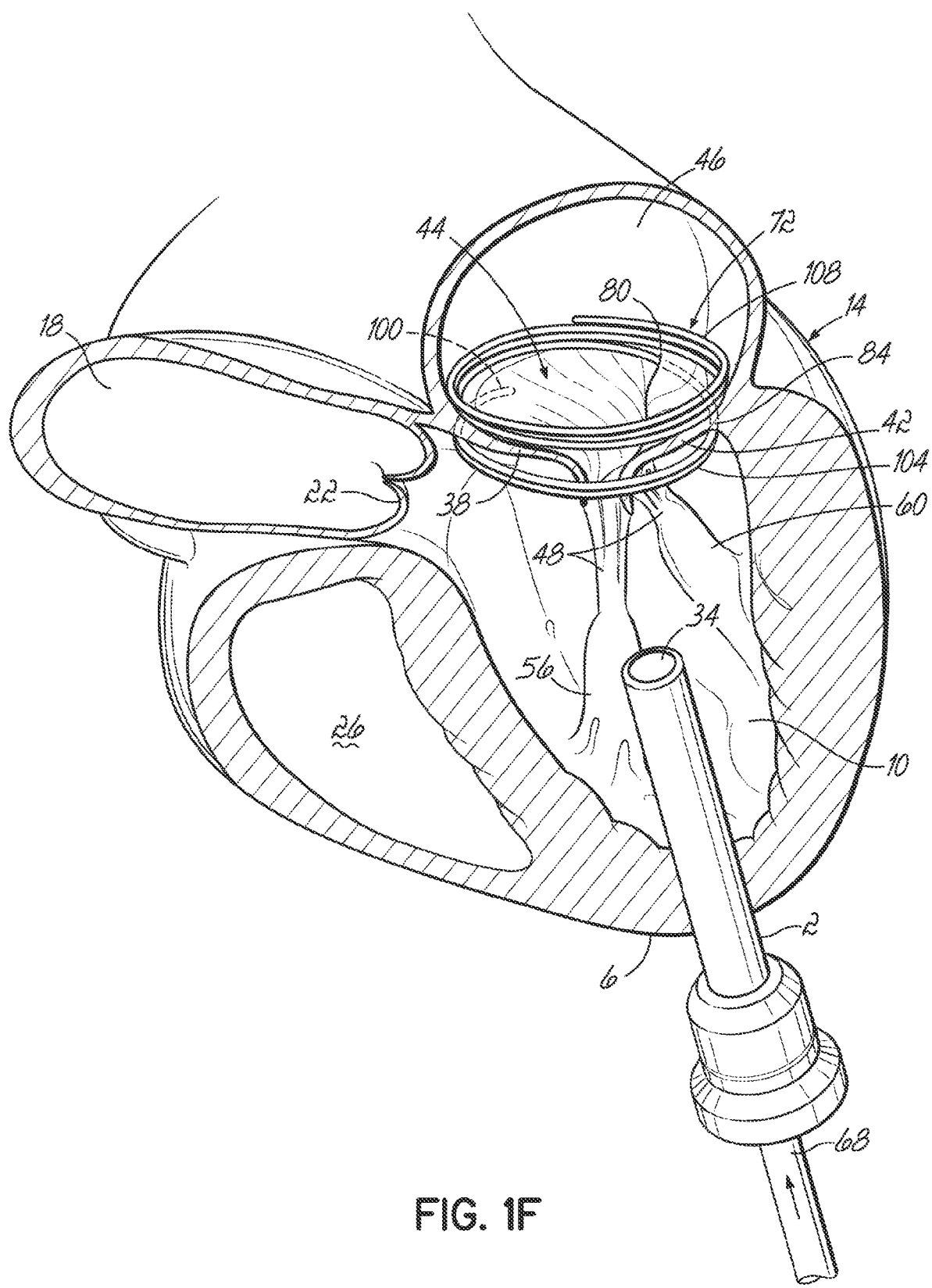

After the helical anchor 72 is implanted, the coil guide catheter 68 is removed. FIG. 1F shows that about two coils 108 have been placed above the mitral valve annulus 84 and about two coils 104 have been placed below the mitral valve annulus 84. In other embodiments, the arrangement shown can be varied. There may be any number of coils 104, 108 as the operator sees fit. It should be noted that even a portion of a coil 104,108 above or below the annulus 84 may be sufficient to retain the helical anchor 72. It should be noted that the size of the helical anchor 72 can be preselected before placement so that it closely matches the diameter of the annulus 84. This maximizes the size of the replacement valve implant that can be placed inside the helical anchor 72 and helps reduce the risk of a leak at the commissures 80.

The gap between the coils 104, 108 can be adjusted when making the helical anchor 72. By leaving a slightly larger gap between the coils 104, 108 sitting above and below the annulus, it is possible to allow the valve tissue 44 to close at the commissures 80 by permitting a small amount of motion of the leaflets 38, 42 as the heart 14 contracts. This is one strategy to ensure there is no leak around the helical anchor 72. The coils 104, 108 do not need to trap the leaflet tissue 38, 42. In fact, leaving a gap between the ventricular and atrial coils 104, 108 may be advantageous in permitting the leaflet tissue 38, 42 to close at the commissures 80 and prevent blood flow leakage at these locations. In addition to leaving a sufficient gap between at least the coils 104, 108 (i.e., a gap that spans the annulus 84 when the anchor 72 is implanted, other manners of preventing the trapping of annulus tissue are possible. For example, the atrial coil or coils 108 may be of larger diameter or even shaped differently than a "coil" such that it comprises an extension that engages a portion of the atrial wall 46 *a* above the annulus 84. Various other designs for atrial and/or ventricular anchor stabilization are possible as well.

FIG. 1F shows the coils 104 wrapping around the anterior leaflet 38 of the mitral valve 46 which is near the aortic valve 22. The anterior leaflet 38 is engaged by the lower coils 104 of the helical anchor 72 and is thereby restricted from obstructing the flow of blood into the aortic valve 22. The coils 104 can also be adjusted to sit even lower than shown if additional control of the anterior mitral leaflet 38 is desired. In other embodiments, the number of lower coils 104 in the helical anchor 72 can be adjusted to cover more of the anterior mitral leaflet 38. The lower coils 104 can sit high against the annulus 84, or lower in the ventricle 10.

It should be noted that once a helical anchor 72 has been inserted as described herein, the patient's native mitral valve 44 continues to work, i.e., the leaflets 38, 42 continue to open and close during the heart cycle as required. The valve 44 can open and close normally despite some restriction of the opening by the coils 104, so that functionally the patient can remain stable. This allows an operator to implant a valve prosthesis within the anchor 72 without the risk of the patient being in a position of hemodynamic compromise. Therefore, the procedure can be performed on a beating heart 14 without a heart-lung machine. Another feature of this design is that when the replacement valve (i.e., prosthesis) is positioned, the location of the replacement valve (e.g. in the annulus, relatively higher than the annulus, or in the ventricle) can be chosen by the location of the coils 104, 108 and by the physician's decision about the optimal placement of the valve prosthesis. This allows a valve prosthesis or replacement valve implant to sit lower or higher in the annulus 84 depending on the particular design of the helical anchor 72 and the patient's anatomy and clinical situation.

Figure 1G:
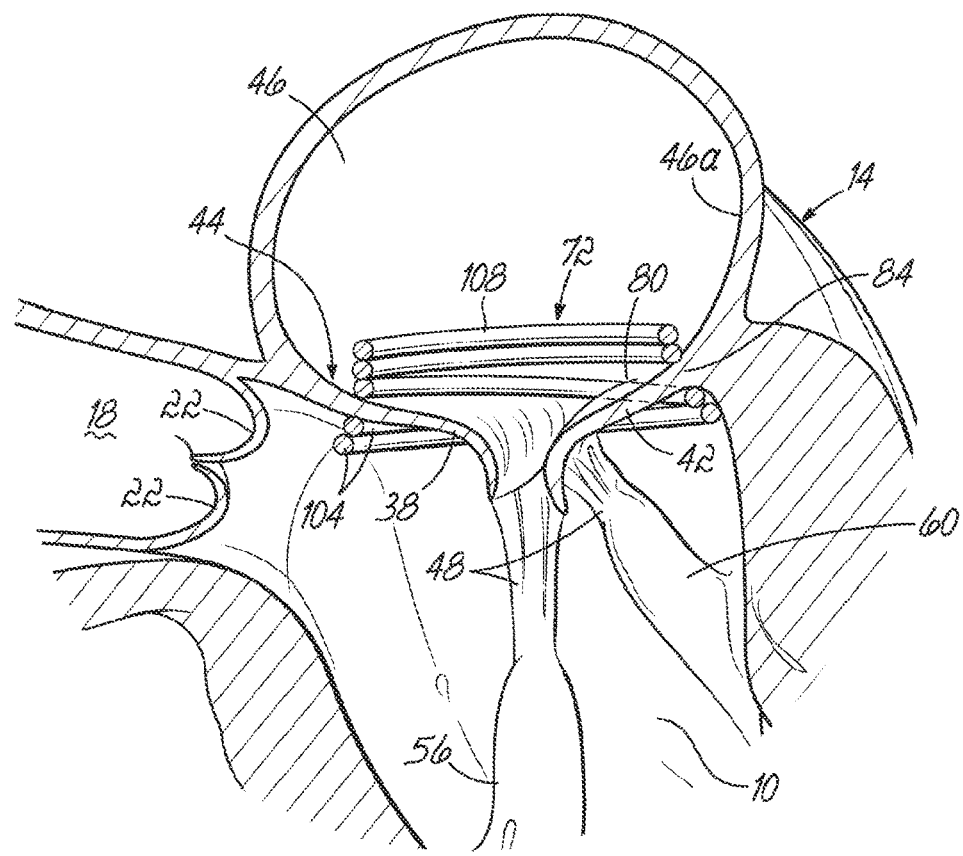
FIG. 1G is a cross sectional view of the helical anchor shown in FIG. 1F.
Figure 1H:
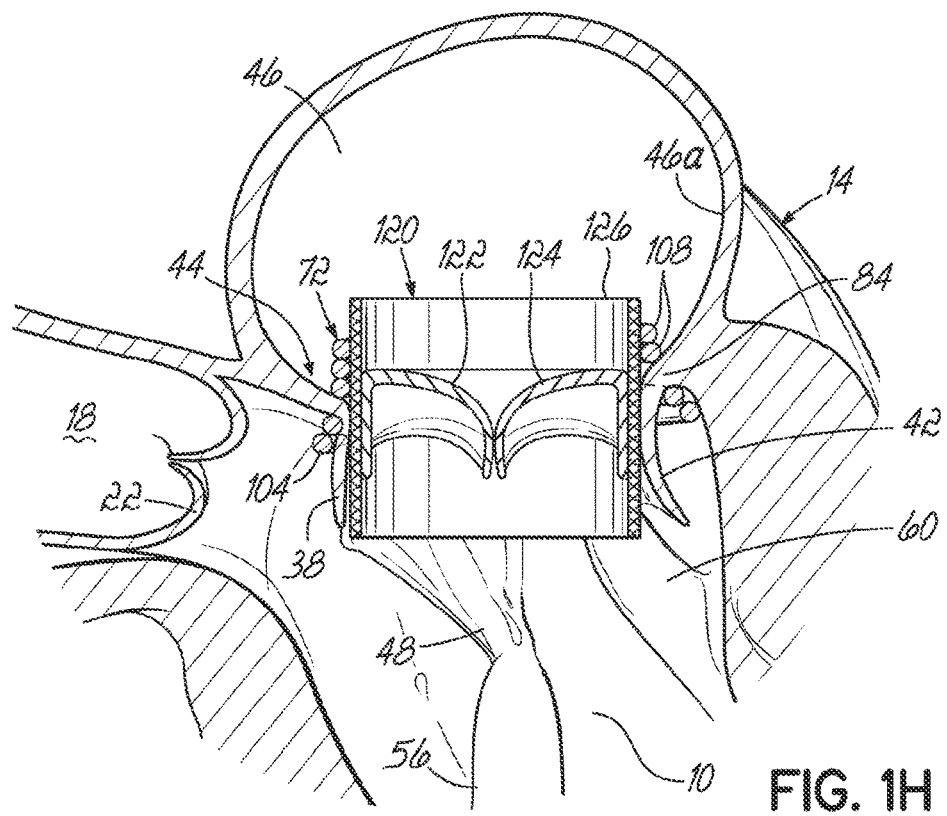
FIG. 1H is a cross sectional view of a valve prosthesis retained by the helical anchor shown in FIGS. 1F and 1G.

FIG. 1G shows a helical anchor 72 that has been implanted with approximately three coils 108 above the mitral valve annulus 84 in the left atrium 46 and approximately two coils 104 below the annulus 84 in the left ventricle 10. The anterior and posterior leaflets 38, 42 are engaged by the coils 104, 108 of the helical anchor 72. In particular, the anterior leaflet 38 is restrained by the coils 104, 108 so that it is prevented from obstructing the flow of blood into the aortic valve 22. In this embodiment, at least one or more of the coils 104 below the annulus have diameters greater than the diameter of at least one or more of the coils 108 above the annulus 84. This type of design can have a number of benefits. For example, it can assist in closing the commissures 80 and thereby prevent leakage of blood at these locations after the procedure is complete. It can also assist with the insertion of the helical anchor 72 to initially start extruding the larger diameter coil(s) and then proceed with smaller diameter coils. Referring to FIG. 1H, the use of smaller diameter coils 108 at the location where a mitral valve prosthesis 120 will be implanted allows for implantation of a smaller sized prosthesis 120, and this can be advantageous for various reasons. Some patients may have a large diameter annulus 84 and a doctor may want to implant a smaller prosthesis 120. This will also help prevent obstruction of the aortic valve 22. The valve prosthesis retention coils 108, e.g. the smaller coils, may also extend higher into the left atrium 46 such that the prosthesis is also positioned higher and away from the aortic valve 22. It should be appreciated that the coils 104, 108 of the helical anchor are not required to have the same diameter. Rather, it may be appropriate for the diameter to vary on each turn or coil 104, 108. Likewise, the coils 104, 108 are not required to be precisely circular. It may be useful for some embodiments to have turns in the coils that are more oval or elliptical in shape. For example, an elliptical shape may be useful if the coils 108 above the annulus 84 seat against the atrial wall 46*a* rather than on the native mitral valve 44 itself.

Still referring to FIG. 1H, a valve prosthesis 120 is retained by a helical anchor 72 in the mitral position. The valve prosthesis 120 comprises a pair of artificial leaflets 122, 124 mounted within an expanded stent structure 126. The artificial leaflets 122, 124 may comprise pliable animal tissue such as cow, pig or horse pericardium or animal valve tissue. Many variations of percutaneous valves 120 have been described for implantation with a catheter, such as those used for aortic valve replacement. The valve prosthesis 120 can be self expanding, such as previously described percutaneous valves based on a shape memory stent such as Nitinol (NiTi), or balloon expandable such as a stainless steel or non-shape memory stent material. The valve prosthesis 120 can be introduced through the same introducer 2 initially shown in the apex 6 of the left ventricle 10. This portion of the procedure is well known since thousands of percutaneous valve implants are performed each year, and all appropriate technologies and methods can be employed to insert the valve prosthesis 120 and anchor it into the helical anchor 72 as shown. The helical anchor 72 can be seen on X-ray, MR, CT and echocardiography to help position the valve prosthesis 120 and perform the procedure. Radiopaque markers such as gold may be added to the surface of the shape memory materials to improve X-ray identification.

In this embodiment, the valve prosthesis 120 is docked to the helical anchor 72 such that the anterior and posterior leaflet tissue 38, 42 is secured between the anchor 72 and the valve prosthesis 120. This serves to lock the anchor 72 in position and prevent it from moving or dislodging. The leaflet tissue 38, 42 also creates a natural seal to prevent blood flow between the valve prosthesis 120 and helical anchor 72. In other embodiments locking of the anchor 72 can also be completed by placing coils 108 of the anchor 72 above the mitral valve 44 such that the upper coils 108 do not compress the valve leaflets 38, 42 but instead abut the atrial wall 46*a*.

The replacement valve 120 can be anchored against the coil(s) 108 of the anchor 72 above the annulus 84, below the annulus 84 or both. FIG. 1H shows a valve 120 that is relatively centered and is anchored against the coils 104, 108 about equal amounts above and below the annulus 84. The precise position can be chosen by the operator. Also, the coils 104, 108 can be adjusted (more coils 104, 108 on the atrial or ventricular side) to help facilitate locating the valve 120.

In order to prevent movement or slipping of the helical anchor 72, it is helpful to compress the leaflets 38, 42 between the valve prosthesis 120 and at least one part of the helical anchor 72 below the annulus 84. The insertion of the valve prosthesis 120 into the helical anchor 72 locks the anchor 72 in position. An advantage of pressing the valve prosthesis 120 against both the coils 104, 108 above and below the valve 44 is that motion of the coils 104, 108 will be stopped. The prosthesis 120 will lock any coils 104, 108 it abuts against into a solid and non-movable position. This can be important because with each heartbeat there is movement in the heart 14. Nitinol and other shape memory materials are strong but are known to have limited resistance to cyclic loads, causing them to fatigue rapidly and fracture. Therefore, preventing movement is very important.

It should be appreciated that in other embodiments the valve prosthesis 120 may not be attached to the helical anchor 72 both above and below the annulus 84. The coils 108 above the annulus 84 do not necessarily need to abut the valve prosthesis 120. Furthermore, anchoring of the valve prosthesis 120 can be achieved by only engaging the anterior and posterior leaflets 38, 42 against the coils 104 below the annulus 84. There can be minimal or no coils 108 of the helical anchor 72 above the annulus.

As described previously, the entire procedure can be performed through the atrium 46 or via a transseptal puncture. More details of a transseptal procedure will be shown and described below.

Figure 1I:
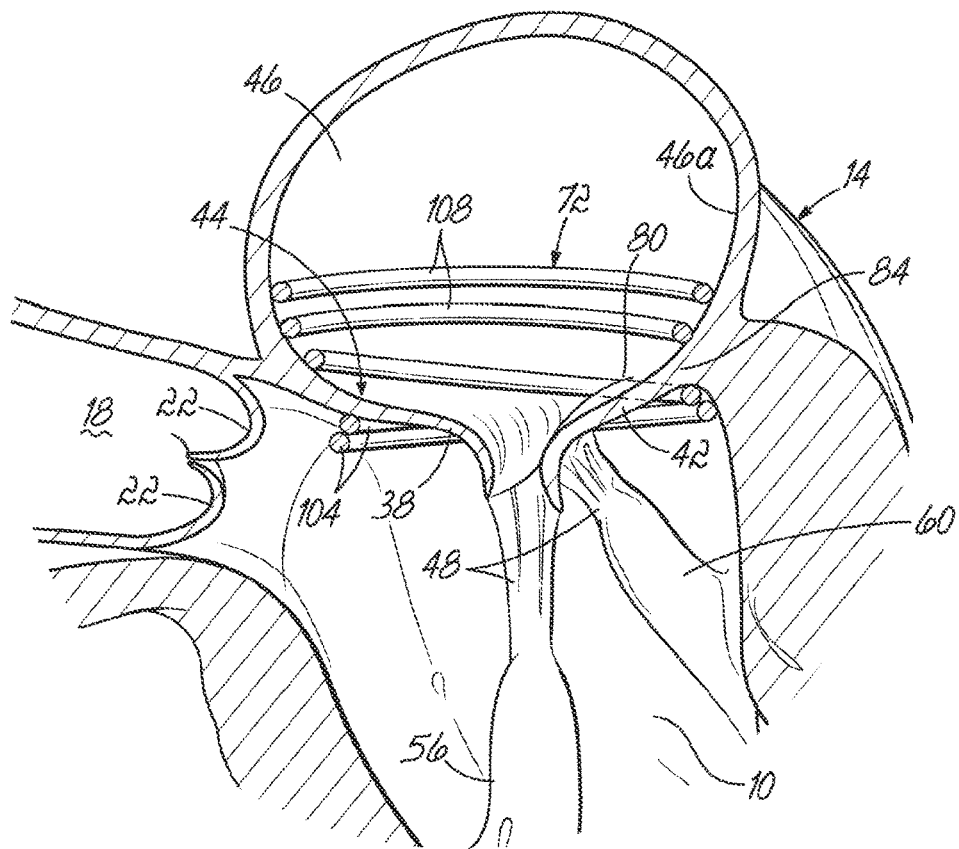
FIG. 1I is a cross sectional view of an alternative embodiment of a helical anchor that has been placed in the mitral position of a heart, wherein the coils located in the atrium do not contact the valve leaflets but anchor against the wall of the atrium.

It is not necessary to have coils 104, 108 of the helical anchor 72 engaged with both sides of the leaflets 38, 42. FIG. 1I shows an embodiment of a helical anchor 72 in accordance with the present invention. The anterior and posterior leaflets 38, 42 are engaged by the coils 104 of the helical anchor 72 below the mitral valve annulus 84 in the left ventricle 10. In particular, the anterior leaflet 38 is restrained by the coils 104 so that it is prevented from obstructing the flow of blood into the aortic valve 22. However, the coils 108 on the opposite side of the valve 44 in the left atrium 46 do not contact the leaflets 38, 42 but anchor against the atrial wall 46a. This arrangement keeps the anchor 72 from moving as in previous descriptions but relies on the atrial wall 46a rather than valve leaflets 38, 42 to support the upper coils 108. The helical anchor 72 cannot move upward toward the atrium 46 due to the contact with the leaflets 38, 42 below the valve 44, and it cannot move downward due to the contact with the atrial wall 46a.

It should be appreciated that combinations of the helical anchor variations could be used in other embodiments and may be easily made. For example, helical anchors 72 could be constructed such that coils 104, 108 sit below the valve 44 and above the valve 44, but there is a gap between the coils 104 below the valve 44 and coils 108 above the valve 44. Valve leaflets 38, 42 would not be trapped between coils 104, 108 of the helical anchor 72. This arrangement allows the mitral valve 44 to approximate naturally at the commissures 80 because the leaflet tissue 38, 42 is not trapped between coils 104, 108 and can prevent leaks at the commissures 80. In another embodiment, additional coils 104, 108 may be added which would extend from the top of the coils 108 previously described in the left atrium 46 to anchor against the atrial wall 46a. This arrangement may allow a valve prosthesis 120 to be fastened to coils 104, 108 above and below the annulus 84 to improve the stability of the valve prosthesis 120 and anchor to the atrial wall 46a. It should be noted that in addition to the gap between coils 104 and 108, both the diameter of the helical anchor 72 and shape of the coils 104, 108 could be varied. The helical anchor 72 does not need to be uniform in diameter or profile. For example, the coils 108 above the annulus 84 might be made thicker than the coils 104 below the annulus 84 for more strength of attachment to the atrial wall 46a. There could be thicker and thinner areas of the coils 104, 108 as needed for strength or function. Furthermore, the cross sectional shape of the coils 104, 108 does not need to be circular.

Figure 1J:
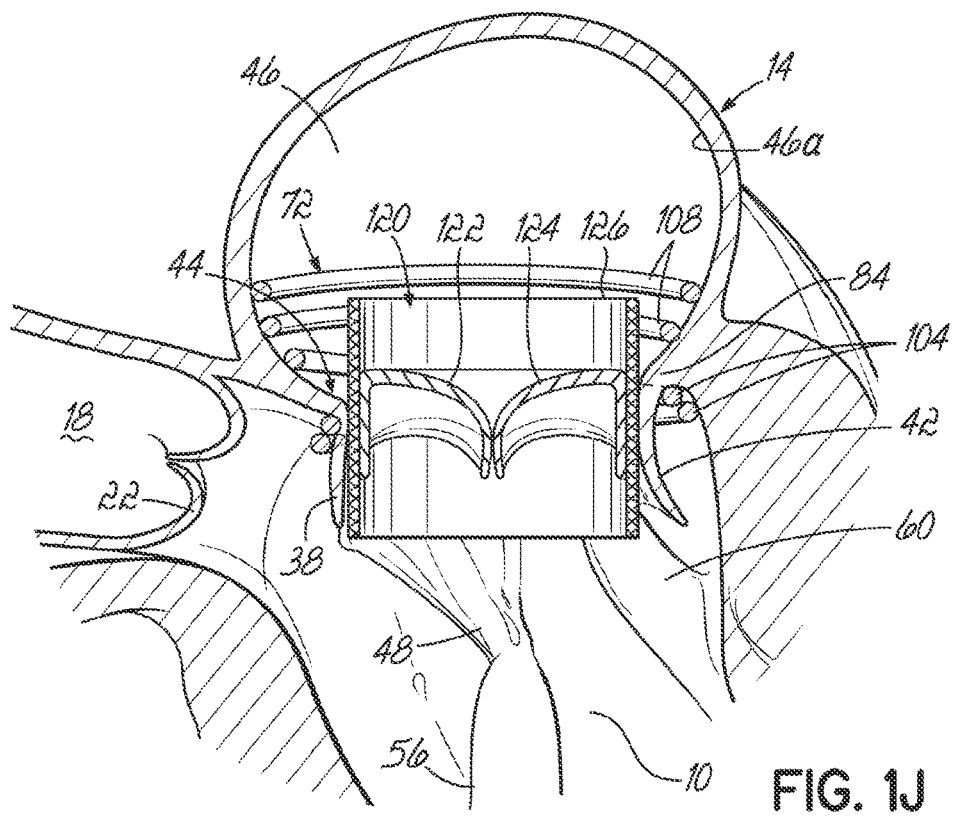
FIG. 1J is a cross sectional view of a valve prosthesis retained by the helical anchor shown in FIG. 1I.

FIG. 1J shows a valve prosthesis 120 that has been anchored to the helical anchor 72 shown in FIG. 1I. In this embodiment, the valve prosthesis 120 comprises a pair of artificial leaflets 122, 124 mounted within an expandable stent structure 126. The artificial leaflets 122, 124 may comprise pliable animal tissue such as cow, pig or horse pericardium or animal valve tissue. Various suitable valve prostheses have been previously described. In this embodiment, the valve prosthesis 120 is docked to the helical anchor 72 such that the anterior and posterior leaflet tissue 38, 42 is secured between the anchor 72 and the valve prosthesis 120. This serves to lock the anchor 72 in position and prevent it from moving or dislodging. The leaflet tissue 38, 42 also creates a natural seal to prevent blood flow between the valve prosthesis 120 and helical anchor 72.

As described, in other embodiments more coils 108 could be placed above the annulus 84 (in addition to the coils 108 which contact the atrial wall 46a) so that the valve prosthesis 120 could anchor to coils 104, 108 of the helical anchor 72 above and below the annulus 84 as previously described with reference to FIG. 1H. The coils 108 above the annulus 84 could easily not abut the leaflets 38, 42, but rather there could be a gap between the coils 108 above and coils 104 below the annulus 84 such that there is no trapping of leaflet tissue 38, 42 between coils 104, 108.

Figure 1K:
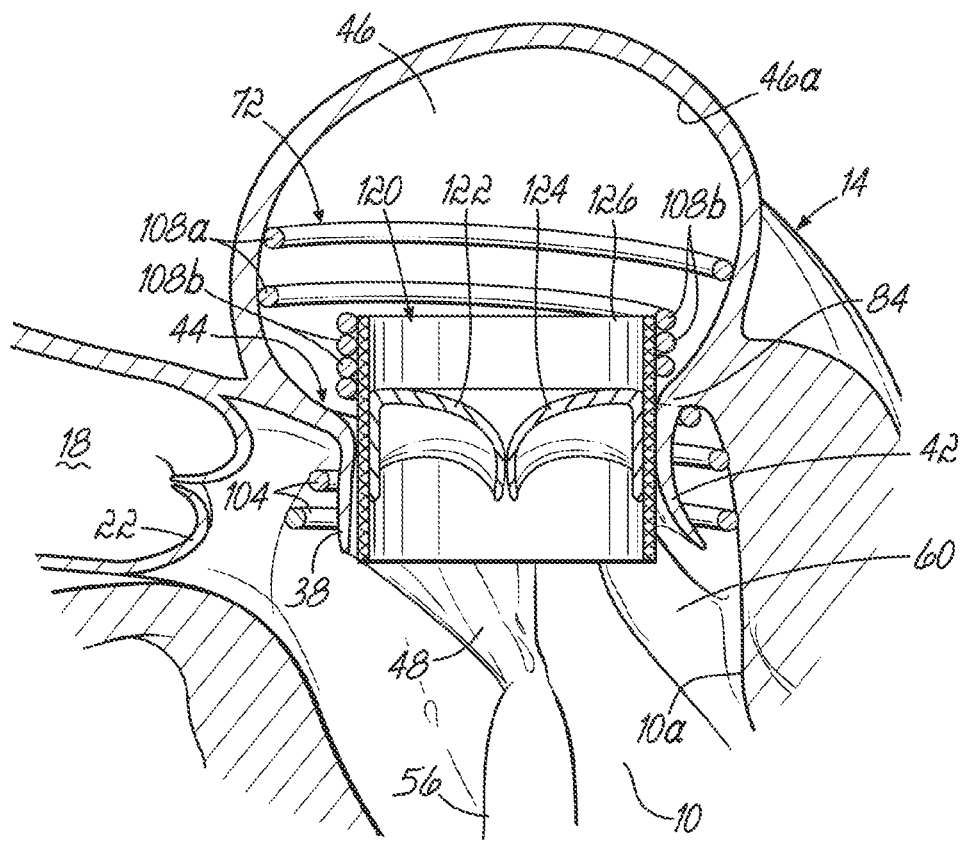
FIG. 1K is a cross sectional view of a valve prosthesis retained by another alternative embodiment of a helical anchor that has been placed in the mitral position of a heart.

FIG. 1K shows an embodiment of a helical anchor 72 having a varied coil configuration. The anchor 72 is held in place by coils 108a extending above the annulus 84 which abut against the atrial wall 46a and by coils 104 extending below the annulus 84 which abut against the ventricular wall 10a. Additional coils 108b above the annulus 84 engage and hold a valve prosthesis 120 without contacting either of the anterior or posterior leaflets 38, 42. The valve prosthesis 120 comprises a pair of artificial leaflets 122, 124 mounted within an expandable stent structure 126. The artificial leaflets 122, 124 may comprise pliable animal tissue such as cow, pig or horse pericardium or animal valve tissue. Various suitable valve prostheses have been previously described. In this embodiment, the coils 104 of the helical anchor 72 below the annulus 84 may not trap the anterior and posterior leaflet tissue 38, 42 between the anchor 72 and the valve prosthesis 120 sufficiently to create a seal between the helical anchor 72 and valve prosthesis 120 or prevent the anterior leaflet 38 from obstructing blood flow into the aortic valve 22. Therefore, in another embodiment the coils 104 below the leaflets 38, 42 may be adjusted to tightly secure the leaflets 38, 42 against the valve prostheses 120, rather than abutting the ventricular wall 10a. Securing the anterior leaflet 38, such as in any of the manners described herein can be important for purposes of preventing obstruction of blood flow from the left ventricle 10 through the aortic valve 22. As previously mentioned, coils 108a and 108b may be configured such that the prosthesis 120 can be implanted at a desired height relative to the annulus 84. In addition to preventing obstruction of the aortic valve 22 with the prosthesis 120, this can prevent the prosthesis from contacting the walls of the left ventricle 10, which could lead to rupture of the left ventricle 10. This latter case can be especially important for patients with small left ventricles.

Figure 2:
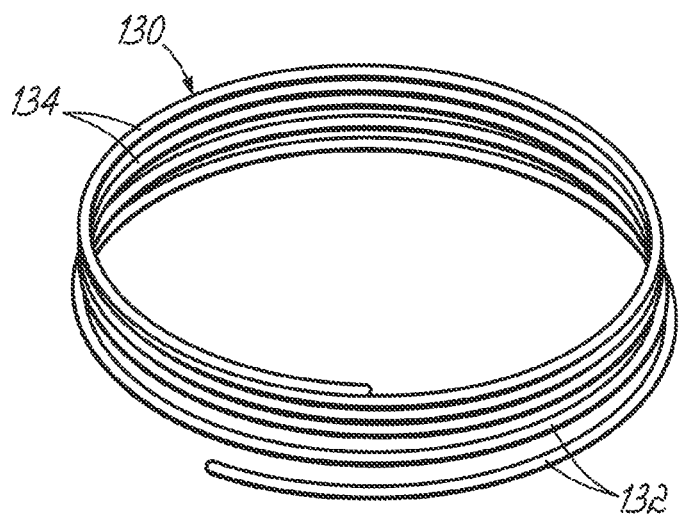
FIG. 2 is a perspective view of another alternative helical anchor for a mitral valve prosthesis, characterized by an initial area extending outward from the coil.
Figure 3:
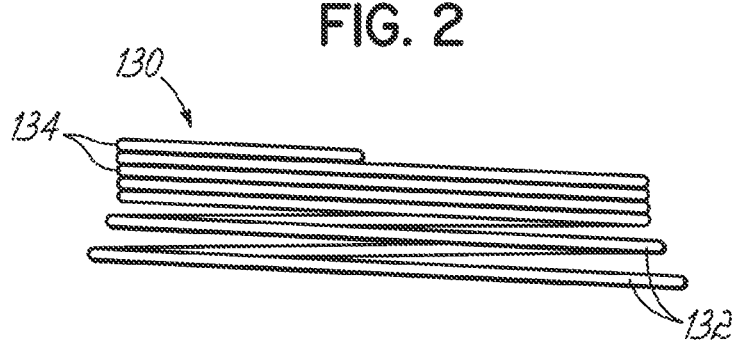
FIG. 3 is a side view of the helical anchor shown in FIG. 2.
Figure 4:
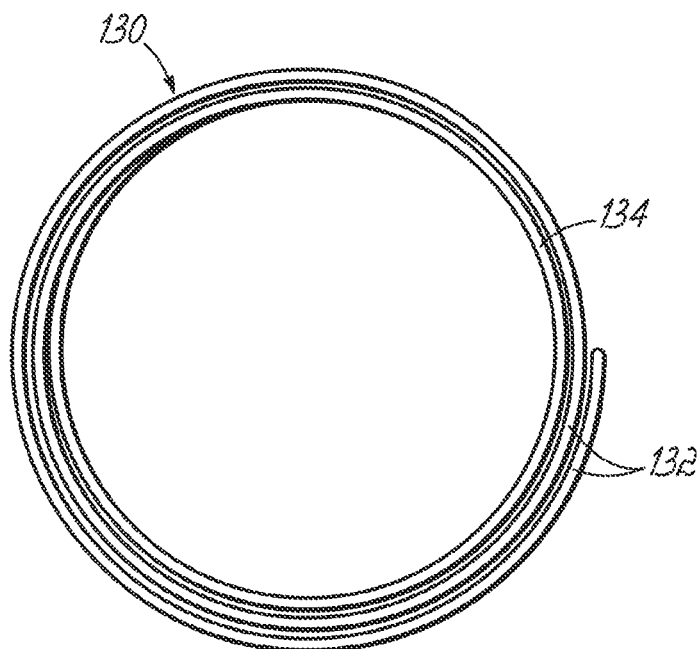
FIG. 4 is a bottom view of the helical anchor shown in FIGS. 2 and 3.

The helical anchor of the present invention can be constructed in a large number of variations. FIGS. 2, 3 and 4 show an embodiment of a helical anchor 130 wherein the lower coils 132, or first approximately two coils, of the anchor 130 have diameters that are greater than the diameter of the remaining upper coils 134. This allows for easy engagement with the mitral annulus 84 (FIG. 1A) during insertion. In addition, the lower coils 132 of the anchor 130 extend slightly downward creating gaps so that the lower coils 132 do not press against each other, while the upper coils 134 are shown contacting each other. This feature allows the initial lower coil 132 to slip to the opposite side of the mitral leaflets 38, 42 as it is inserted and to avoid unwanted friction or drag as the anchor 130 is pushed into place. Both of these variations, whether included together or separately in other embodiments, may help with anchor placement and improve retention. Further embodiments, not shown, can include anchors having coils of varying diameters, coils spaced with varying gap sizes, and coils which taper, expand, or flare larger or smaller. It should be noted that the coils may stretch radially outward when the valve prosthesis 120 (FIG. 1H) is placed or expanded within the helical anchor 72 or 130. This is seen particularly in the middle coils. Therefore, even though the coils may have different diameters initially, the coils may all contact the valve prosthesis 120. It should also be noted that a valve prosthesis 120 may have a varying diameter, which may be designed for optimal contact with a desired number of coils of the helical anchor 72 or 130 to improve retention.

Figure 5:
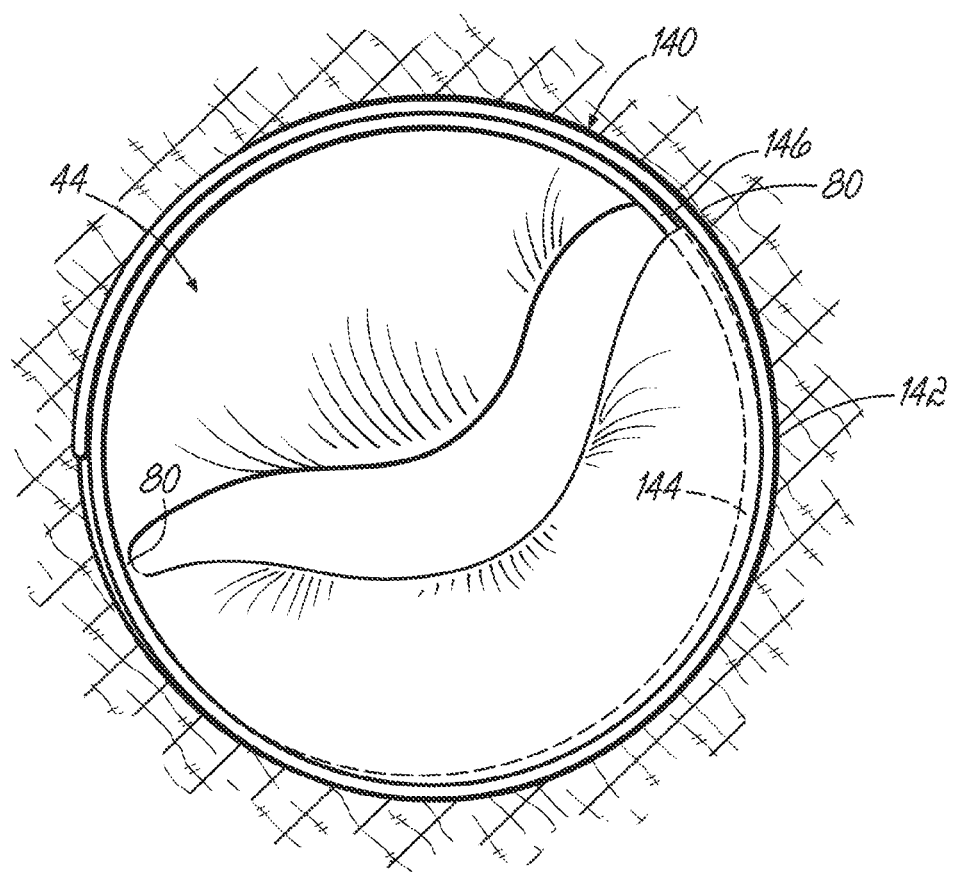
FIG. 5 is an aerial view of a helical anchor that has been placed in the mitral position of a heart via a commissure in the native mitral valve.

FIG. 5 illustrates an embodiment of the present invention in which a helical anchor 140 for docking a valve prosthesis (not shown) passes through one of the two commissures 80 of the mitral valve 44. Coils 142, 144 of the anchor 140 are located above and below the annulus 84, and a connecting segment 146 is located across the commissure 80 without passing through valve tissue.

Figure 6:
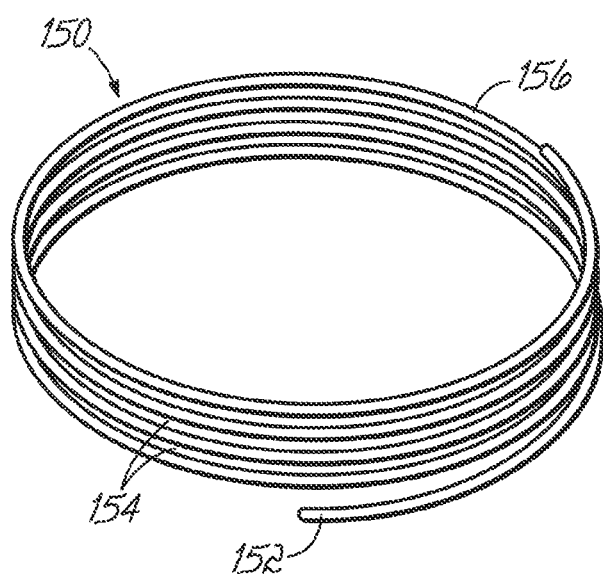
FIG. 6 is a perspective view of another alternative helical anchor of a mitral valve prosthesis, characterized by no taper but having a slight outward turn at the start.

FIG. 6 illustrates another illustrative embodiment of a helical anchor 150, wherein the anchor 150 is shaped as a simple helix with no taper and a slight outward turn 152 at one end to facilitate initial turning of the helical anchor 150 under the annulus 84 (FIG. 1A). In addition, gaps 154 are provided between the coils 156 of the anchor 150 to prevent unwanted friction or drag as the anchor 150 is pushed into place. The slight outward turn, or outward extension has a larger radius from the center of the anchor 150 than the next adjacent coil. The distal end or outward turn 152 may also be oriented downward or away from the next adjacent coil in a direction generally along the central axis of the helical anchor 150, as shown. In this embodiment, the distal end 152 extends radially outward and downward relative to the next adjacent coil 154 to create a gap or spacing between end 152 and coil 154 that exists prior to implantation. This design feature also helps avoid tangling or interference with the chordae tendineae 48 and/or leaflets 38, 42 during insertion of the helical anchor 150 and with downsizing needs when a smaller prosthesis 120 is to be implanted.

Figure 7:
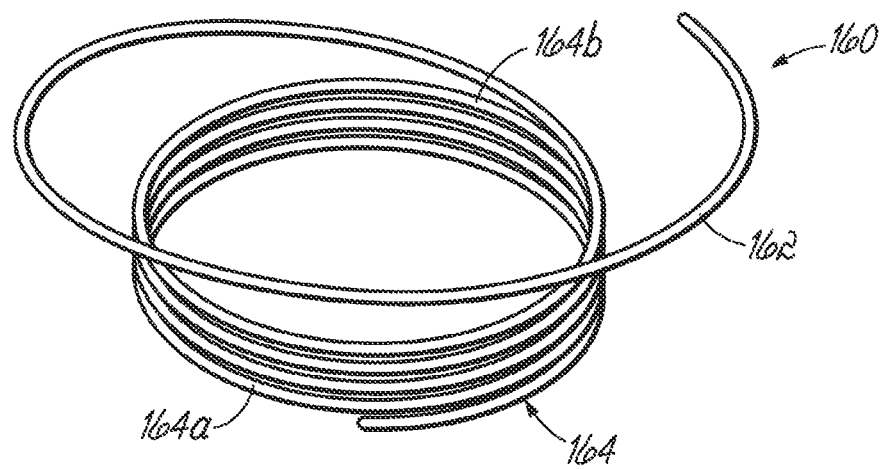
FIG. 7 is a perspective view of another alternative helical anchor having a wide tail portion or extension capable of engaging the atrial wall.
Figure 8:
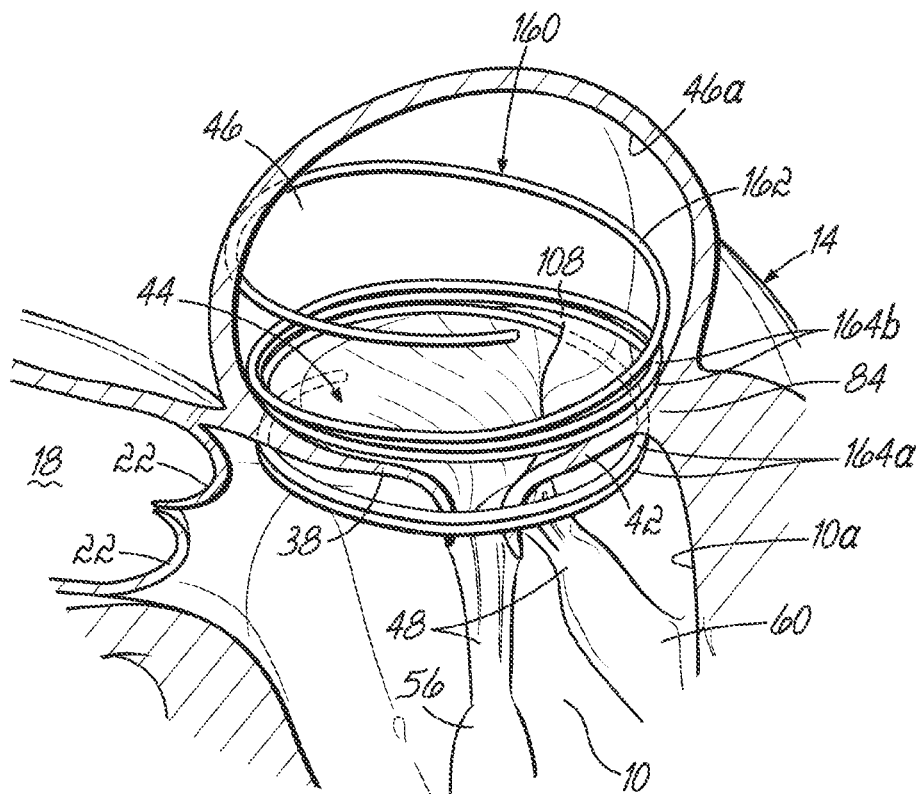
FIG. 8 is a perspective view of another alternative helical anchor having a tail portion or extension that is substantially wider than the tail portion of FIG. 7, shown placed in the mitral position of a heart.

After a helical anchor has been implanted and prior to a valve prosthesis being fastened therein, the anchor may slip out of position or dislodge completely. Atrial anchoring features can be added to prevent this unwanted movement. For example, a helical anchor 160 may include a tail-like extension 162 as shown in FIG. 7. The uppermost helical convolution 162 is of larger diameter than lower coils 164 so as to make contact with or abut the atrial wall 46a as shown in FIG. 8. As previously described, the coils 164a of the helical anchor 160 below the mitral valve annulus 84 in the left ventricle 10 engage the anterior and posterior leaflets 38, 42. In particular, the anterior leaflet 38 is restrained by coils 164a so that it is prevented from obstructing the flow of blood into the aortic valve 22. By applying a spring force against the atrial wall 46a, the tail-like extension 162 assists in preventing the helical anchor 160 from moving. It should be appreciated that in other embodiments the tail-like extension 162 may not comprise a helical shape. For example, the tail-like extension 162 can comprise a simple straight segment passing outward from the helical anchor 160 at an angle of approximately 90 degrees. A wide variety of tail-like extensions or other atrial anchoring features could be incorporated in various embodiments. The tail-like extension 162 could eliminate entirely the need for coils 164b above the valve leaflets 38, 42 to engage the leaflets 38, 42. The coils 164b above the leaflets 38, 42 could be eliminated or the coils 164b above the leaflets 38, 42 could be arranged to produce a gap above the leaflets 38, 42. The gap can allow the helical anchor 160 to have a much longer contact with the valve prosthesis 120 (FIG. 1H). This can help to orient the valve prosthesis 120 so that it is aimed appropriately into the left ventricle 10 and atrium 46. It is important to ensure that the inflow of the valve prosthesis 120 into the ventricle does not abut against the posterior wall 10a of the left ventricle 10, as this may cause wear and rupture of the heart 14, or an impairment of flow into the left ventricle 10.

If an embodiment of the invention incorporates a gap between the upper and lower coils of a helical anchor, as described previously herein, there may be a weak point in the system that is prone to fracture. The segment of the helical anchor that connects the coil above the valve 44 to that below the valve 44 may move rhythmically with the heart's contraction and fracture. To prevent this unwanted movement, anchoring the valve prosthesis 120 to coils both above and below the leaflets 38, 42 will lock these two helical coil portions together, preventing relative motion. Even if a connecting segment between upper and lower coil portions were to fracture, the valve prosthesis 120 would hold coils above the leaflets 38, 42 and below the leaflets 38, 42 together, like a splint. This would prevent embolization of parts. It is also possible that a connecting segment between upper and lower helices would not be needed after replacement valve implantation. Connection of upper and lower coil portions is necessary only for the insertion of the helical anchor. The connecting segment between upper and lower coil portions could be purposely made expendable (small and thin) or removable.

Referring now to FIGS. 9A-9C, an embodiment of the present invention is depicted wherein a delivery apparatus 180 comprises an external sheath 182 and an internal shaft 184 having a converging tip 186. A helical anchor 190 is placed over the shaft 184 and restrained within the sheath 182, shown in dash-dot lines, in order to tighten the coils 192 of the anchor 190 prior to implanting. The converging tip 186 is provided to assist an operator with guiding the apparatus 180 through a patient's venous system, if used percutaneously, or through the patient's heart. Anchoring arms 194 such as hooks are provided along a coil 192a of the helical anchor 190, and are constructed of a shape memory material. The anchoring arms 194 have two spaced apart wire portions 194a, 194b to provide a strong anchor point to hold tissue. The anchoring arms 194 are restrained and straightened in a downward orientation within the external sheath 182. When the delivery apparatus 180 is removed, the coils 192 of the anchor 190 are released and spring radially outward to their natural diameter and the anchoring arms 194 fold in an upward direction forming hooks to engage tissue, as shown in FIGS. 9B and 9C.

Figure 10A:
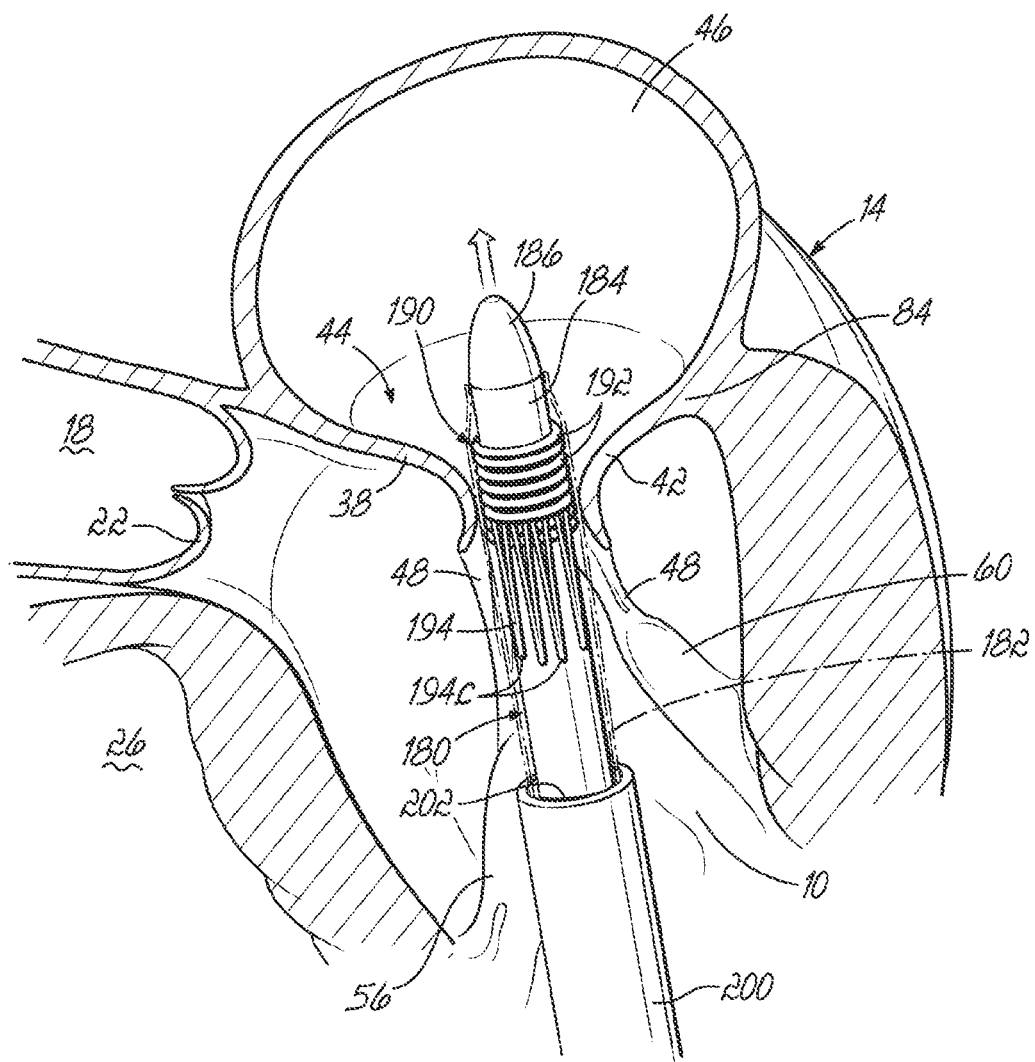
FIG. 10A is a perspective view of the helical anchor of FIG. 9A retained within a sheath and being placed in the mitral position of a heart, which is shown in partial cross section.
Figure 10B:
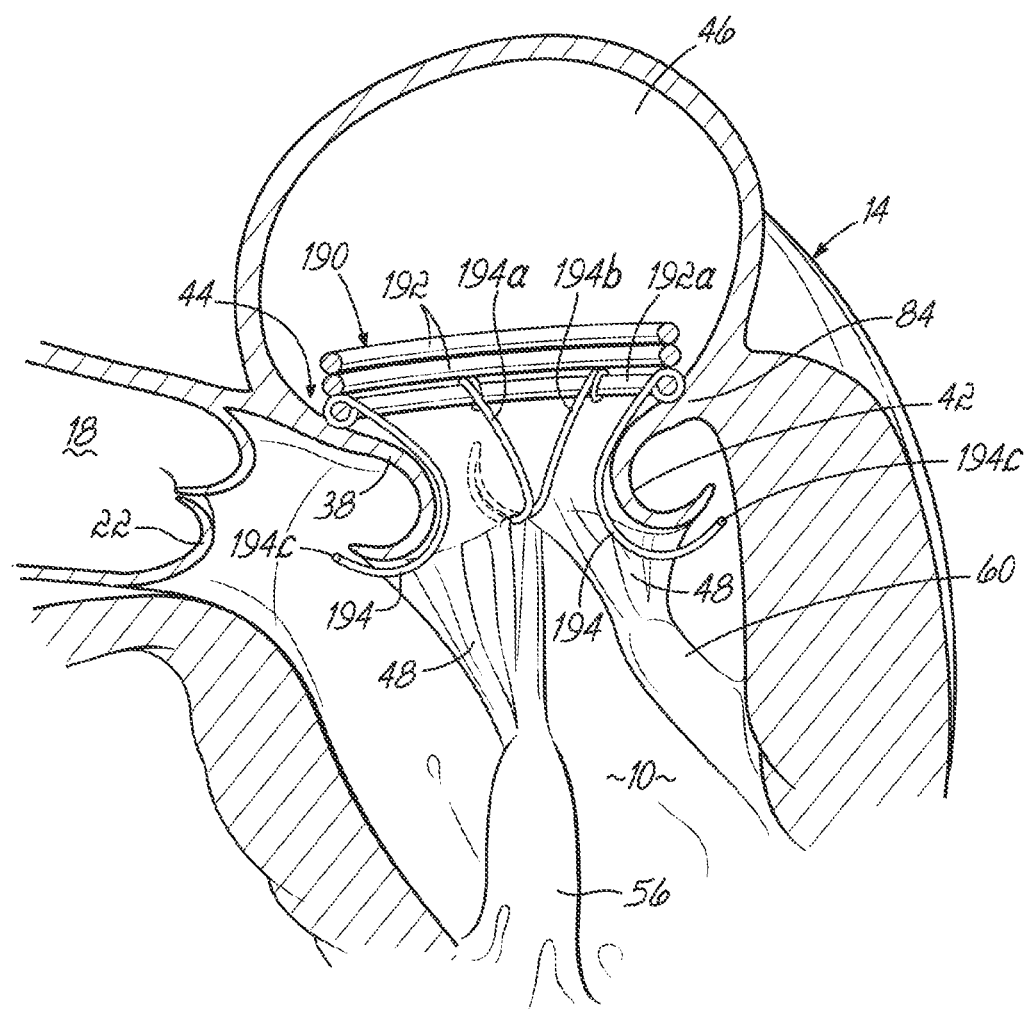
FIG. 10B is a cross sectional view of the helical anchor of FIGS. 9A-10A placed in the mitral position of heart showing the anchoring arms engaging the valve leaflets.
Figure 10C:
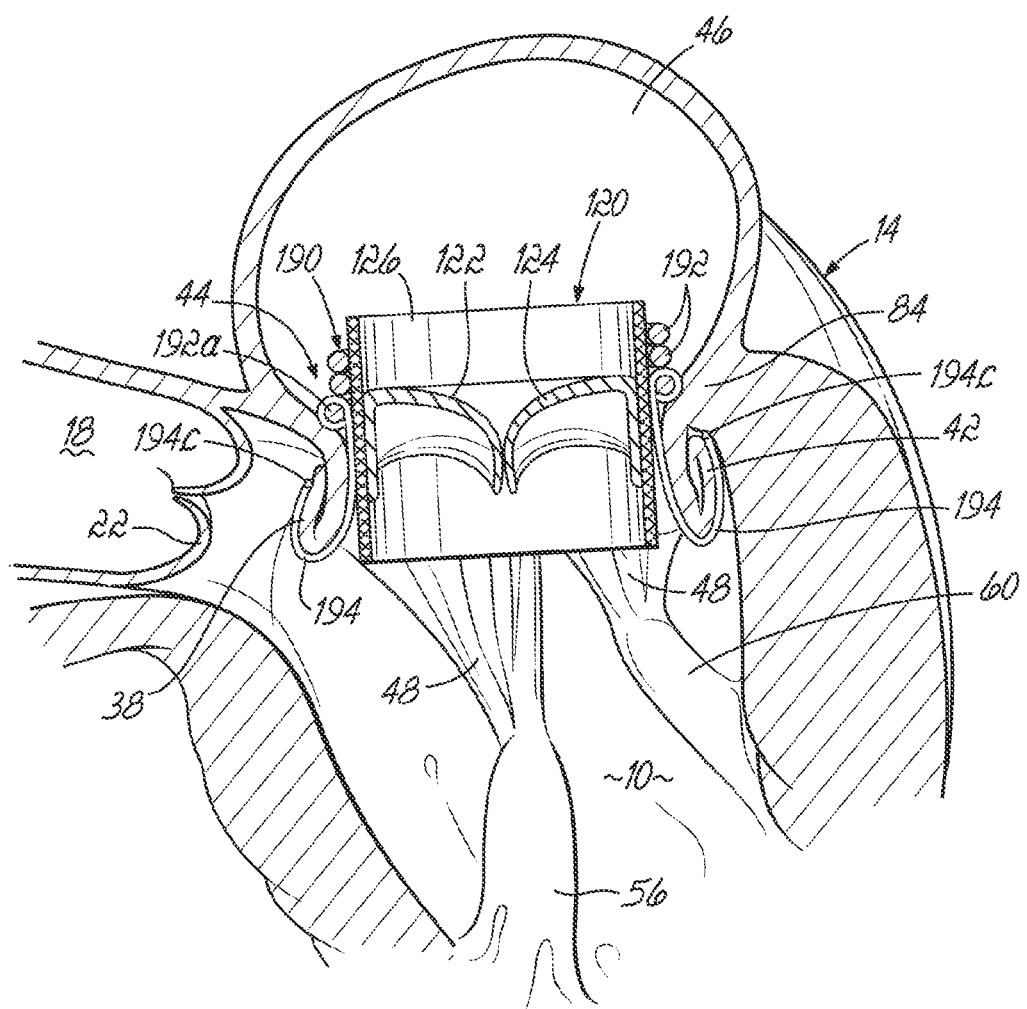
FIG. 10C is a cross sectional view of a valve prosthesis retained by the helical anchor of FIGS. 9A-10C.
Figure 20:
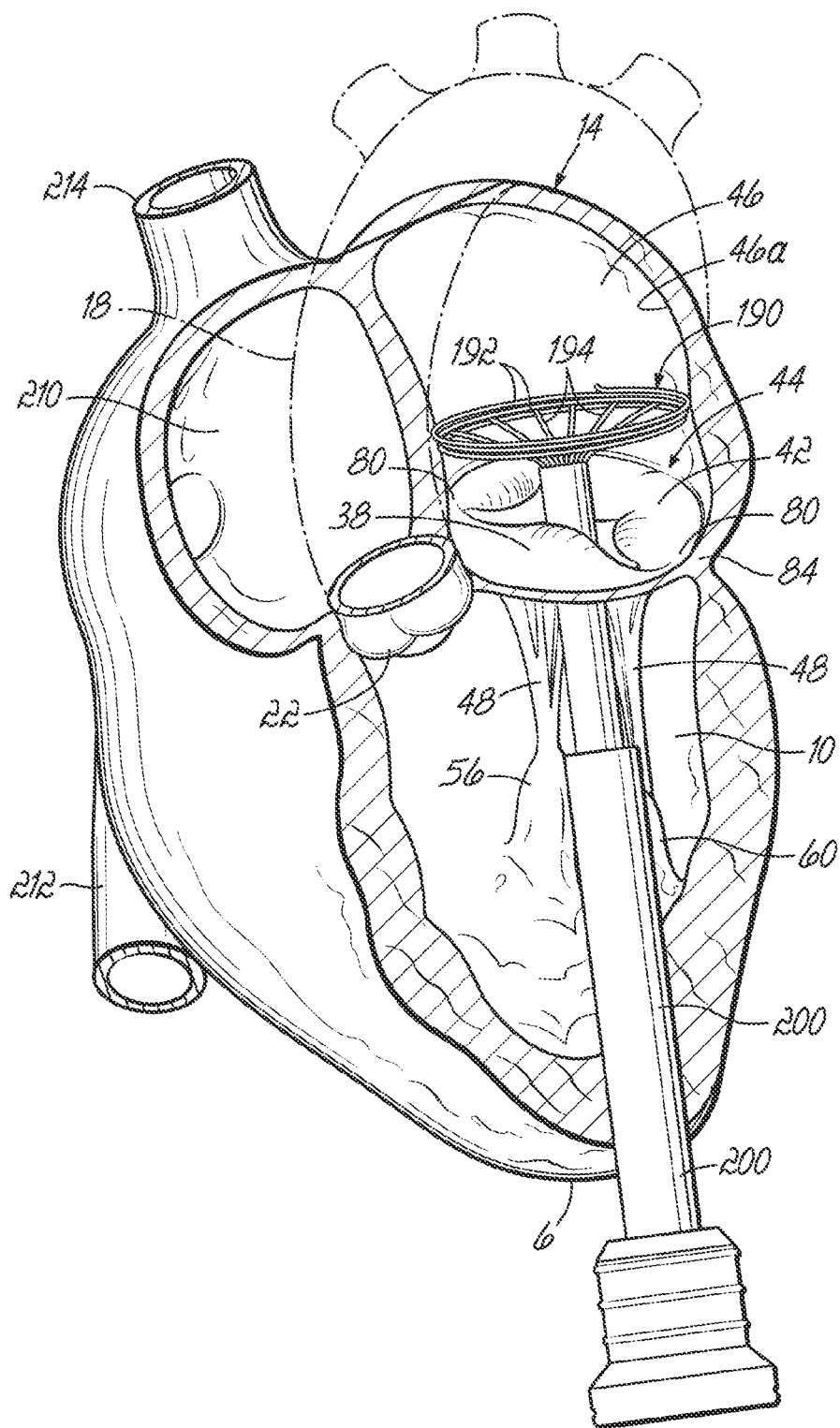
FIG. 20 illustrates in perspective the placement of an embodiment of a helical anchor in the mitral position of a heart, which is shown in partial cross section, where the helical portion of the anchor is deployed and the anchoring loops are retained within a sheath.
Figure 21:
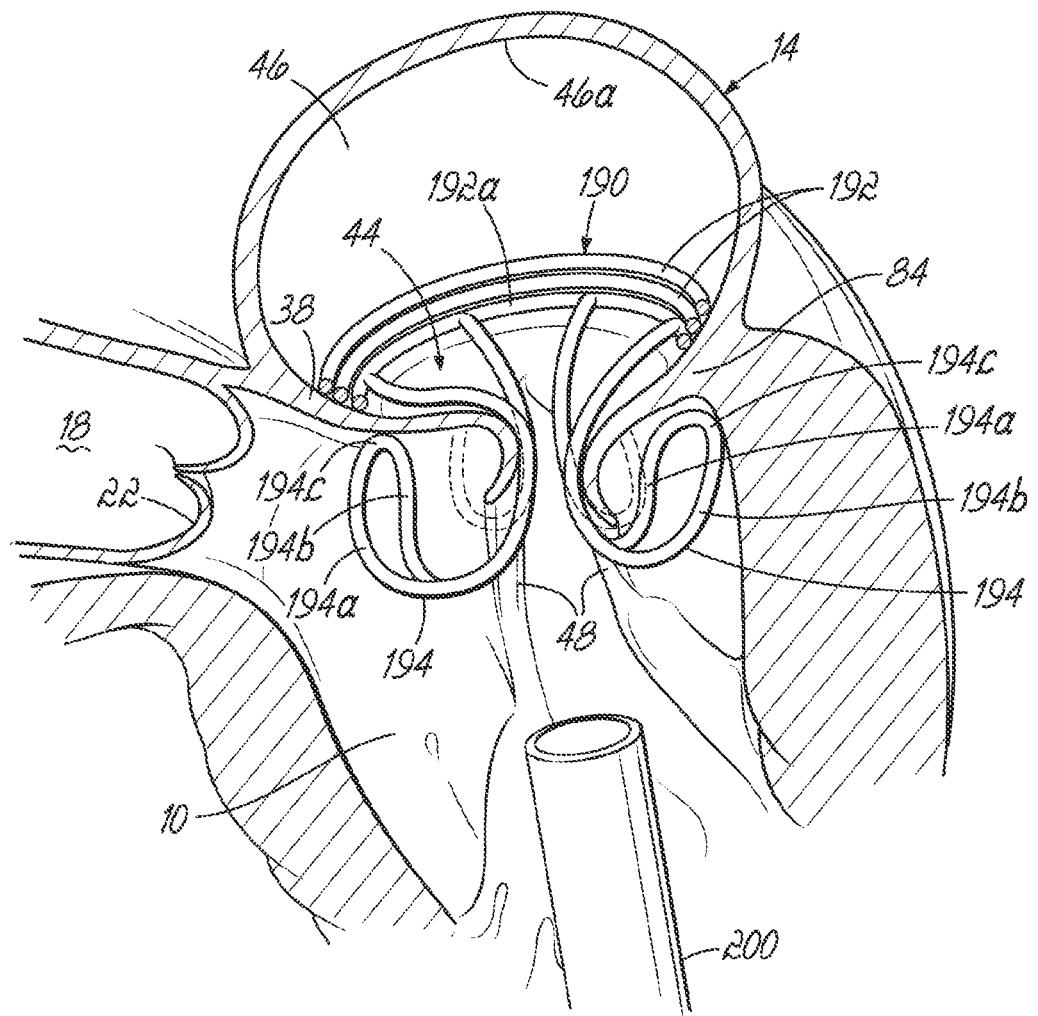
FIG. 21 is a close-up view of the helical anchor of FIG. 20 placed in the mitral position of a heart, which is shown in partial cross section, where the sheath has been retracted to deploy the helical portion in the atrium and the anchoring loops in the ventricle.
Figure 22:
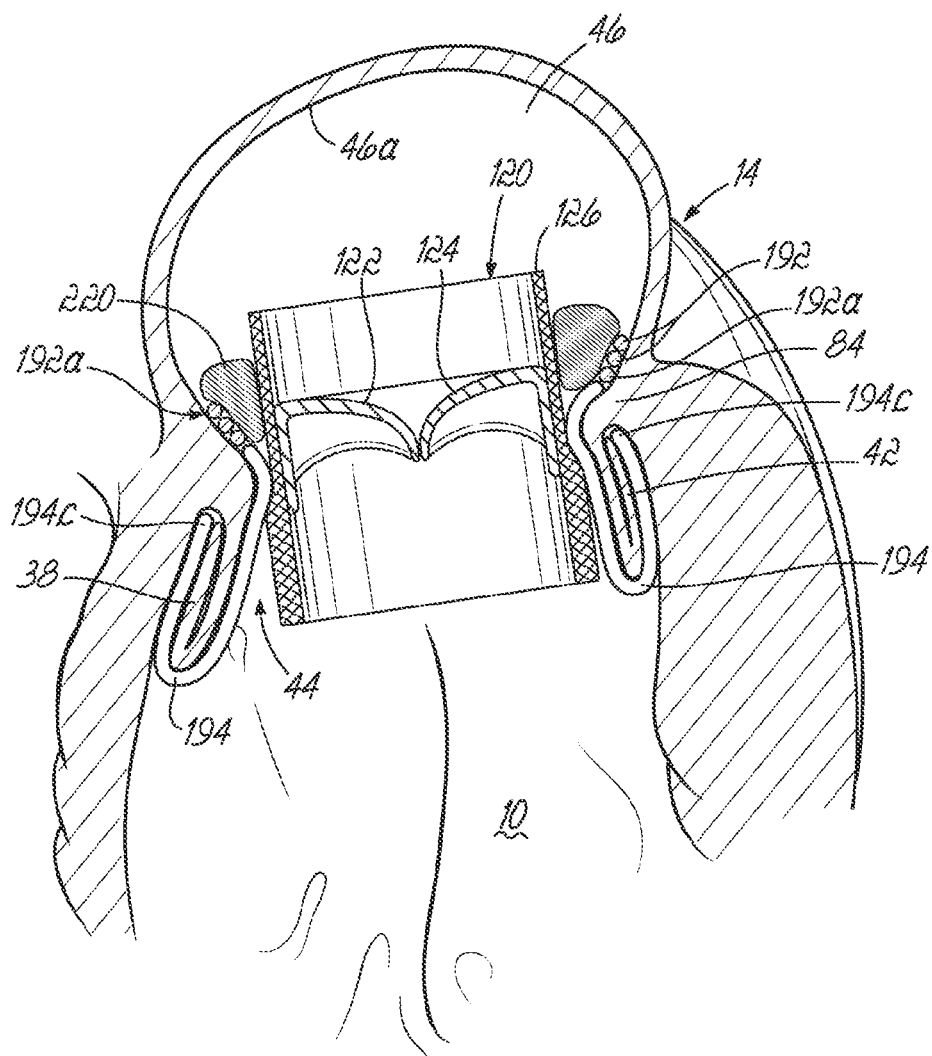
FIG. 22 is a cross sectional view of a valve prosthesis retained by the helical anchor of FIGS. 20-21 with the assistance of a cuff.

Referring now to FIGS. 10A-10C and 20-22, in one embodiment of the present invention a delivery catheter 200 is inserted into the left ventricle 10 of a patient's heart 14. The delivery catheter 200 includes a lumen 202 which carries a delivery apparatus 180 as previously described, for example, having an external sheath 182 and a shaft 184 with a converging tip 186. A helical anchor 190 having anchoring arms 194 is compressed over the shaft 184 and retained by the sheath 182 such that the coils 192 of the anchor 190 are tightened. The tip 186 assists the advancement of the delivery apparatus 180 between the anterior and posterior leaflets 38, 42 of the mitral valve 44 from the left ventricle 10 into the left atrium 46 as shown in FIG. 10A. As the external sheath 182 is retracted, the helical anchor 190 springs open to its original size as shown in FIGS. 10B and 20. This helical anchor 190, as with other embodiments, may take various forms, such as with different diameter coils 192 instead of constant diameter coils, and/or coils that engage the atrial wall 46a as opposed to contacting or engaging leaflet tissue. For environmental purposes, FIG. 20 shows the right atrium 210, inferior vena cava 212, superior vena cava 214, aortic valve 22, and aorta 18 (in dash-dot lines). As the external sheath 182 is slid downward relative to the anchor 190, the anchoring arms 194 unfold and expand, for example, into hooks. The hooks 194 wrap around the anterior and posterior leaflets 38, 42 and hold the anchor 190 in position, as shown in FIGS. 10B and 21. The anchoring arms, or hooks in this embodiment, also capture or otherwise secure the leaflets 38, 42 and help prevent the anterior leaflet 38 from obstructing blood flow out of the left ventricle 10 through the aortic valve 22. It should be noted that the edges of the valve leaflets 38, 42 are attached to chordae tendineae 48 which extend from papillary muscles 56, 60. In this embodiment, the hooks 194 are constructed in a shape that is relatively narrow at the distal ends 194c in order to pass between the chordae tendineae 48 (see FIGS. 9B and 9C). However, it is appreciated that the hooks 194 may be constructed in a wide variety of shapes without departing from the scope of the invention. For example, FIG. 21 shows an alternative embodiment having hooks 194 that are wide at the distal ends 194c to form loops. The wide-loop hooks 194 of FIG. 21 provide improved retention of the valve leaflets but may be difficult to position around the chordae tendineae 48. Referring again to FIGS. 10A-10C, a valve prosthesis 120 is positioned and retained within the helical anchor 190 as shown in FIGS. 10C and 22. In the embodiments of FIGS. 10C and 22, the valve prosthesis 120 is mounted in a stent 126 and comprises a pair of artificial leaflets 122, 124. The artificial leaflets 122, 124 may comprise pliable animal tissue such as cow, pig or horse pericardium or animal valve tissue. The valve prosthesis 120 may be self expanding or balloon expandable. Leaflet tissue 38, 42 is retained by hooks 194 toward the valve prosthesis 120, preventing the anterior leaflet 38 from obstructing blood flow through the aortic valve 22. In the embodiment shown in FIG. 22, a circumferential cuff 220 is inserted between the helical anchor 190 and the valve prosthesis 120 in order to improve retention of the valve prosthesis 120 in the atrium 46 and to provide a seal between the anchor 190 and the valve prosthesis 120 to prevent leakage.

Figure 11A:
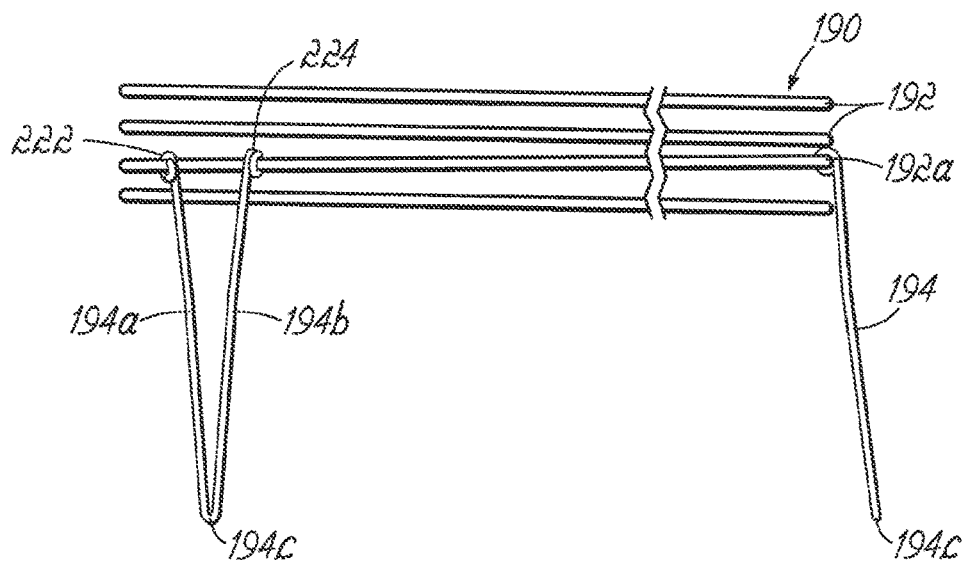
FIGS. 11A-11C are side views of the helical anchor of FIGS. 9A-9C, showing the anchoring arms expanding from a compressed state to a deployed state (most anchoring arms removed for clarity).
Figure 11B:
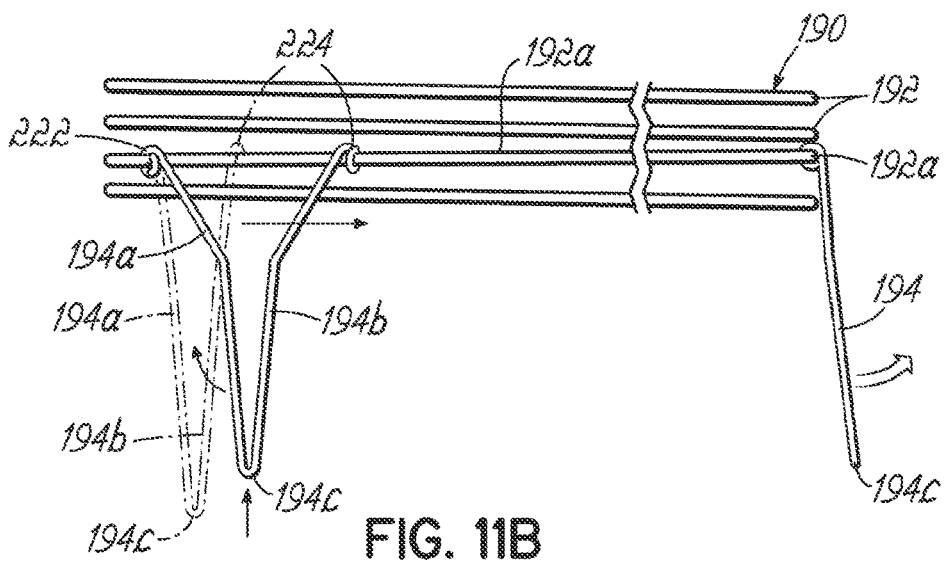
Figure 11C:
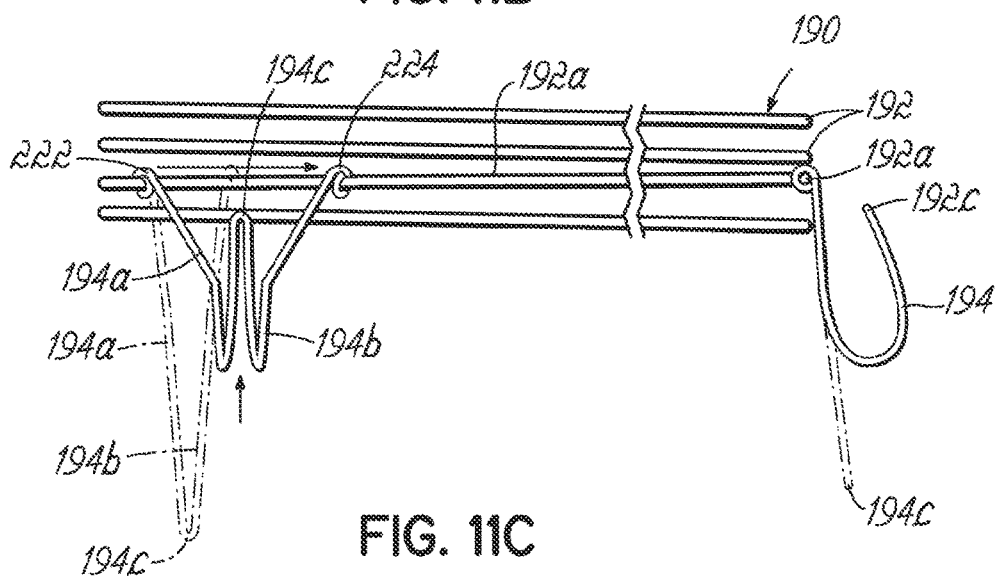

FIGS. 11A-11C illustrate the transition of an anchoring arm 194 from a straightened position (FIG. 11A) to an activated position (FIG. 11C). As stated previously, the anchoring arm 194 may be constructed of shape memory materials. FIG. 11A shows anchoring arms 194 each having a fixed end 222 and a free end 224 located along a coil 192a. When the anchoring arm 194 is released from a straightened position (FIG. 10A), the free end 224 may move away from the fixed end 222, causing the base of the anchoring arm 194 to elongate, and the distal tip 194c of the anchoring arm 194 may begin to bend or fold upward as shown in FIG. 11B. The anchoring arm 194 is activated when the distal tip 194c is bent to its original shape forming a hook as shown in FIG. 11C. In another embodiment, the anchoring arm 194 may have no fixed end 222, but rather two free ends 224 so that it may slide along the helical anchor 194 at both ends. The number and configuration of anchoring arms 194 provided may vary.

Figure 12A:
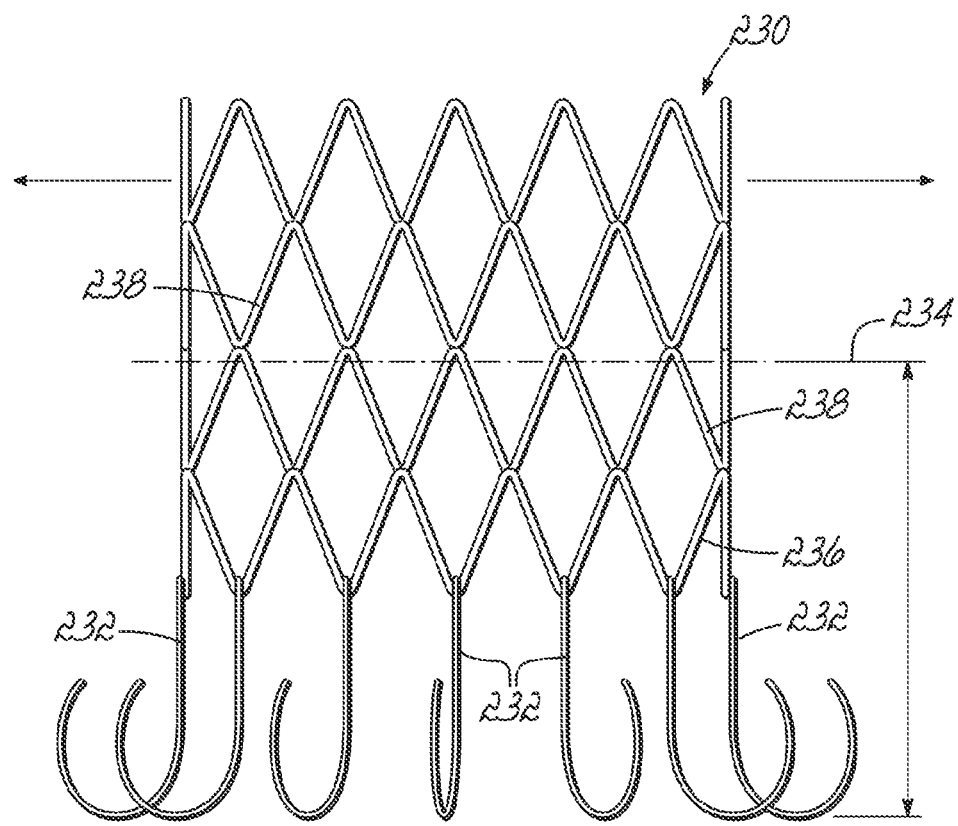
FIG. 12A is a side view of one embodiment of a stent docking having hooks which are lifted as the stent docking expands and shortens.

FIG. 12A shows a stent dock 230 with anchoring arms such as hooks 232 at the bottom in accordance with another embodiment of the present invention. The hooks 232 may be separately attached or integrated into the construction of the stent dock 230. The midpoint of the stent dock 230 is shown as dash-dot line or axis 234. The hooks 232 are attached to the apex 236 of each lowermost cell 238 of the stent dock 230. Other embodiments may incorporate double sided hooks (such as shown in FIGS. 11A-11C) that are anchored with one base on one cell 238 and one base on another cell 238. As the stent dock 230 is expanded, the cells 238 collapse vertically causing the hooks 232 to rise such as to engage leaflet tissue. In this manner shortening of the stent dock 230 (i.e., radial expansion thereof) is used in a functional way to activate the hooks 232.

Figure 12B:
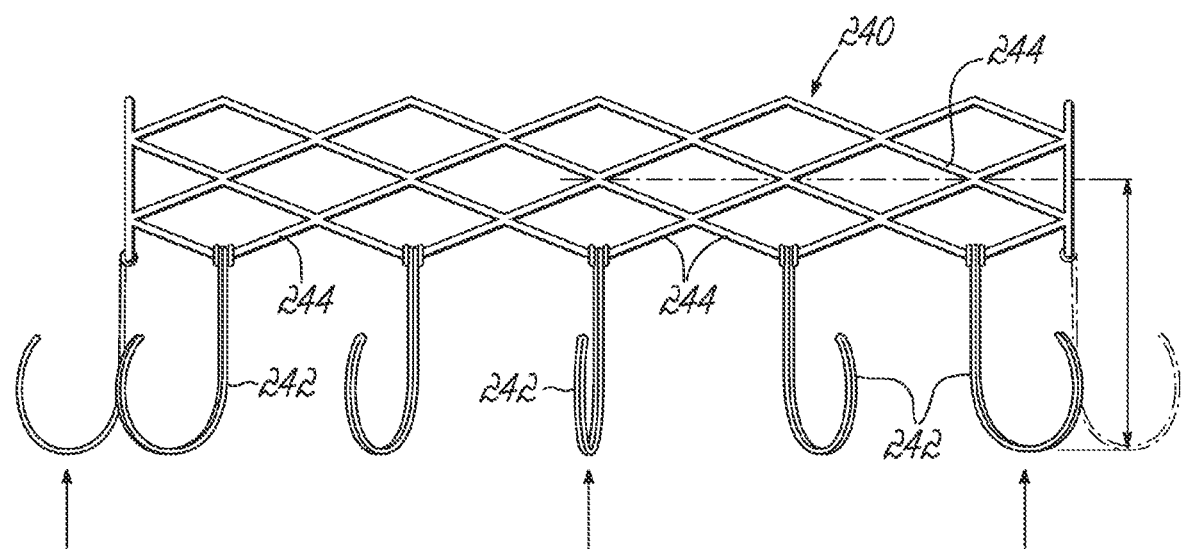
FIG. 12B is a side view of another embodiment of a stent docking having double-wire hooks which are lifted as the stent docking expands and shortens.

FIG. 12B shows another embodiment of a stent dock 240 as it expands so that the stent dock 240 shortens and anchoring arms such as double-hooks 242 are lifted in a manner similar to that described with reference to FIG. 12A. Additional embodiments may include a wide variety of hook types and attachment structure. For example, double-wire hooks may be attached with one wire end at the bottom of a first cell 244 of the stent dock 240, and another wire end at the bottom of an adjacent cell 244 of the stent dock 240. This arrangement would cause the base of the hook 242 to lengthen as the stent dock 240 is expanded. In this manner a hook 242 could start to engage tissue with a narrow shape and then widen as the stent dock 240 is expanded. This may be a useful feature when a hook 242 is attached to a valve leaflet between chordae tendineae.

Figure 13A:
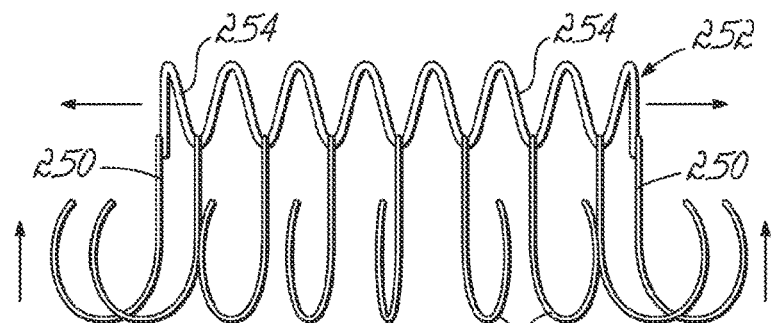
FIGS. 13A and 13B are side views of hooks spread along a serpentine wire, which are lifted upward as the wire is straightened and which can be incorporated in a stent docking.
Figure 13B:
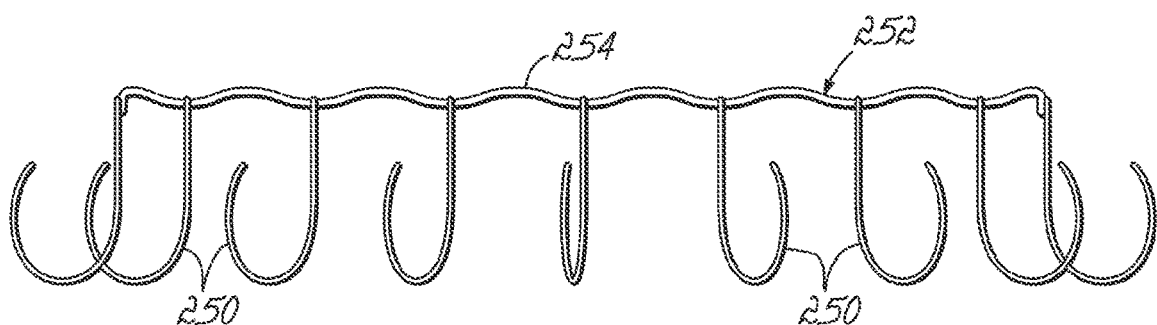

Referring now to FIGS. 13A and 13B, hooks 250 are shown spread along a serpentine wire 252. The turns 254 of the wire 252 separate the hooks 250. As the wire 252 is straightened, the hooks 250 spread apart and become elevated as shown in FIG. 13B. In this manner the hooks 250 may be activated to retain tissue.

Figure 14A:
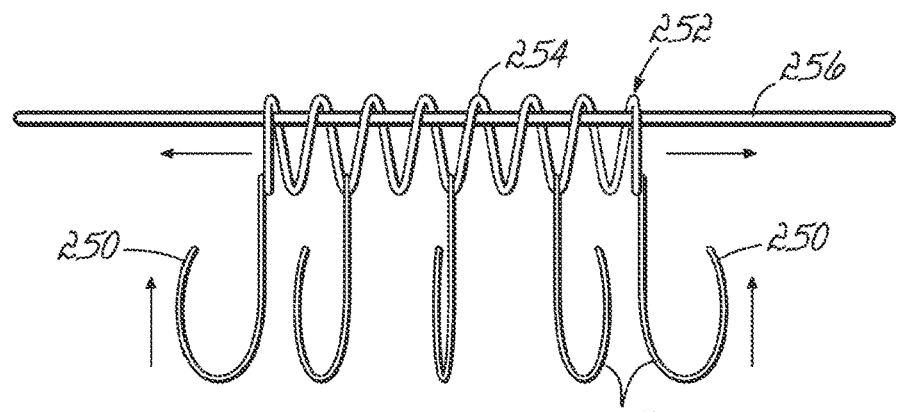
FIGS. 14A and 14B are side views of a serpentine wire mounted on a central retaining wire and hooks spread along the serpentine wire, which are lifted upward as the serpentine wire is straightened and which can be incorporated in a helical anchor.
Figure 14B:
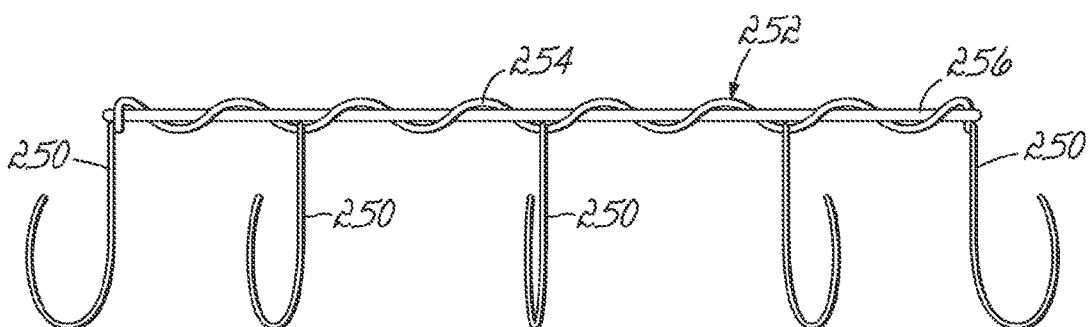

Similarly, FIGS. 14A and 14B illustrate hooks 250 spread along a serpentine wire 252 which is mounted on a central retaining wire 256. The hooks 250 spread apart and become elevated as the serpentine wire 252 is straightened along the central retaining wire 256 as shown in FIG. 14B. The central retaining wire 256 may, for example, comprise a helical anchor (such as described herein) which carries a serpentine wire 252 thereon.

Figure 14C:
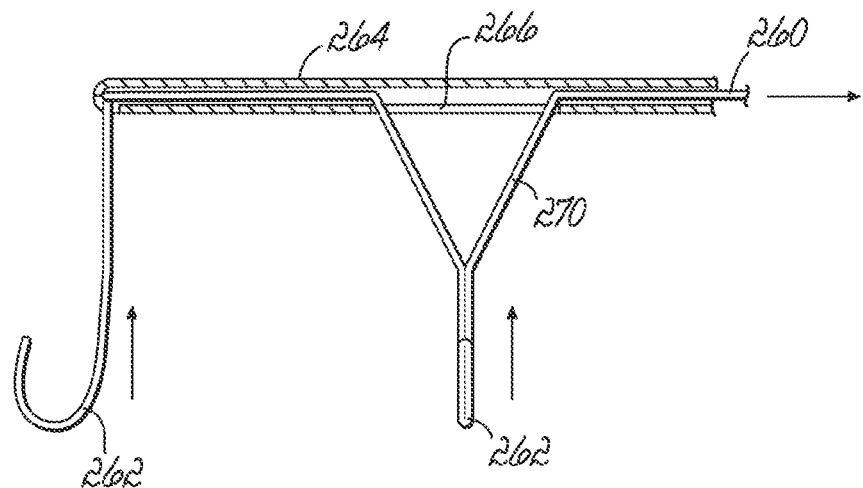
FIGS. 14C and 14D are cross sectional views of hooks shaped on a wire that is placed within a sheath and which are lifted upward as the wire is pulled through the sheath.
Figure 14D:
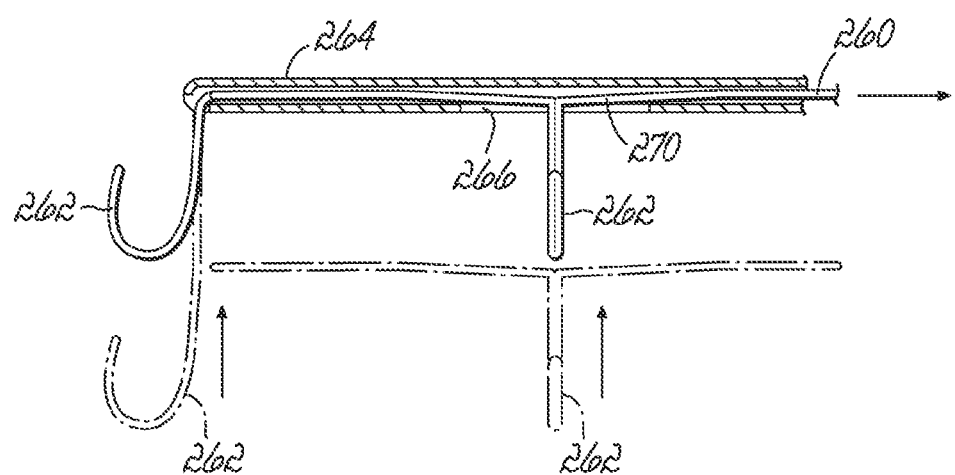

FIGS. 14C and 14D illustrate yet another method of hook deployment in accordance with optional aspects of the present invention. A wire 260 is folded such that a plurality of anchoring arms such as hooks 262 having V-shaped portions are provided. The wire 260 is placed within an outer shell or hollow structure 264 having apertures 266 such that the hooks 262 are permitted to extend through the apertures 266 as shown in FIG. 14C. As the wire 260 is pulled through the shell 264, V-shaped portions 270 retract and straighten within the shell 264 causing the hooks 262 to lift upward as shown in FIG. 14D. There are many other ways to activate a hook associated with the lengthening of a wire, stent dock or helical anchor in accordance with the inventive principles.

Figure 15A:
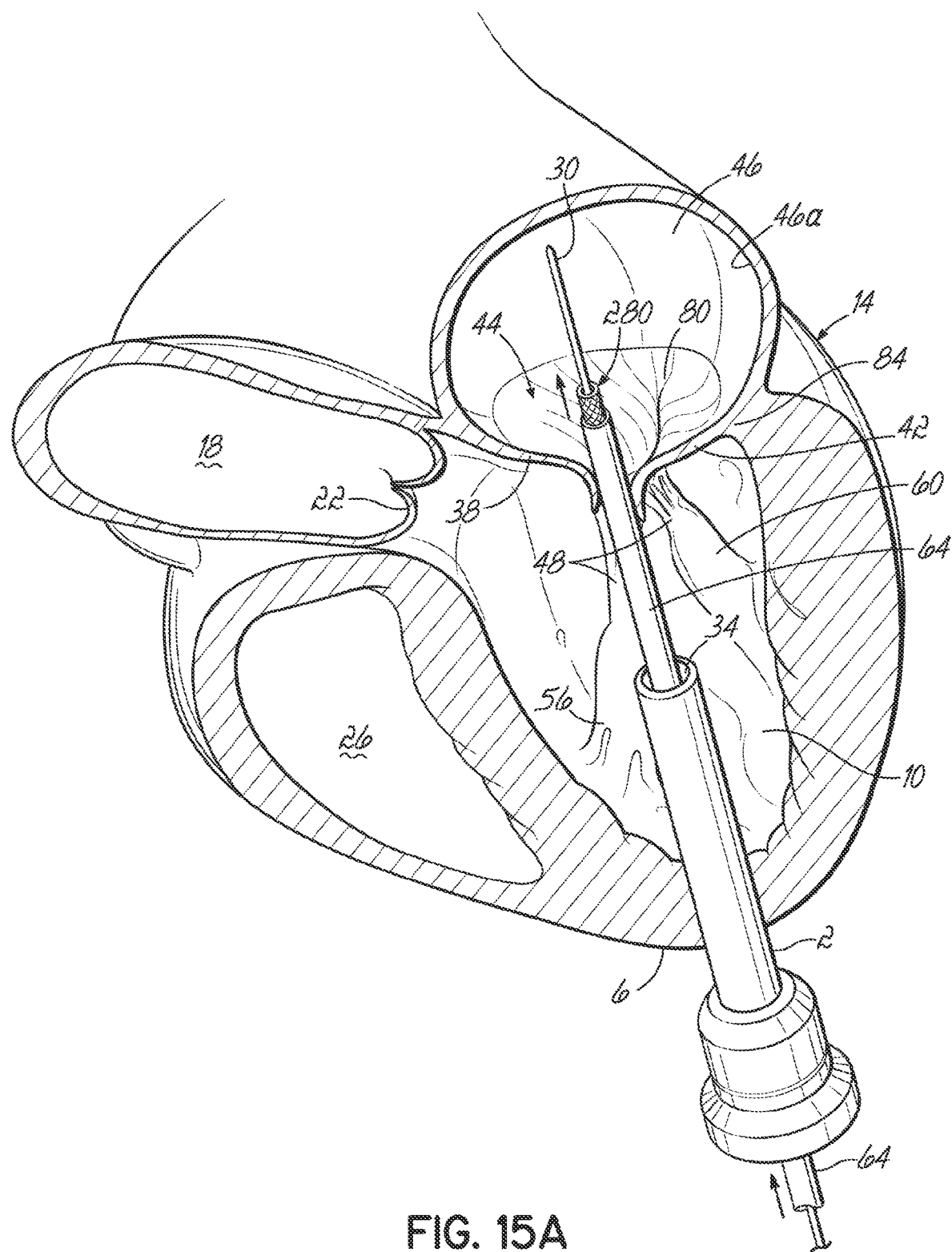
FIGS. 15A-15E illustrate in perspective the placement of one embodiment of a stent docking in the mitral position of a heart, which is shown in partial cross section.

Referring now to FIGS. 15A-15F, a system and method for positioning a stent dock 280 in the mitral position or location of a patient's heart 14 is shown. FIG. 15A shows an introducer 2 inserted into the apex 6 of the left ventricle 10 by a small thoracotomy, a sternotomy, or from below the diaphragm with an upper abdominal incision. One particularly favorable approach is to make a small incision on the patient's chest near the apex 6 of the left ventricle 10 and then through the apex 6 of the heart 14. To prevent blood leakage from the apex 6, a standard purse string suture could be used to hold an introducer 2 in place and close the defect on removal. It is also possible to use an occluder device for entry and exit. A guidewire 30 is advanced such that a portion of the guidewire 30 is positioned in the left atrium 46. Care should be taken when advancing the guidewire 30 to avoid entanglement of the guidewire 30 with the chordae tendineae 48 or their associated papillary muscles 56, 60. A delivery catheter 64 may then be advanced upon the guidewire 30.

Figure 15B:
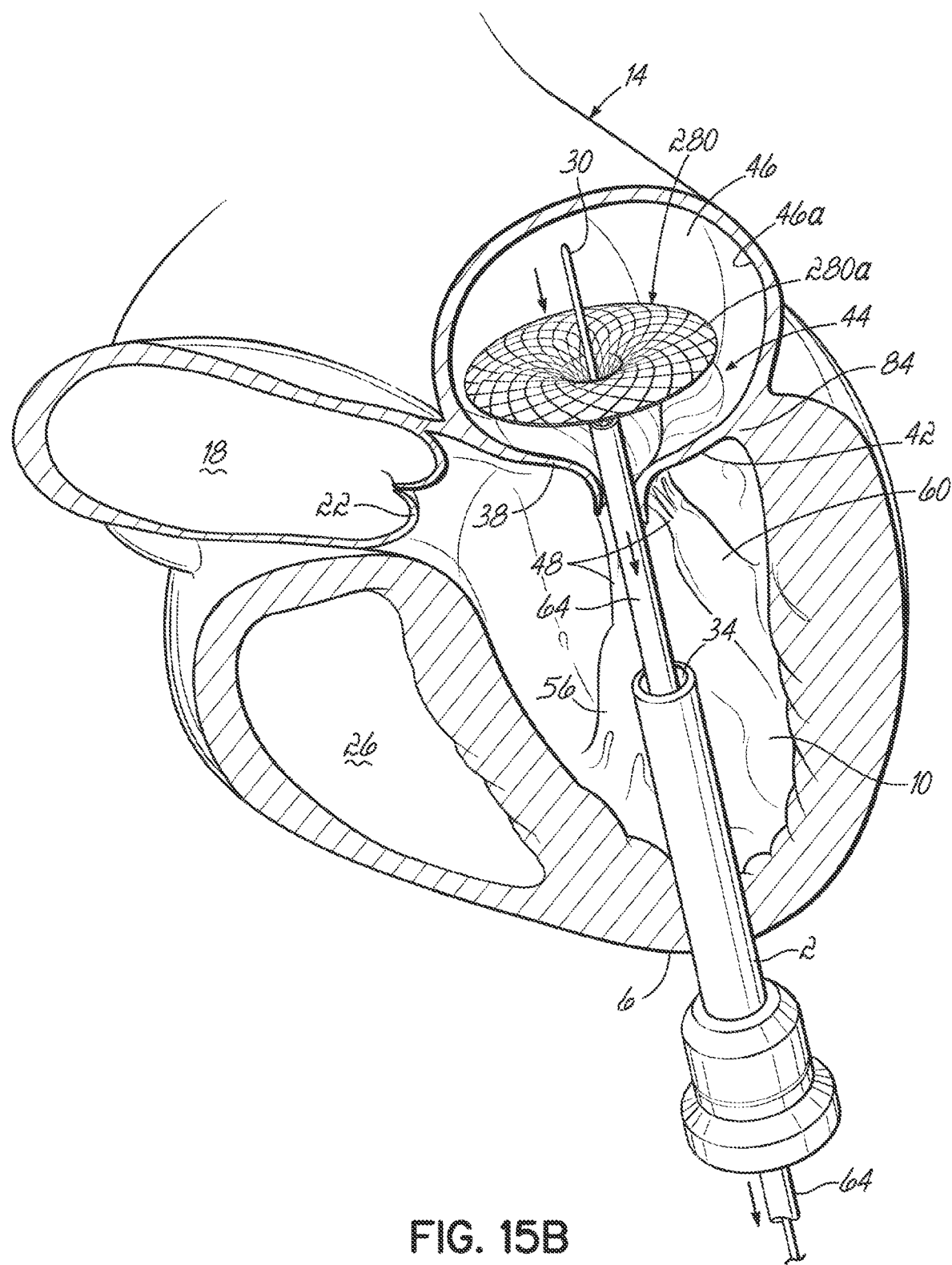
Figure 15C:
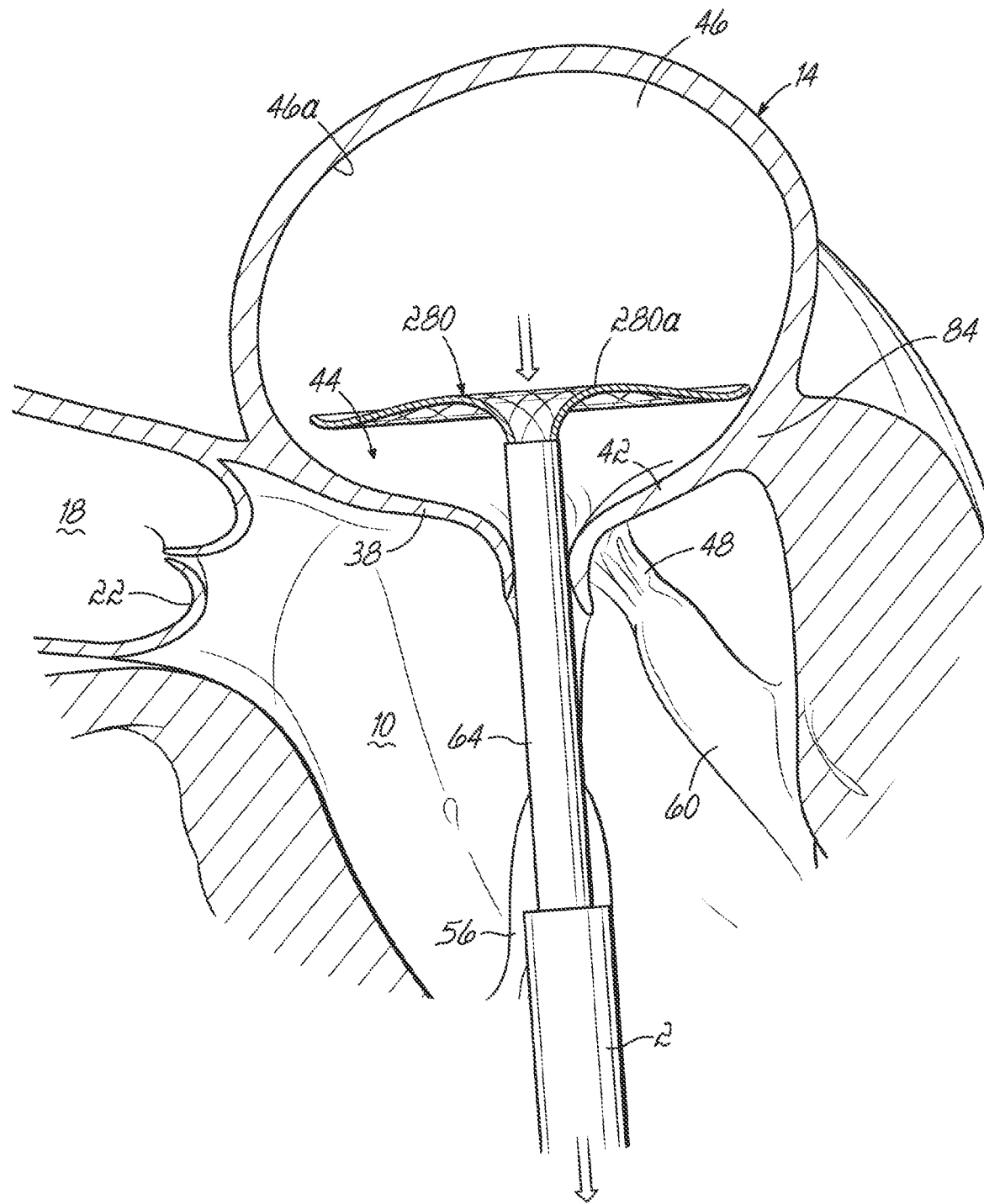

The delivery catheter 64 contains the stent dock 280 and is directed into the left atrium 46. An atrial portion 280a of the stent dock 280 is extruded (i.e., extended) by withdrawing the delivery catheter 64 as the stent dock 280 is held in place as shown in FIGS. 15B and 15C. This could also be accomplished by pushing the stent dock 280 outward from the delivery catheter 64. It is appreciated that, although the stent dock 280 can be constructed in a variety of ways, it is useful to construct the stent dock 280 from a shape memory material such as Nitinol. It should be noted that the stent dock 280 may be cut from a tube or piece of material, or may be woven from threads or pieces of shape memory material. Preferably, the stent dock 280 has an option of allowing blood to flow around it and through it. This is facilitated by the stent matrix as shown in FIG. 15B. In one embodiment of the invention, portions of the stent dock 280 may be coated with one or more of fabric, polymers, and biologic material. It is noted that a fabric coating may be particularly useful to prevent leaks and encourage tissue ingrowth around the annulus 84 of the mitral valve 44. Suitable fabrics may include Dacron and Teflon materials.

Figure 15D:
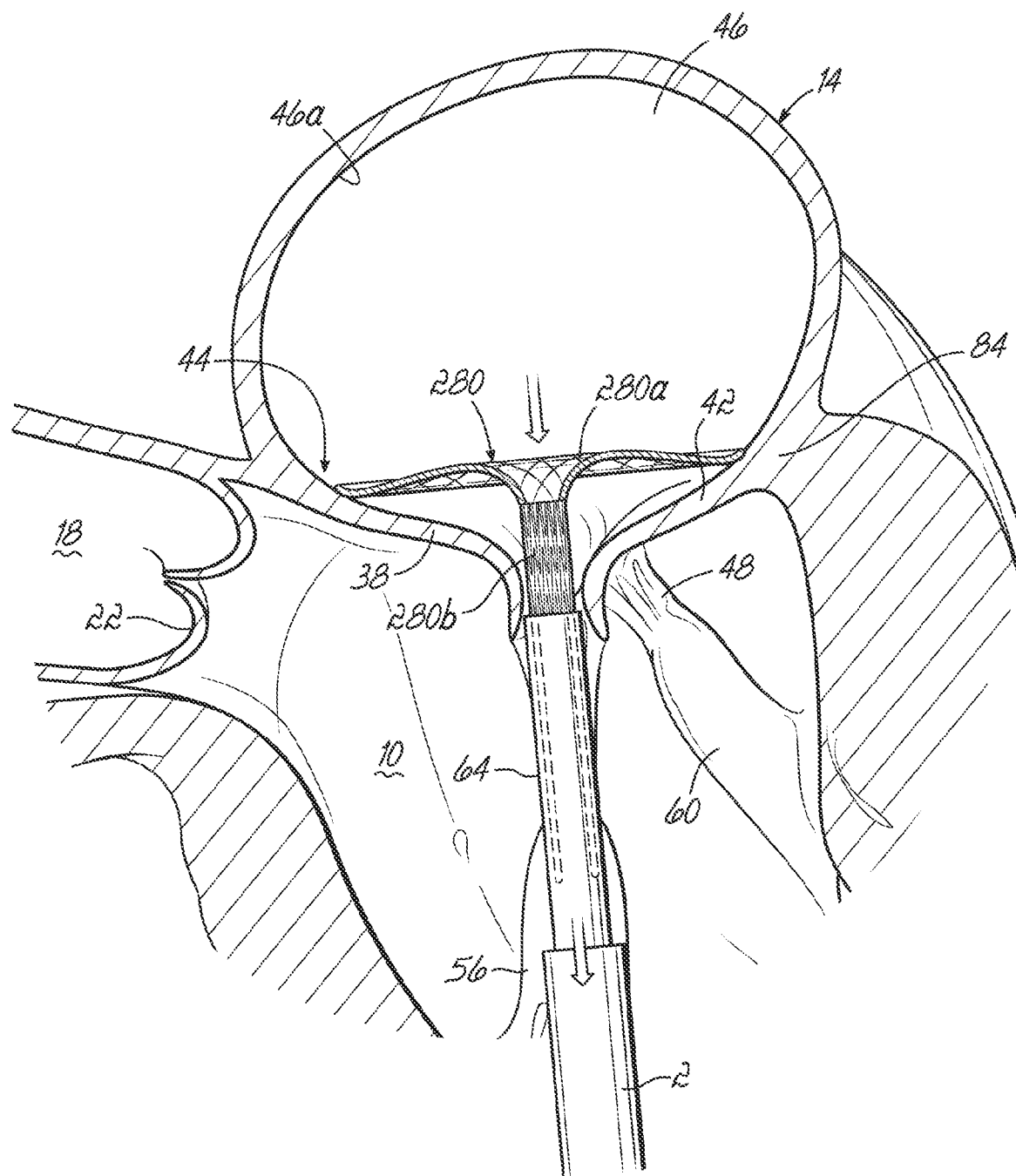
Figure 15E:
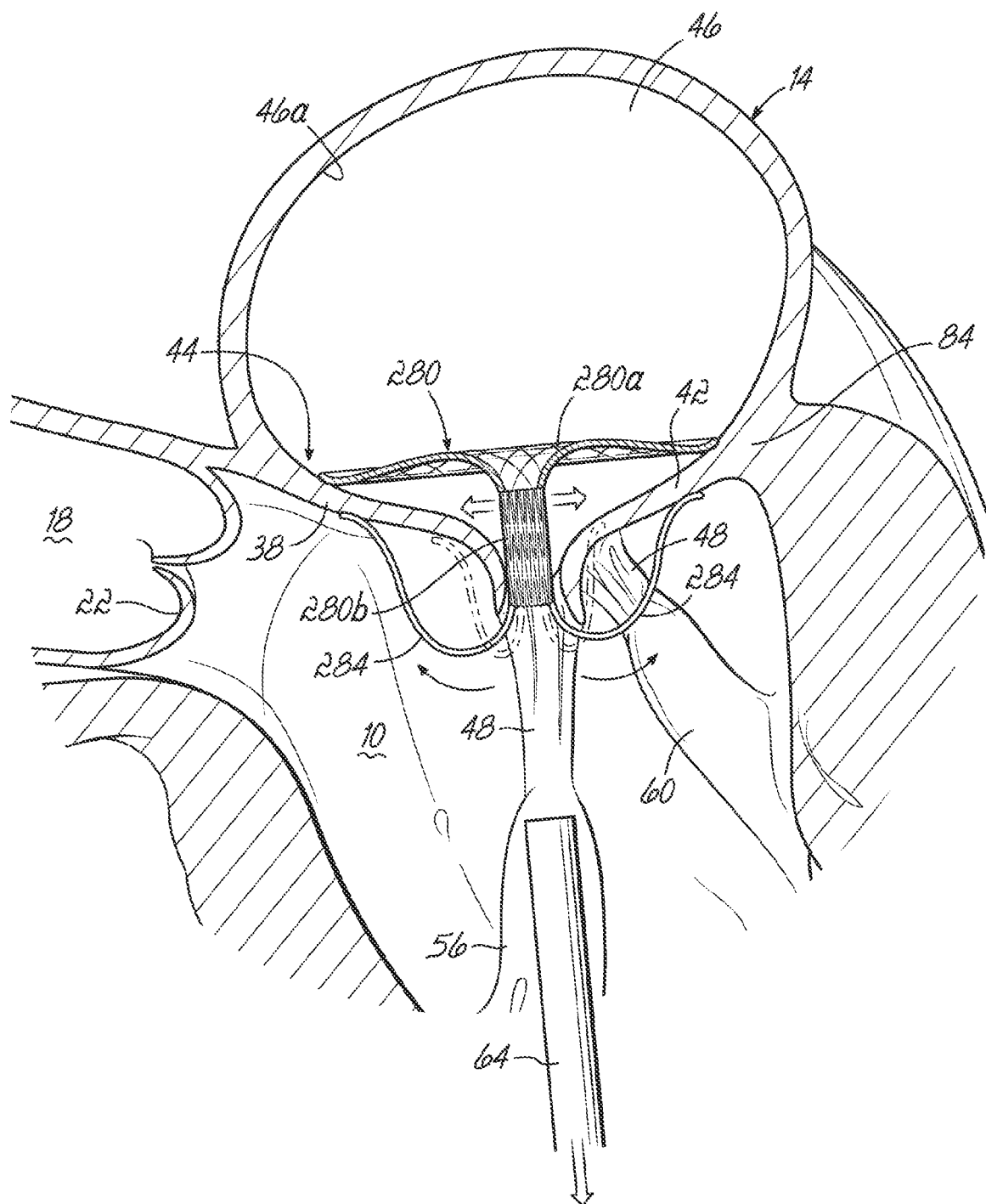

After the atrial portion 280a of the stent dock 280 is released, the stent dock 280 and delivery catheter 64 are lowered together as shown in FIGS. 15C and 15D so that the atrial portion 280a of the stent dock 280 may contact the atrial wall 46a and the valve anchoring portion 280b of the stent dock 280 is positioned within the mitral valve 44 as shown in FIG. 15D. The valve anchoring portion 280b may also be coated with material such as Dacron or Teflon to promote tissue ingrowth and help prevent leaks. As illustrated in FIG. 15E, the delivery catheter 64 is retracted further and releases anchoring arms in the form of ventricular hooks 284 of the stent dock 280, allowing the hooks 284 to travel between the chordae tendineae 48 and wrap around the mitral valve leaflets 38, 42. The atrial portion 280a retains the stent dock 280 in the left atrium 46 and the stent dock 280 is held stable inside the heart 14. The valve anchoring portion 280b is in a closed position, but may expand in the direction of the arrows upon insertion of a valve prosthesis 120 (FIG. 15G). It should be noted that the native mitral valve 44 may still open and close so that the heart 14 still functions and the patient remains stable during the procedure. Therefore, there is no critical time constraint placed on the operator while preparing to implant the valve prosthesis 120.

It is appreciated that other methods of stent dock deployment may be used within the scope of the present invention. For example, other embodiments (not shown) may incorporate a delivery catheter device or devices constructed so that the stent dock 280 can be released from two ends. In one embodiment a catheter could retain the atrial portion 280a with or without the valve anchoring portion 280b of the device and a separate catheter could retain the ventricular hooks 284. The more proximal catheter could be withdrawn to allow the hooks 284 to open first. This step could be performed with the hooks 284 low in the ventricle 10 and the entire stent dock 280 could be pushed forward toward the valve 44, ensuring that the valve leaflets 38, 42 are retained by the hooks 284. If imaging (for example, echocardiography) is used and shows that part of a valve leaflet 38, 42 is not hooked, the stent dock 280 can be pulled back and re-positioned. When the hooks 284 have properly engaged the valve leaflets 38, 42, the more distal catheter could be withdrawn to allow the atrial portion 280a to expand.

Additional maneuvers may assist positioning of the stent dock 280. For example, restricting leaflet motion may help to allow the hooks 284 to secure all leaflet components. This could be performed pharmacologically by reducing flow through the mitral valve via negative inotropes or vasodilators to pool blood in the periphery of the patient or by table positioning. Mechanical devices such as occluders or balloons could be inflated near the mitral valve to limit flow. Alternatively, the atrial portion 280a of the stent dock 280 could be adapted to impair flow, or a flow impairing stent structure could be incorporated thereon. In another embodiment, the atrial portion 280a could have fabric attached in part or covering its entire surface to restrict flow. This fabric could also be used to promote tissue ingrowth and long term biocompatibility.

Figure 15F:
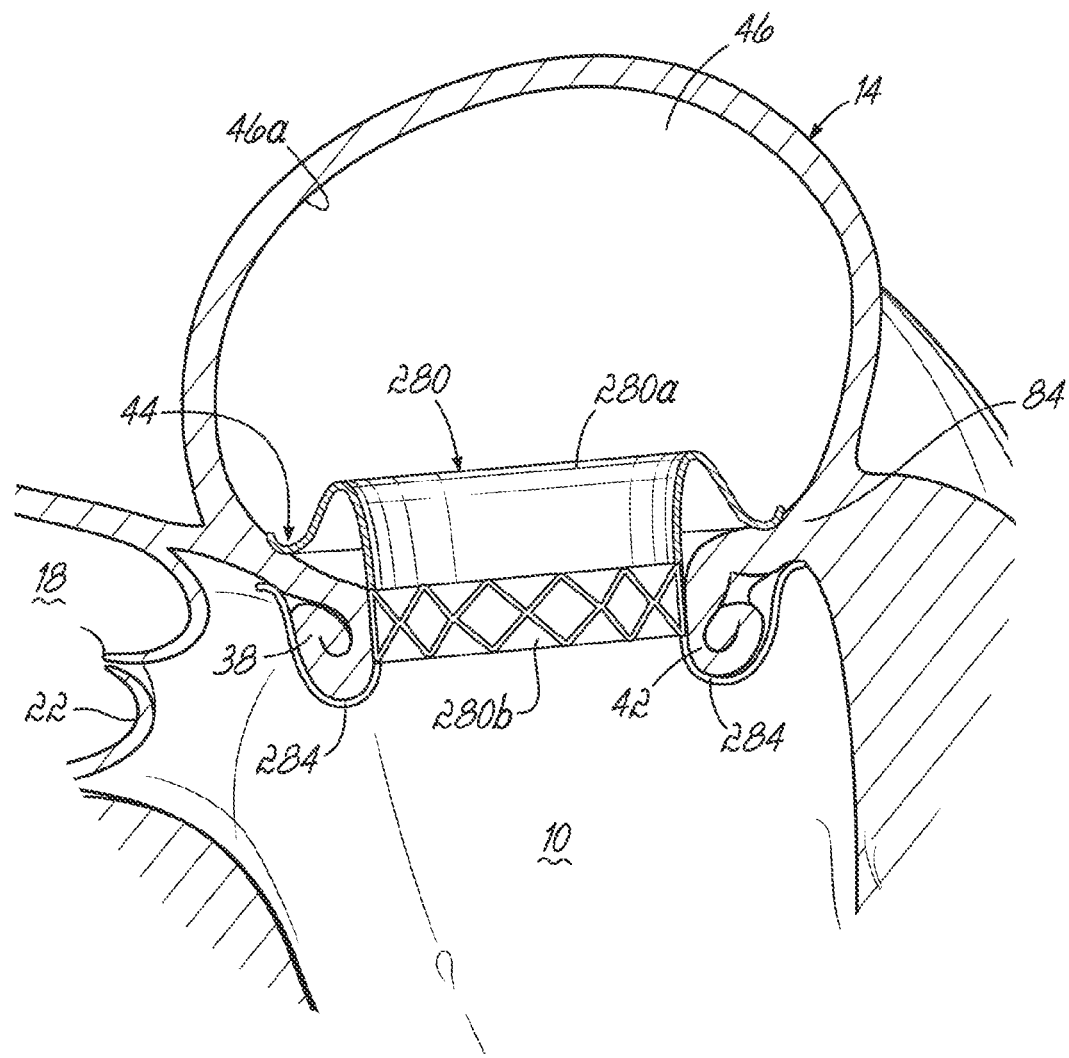
FIG. 15F is a cross sectional view of the stent docking of FIG. 15E as it engages with the valve leaflets and atrial wall.
Figure 15G:
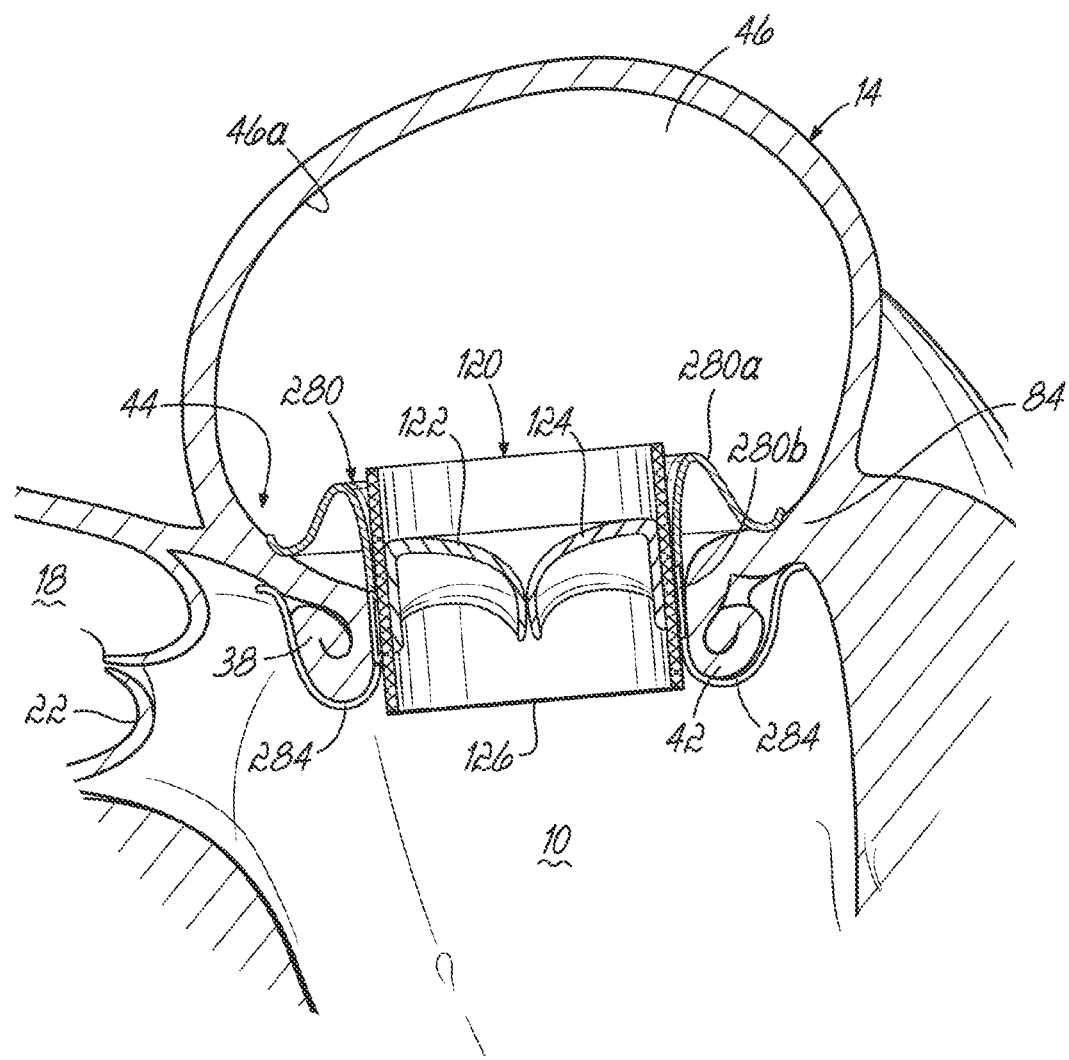
FIG. 15G is a cross sectional view of a valve prosthesis retained by the stent docking shown in FIG. 15F.

Referring now to FIG. 15F, the stent dock 280 has been positioned. The valve retaining portion 280b of the dock 280 has expanded or dilated, causing the hooks 284 to lift or move upward toward the atrial portion 280a of the dock 280. The hooks 284 pull upward on the mitral valve tissue so that the valve 44 may no longer open and close. Also, the mitral valve leaflet tissue 38, 42 is compressed by the hooks 284 to form an excellent gasket or seal around the stent dock 280. The mitral leaflet tissue 38, 42 forms a ring of compressed native biologic material that strengthens the dock 280 and prevents any leaks around the stent dock 280. Therefore the expansion of the valve retaining portion 280b causes the atrial portion 280a and hooks 284 to hold the dock 280 in place. The expansion of the valve retaining portion 280b can be effected by a variety of means. In one embodiment a draw string (not shown) could be used to pull the hooks 284 toward the atrial portion. Similarly, in another embodiment a series of draw strings (not shown) could be used to pull hooks 284 and segments of the atrial portion 280a together.

It should be noted that both the atrial portion 280a and the ventricular hooks 284 of this device 280 could have many variations. For example, the atrial portion 280a may not be composed of complete cells. In one embodiment the atrial portion 280a may comprise radial arms (not shown) extending outward and not a complete circle of stent material. In another embodiment the atrial portion 280a could comprise a spiral of material similar to the tail-like extension 162 shown previously to anchor the helical anchor in the atrium in FIG. 8.

Following successful placement of the stent dock 280, a separate valve prosthesis 120 is implanted within the valve retaining portion 280b as shown in FIG. 15G. The valve prosthesis 120 may be as previously described, for example. The expansion of the valve prosthesis 120 may cause the retaining portion 280b to expand, which allows the hooks 284 and atrial portion 280a to firmly retain the stent dock 280. Alternatively, the valve prosthesis 120 may be integrated within the stent dock 280 prior to implantation to avoid the secondary step.

Figure 16A:
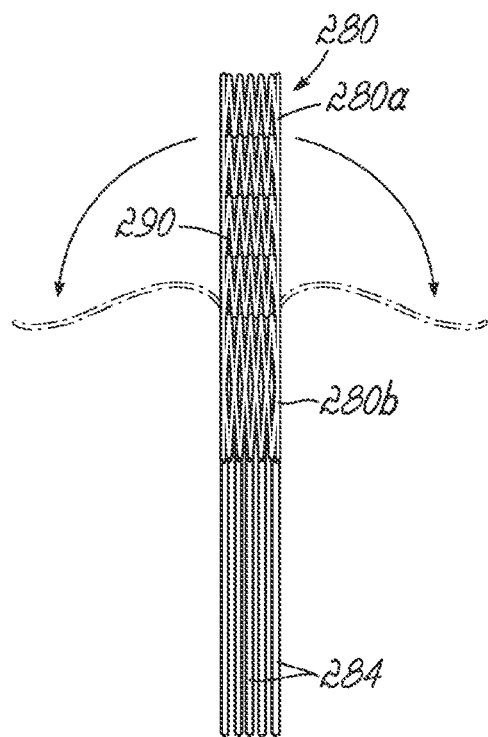
FIGS. 16A and 16B illustrate in perspective a stent docking having an atrial component transitioning from a closed state to an open state.
Figure 16B:
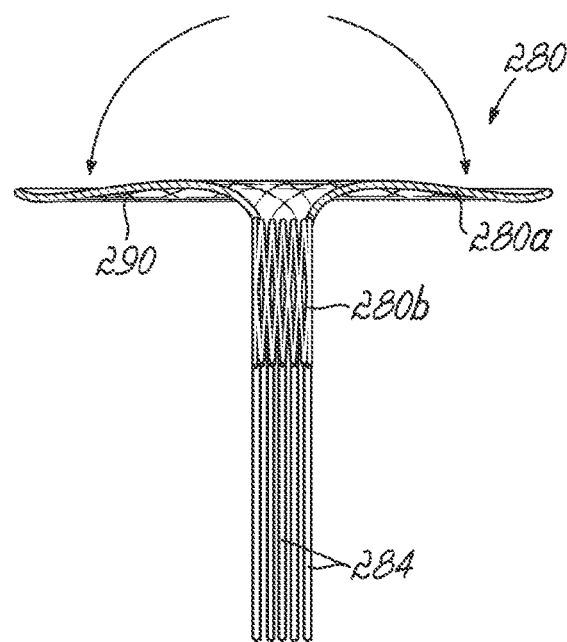
Figure 16C:
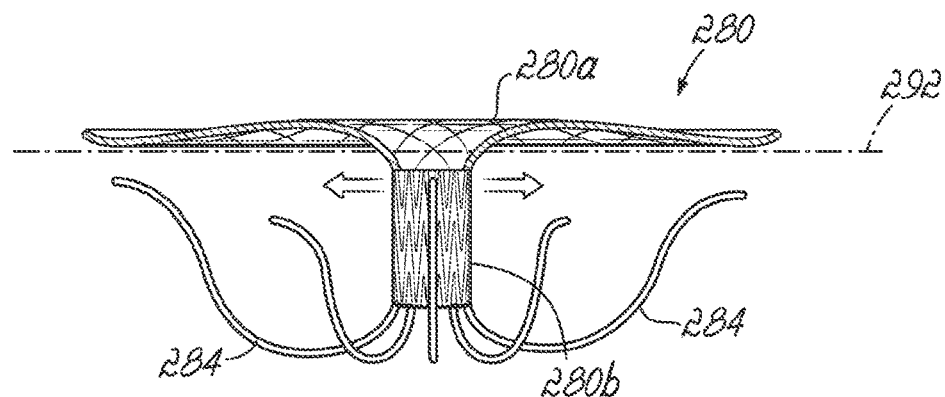
FIG. 16C is a perspective view of the stent docking of FIGS. 16A and 16B as the valve retaining portion expands and the hooks deploy.
Figure 16D:
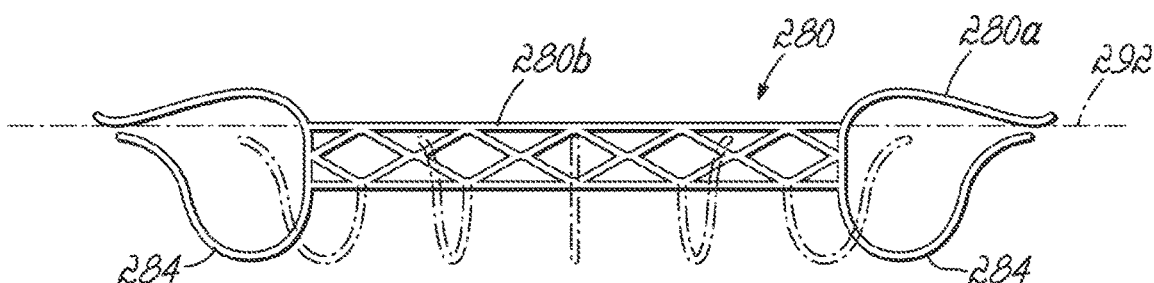
FIG. 16D is a cross sectional view of the fully deployed stent docking of FIGS. 16A-16C with the valve retaining portion expanded.

FIGS. 16A-16C show the stent dock deployment without a delivery catheter to provide closer detail. The atrial portion 280a is shown opening in FIGS. 16A and 16B. The spaces between the struts 290 of the atrial portion allow for minimal or no interruption of blood flow. FIG. 16C shows the atrial portion 280a resting in the plane 292 of the mitral valve, shown in dash-dot lines. The valve retaining portion 280a is beginning to expand, causing the hooks 284 to elevate. FIG. 16D illustrates the valve retaining portion 280b is fully expanded, resulting in the hooks 284 being lifted to their deployed position.

Figure 17A:
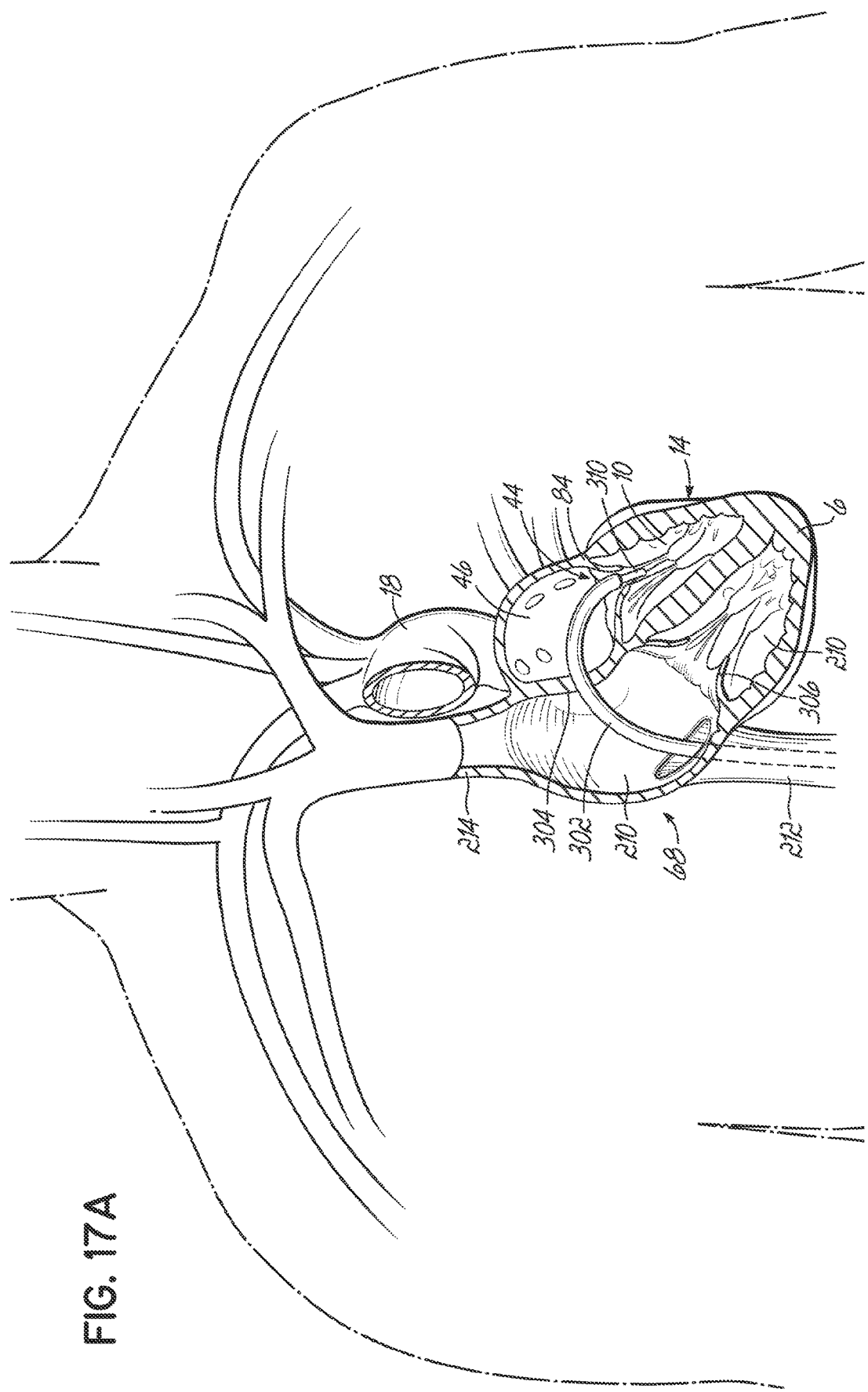
FIGS. 17A-17D illustrate in perspective an alternative procedure of placing a helical anchor by way of the venous system in the mitral position of a heart, which is shown in cross section.

Referring now to FIGS. 17A-17D, a system and method for positioning a helical anchor 300 in the mitral position of a patient's heart 14 is shown. A catheter 302 is introduced into a patient's venous system by percutaneous puncture or by a small surgical cut down at the patient's groin, as is commonly known. Alternatively, the catheter 302 may be introduced anywhere in the lower abdomen or retroperitoneal region, or in the neck or shoulder regions via the subclavian or axillary veins or the jugular system in the neck. In this embodiment, the catheter 302 is advanced up the inferior vena cava 212, into the right atrium 210, across the atrial septum 304, and into the left atrium 46 as shown in FIG. 17A. The tricuspid valve 306, right ventricle 210, superior vena cava 214, and aorta 18 of the patient's heart 14 are show for illustrative purposes. A coil guide catheter 310 is carried by the catheter and extends between the anterior and posterior leaflets 38, 42 of the mitral valve 44 into the left ventricle.

In this embodiment the system is preferably inserted via the venous system, which is low in pressure and can accommodate large catheters and guides. This allows flexibility in developing and introducing catheters, systems, devices and methods for remote mitral valve replacement. However, it is appreciated that the system may be introduced directly into the left atrium 46 without a transvenous approach, or via the aorta 18. For example, the catheter 302 can be passed from the aorta 18 to the left ventricle 10 and then into the left atrium 46. The aorta 18 can be accessed directly as in an open surgical procedure, or from any of its branches so that the system may be introduced in the groin, shoulder, retro peritoneum, chest, or abdomen of the patient.

Figure 17B:
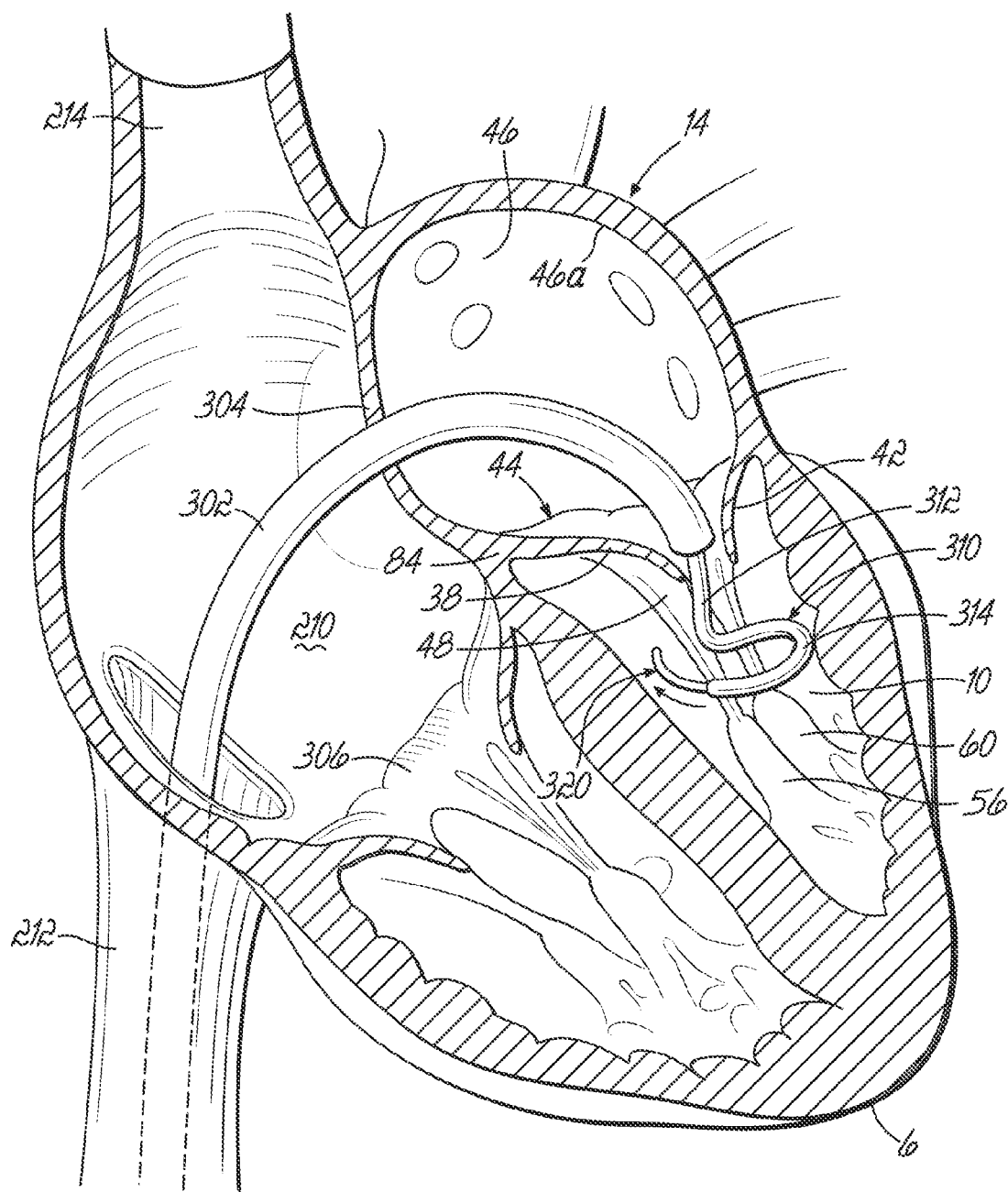

In FIG. 17B a coil guide catheter 310 is extended into the left ventricle 10 and assumes its original shape. In this embodiment, the coil guide catheter 310 comprises a stem 312 and a U-shaped portion 314. The lower coils 316 (FIG. 17C) of a helical anchor 320 are extruded (i.e., extended) from the coil guide catheter 310 inside the ventricle 10. The lower coils 316 wrap around the chordae tendineae 48 and the mitral valve 44. The precise level at which the lower coils 316 are extruded can be determined by adjusting the level of the coil guide catheter 310 in the left ventricle 10. In this embodiment the extrusion is commenced below the level of the valve 44 such that the chordae tendineae 48 and the valve 44 are encircled. It may be more convenient to encircle at a higher level. The chordae tendineae 48 originate from two papillary muscle heads 56, 60 located substantially below the mitral valve 44. Due to the higher concentration of the chordae tendineae 48 near the papillary muscle heads 56, 60, it may be desirable to encircle the chordae tendineae 48 at a lower level.

Figure 17C:
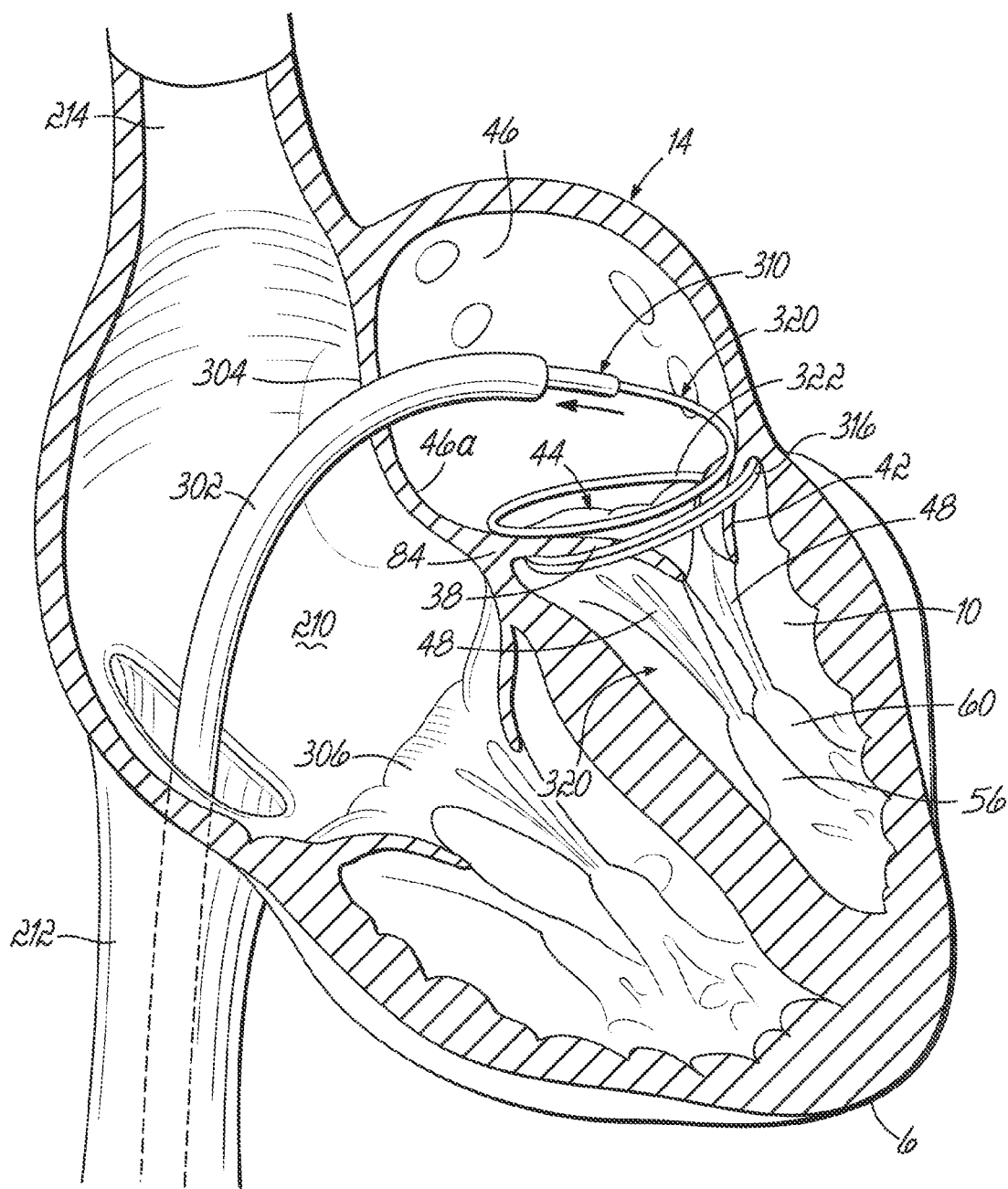
Figure 17D:
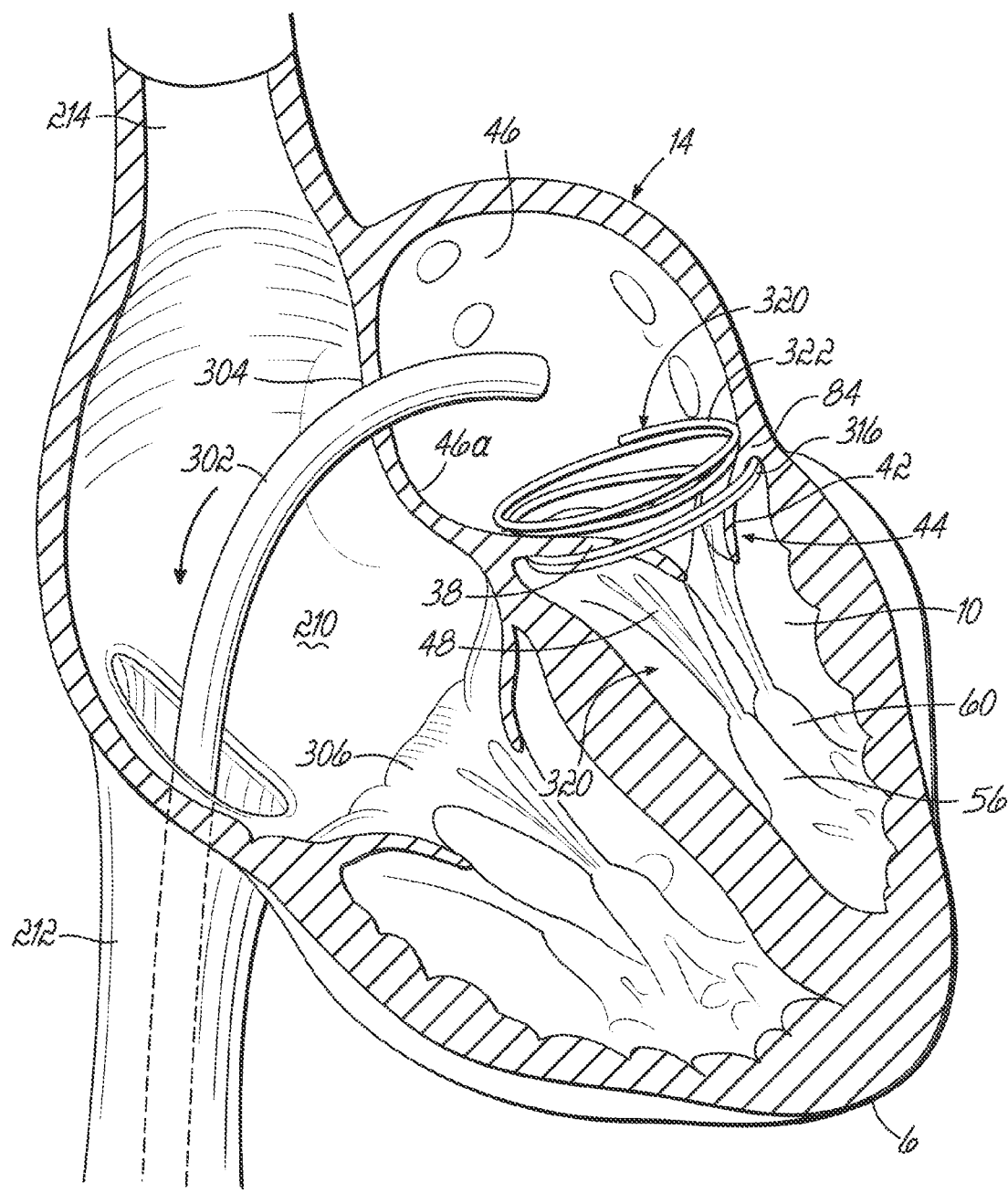

When the lower coils 316 of the helical anchor 320 have been delivered below the mitral valve 44 as desired, the coil guide catheter 310 is drawn up into the left atrium 46. See FIG. 17C. The act of withdrawing the coil guide catheter 310 into the atrium 46 can be used to pull the lower coils 316 of the helical anchor 320 placed in the ventricle 10 to a higher level in order to contact the mitral valve 44 as shown in FIG. 17C. The upper coils 322 of the helical anchor 320 are released in the atrium 46 by retracting the coil guide catheter 310 inside the catheter 302. When the helical anchor 320 has been delivered in place as shown in FIG. 17D, the coil guide catheter 310 is retracted and the catheter 302 is withdrawn. In this embodiment, coils 316, 322 of the anchor 320 contact the mitral valve 44 both above and below the leaflets 38, 42. However, it is appreciated that other embodiments may have a variety of arrangements including those previously described. For example, the upper coils 322 may not contact the mitral valve 44 but may be supported against the atrial wall 46a. Also, a helical anchor having a gap between the lower and upper coils 316, 322 could be positioned so that the leaflets 38, 42 are not trapped between coils 316, 322 and to improve orientation of a subsequently placed valve prosthesis (not shown). FIG. 17D also illustrates that ventricular coils 316 contain leaflets 38, 42. It will be appreciated that there may be gaps between coils 316 and/or gaps between coils 322, and that different numbers of coils than those shown in the drawings may be utilized. As one further example, if additional coils 316 are used in the ventricle 10, this can provide further prosthetic valve support and help further contain the anterior leaflet 38 from obstructing the aortic valve 22. Additional coils 322 in the atrium 46 can also provide further prosthetic valve stabilization and also allow the prosthetic valve to be positioned higher in the atrium 46 so that it does not obstruct the aortic valve 22.

It should be noted that when the helical anchor 320 is delivered this way, the lower and upper coils (i.e., ventricular and atrial coils) 316, 322 are joined by a segment of the anchor that is located at the leaflets 38, 42. This may impair leaflet closure and cause a leak in the valve 44. However, this situation will not persist for a long time since a percutaneous replacement valve 120 can be deployed immediately after placing the anchor 320. Also, the segment of the anchor 320 joining the atrial coils 322 and ventricular coils 316 may sit near a commissure 80 (FIG. 15A) and not interfere with valve closure. In another embodiment the wire of the anchor 320 could be preformed so that it would travel through the center of the native mitral valve 44 and allow the two mitral valve leaflets 38, 42 to approximate each other. A wide variety of helical anchor configurations, such as those previously described herein, may be incorporated.

Figure 18A:
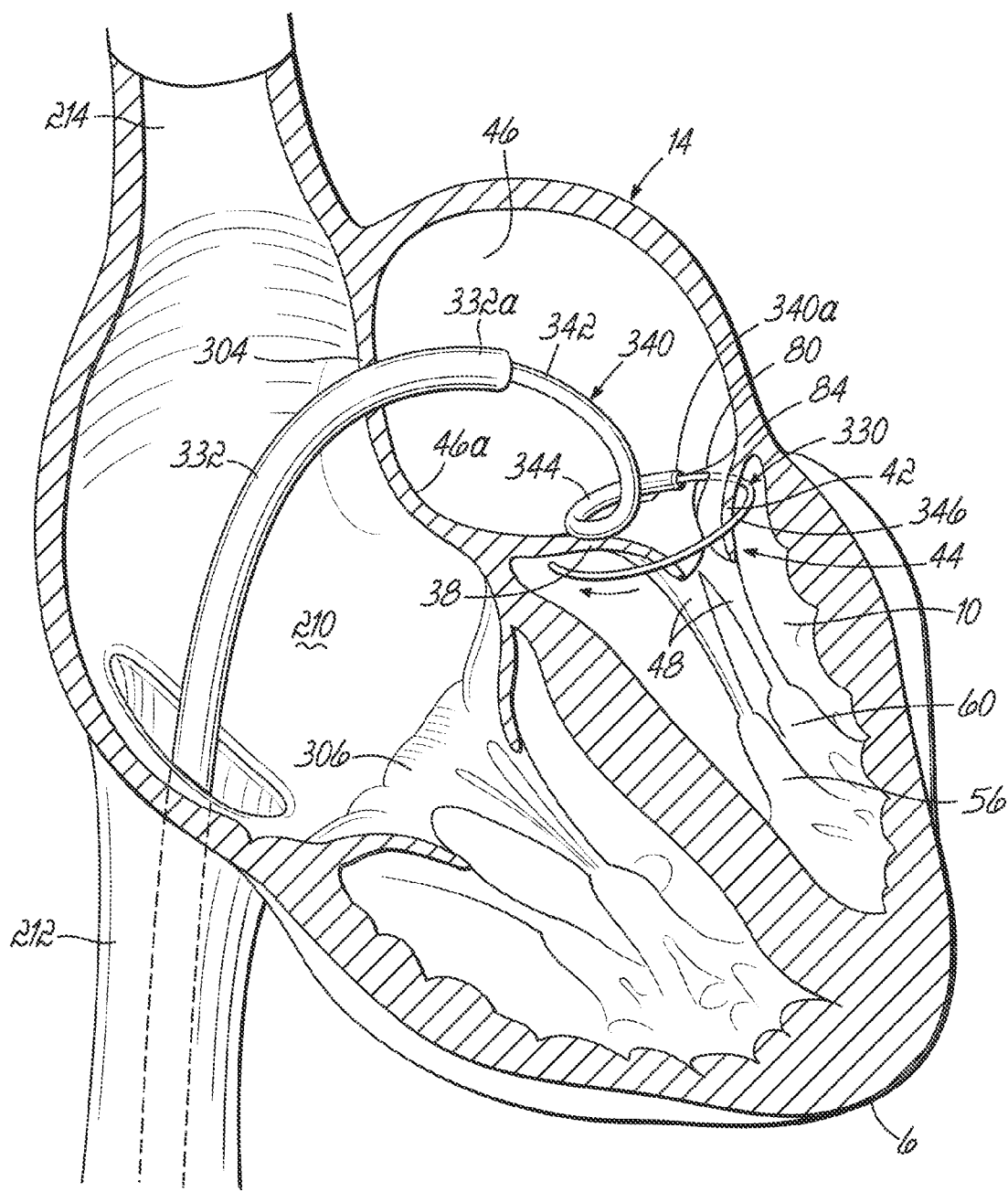
FIGS. 18A-18C illustrate in perspective another alternative procedure of placing a helical anchor by way of the venous system in the mitral position of a heart, which is shown in cross section.
Figure 18B:
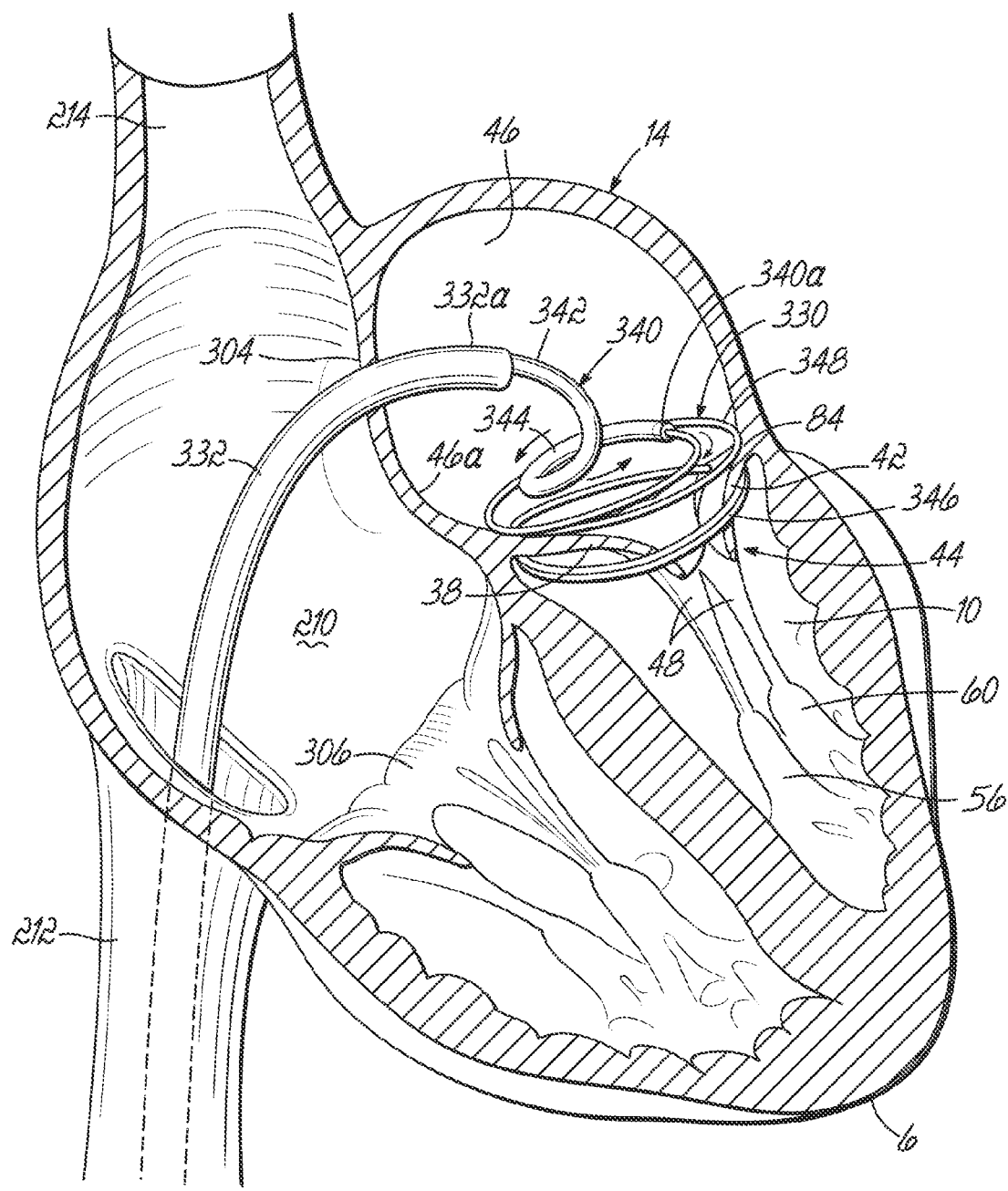
Figure 18C:
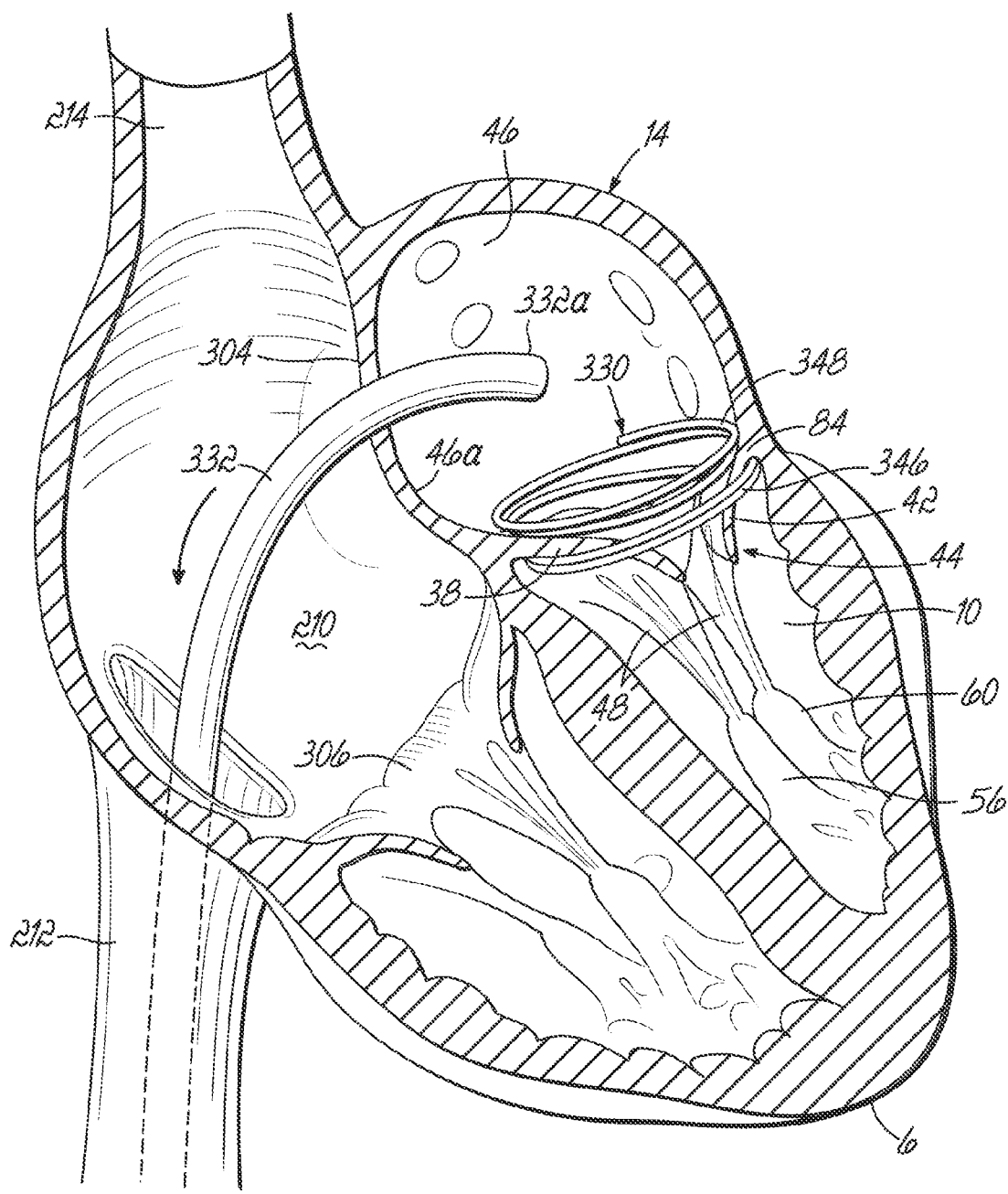

Referring now to FIGS. 18A-18C, a system and method for positioning a helical anchor 330 in the mitral position of a patient's heart 14 is shown. A catheter 332 is introduced into a patient's venous system by percutaneous puncture or by a small surgical cut down at the patient's groin, as is commonly known. Alternatively, the catheter 332 may be introduced anywhere in the lower abdomen or retroperitoneal region, or in the neck or shoulder regions via the subclavian or axillary veins or the jugular system in the neck. In this embodiment, the catheter 332 is advanced up the inferior vena 212 cava, into the right atrium 210, across the atrial septum, and into the left atrium 46 as shown in FIG. 18A. A coil guide catheter 340 extends from the catheter 332 into the left atrium 46 with its distal tip 340a at or near the mitral valve 44. The helical anchor 330 is extruded from the tip 340a of the coil guide catheter 340 under the mitral valve 44 through a commissure 80 between the anterior and posterior leaflets 38, 42. The coil guide catheter 340 comprises a stem 342 and a U-shaped portion 344 to assist in the extrusion of the helical anchor 330.

In this embodiment the system is preferably inserted via the venous system, which is low in pressure and can accommodate large catheters and guides. This allows flexibility in developing and introducing catheters, systems, devices and methods for remote mitral valve replacement. However, it is appreciated that the system may be introduced directly into the left atrium 46 without a transvenous approach, or via the aorta 18. For example, the catheter 332 can be passed from the aorta 18 to the left ventricle 10 and then into the left atrium 46. The aorta 18 can be accessed directly as in an open surgical procedure, or from any of its branches so that the system may be introduced in the groin, shoulder, retro peritoneum, chest, or abdomen of the patient.

After the lower coils 346 have been positioned under the mitral valve 44 in the ventricle 10 as desired, upper coils 348 may be positioned above the mitral valve 44 in the atrium 46. In this embodiment, approximately two lower coils 346 of the anchor 330 are positioned under the mitral valve 44. It is appreciated that any desired number of coils 346 may be positioned under the mitral valve 44. The upper coils 348 of the anchor 330 are released from the coil guide catheter 340 above the mitral valve 44 by rotating the coil guide catheter 340 as shown in FIG. 18B. In this embodiment, the catheter 332 has a turn 332a at its distal end. In other embodiments, the turn 332a may be deactivated so that the upper coils 348 are delivered above the valve 44 from a location closer to the atrial septum 304. This would allow the coils 348 to assume their preformed position with relative ease, and would eliminate the need to rotate the catheter 332. FIG. 18C illustrates the completed placement of the helical anchor 330 in the mitral position, such that approximately two lower coils 346 of the anchor 330 are positioned under the mitral valve 44 and approximately two upper coils 348 are positioned above the mitral valve 44. In this embodiment, coils 346, 348 on both sides of the valve 44 contact the valve leaflets 38, 42. After anchor placement is complete, the coil guide catheter 340 is retracted and the catheter 342 may be withdrawn.

Figure 19A:
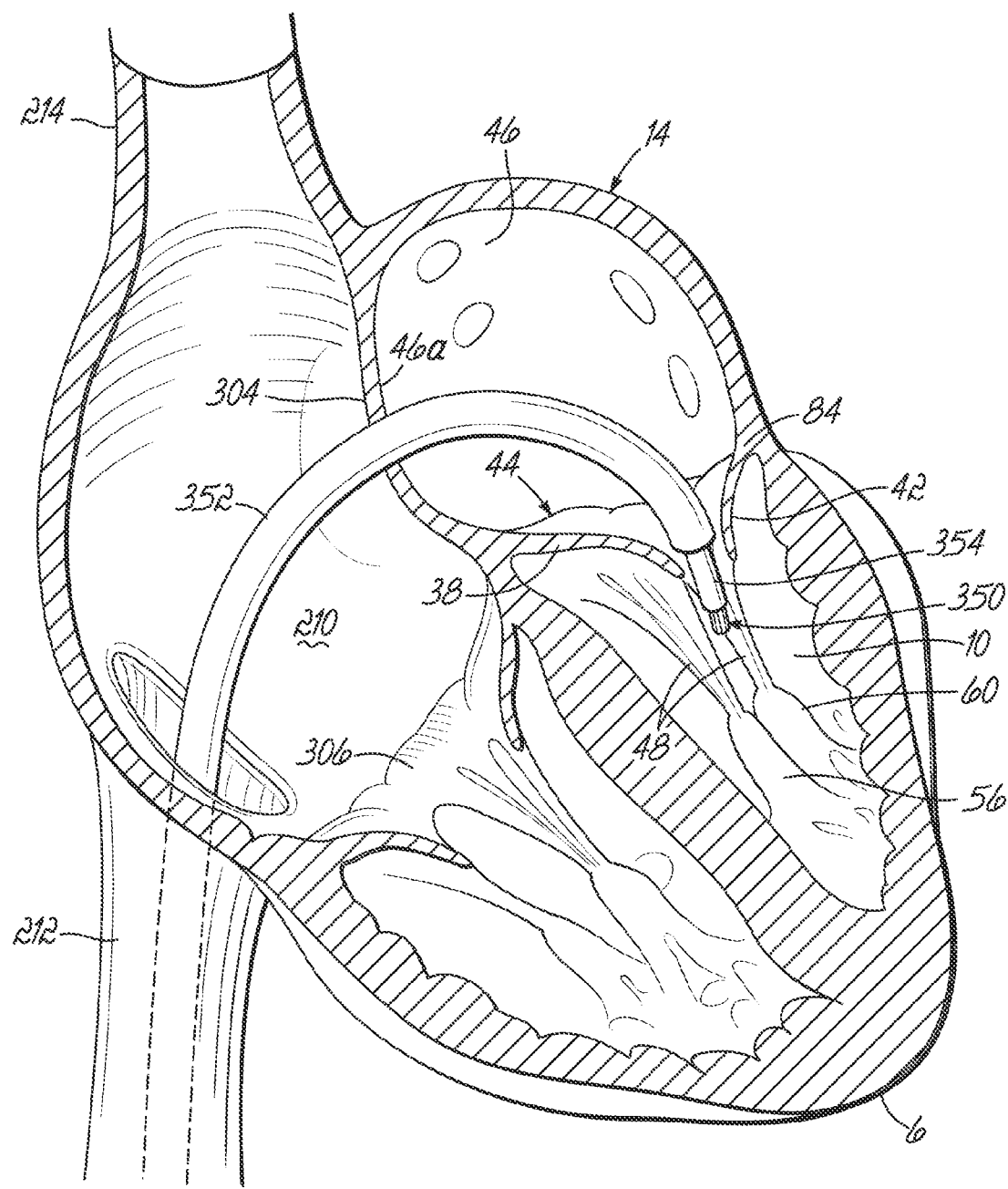
FIGS. 19A-19D illustrate in perspective an alternative procedure of placing a stent docking by way of the venous system in the mitral position of a heart, which is shown in cross section.
Figure 19B:
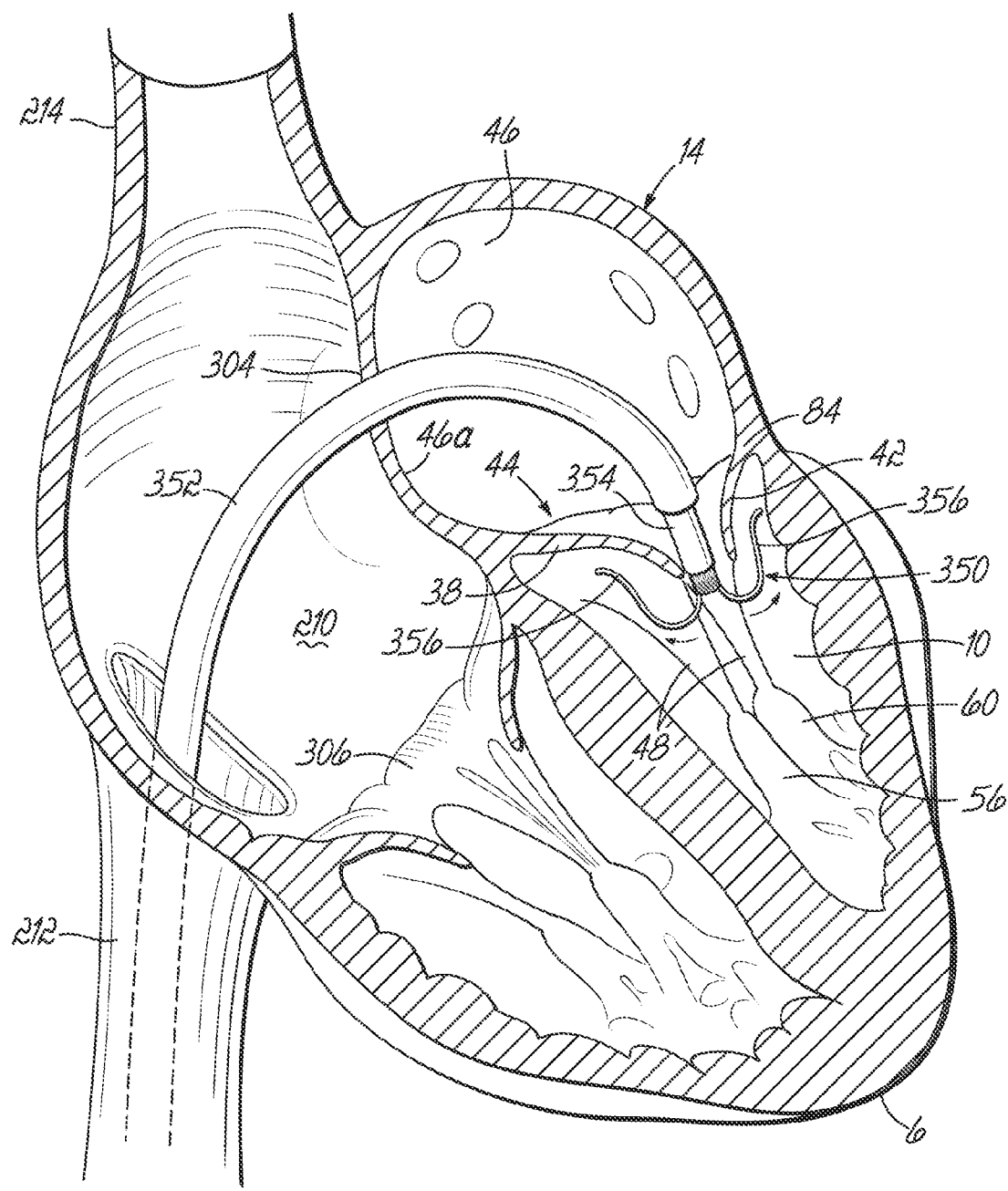
Figure 19C:
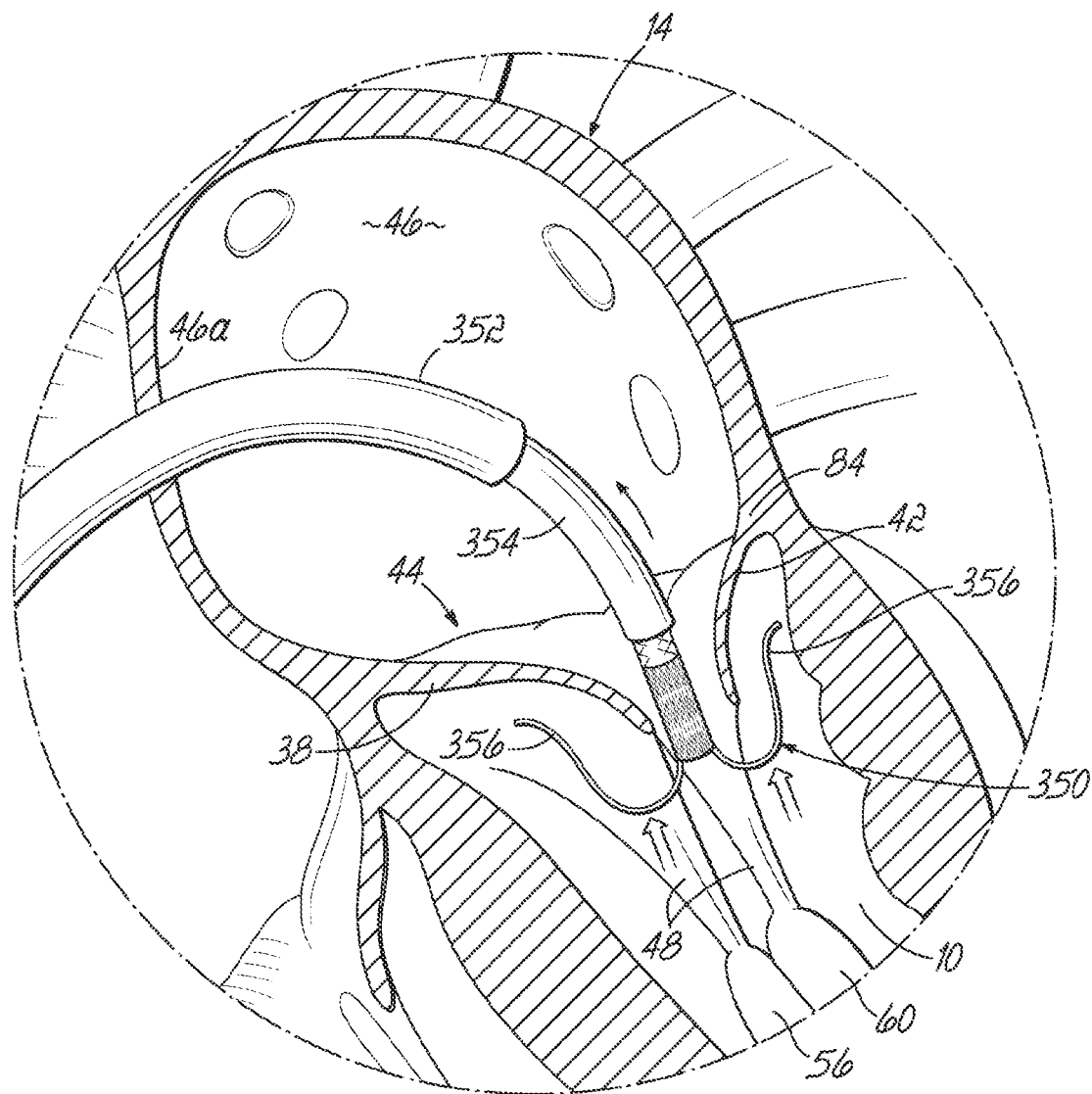
Figure 19D:
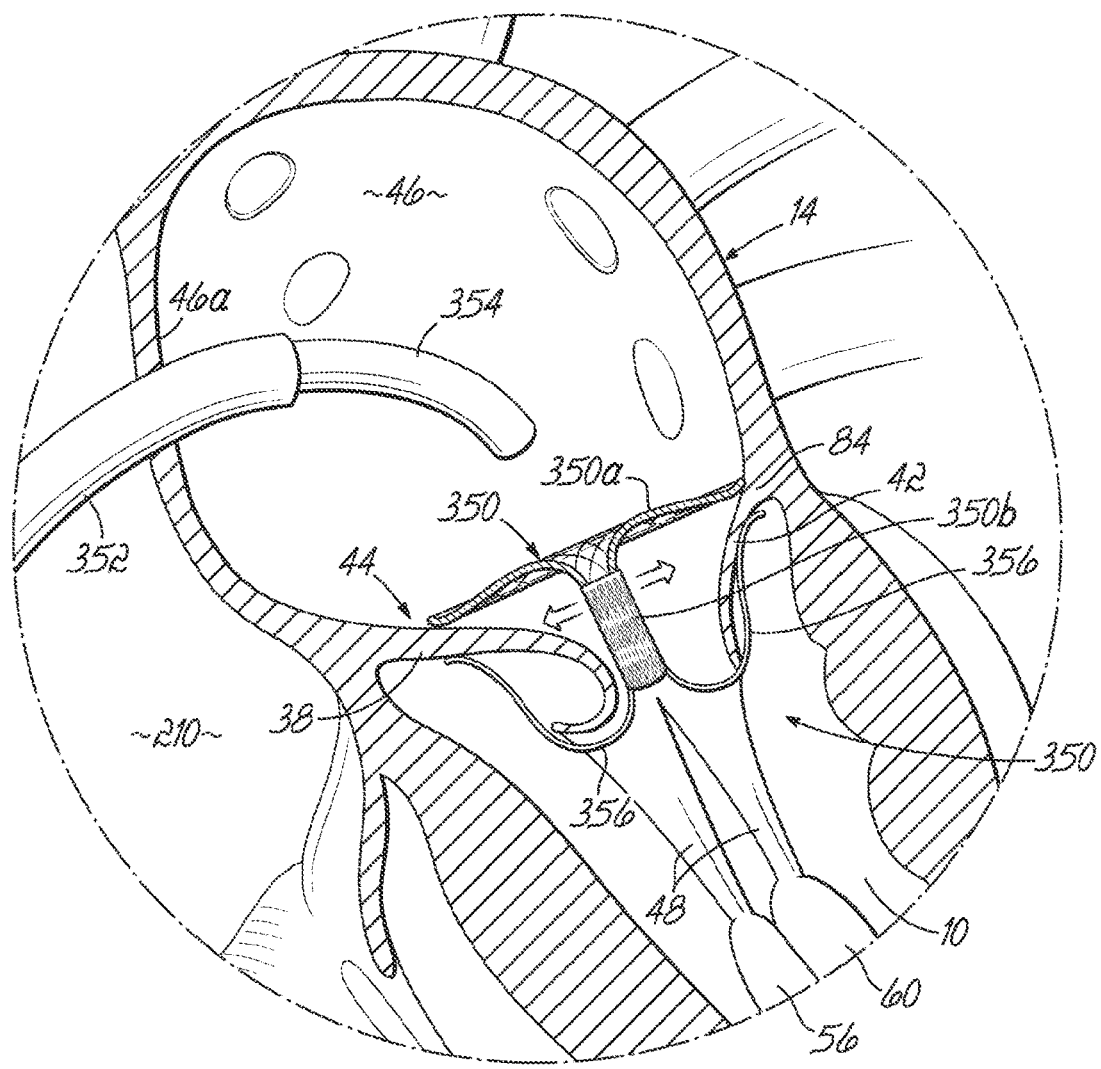
Figure 19E:
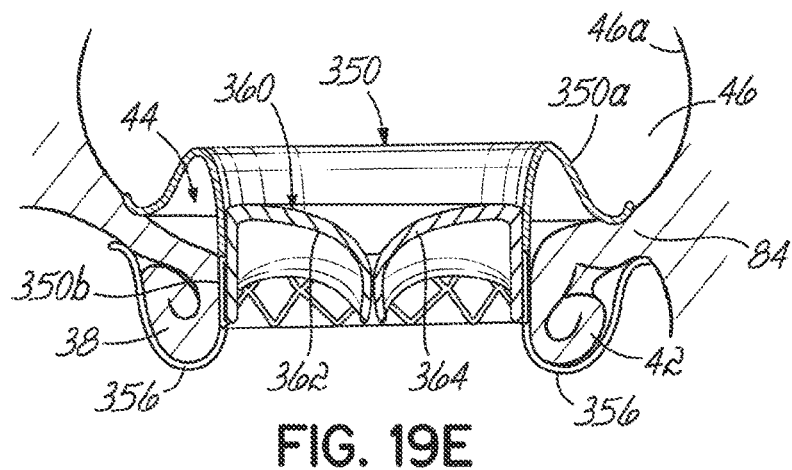
FIG. 19E is a cross sectional view of an alternative embodiment of the present invention, wherein a valve prosthesis is integrated into the valve retaining portion of a stent docking and is placed in the mitral position of a heart, shown in partial cross section.

Referring now to FIGS. 19A-19E, a system and method for positioning a stent dock 350 in the mitral position of a patient's heart is shown. The stent dock 350 may be constructed as described in connection with FIGS. 16A-16D, or in any other suitable manner to carry out the inventive principles as described herein. A catheter 352 is introduced into a patient's venous system by percutaneous puncture or by a small surgical cut down at the patient's groin, as is commonly known. Alternatively, the catheter 352 may be introduced anywhere in the lower abdomen or retroperitoneal region, or in the neck or shoulder regions via the subclavian or axillary veins or the jugular system in the neck. In this embodiment, the catheter 352 is advanced up the inferior vena cava 212, into the right atrium 210, across the atrial septum 304, and into the left atrium 46 toward the mitral valve 44 as shown in FIG. 19A. A delivery catheter 354 extends from the catheter 352 across the mitral valve 44 into the left ventricle 10. The stent dock 350 is extruded from the delivery catheter 354 within the left ventricle 10 such that hooks 356 of the stent dock 350 are released from the delivery catheter 354 and are positioned around the mitral valve leaflets 38, 42 as shown in FIG. 19B. To ensure that all parts of both the anterior and posterior leaflets 38, 42 are engaged by the hooks 356, the stent dock 350 can be pulled toward the valve 44 as shown in FIG. 19C. If this method fails, the stent dock 350 can be pushed forward and the process repeated. Furthermore, the hooks 356 can be retracted back into the delivery catheter 354 in order to restart or abandon the process if there is difficulty in engaging both leaflets 38, 42. After the hooks 356 have been successfully positioned, the entire stent dock 350 is released from the delivery catheter 354 such that a valve retaining portion 350 is placed between the anterior and posterior leaflets 38, 42 of the mitral valve 44 and an atrial portion 350a expands to its original shape within the left atrium 46 as shown in FIG. 19D. A valve retaining portion 350b may have shape memory characteristics that allow it to expand spontaneously, or the valve retaining portion 350b may be expanded by a balloon. The expansion of the valve retaining portion 350b causes the hooks 356 to move upward and secure the valve leaflets 38, 42 such that the hooks 356 and atrial portion 350a of the stent dock 350 clamp upon the mitral valve 44, stabilizing the stent dock 350 in place and forming a seal around the stent dock 350. In this embodiment a valve prosthesis 360 is integrated into the system as shown in FIG. 19E. The valve prosthesis 360 comprises two artificial leaflets 362, 364 which are mounted within the valve retaining portion 350b. The artificial leaflets 362, 364 may comprise pliable animal tissue such as cow, pig or horse pericardium or animal valve tissue or any other suitable material, as with all other embodiments. It is appreciated that other embodiments may require the additional step of implanting a separate valve prosthesis within the valve retaining portion 350b of the stent dock 350.

In another embodiment, orientation relative to the mitral valve 44 can be provided. The anterior leaflet 38 is larger than the posterior leaflet 42 and is situated adjacent to the aortic valve 22 whereas the posterior leaflet 42 is closely associated with the posterior wall of the heart 14. It may be useful for example, to provide longer hooks 356 on the stent dock 350 where it attaches to the anterior mitral leaflet 38. To orient the prosthesis 360, an operator can direct a guidewire or other orienting object (not shown) through the aortic valve 44. This will give the operator an orientation on how to turn the prosthesis 360 for optimal alignment. More specifically, the aortic valve 22 is located adjacent the anterior leaflet 38. Therefore, passing a guidewire into and through the aortic valve 22 will allow visualization, for example, on fluoroscopy and show the operator how to orient the stent dock 350 and properly orient or place the anchoring arms, e.g., hooks 356 to retain and secure the anterior leaflet 38 such that it does not obstruct the aortic valve 22. Alternatively, the orientation can be performed automatically by directing a guidewire through the aortic valve 44 such that the guidewire is passed through a lumen on the delivery system, e.g., a delivery catheter 352, for the stent dock 350. A guide wire (not shown) may be passed through the delivery catheter 352 and out through the aortic valve 22 via the left ventricle 10. This will give the operator an orientation view of the delivery system by way of a fluoroscope, for example. The stent dock 350 can then be directed through the delivery catheter 352 such that a channel in the delivery catheter that holds the guide wire is adjacent to a portion of the stent dock 350 that will abut the anterior leaflet 38, and adjacent to those hooks or other anchoring arms that will secure the anterior leaflet 38. The location of the guidewire or other orienting structure turns the stent dock 350 so that it orients to the anterior mitral valve leaflet 38 in this manner.

Figure 23A:
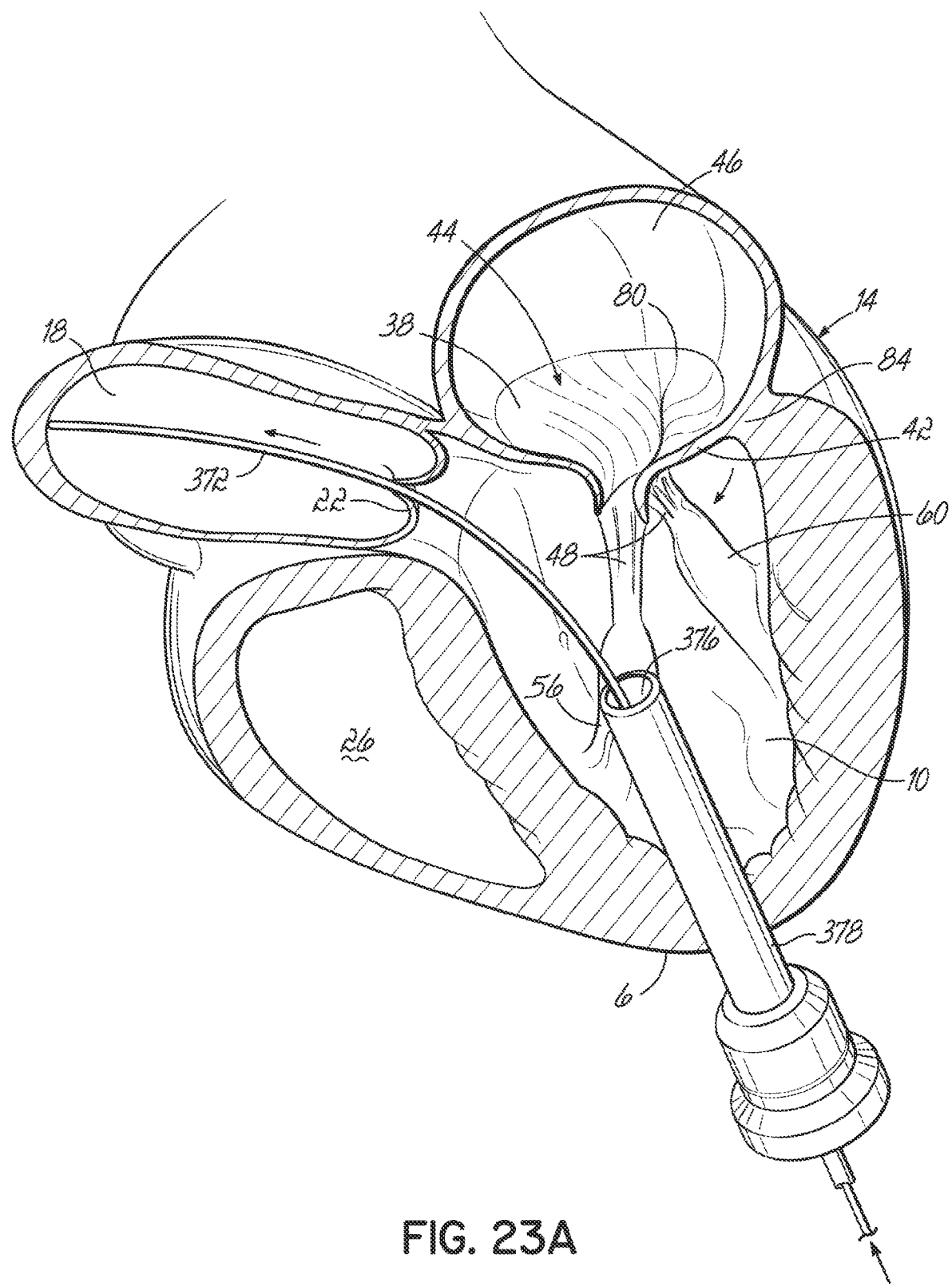
FIGS. 23A-23D illustrate in perspective the placement of an embodiment of a helical anchor in the mitral position of a heart, which is shown in partial cross section, with the assistance of a guidewire placed within the right atrium and a positioning helix placed within the left atrium via the left ventricle.
Figure 23B:
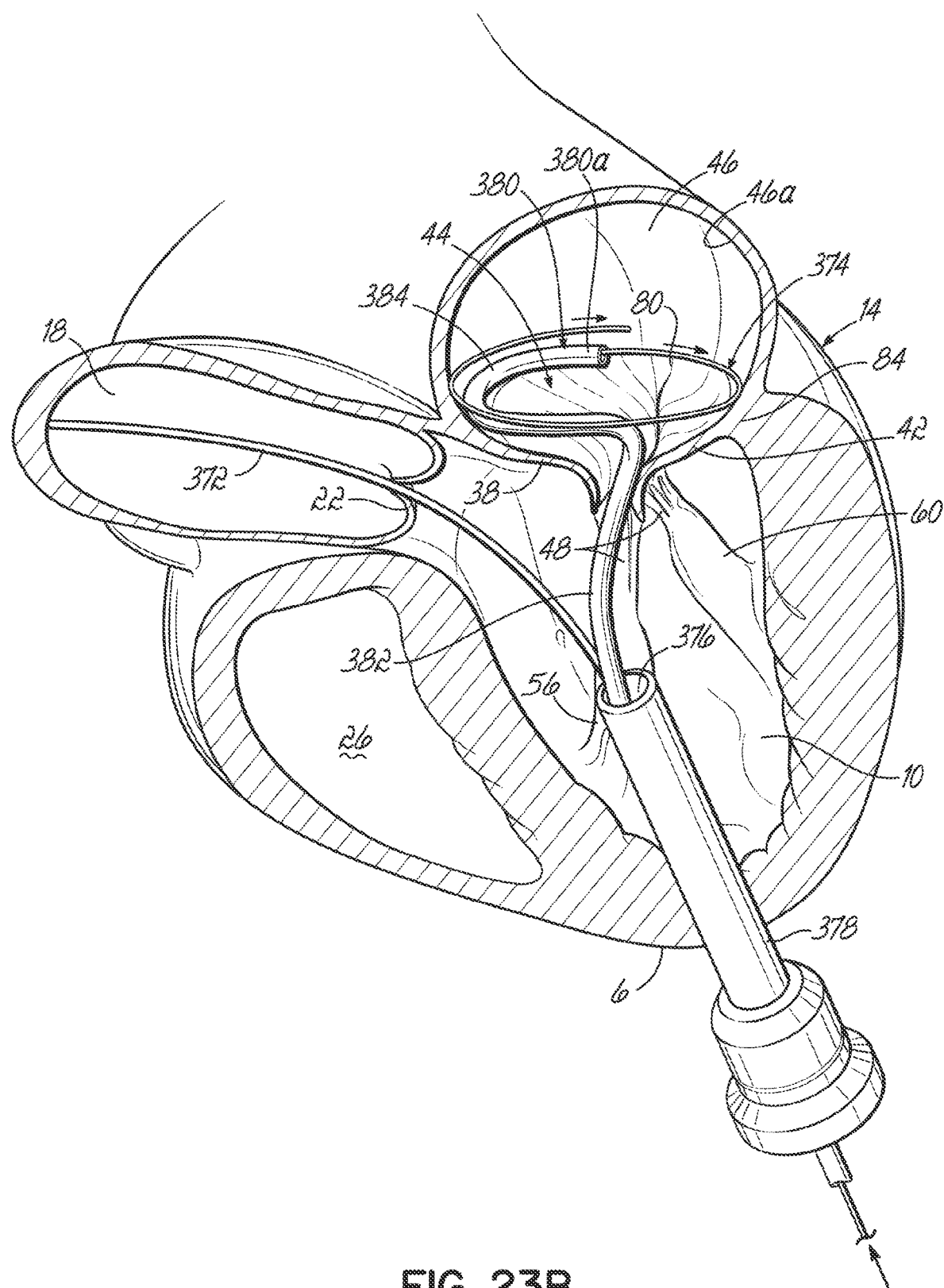

Referring now to FIGS. 23A-23D, a system and method for positioning a helical anchor 370 in the mitral position of a patient's heart 14 with the assistance of an aortic guidewire 372 and a positioning helix 374 is shown. A guidewire 372 is advanced from a lumen 376 of an introducer 378 into the left ventricle 10, across the aortic valve 22, and into the aorta 18. The right ventricle 210 is shown for illustrative purposes. The guidewire 372 may be used to locate the anterior leaflet 38, which is proximate the aortic valve 22. A coil guide catheter 380 having a stem 382 and a U-shaped portion 384 is advanced from the lumen 376 of the introducer 378 and is positioned with its distal tip 380a in the left atrium 46 as shown in FIG. 23B, so that the distal tip 380a of the coil guide catheter 380 may be aimed away from the guidewire 372, as shown, or it may be aimed toward the guidewire 372. An operator may use fluoroscopy or echocardiography to determine the direction of the distal tip 380a relative to the guidewire 372. If the distal tip 380a is aimed away from the guidewire 372, then the operator is assured that a subsequent positioning helix 374 will be extruded from the coil guide catheter 380 toward the posterior leaflet 42. Conversely, if the distal tip 380a is aimed toward the guidewire 372, then a subsequent positioning helix 374 will be extruded from the coil guide catheter 380 toward the anterior leaflet 38. It will be appreciated that this type of guide wire assistance may also be used via an atrial approach wherein the guide wire 372 is delivered via a catheter from the atrium 46 and then through the mitral valve 44 and turned upward through the aortic valve 22.

Prior to placing a helical anchor 370 in the mitral position, a positioning helix or spring 374 can be advanced from the coil guide catheter 380 into the left atrium 46 as shown in FIG. 23B. The left atrium 46 narrows at the location of the mitral valve 44 such that the valve 44 resembles a drain. The positioning helix 374 shown is larger than the diameter of the annulus 84. For example, a positioning helix 374 with a maximum diameter of 40 mm may be used for a 30 mm annulus 84. The positioning helix 374 is advanced when the coil guide catheter 380 is in the middle of the atrium 46 so that the helix 374 will fully expand. When the coil guide catheter 380 is retracted toward the mitral valve 44, the operator can feel the force of the helix 374 against the atrial wall 46a adjacent to the annulus 84 and may also see a deflection of the helix 374 away from the plane of the valve 44 when fluoroscopy or echocardiography is used. This positioning helix or spring 374 serves to identify the location of the mitral valve 44 to make it easier to locate the annulus 84. The helix 374 can be made from any appropriate metal and particularly a shape memory material. The helix 374 shown has approximately one turn or coil, although any number of coils could be incorporated.

Figure 23C:
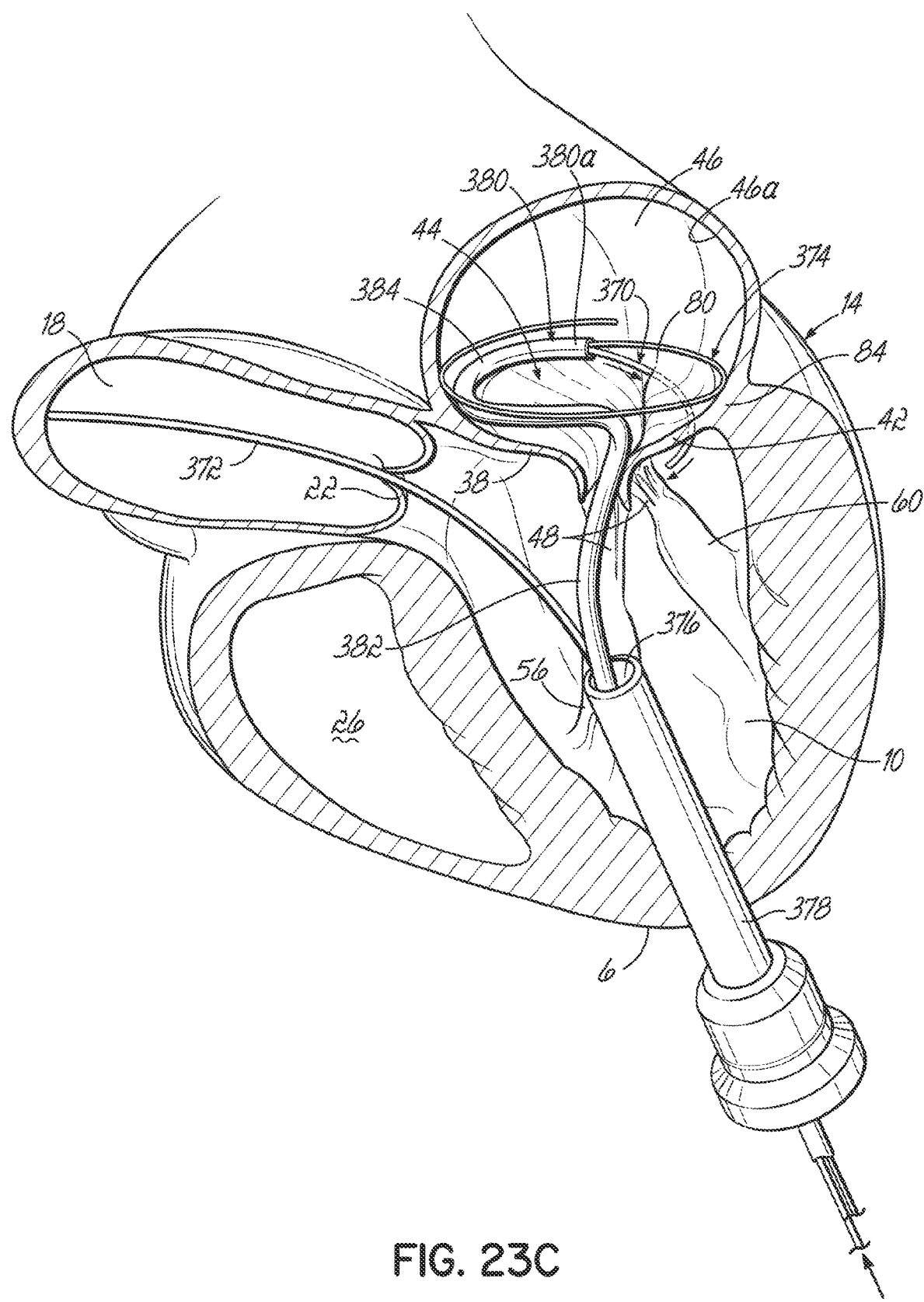
Figure 23D:
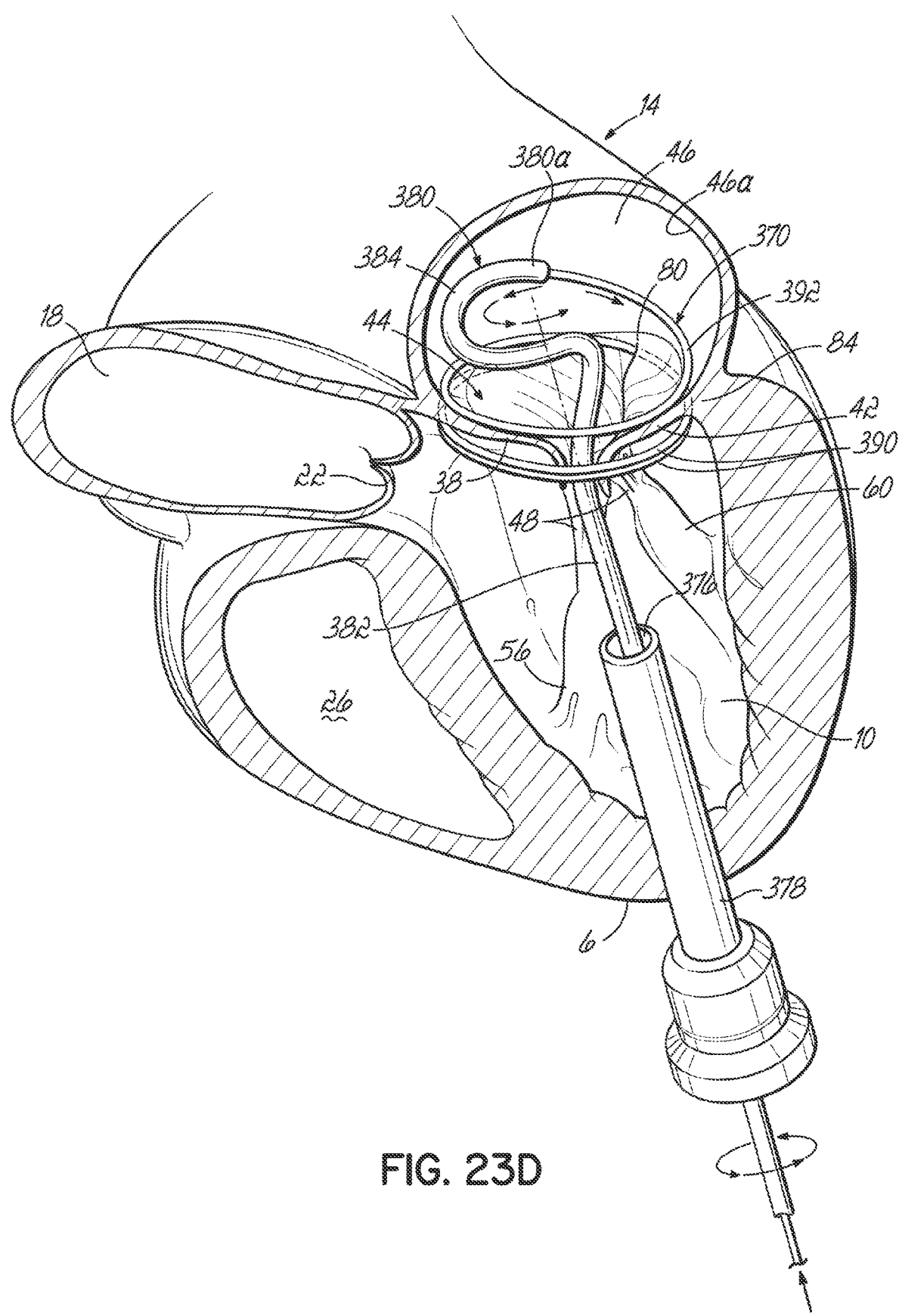

After the positioning helix 374 has located the mitral valve 44, a helical anchor 370 is advanced from the coil guide catheter 380 into the atrium 46, through a commissure 80 of the mitral valve 44, and into the ventricle 10 below the valve 44 as shown in FIG. 23C. The positioning spring 374 can then be removed from the atrium 46. In this embodiment, approximately two lower coils 390 of the helical anchor 370 are placed below the valve 44 by extruding the helical anchor 370 from the coil guide catheter 380. Upper coils 392 of the helical anchor 370 are then placed above the valve 44 by rotating the coil guide catheter 380 as the helical anchor 380 is pushed forward as shown in FIG. 23D. A positioning helix or spring 374 can be incorporated into any of the systems and methods for positioning a helical anchor in the mitral position of a patient's heart described herein.

Figure 24A:
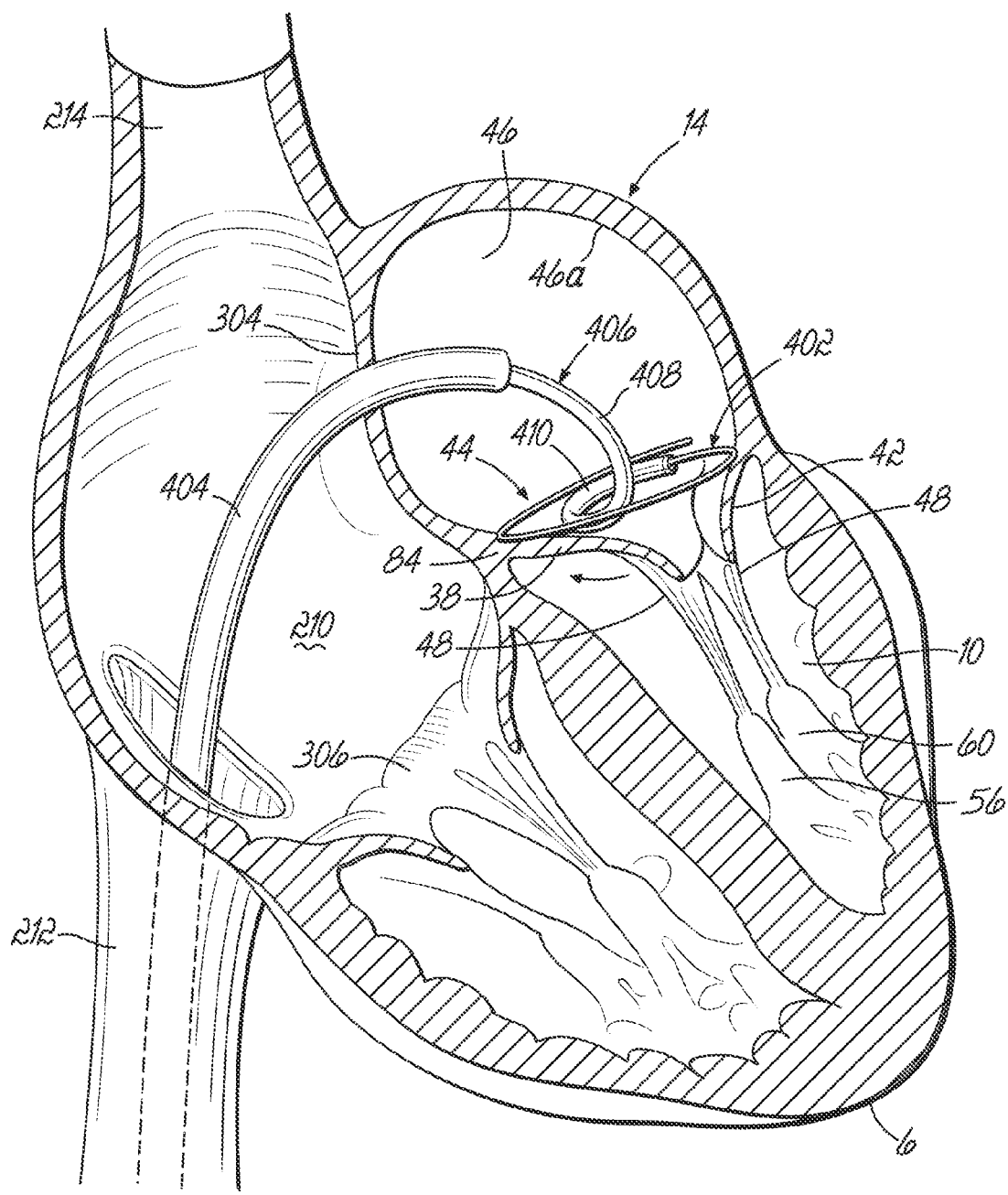
FIGS. 24A-24C illustrate in perspective the placement of an embodiment of a helical anchor in the mitral position of a heart, which is shown in cross section, with the assistance of a positioning helix placed within the left atrium via a transseptal delivery.
Figure 24B:
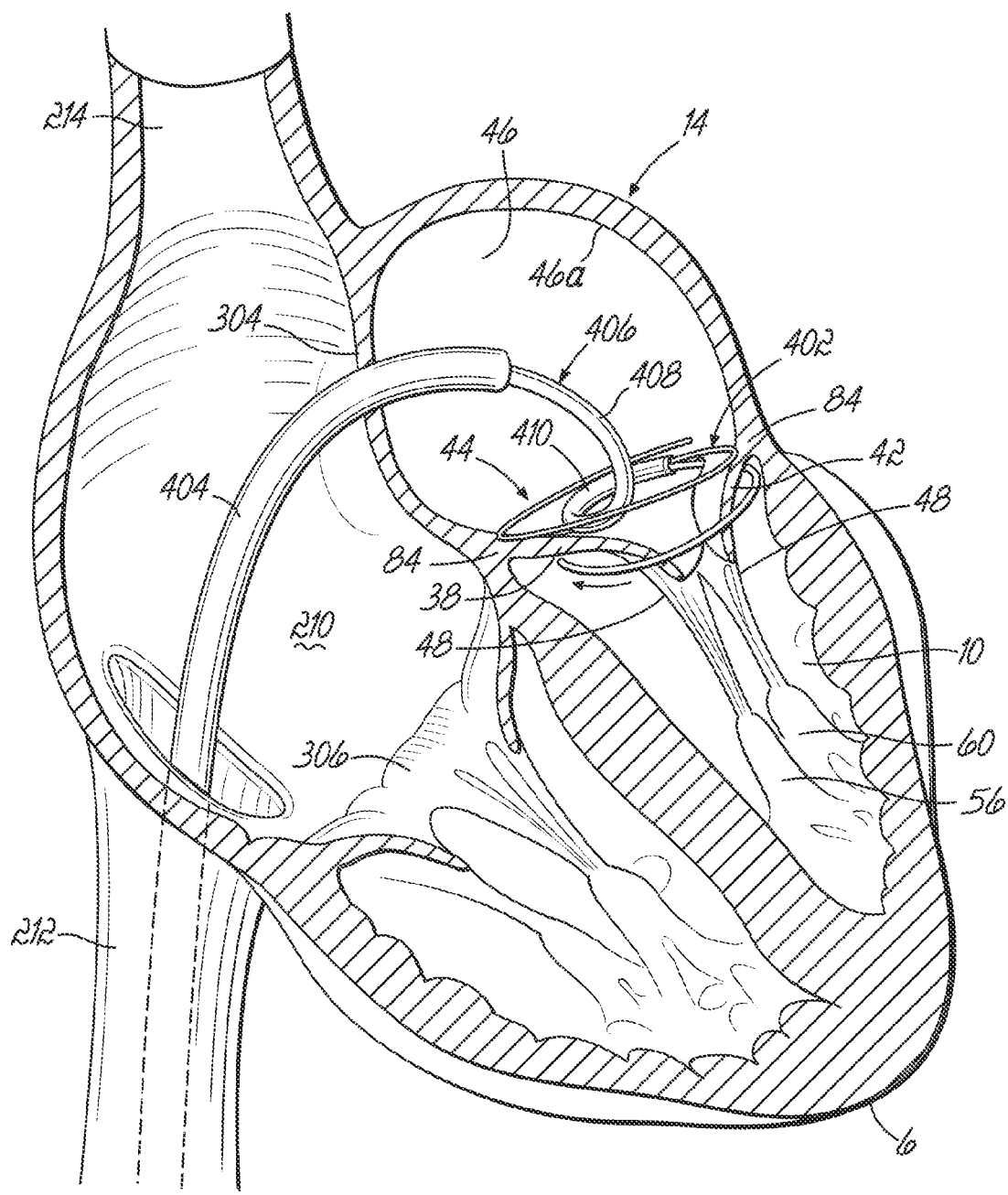
Figure 24C:
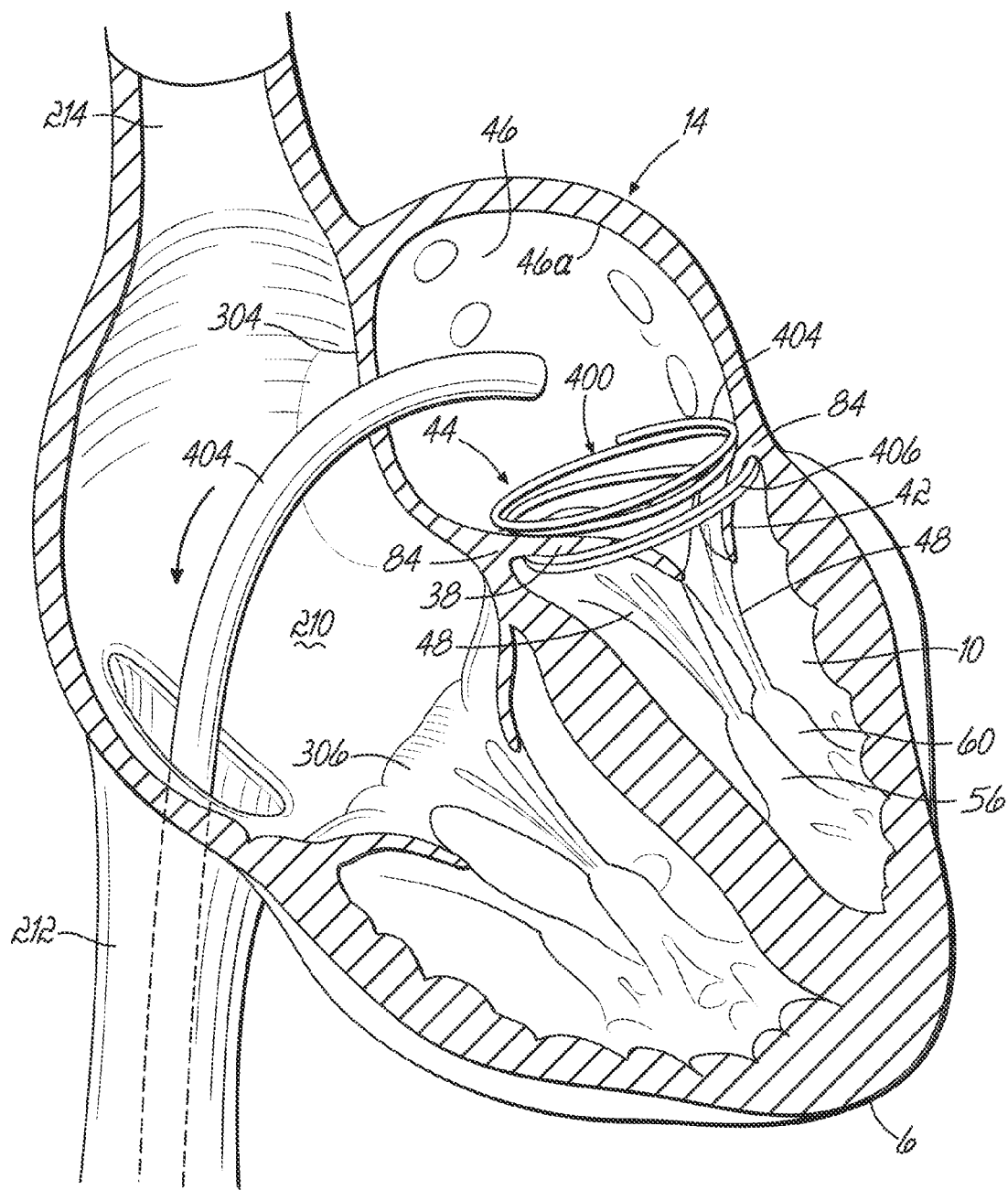

Referring now to FIGS. 24A, 24B, and 24C, another embodiment of a system and method for positioning a helical anchor 400 in the mitral position of a patient's heart 14 with the assistance of a positioning helix 402 is shown. A catheter 404 is introduced into a patient's venous system by percutaneous puncture or by a small surgical cut down at the patient's groin, as is commonly known. Alternatively, the catheter 404 may be introduced anywhere in the lower abdomen or retroperitoneal region, or in the neck or shoulder regions via the subclavian or axillary veins or the jugular system in the neck. In this embodiment, the catheter 404 is advanced up the inferior vena cava 212, into the right atrium 210, across the atrial septum 304 and into the left atrium 46 as shown in FIG. 24A. A coil guide catheter 406 extends from the catheter 404 into the left atrium 46 toward the mitral valve 44. The coil guide catheter 406 comprises a stem 408 and a U-shaped portion 410 for assisting the extrusion of the positioning helix 402 and a helical anchor 400 therefrom. A positioning helix 402 is extruded from the coil guide catheter 406 and is pushed against the bottom of the left atrium 46 near the mitral valve 44. This causes a backforce that can be felt by the operator to confirm the location of the mitral valve 44. A helical anchor 400 is then extruded from the coil guide catheter 406 under the mitral valve leaflets 38, 42 using the positioning helix 402 as a guide as shown in FIG. 24B. The positioning helix 402 can be removed after a portion of the helical anchor 400 is placed below the leaflets 38, 42. The removal of the catheter 404 following the completed placement of the helical anchor 400 with coils 404, 406 respectively above and below the valve is shown in FIG. 24C. It should be noted that in other embodiments the positioning helix 402 could have additional features. For example, it may incorporate a tail-like extension which can pass through the left ventricle and into the aorta (not shown) at its distal end. This feature would ensure that the positioning helix 402 is substantially centered around the mitral annulus 84. In addition the positioning helix 402 would deviate when pushed against the base of the atrium 46. Such a deviation would show up to the operator on the fluoroscope and show the position of the helix 402.

As previously described herein, when the end of an anchor delivery system is located inside the atrium 46, the helical anchor must be directed under the valve leaflets 38, 42. Therefore, additional devices and methods which will now be described are useful to assist the positioning of the start of the helical anchor under the valve leaflets 38, 42 without the need for visualization or with minimal visualization and maximal assurance of the location of the starting point of the anchor so that coils of the anchor will ultimately be located both above and below the leaflets 38, 42.

Figure 25A:
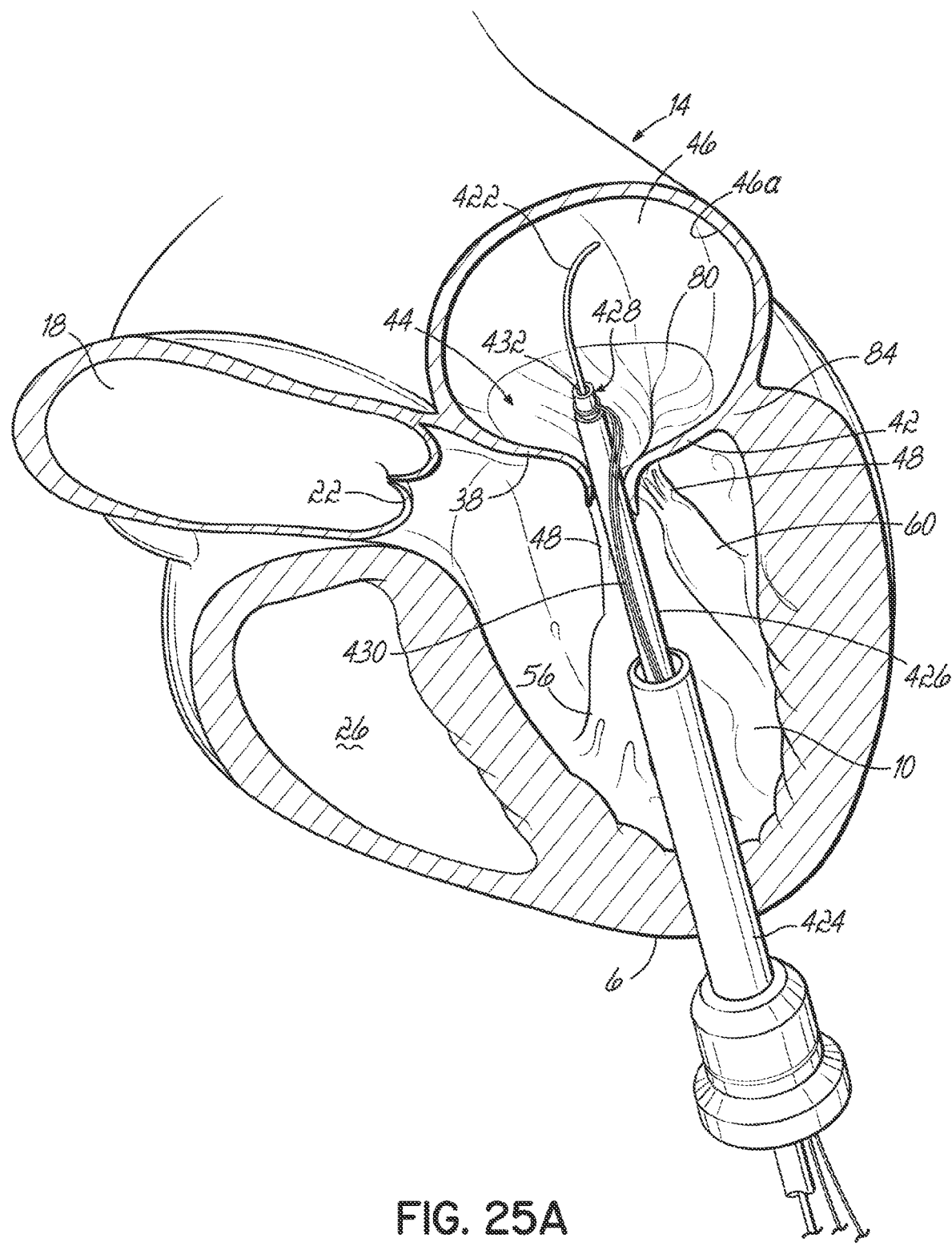
FIGS. 25A-25C illustrate in perspective the placement of an embodiment of a helical anchor in the mitral position of a heart, which is shown in partial cross section, with the assistance of a drawstring to draw a coil delivery catheter or coil guide catheter under a leaflet of the native mitral valve.
Figure 25B:
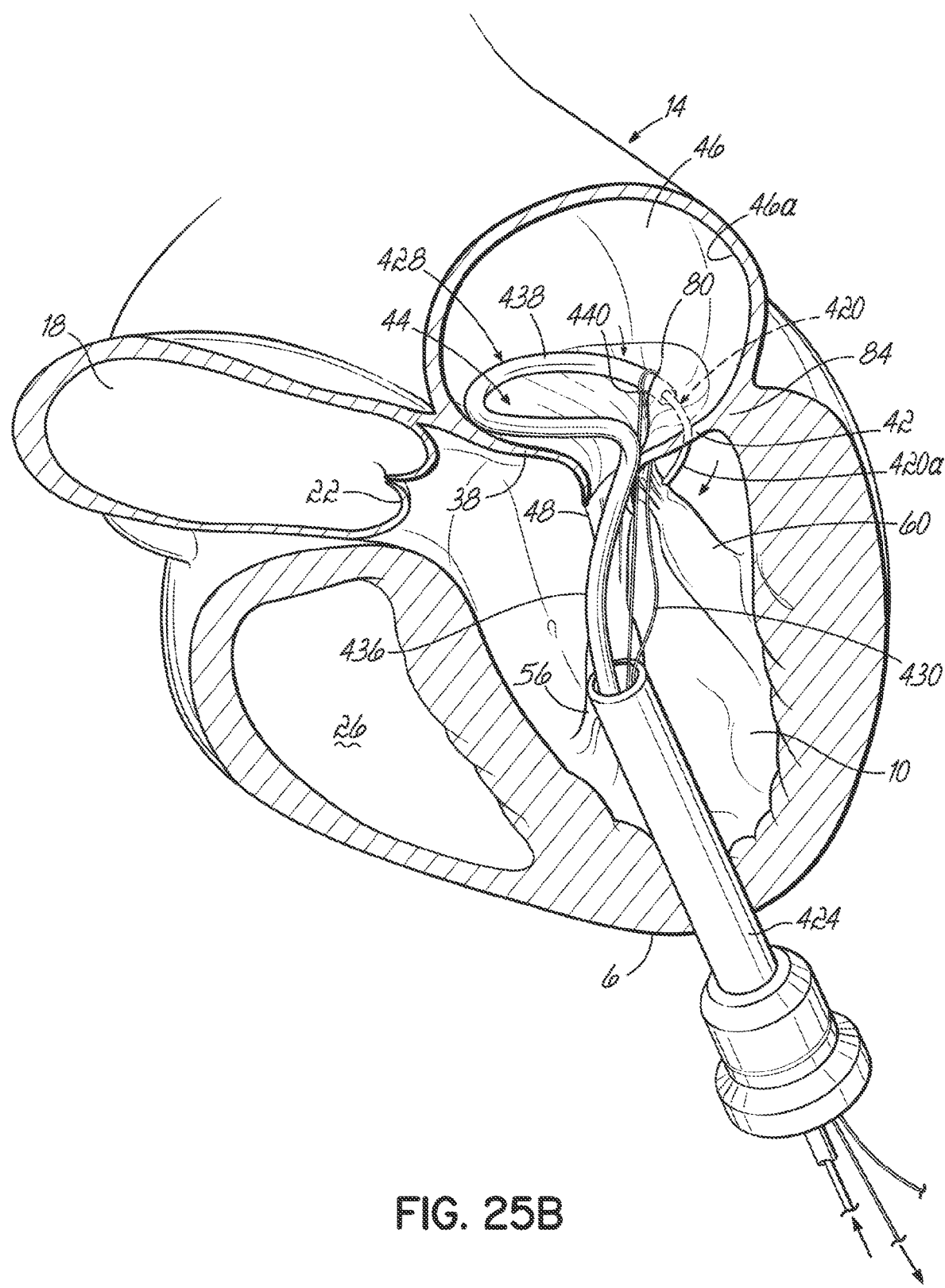
Figure 25C:
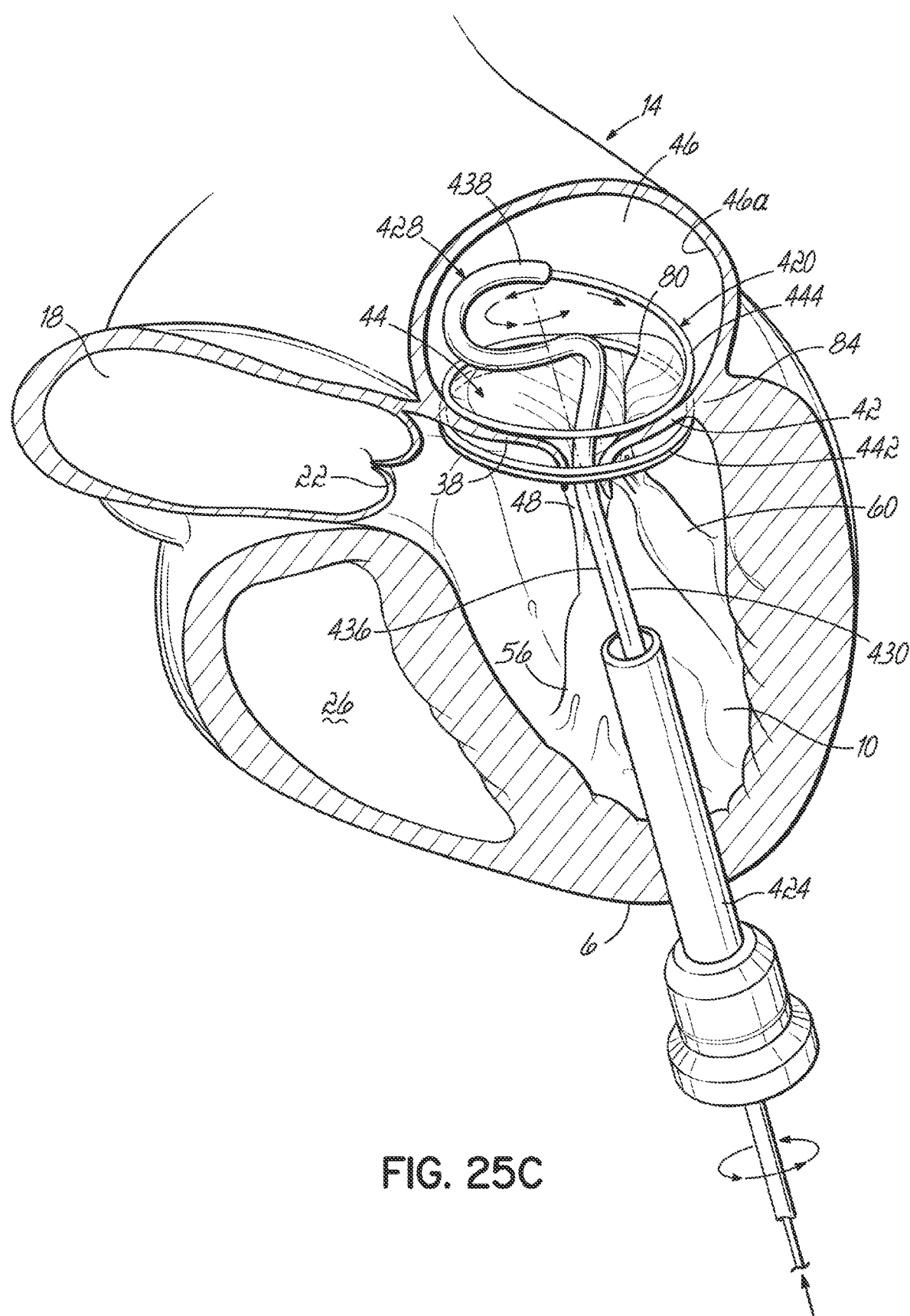

Referring now to FIGS. 25A-25C, a system and method for positioning a helical anchor 420 in the mitral position of a patient's heart 14 is shown. A guidewire 422 is advanced from an introducer 424 through the left ventricle 10 and into the left atrium 46 via the mitral valve 44. A catheter 426 containing a coil guide catheter 428 having an attached drawstring 430 and a central lumen 432 is advanced over the guidewire 422 so that the coil guide catheter 428 extends into the left atrium 46 as shown in FIG. 25A. In another embodiment, the coil guide catheter 428 may have two lumens for each of the guidewire 422 and the helical anchor 420. This variation prevents the two wires 420, 422 from interfering with easy passage of one another if they are in place at the same time. Interference might be particularly problematic in a coil guide catheter 428 having a single lumen when inserting a helical anchor 420 comprising a shape memory material, which could create kinks that would impair the movement of a guidewire 422 through the lumen 432. Both lumens are not required to pass to the end of the coil guide catheter 428. The drawstring 430 may be tied around the coil guide catheter 428 or incorporated into the structure of the coil guide catheter 428, or it may pass through a loop (not shown) in the coil guide catheter 428 for fixation.

The coil guide catheter 428 is initially straight and is activated to a complex curved shape to facilitate delivery of the helical anchor 420 as shown in FIG. 25B. In general, the activated coil guide catheter 428 features curves in two directions. Specifically, a stem 436 of the coil guide catheter 428 is curved to bring the distal end thereof into a plane roughly parallel with the mitral valve 44. A second curve 438 roughly parallels the path of the mitral annulus 84. The helical anchor 420 is shown passing out of the coil guide catheter 428 and under the mitral valve leaflets 38, 42. Anchor delivery under the leaflets 38, 42 has been facilitated by the drawstring 430. The drawstring 430 is pulled from inside the introducer 424 to draw the coil guide catheter 428 under the leaflets of the mitral valve 44. The coil guide catheter 428 can be temporarily pulled down inside the left ventricle 10, until it sits under the leaflets 38, 42. The helical anchor 420 can be pushed out of the coil guide catheter 428 and its turns or coils are started under the leaflets 38, 42. It should be noted that the drawstring 430 passes between the leaflets 38, 42 to ensure that the coil guide catheter 428 will be drawn down between the leaflets 38, 42. The coil guide catheter 428 can be drawn downward in an exaggerated manner (i.e., far into the left ventricle 10) to ensure the helical anchor 420 starts its turns under the leaflets 38, 42. After a segment of the anchor 420 is delivered, the tension on the drawstring 430 can be released so that the coil guide catheter 428 will return to its position just under the leaflets 38, 42 and the helical anchor 420 will be positioned just under the leaflets 38, 42 by simply pushing it out from the coil guide catheter 428. In this embodiment the procedure is performed via the apex 6 of the left ventricle 10. If this procedure is performed via a trans septal puncture, the pulling motion will not work. A pushing motion will be necessary and so a device with some stiffness would be required to move the end of the coil guide catheter 428 under the leaflets 38, 42. In one embodiment this could be accomplished simply by running the drawstring 430 through a tube or catheter and pushing on the catheter (not shown). As shown in FIG. 25B, pulling on the end of the drawstring 430 releases a knot 440 and allows the drawstring 430 to be removed. There are other options including cutting the knot 440 or passing the drawstring 430 through a loop that allows it to be pulled free.

FIG. 25C shows the placement of the helical anchor 420 above the valve 44 following the removal of the drawstring 430 and completed anchor placement below the valve 44. Two coils or turns 442 of the helical anchor 420 sit under the mitral valve 44 and additional turns 444 are placed above the valve 44 by simultaneously pushing out the helical anchor 420 and turning the coil guide catheter 428. It is not necessary to simultaneously push out the helical anchor 420 and turn the coil guide catheter 428 at the same time. The two steps can be performed separately. In another embodiment, coils of the helical anchor 420 can be delivered into the atrium 46 before the tip 420a of the anchor 420 is pushed under the leaflets 38, 42 (FIG. 25B). For example, two coils of the anchor 420 could be extruded from the coil guide catheter 428 into the left atrium 46 before the end 420a of the anchor 420 is directed under the mitral leaflets 38, 42. The tip 420a of the anchor 420 could then be passed under the valve leaflets 38, 42 and two more turns advanced by simply pushing on the helical anchor 420. This would result in a helical anchor 420 positioned with two turns above the leaflets 38, 42 and two turns below the leaflets 38, 42. As stated previously, a different number of turns may be provided above and/or below the valve 44. By delivering the turns of the anchor 420 before engaging the mitral leaflets 38, 42, the need to rotate the coil guide catheter 428 is eliminated. Only a pushing motion is required. This arrangement will allow a helical anchor 428 to be implanted with the operator only needing to push catheters and tools in and out of the patient. Any need to turn and rotate catheters, particularly remotely, makes the procedure more difficult. Transferring torque along a catheter is difficult and unpredictable and can result in the catheter either not moving at all or jumping unpredictably with a risk of heart injury. A catheter procedure performed with only in-and-out motions is much easier and safer.

Figure 26A:
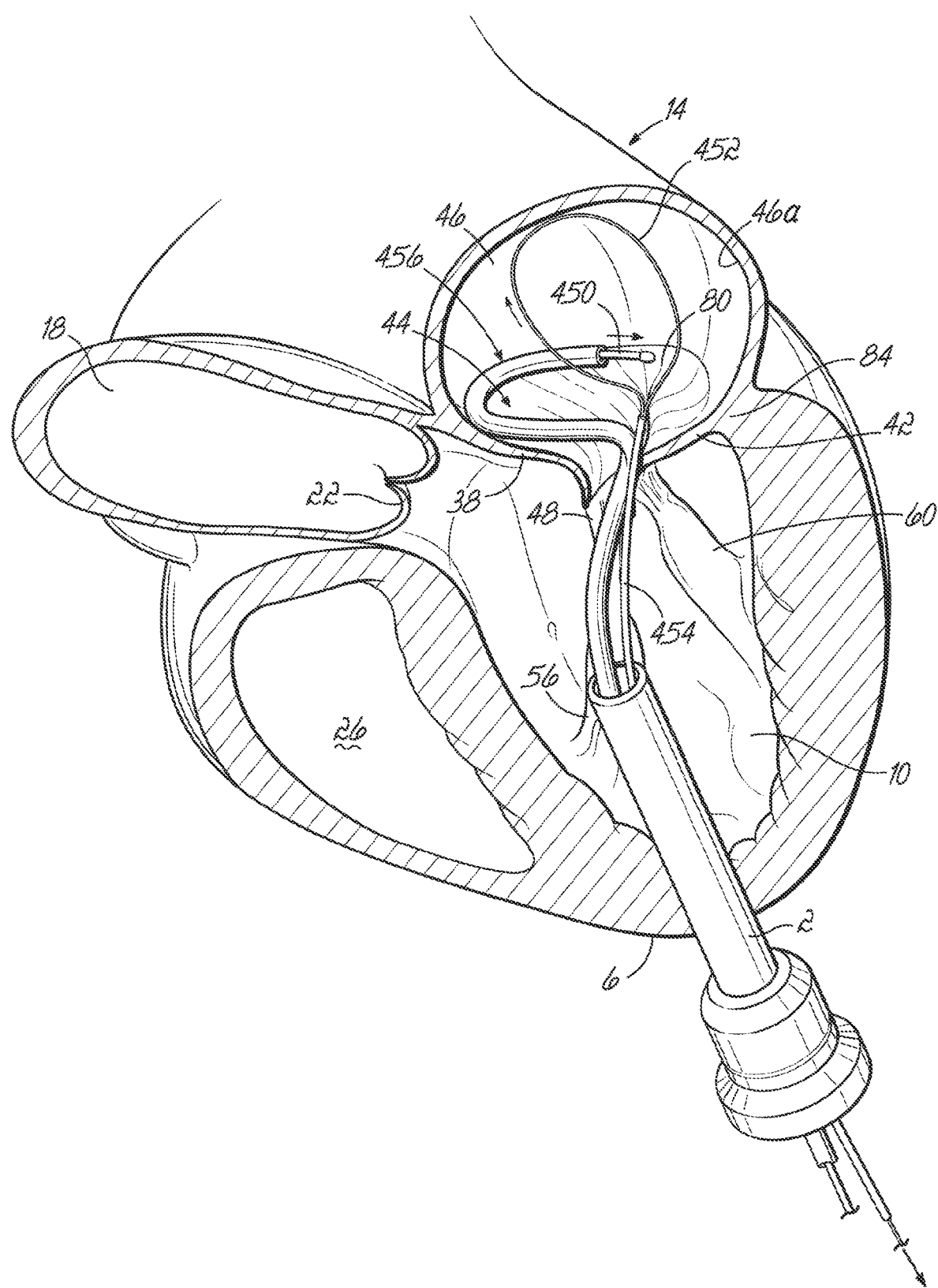
FIGS. 26A-26C illustrate in perspective the placement of an embodiment of a helical anchor in the mitral position of a heart, which is shown in partial cross section, with the assistance of a snare to draw the helical anchor under a leaflet of the native mitral valve.
Figure 26B:
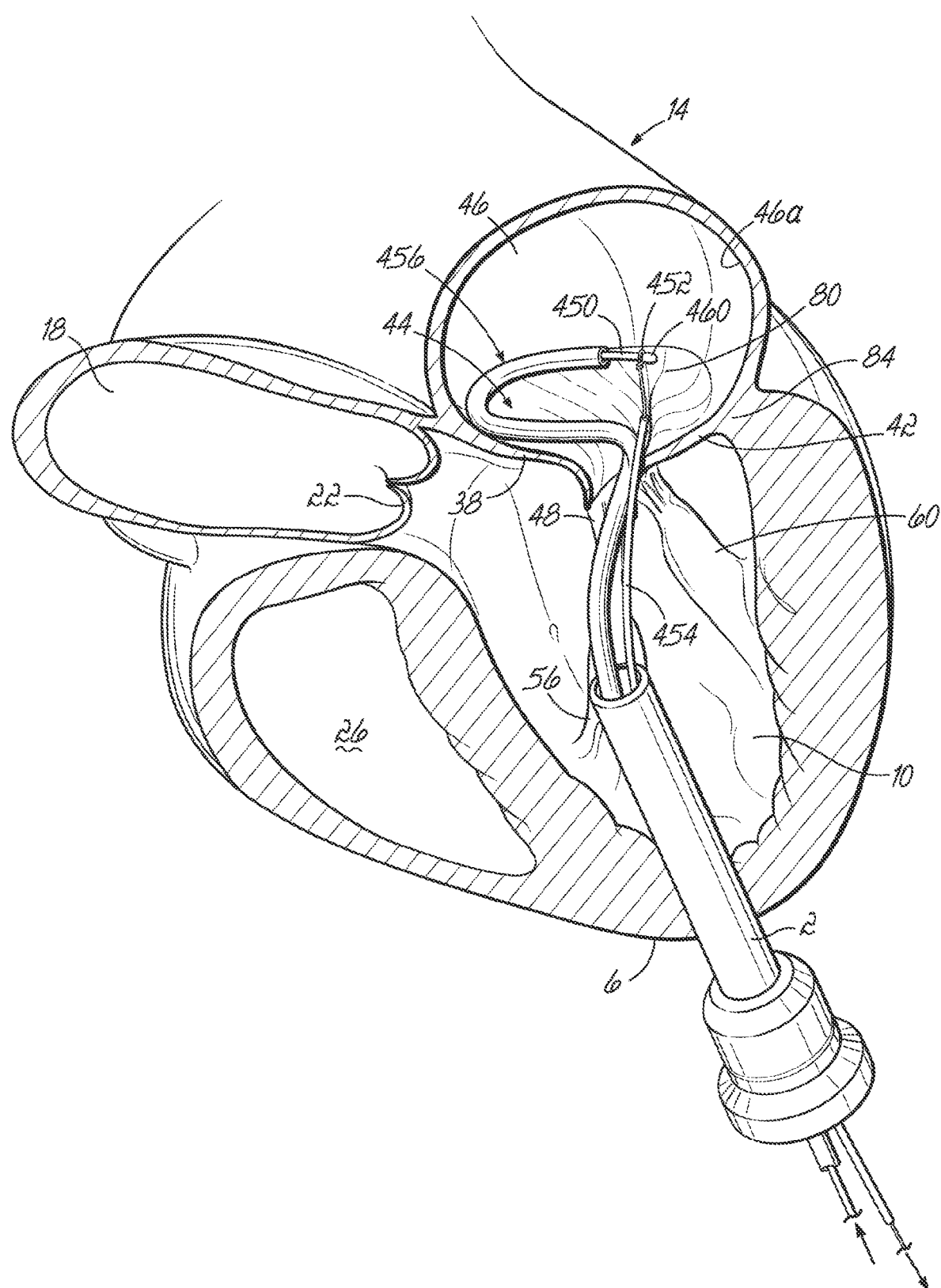
Figure 26C:
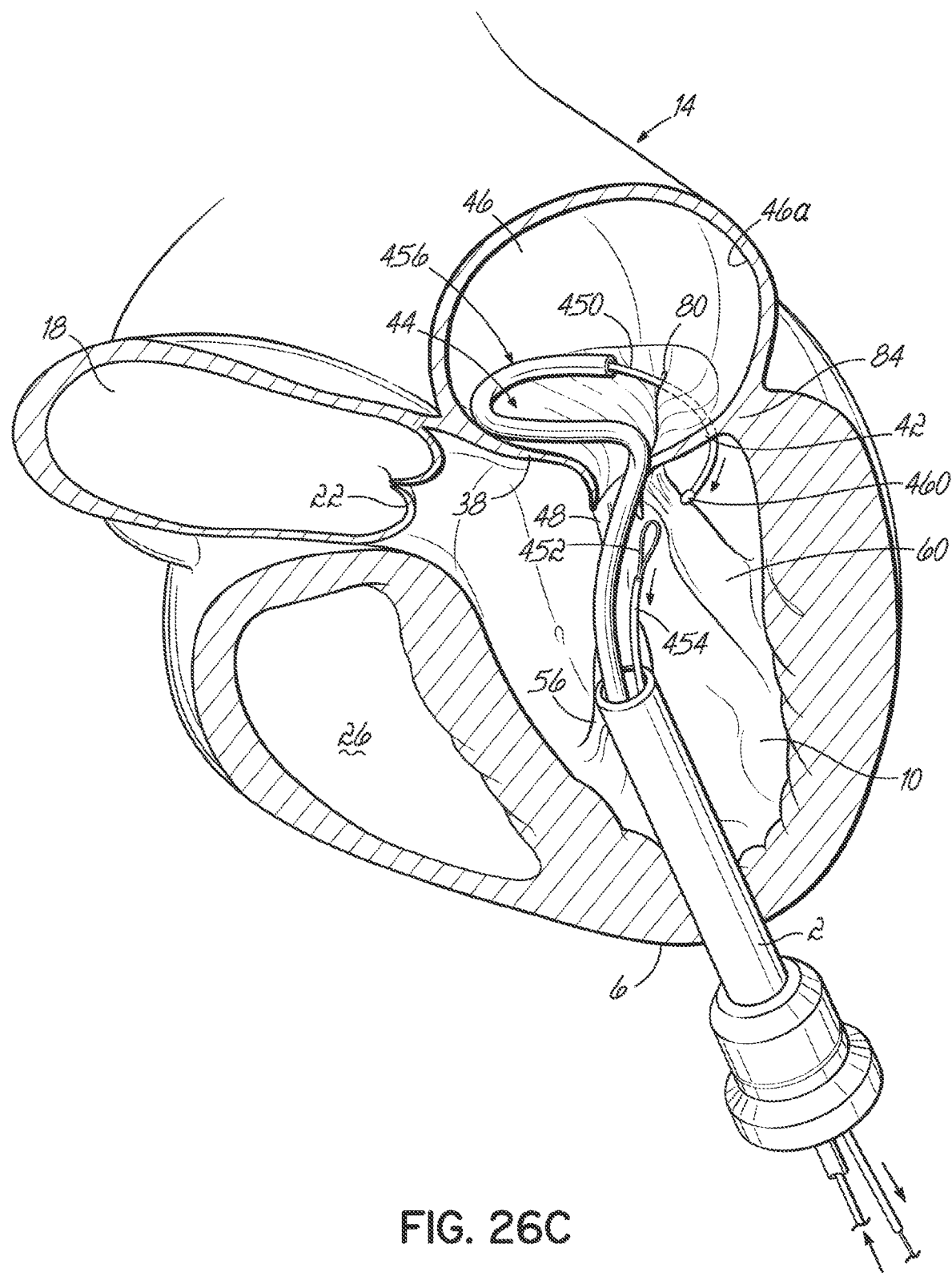

Referring now to FIGS. 26A-26C, a system and method of directing a helical anchor 450 under the mitral valve leaflets 38, 42 is shown. This series of figures shows the helical anchor 450 itself being sprung out of its neutral position and pulled under the leaflets 38, 42. A snare 452 is comprised of a loop of suture or wire which can be choked down upon within a catheter or tube 454. In one embodiment, materials may be added to the loop 452 to allow it to be visualized on fluoroscopy (i.e. radiopaque). Alternatively, the snare 452 could be composed of wire or wire inside a cover such as a suture or a polymer coating. The snare 452 can be applied as shown by inserting the snare catheter 454 into the left atrium 46 and then widely opening the loop 452 to create a substantially large target to pass the helical anchor 450 through. FIG. 26A shows the snare 452 being attached to the end of the anchor 450 inside the heart 14. However, this may be difficult to do. Alternatively, the snare 452 could be inserted in a patient with the snare 452 pre-attached to the end of the helical anchor 450 (which could be slightly extruded from the end of a coil guide catheter 456 and cinched to the end of the coil guide catheter 456 before it is placed inside the introducer 2). Alternatively, the loop 452 may be coupled to the end of the coil guide catheter either before entering the patient, or when in the heart. It will be appreciated that pre-snaring the loop 452 to the tip of the coil guide catheter 456 or to the tip or end of the helical anchor 450, will generally be easier.

The snare catheter 454 and the coil guide catheter 456 pass through the same introducer 2 in the apex 6 of the left ventricle 10. When two objects pass through the same introducer, there is a tendency for blood to leak as the closure mechanism cannot seal around the space between the two objects. It may be useful to alter the design of the wall of the coil guide catheter 456 and/or the snare catheter 454 so the two together form a perimeter that is easy to close. For example, the snare catheter 454 might be made flat or elliptical or crescent shaped where it passes through the introducer 2 to reduce the risk of blood leaking by improving sealing. There could also be a groove in the introducer 2 to accommodate the snare catheter 454.

In FIG. 26B the snare 452 has tightened around the end of the helical anchor 450 which has been extruded beyond the end of the coil guide catheter 456. The helical anchor 450 has an enlarged tip 460 to prevent the snare 452 from sliding off of the end of the anchor 450. The operator pulls on the snare 452 to deliver the tip 460 of the helical anchor 450 below the mitral valve 44. Since the snare 452 passes between the mitral valve leaflets 38, 42, the helical anchor 450 will also pass between the mitral valve leaflets 38, 42. To ensure that the anchor 450 is truly under the valve leaflets 38, 42, the anchor 450 can be tugged in an exaggerated fashion into the ventricle 10 before the coil 450 is advanced out of the coil guide catheter 456. The snare 452 can be released by pulling through a loop of suture or cutting the suture inside or outside the patient.

In another embodiment it may be useful to allow the snare 452 to be directed and deflectable. Once the anchor 450 is pulled under the leaflets 38, 42, it may be useful to direct the tip 460 of the anchor 450 to the perimeter of the valve 44, particularly to avoid entanglement with the chordae tendineae. 48 This could be accomplished, for example, by passing a preshaped or malleable rod down the snare catheter 454 to give it a preferred shape. A malleable rod allows the operator to change its curve. The snare system could also have steerable features such as those previously described in relation to the coil guide catheters. A handle on the outside of the patient could be used to adjust the turn on the snare system.

To be sure the helical anchor 450 passes wide to all of the chordae tendineae 48, it would be useful to allow the snare 452 or suture to be deflected toward the perimeter of the valve 44 once the helical anchor 450 is pulled under the leaflets 38, 42. This could be done with a stylet inside the snare tube 454 or the snare 452 could have features such as those previously described with relation to the coil guide catheters, allowing it to change shape with a slight bend outward. The anchor 450 can then be pushed out until it is safely under the leaflets 38, 42 for perhaps 2 or 3 cm or about a quarter of a turn (i.e. so the anchor 450 will not spring back into the left atrium 46). After a safe amount of the anchor 450 is pushed under the leaflets 38, 42, the snare 452 can be released. The anchor delivery is continued by pushing the anchor 450 out until the desired number of turns are under the leaflets 38, 42. If a suture is used, it could be cut. The stiffening rod could also be passed through a lumen separate from the suture 452 and still provide the same benefit.

FIG. 26C shows the tip 460 of the helical anchor 450 positioned under the valve 44 and released from the snare 452. An easy way to disengage the anchor tip 460 from the snare is to pull down on the snare 452 until the anchor is bent down into the left ventricle 10 and then release the snare 452, allowing the anchor 450 to spring out of the snare 452. The suture could also be cut outside the patient and then pulled through the snare 452. The suture could also pass through a preformed loop (not shown) in the tip 460 of the anchor 450. Alternatively, the distal end of the coil guide catheter 456 can be advanced under the leaflets 38, 42 by rotating it once the tip 460 of the anchor 450 is under the leaflets 38, 42. The snare 452 is then released slightly and the helical anchor 450 is then withdrawn back inside the coil guide catheter 456, forcing the snare 452 off the end of the anchor 450. The suture 452 and snare tubing 454 can be withdrawn through the introducer 2 in the apex 6 of the left ventricle 10. The anchor insertion can be completed by pushing out the remainder of the anchor 450 under the leaflets 38, 42, as previously described herein.

Figure 27A:
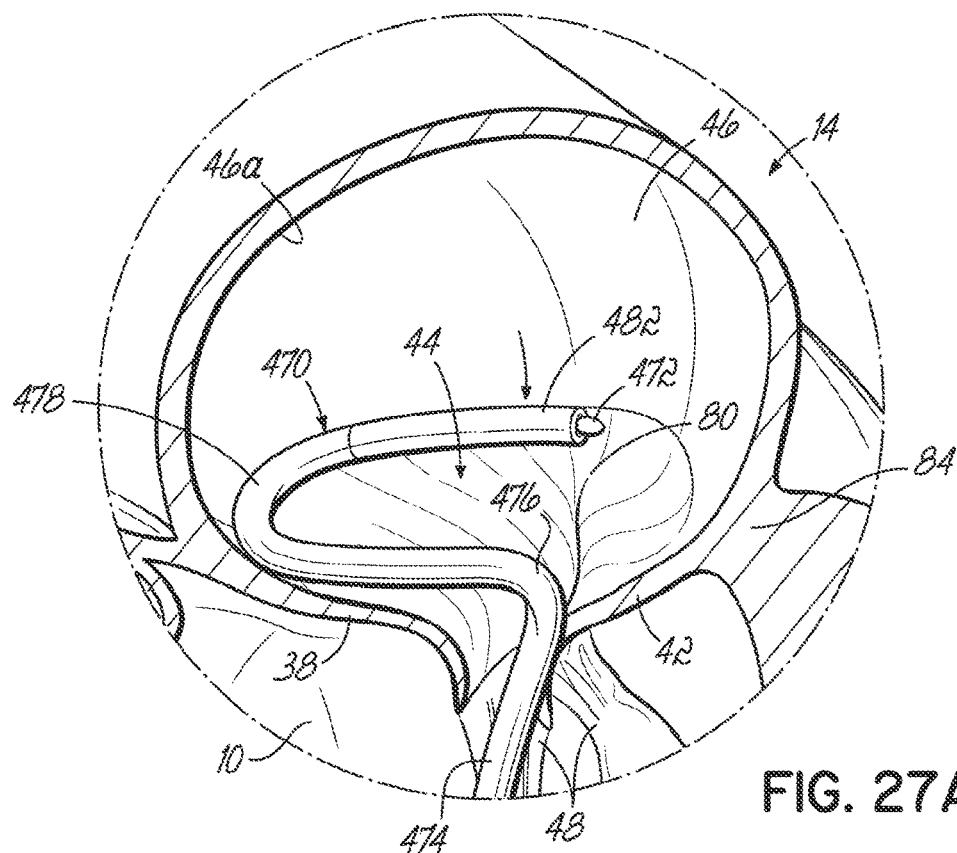
FIG. 27A is a close-up view of the coil delivery catheter or coil guide catheter shown in FIGS. 26A-26C.
Figure 27B:
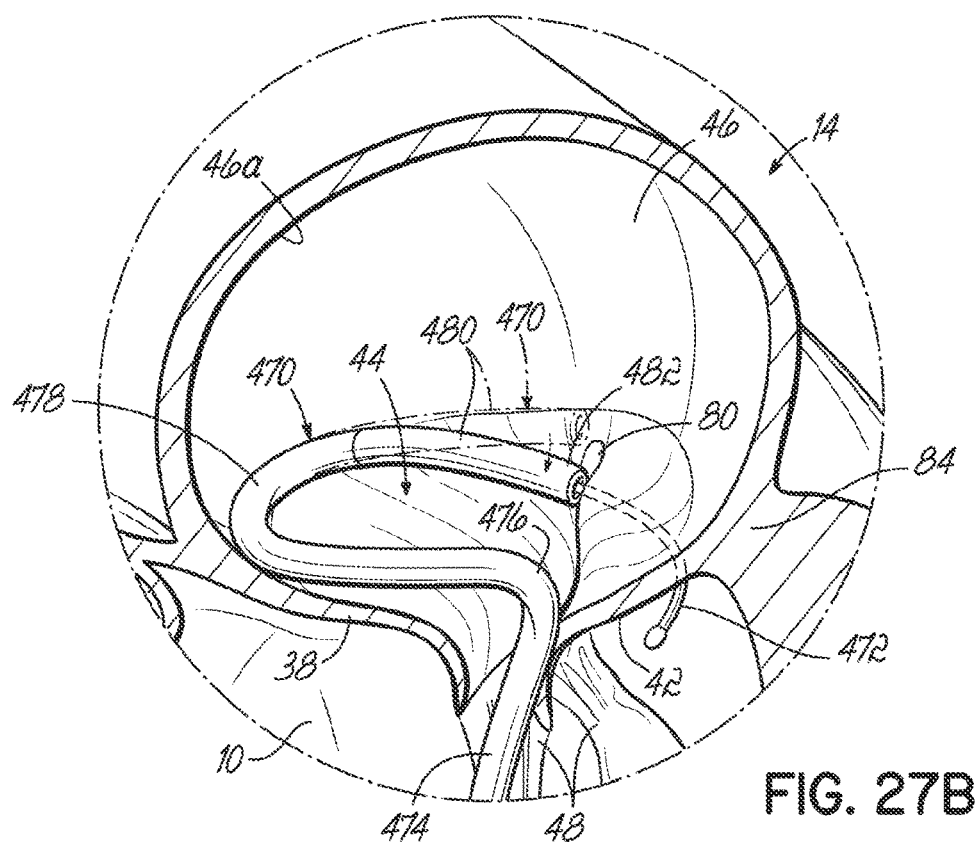
FIG. 27B illustrates the coil delivery catheter or coil guide catheter of FIG. 27A having a tip which is deflected downward.

Referring now to FIGS. 27A and 27B, a coil guide catheter 470 as previously described is shown with an additional position setting feature. FIG. 27A shows the coil guide catheter 470 activated to a complex curved shape to facilitate delivery of a helical anchor 472. The activated coil guide catheter 470 features curves in two directions. Specifically, the stem 474 of the coil guide catheter is curved to bring the distal end 476 of the coil guide catheter 470 into a plane roughly parallel with the mitral valve 44. A second curve 478 roughly parallels the path of the mitral annulus 84. In FIG. 27B the coil guide catheter 470 is shown with an additional curve 480 so that its tip 482 is deflected further downward. This downward deflection allows the tip 482 of the coil guide catheter 470 to pass easily under the mitral valve leaflets 38, 42. For example, the coil guide catheter 470 may assume the shape illustrated in FIG. 27B while a helical anchor is delivered under the mitral valve leaflets 38, 42 for several centimeters, and then may be returned to the shape shown in FIG. 27A to ensure that the anchor 472 sits correctly under the leaflets 38, 42.

Figure 28A:
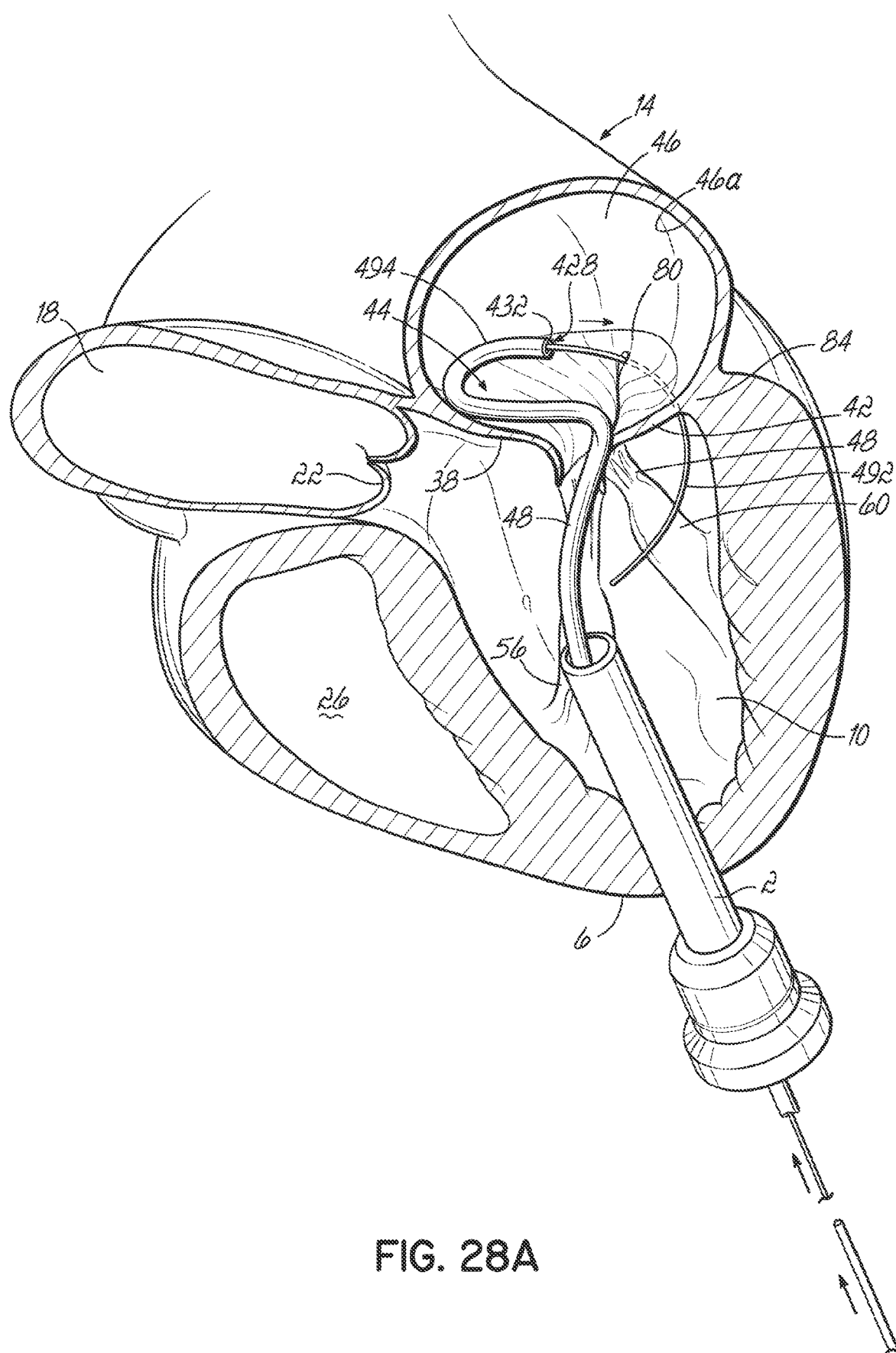
FIGS. 28A and 28B illustrate in perspective the placement of an embodiment of a helical anchor in the mitral position of a heart, which is shown in partial cross section, with the assistance of a guidewire extending from the left atrium into the left ventricle under the native mitral valve leaflets.
Figure 28B:
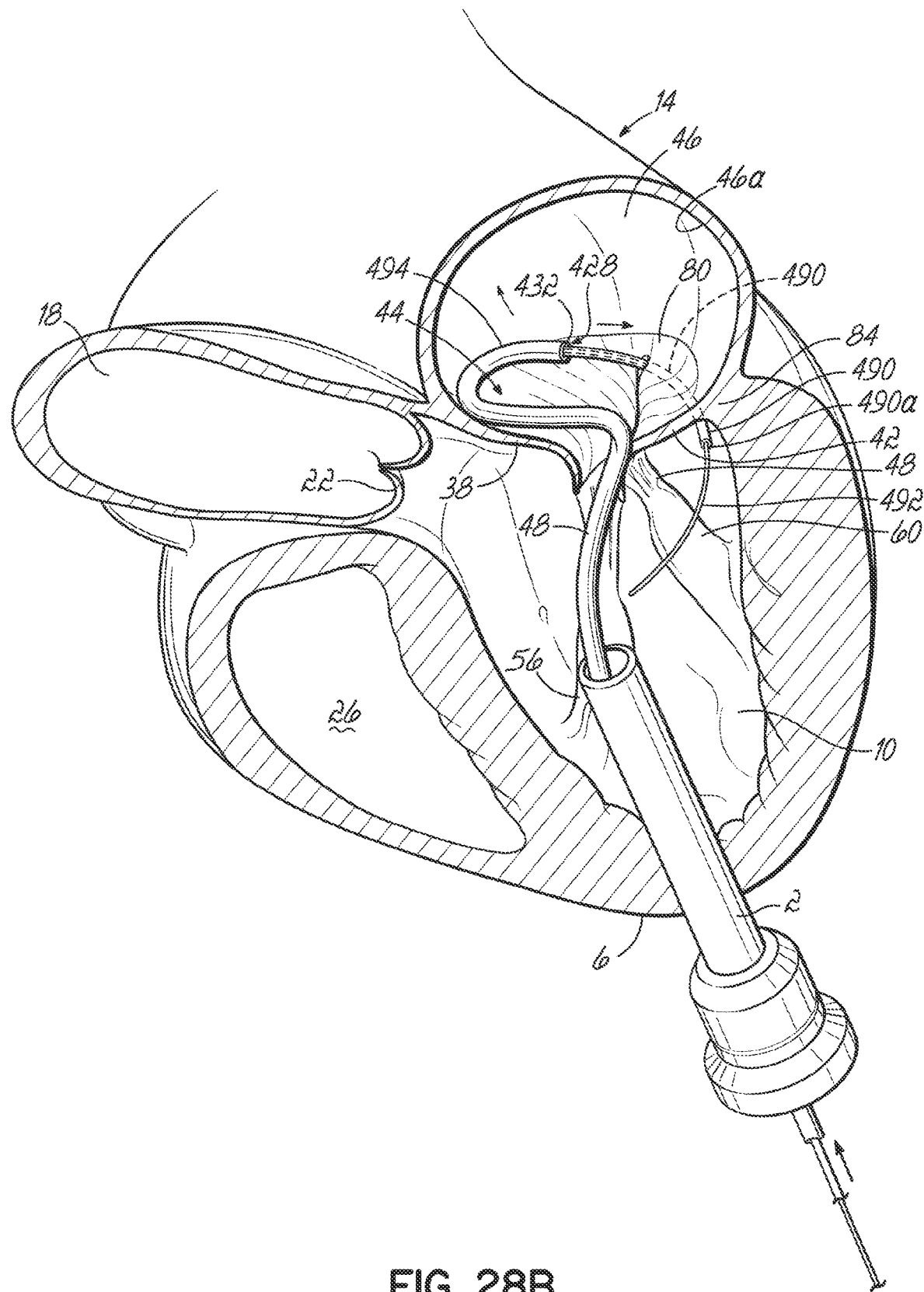

Referring now to FIGS. 28A and 28B, a system and method of directing a helical anchor 490 under the mitral valve leaflets 38, 42 is shown. This series of figures shows the helical anchor 490 being delivered over a guidewire 492. The guidewire 492 is delivered through the end of a coil guide catheter 494 such that the guidewire 492 passes under the mitral valve leaflets 38, 42 into the left ventricle 10, as shown in FIG. 28A. The helical anchor 490 having a lumen 490a is then advanced over the guide wire 492 such that the anchor 490 passes under the mitral valve leaflets 38, 42 into the left ventricle 10, as shown in FIG. 28B. The guidewire 492 may be withdrawn at any time after the anchor 490 has successfully passed into the left ventricle 10. In this embodiment the helical anchor 490 is constructed of a solid tube or a stent-like structure.

Figure 29A:
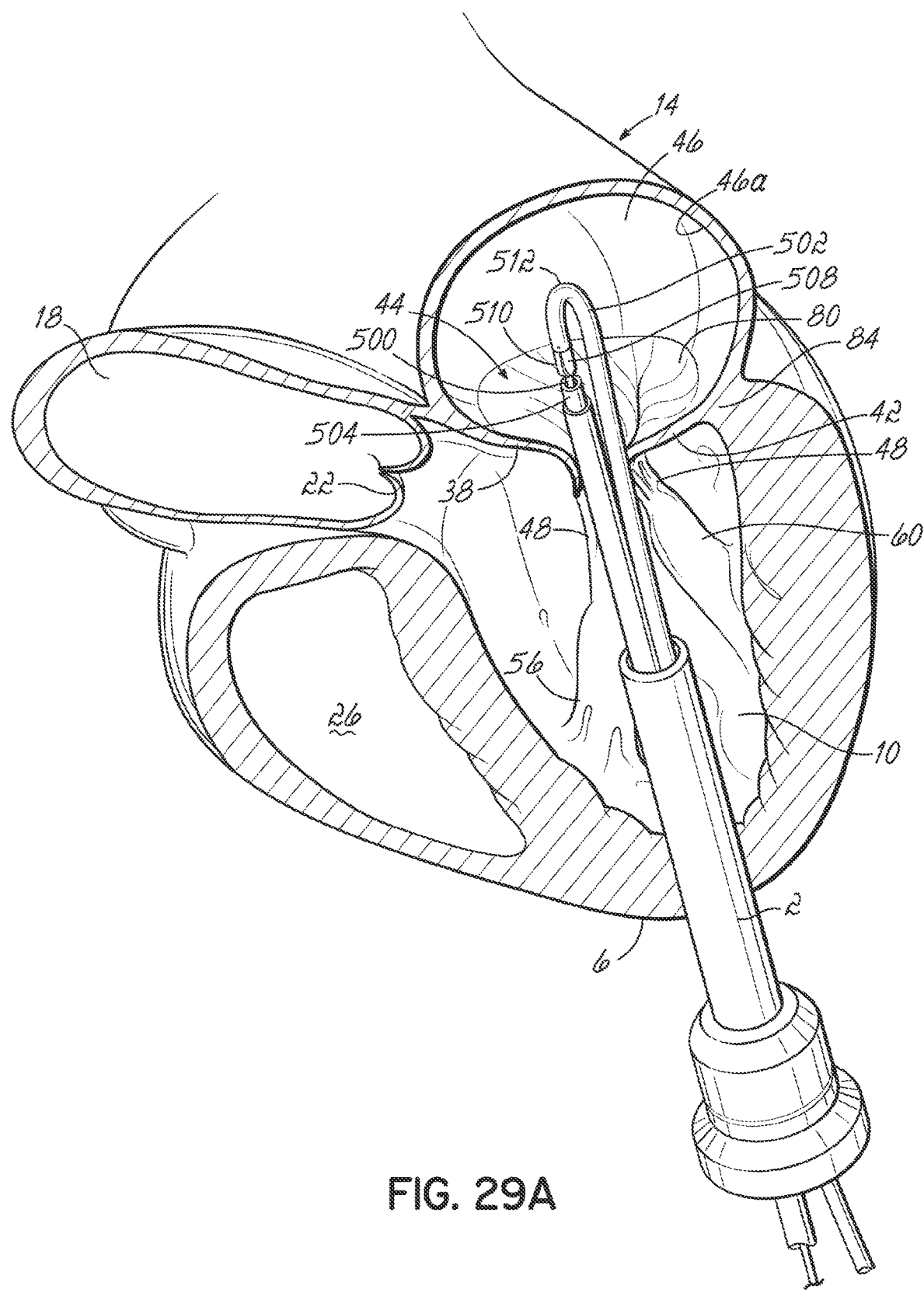
FIGS. 29A-29C illustrate in perspective the placement of an embodiment of a helical anchor in the mitral position of a heart, which is shown in partial cross section, with the assistance of a grasping tool to draw the helical anchor under a leaflet of the native mitral valve.
Figure 29B:
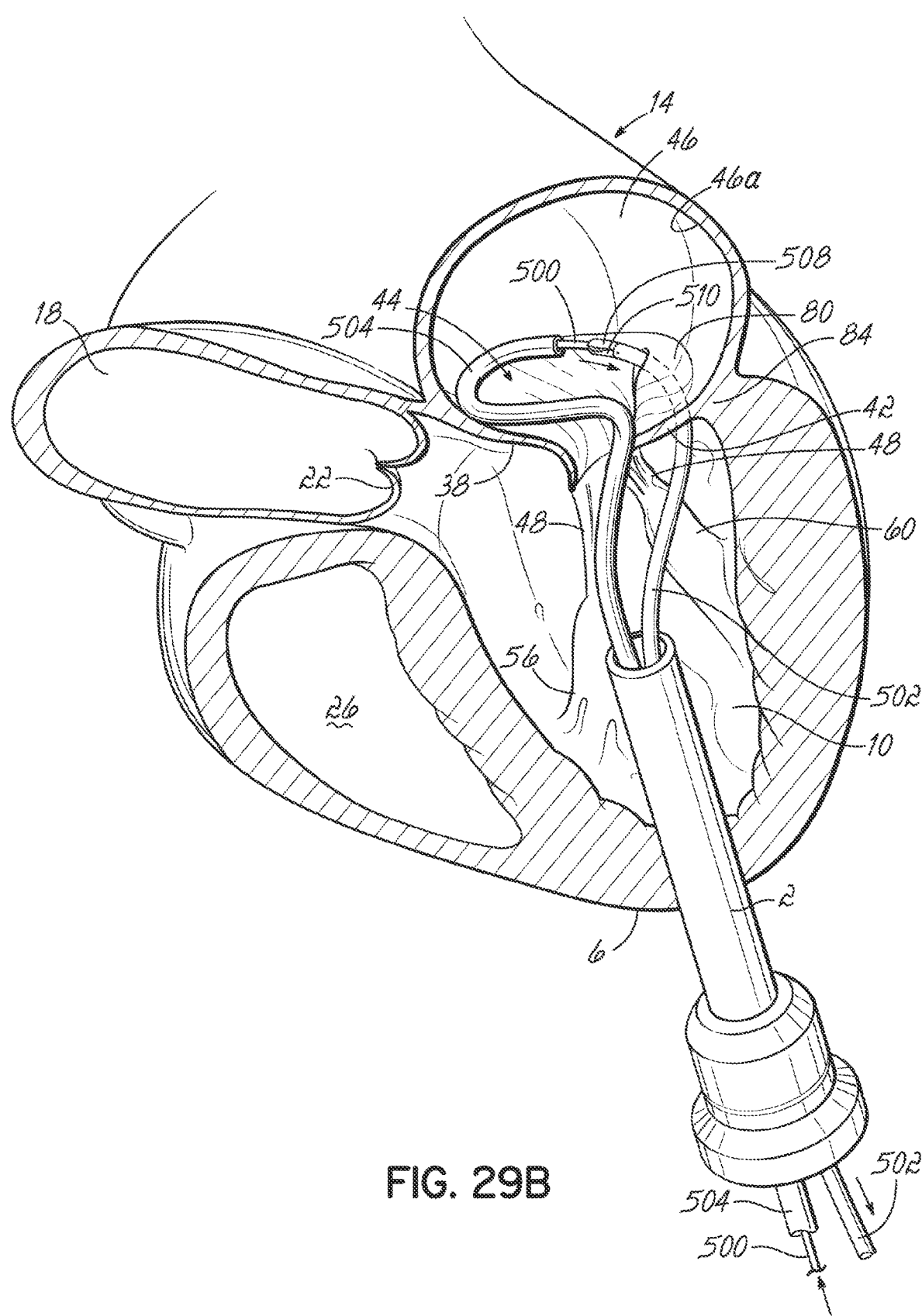
Figure 29C:
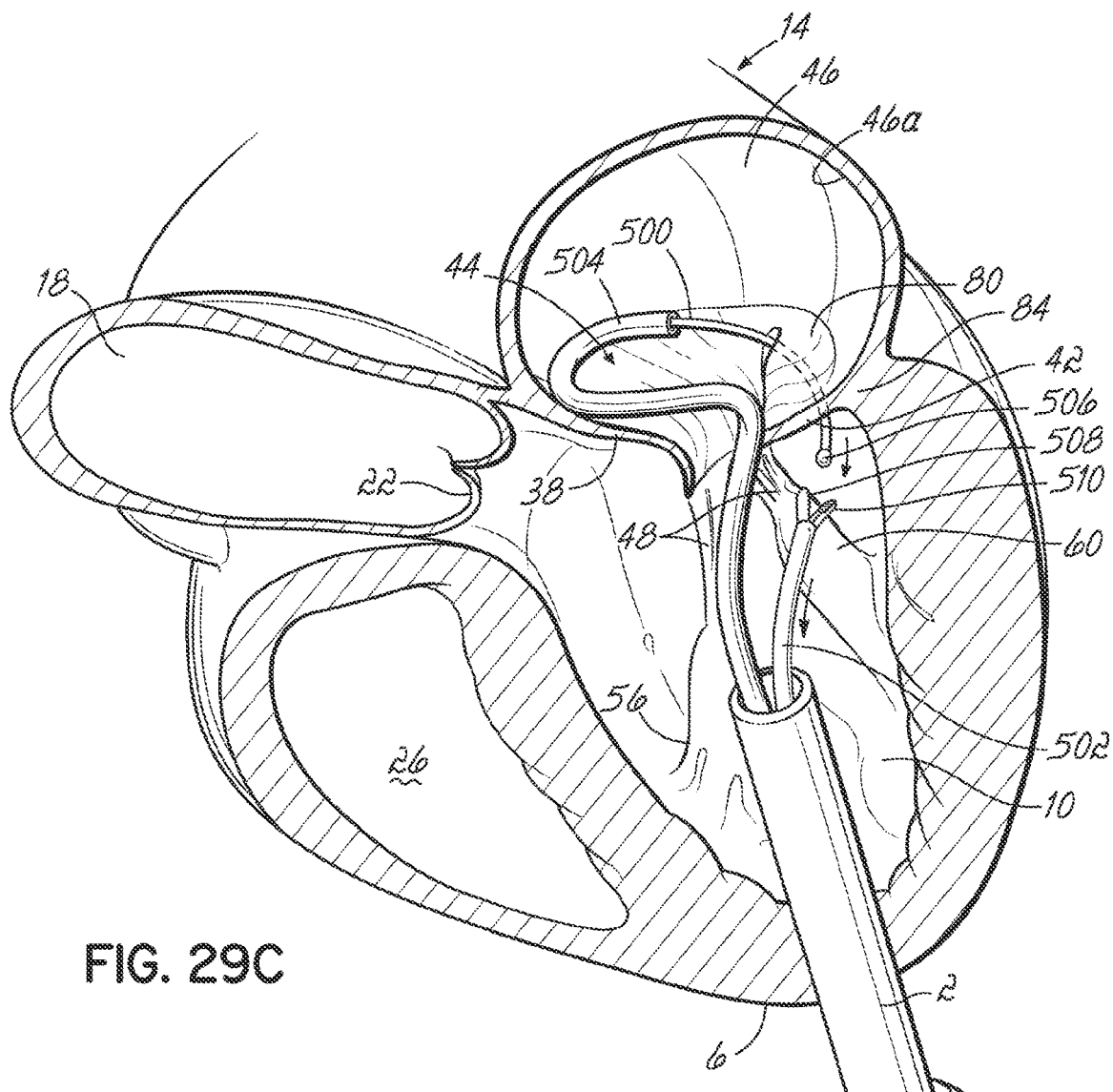

Referring now to FIGS. 29A-29C, a system and method of directing a helical anchor 500 under the mitral valve leaflets 38, 42 is shown. This series of figures shows the helical anchor 500 being withdrawn from its neutral position and pulled under the leaflets 38, 42 by a grasping tool 502. A coil guide catheter 504 is shown inside the left atrium 46 with a helical anchor 500 retained therein. The end 506 (FIG. 29C) of the helical anchor 500 is held by the jaws 508, 510 of a separate grasping tool 502. Alternatively, the grasping tool 502 can attach to the helical anchor 500 along the length of the anchor 500. The grasping tool 502 functions similarly to the snare previously described herein, and can extend to the inside of the coil guide catheter 504 or it can hold the end 506 of the helical anchor 500 outside the coil guide catheter 504 as shown in FIG. 29A.

In this illustrative example, the grasping tool 502 features a U turn 512 to properly position the jaws 508, 510 of the tool 502 for gripping the end 506 of the helical anchor 500. The need for a U turn 512 could be eliminated simply by having a pivoting joint, such as a universal joint connection between the end of the grasping tool 502 and the end 506 of the helical anchor 500. Alternatively, the ball on the end 506 of the helical anchor 500 could mate with a groove in the jaws 508, 510 of the grasping tool 502 allowing it to engage at any angle. The grasping tool 502 can be used to draw the helical anchor 500 below the mitral valve leaflets 38, 42 as shown in FIG. 29B. The grasping tool 502 does not need to curve, but rather may pass in a straight course into the left atrium 46. When the helical anchor 500 is positioned under the leaflets 38, 42, the grasping tool 502 is released and may be withdrawn from the heart 14 as shown in FIG. 29C. The anchor 500 may then be advanced into position under the mitral leaflets 38, 42 as previously described herein. The grasping tool 502 may function similarly to biopsy forceps.

Figure 30A:
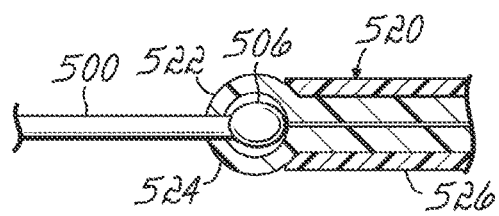
FIG. 30A is a close-up view of the grasping tool of FIGS. 29A-29C, shown with jaws closed to hold the end of the helical anchor.
Figure 30B:
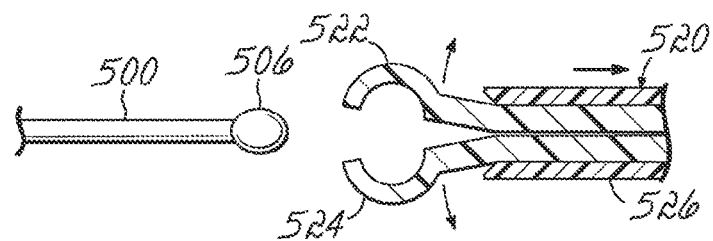
FIG. 30B is a close-up view of the grasping tool of FIGS. 29A-29C, shown with jaws open to release the end of the helical anchor.

FIGS. 30A and 30B illustrate an alternative grasping tool 520 in accordance with the present invention. The grasping tool 520 comprises a pair of a jaws 522, 524 and a catheter 526 which allows the jaws 522, 524 to open and close. The catheter 526 is advance toward the jaws 522, 524 in order to close them and hold the end 506 of the helical anchor 500, shown in FIG. 30A. When the catheter 526 is retracted, the jaws 522, 524 open and the helical anchor 500 is released, as shown in FIG. 30B. This grasping tool 520 is much more flexible and thinner than biopsy forceps. Also, the anchor 500 is able to rotate inside the jaws 522, 524 of the grasping tool 520. This junction acts as a universal joint with a ball-shaped end 506 of the helical anchor 500 allowed to swivel inside the grasping tool 520. This allows the coil guide catheter 504 and grasping tool 520 to be inserted in a parallel path without the need for the U turn 512 of FIG. 29A. As previously described herein, it is not necessary for the grasping tool 520 to hold the end 506 of the helical anchor 500. Rather, the grasping tool 520 may latch onto the helical anchor 500 at any point along its length. With the grasping tool 520 latched on to the side of the helical anchor 500 it is possible to allow the anchor 500 to slide through the jaws 522, 524 so the anchor 500 can be pushed into place while the jaws 522, 524 are closed and the grasping tool 520 is held in place.

Figure 31A:
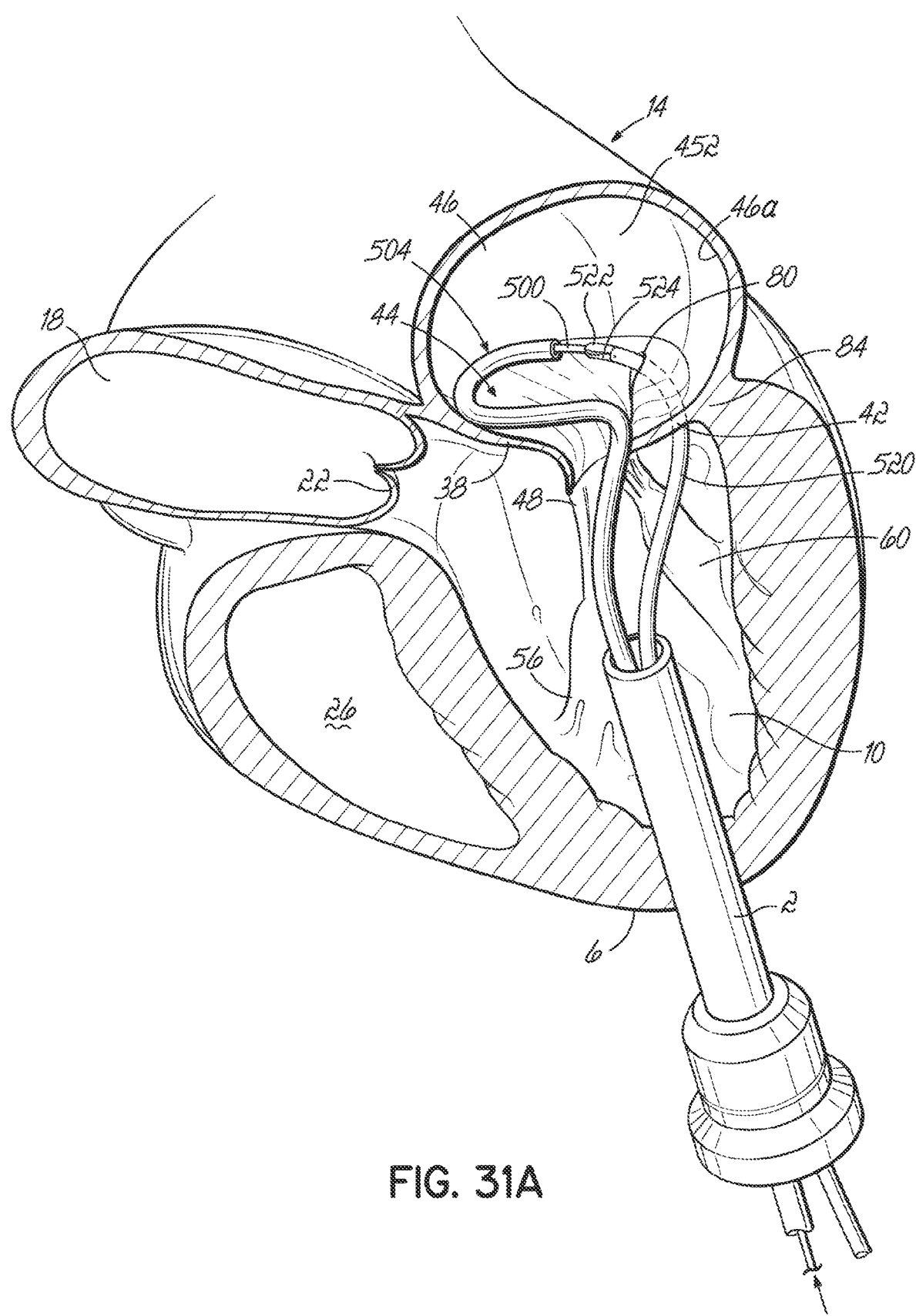
FIGS. 31A-31D illustrate in perspective the placement of an embodiment of a helical anchor in the mitral position of a heart, which is shown in partial cross section, with the assistance of a grasping tool to center the system relative to the native mitral valve and draw the helical anchor under a leaflet of the mitral valve.
Figure 31B:
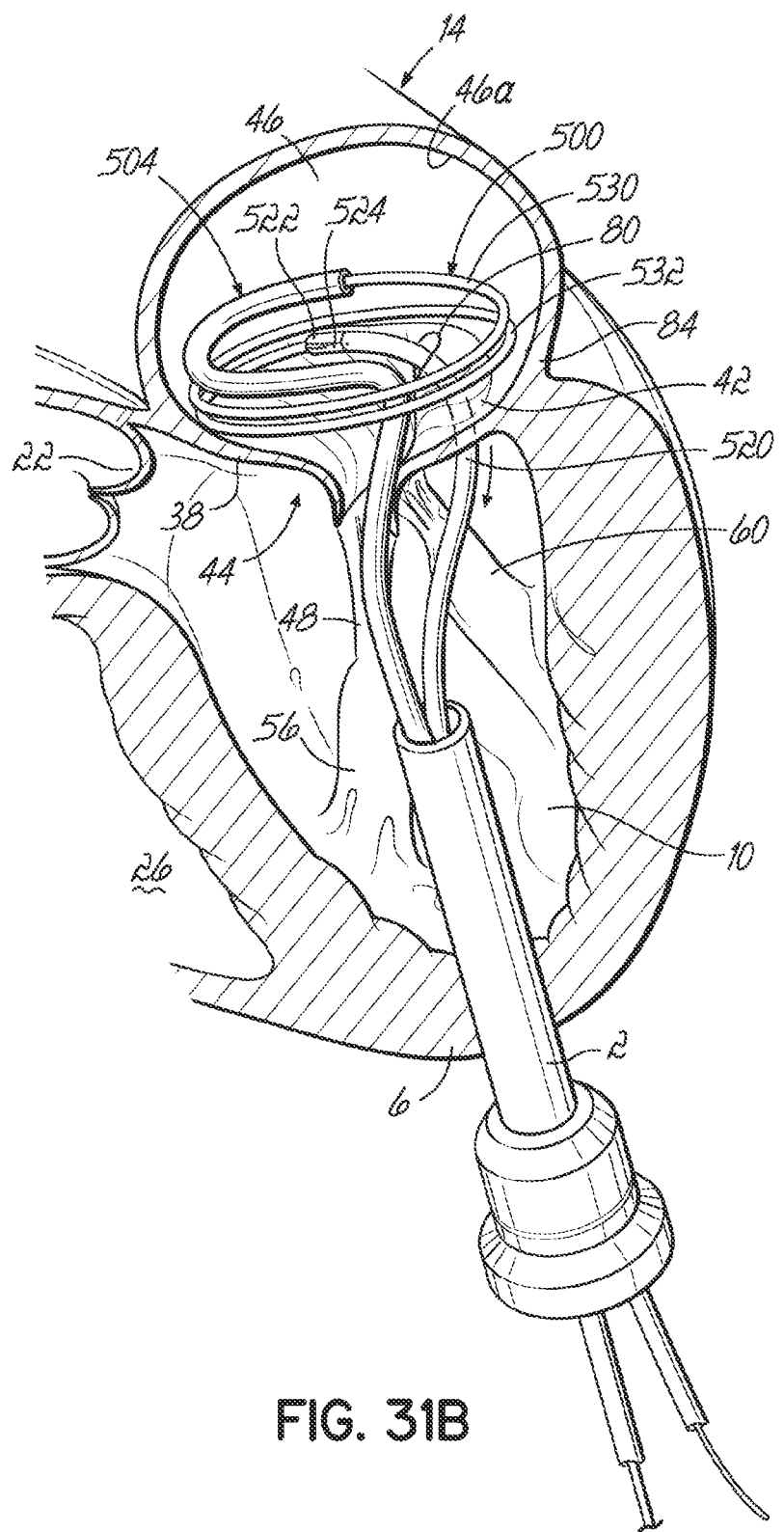
Figure 31C:
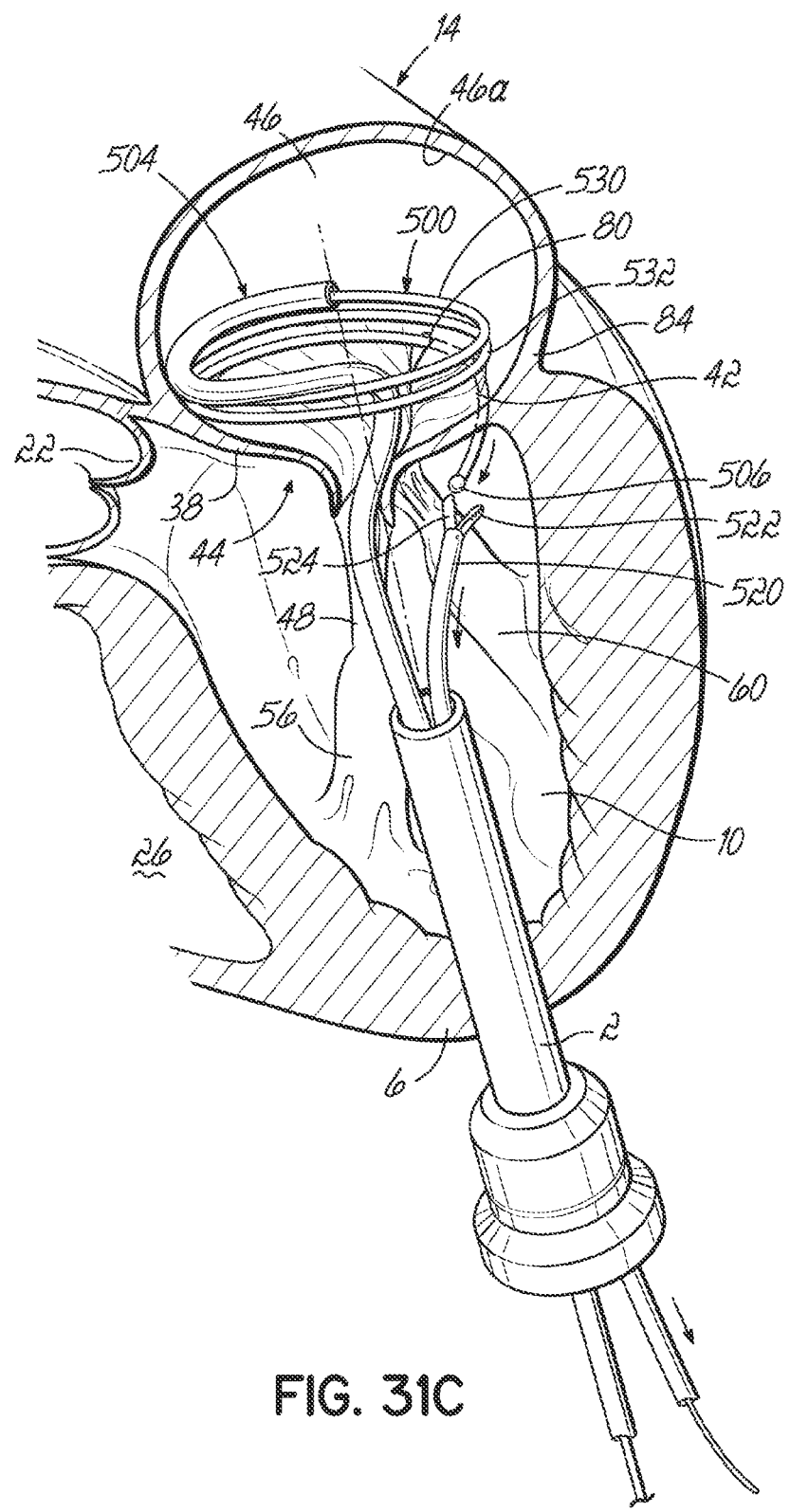
Figure 31D:
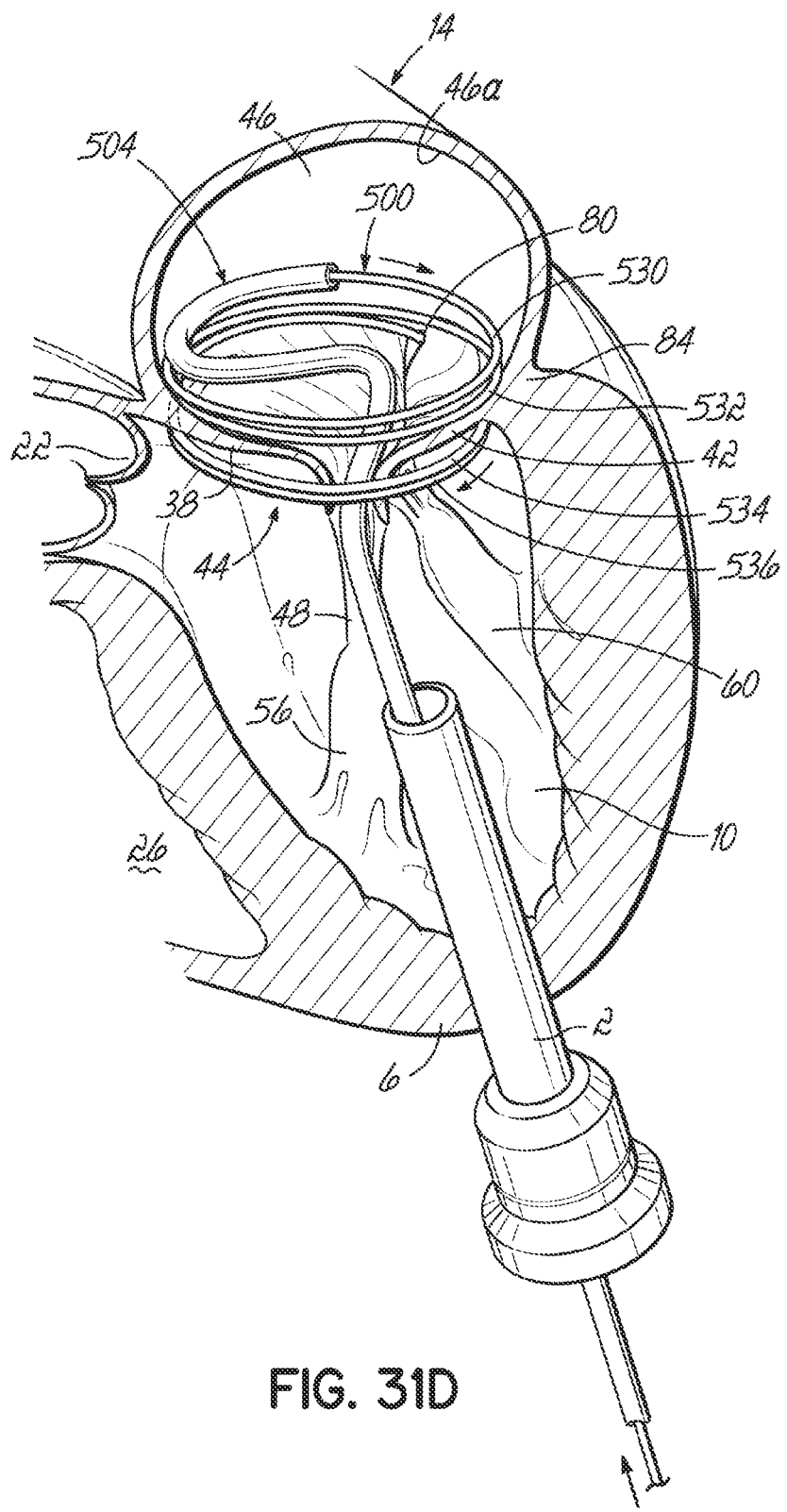

Referring now to FIGS. 31A-31D, a system and method of positioning the helical anchor 500 in the mitral position of a heart 14 is shown. A coil guide catheter 504 and a separate grasping tool 520 are advanced into the left atrium 46 through an introducer 2. The end 506 (FIG. 31C) of the helical anchor 500 comprises a ball shaped tip which extends from the coil guide catheter 504 and is held by the jaws 522, 524 of the grasping tool 520. A portion of the helical anchor 500 is positioned in the atrium 46 by pushing the anchor 500 through the coil guide catheter 504, as shown in FIG. 31A. After approximately two coils 530, 532 have been positioned in the atrium 46, the grasping tool 520 is retracted through a commissure 80 to draw the end 506 under the mitral annulus 84 as shown in FIG. 31B. When the end 506 of the helical anchor 500 has been drawn under the annulus 84, the grasping tool 520 releases the end 506 of the anchor 500 and is withdrawn from the heart 14 as shown in FIG. 31C. The helical anchor 500 is then further extruded from the coil guide catheter 504 such that approximately two coils 534, 536 of the anchor 500 are positioned below the annulus as shown in FIG. 31D. It should be noted that this embodiment does not require any twisting or turning of the coil guide catheter 504, but rather the delivery of the helical anchor 500 is accomplished only by extrusion.

It should be noted that when the grasping tool 520 is clamped to the tip 506 of a helical anchor 500, the grasping tool 520 may wrap around the stem of the coil guide catheter 504 as the turns of the anchor 500 are extruded. This wrapping could be counteracted by simply pre-wrapping the grasping tool 520 around the stem of the coil guide catheter 504 in an opposite direction before it is inserted inside the heart. Alternatively, the grasping tool 520 may be clamped to the tip 506 of the helical anchor 500 after the turns or coils 530, 532 of the anchor 500 have been extruded into the atrium 46. However, this may be very difficult to perform with minimal or no visualization. It is also possible to add magnetic materials to the ends of the grasping tool 520 and helical anchor 500 so that they can be joined by bringing their distal ends in proximity. One or both of the distal end(s) of the grasping tool and the anchor 500 could be magnetic. If only one is magnetic, then the other end must contain a material that can be induced to have a magnetic field such as iron. Even with the aid of magnets, the process may still be very difficult to perform with minimal or visualization. Therefore, other means may be provided to prevent the entanglement of the grasping tool and the coil guide catheter. It should also be understood that while grasping tools and snare catheters are specifically disclosed herein as suitable control elements used for purposes of guiding other components of the system, such as the coil guide catheters and/or the helical anchors, other control elements may be used instead. As one other possible option, a simple cable, suture or other tensile member may be used for pulling on the distal end of a catheter, such as the coil guide catheters of this invention, or otherwise pulling directly or indirectly on the helical anchor itself for positioning purposes.

Figure 32A:
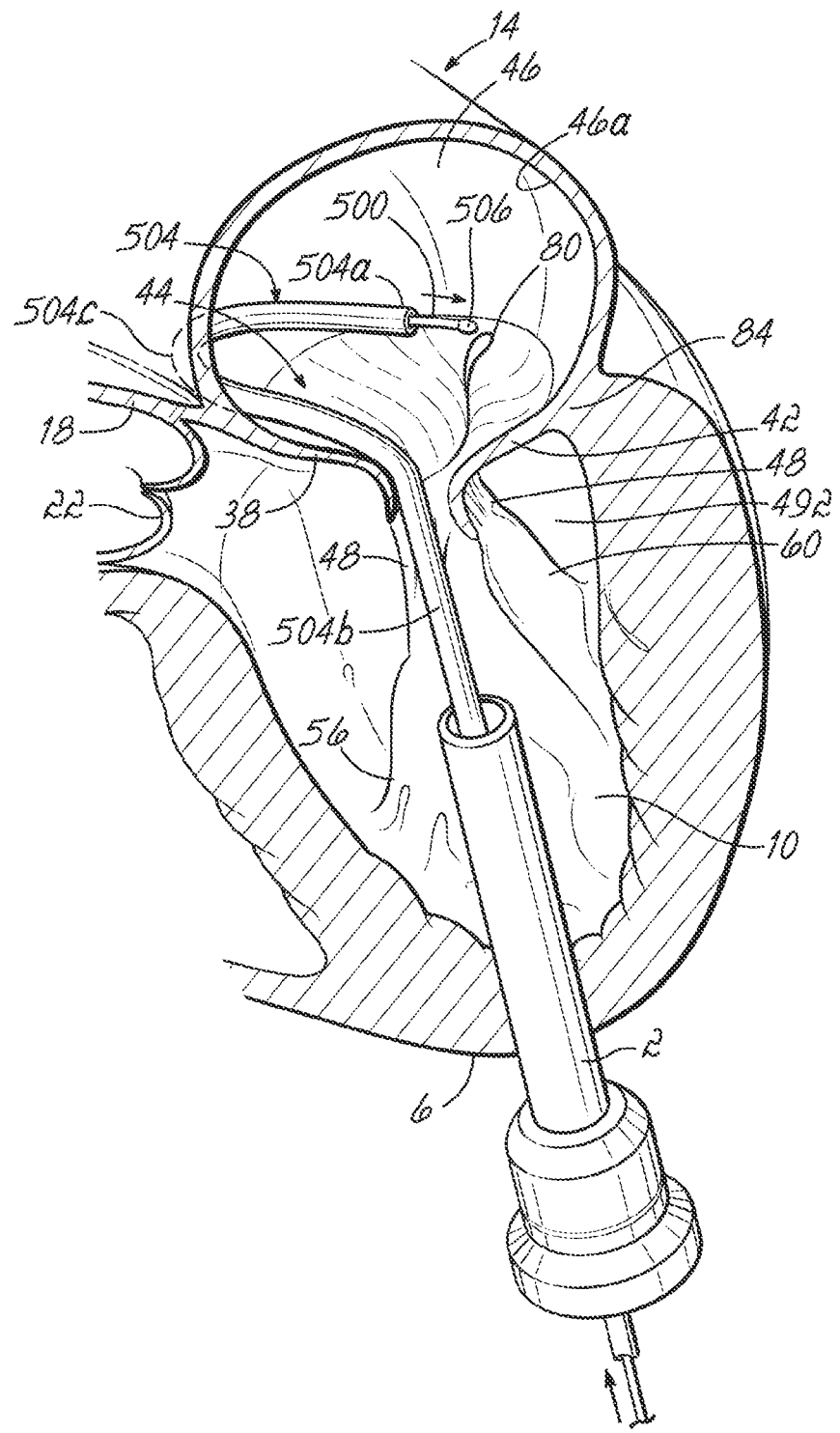
FIG. 32A is a perspective view of one embodiment of a coil delivery catheter or coil guide catheter having a terminal end shaped such that when the stem of the catheter is placed within a first commissure of the mitral valve of a heart, shown in partial cross section, the tip of the terminal end is located at a position substantially close to a second commissure of the mitral valve.

Referring now to FIGS. 32A-32E, a system and method of directing a helical anchor 500 under the mitral valve leaflets 38, 42 is shown. A coil guide catheter 504 is advanced into the left atrium 46 by means of an introducer 2 such that the stem of the coil guide catheter 504 is placed in a commissure 80 of the mitral valve 44. The terminal end 504a of the coil guide catheter 504 is shaped so that it is located near the other commissure 80. The length of the coil guide catheter 504 is chosen so that when the helical anchor 500 is extruded as shown in FIG. 32A, the end 506 of the anchor 500 may be grabbed by a grasping tool 504 that passes quite precisely through the commissure 80. A plurality of coil guide catheters can be manufactured in a variety of dimensions to match different sizes of mitral valves. For example, an operator could select a coil guide catheter 504 having a length of about 30 mm between the end of the stem and the tip 504a of the guide 504 when performing the procedure on a patient with a mitral valve diameter of about 30 mm (shown generally on echocardiography and also on CT and MR scanning).

Figure 32B:
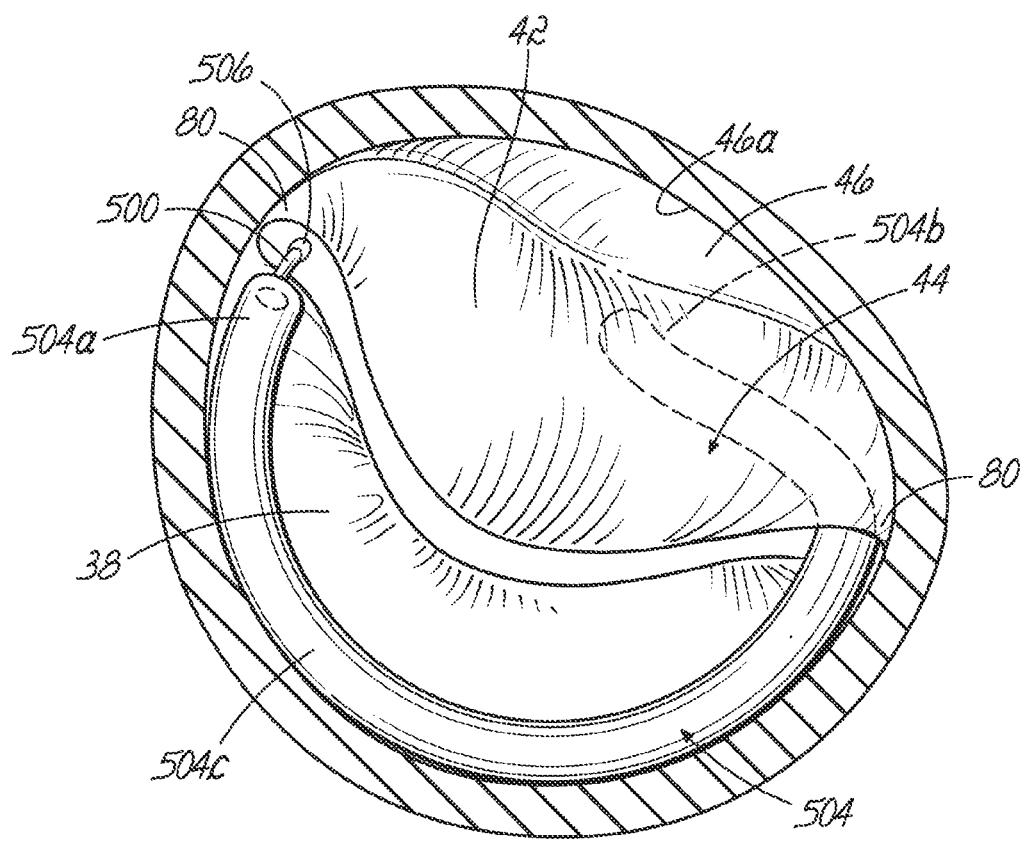
FIG. 32B is a top view of the coil delivery catheter or coil guide catheter of FIG. 32A showing that the U-shaped portion of the coil delivery catheter or coil guide catheter tracks the annulus of the mitral valve.

FIG. 32B shows a view of the mitral valve 44 from above. The coil guide catheter 504 is passing through the mitral valve 44 at the commissure 80 shown on the right. The stem 504b of the coil guide catheter 504 can be guided by echocardiography to reach one of the commissures 80. The end of the coil guide catheter 504 has a U-shaped portion 504c which is similar to the arc of the posterior mitral annulus and the distal tip 504a sits near the other commissure 80 so that a helical anchor 500 may be extruded therefrom and pulled under the leaflets 38, 42 by the grasping tool 540. It should be noted that it is not necessary to position the entry point of the anchor 500 at a commissure 80. However, it is important to recognize that if, for example, the helical anchor 500 is started in the middle region of the anterior mitral valve leaflet 38, this part of the leaflet 38 may become trapped in the coils and cause problems such as causing the valve 44 to leak after the anchor 500 is inserted. If the valve 44 leaks, then the patient may become hemodynamically unstable and the procedure to insert a mitral valve prosthesis may become rushed.

As shown in FIG. 32B, the U-shaped portion 504c of the coil guide catheter 504 tracks the annulus 84 of the valve 44. The U-shaped portion 504c could also track beyond the annulus 84, so that the coil guide catheter 504 sits against the left atrial wall 46a over the base of the heart 14. This provides a type of shelf for the coil guide catheter 504 to abut on. The operator can pull down on the stem 504b of the coil guide catheter 504 and feel the coil guide catheter 504 engage against the base of the heart 14. This will allow a relatively blind positioning of the depth of the coil guide catheter 504 inside the heart 14.

Figures 32C, 32D:
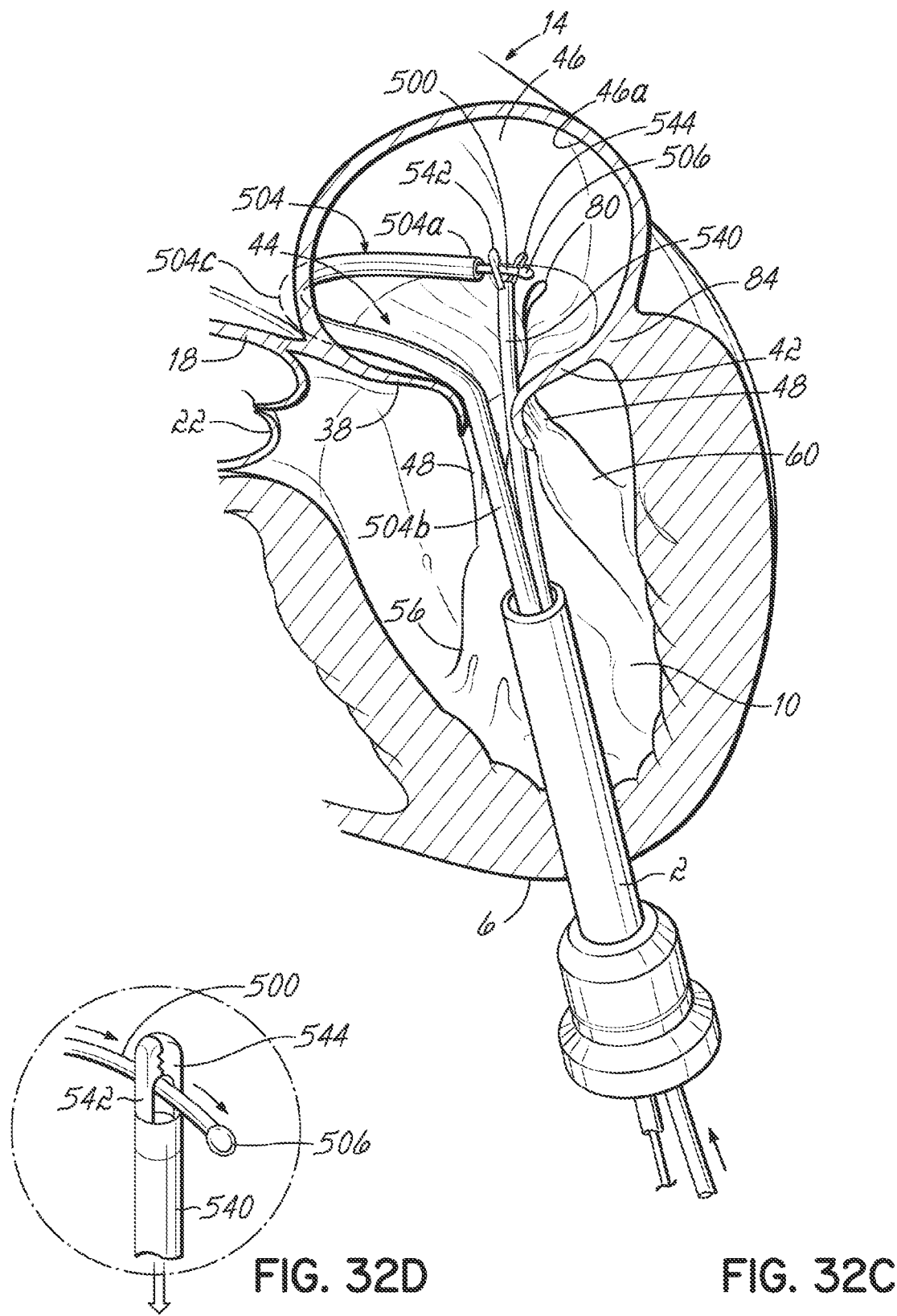
FIG. 32C illustrates in perspective a grasping tool inserted into the atrium to attach to a helical anchor proximal to its tip as the anchor is extruded from the coil delivery catheter or coil guide catheter of FIG. 32A.
FIG. 32D is a close-up view of the grasping tool of FIG. 32C as it attaches to a helical anchor proximal to its tip.
Figure 32E:
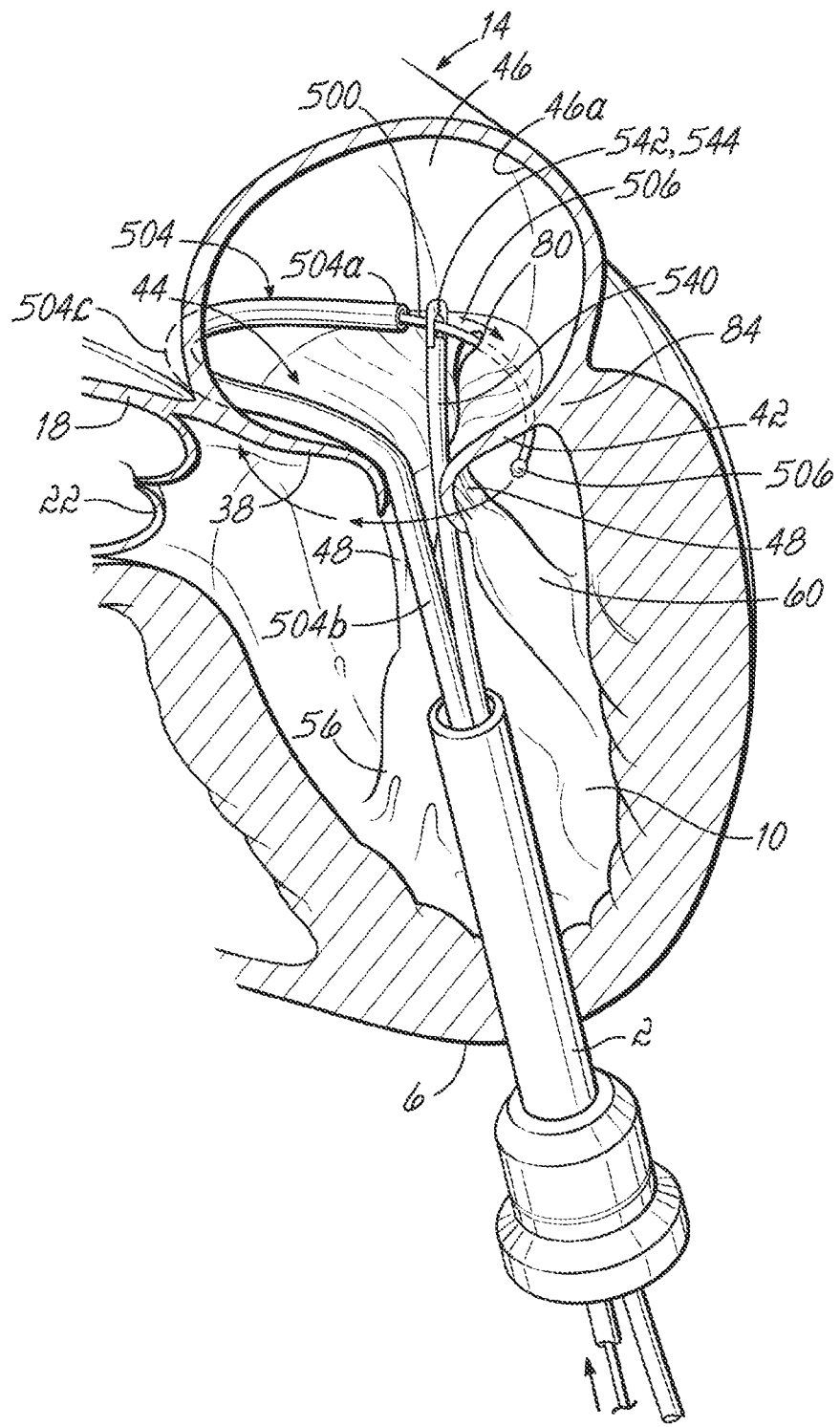
FIG. 32E illustrates in perspective the system of FIG. 32E, where the grasping tool has been attached to the helical anchor and is being used to guide the helical anchor as the anchor is being extruded from the coil delivery catheter or coil guide catheter.

The grasping tool 540 is advanced into the left atrium 46 through the introducer 2 so that the grasping tool 540 passes through the mitral annulus 84 close to a commissure 80 as shown in FIG. 32C. The grasping tool 540 comprises jaws 542, 544 which are initially open for receiving the helical anchor 500. The grasping tool 540 can then clamp the helical anchor 500 proximate its tip 506 so that the anchor 500 may slide through the jaws 542, 544 of the grasping tool 540, as shown in FIG. 32D. In one embodiment, the grasping tool 540 may have a lock on the jaws 542, 544 so that the operator does not have to hold the tool 540 closed. Such locks are well known and have been described on many tools such as endoscopic biopsy forceps. It should be noted that a operator may prefer to clamp the grasping tool 540 upon the helical anchor 500 outside the patient prior to inserting the coil guide catheter 504 and grasping tool 540 inside the heart 14. FIG. 32E shows the helical anchor 500 sliding between the jaws 542, 544 such that the grasping tool 540 guides the advancement of the anchor 500 under the valve leaflets 38, 42. The jaws 542, 544 are located above the valve 44, but it is appreciated that the jaws 542, 544 may alternatively be below the valve 44 or at the same level as the valve 44 to aim the path of the anchor 500. The grasping tool 540 is useful not only to pull the anchor 500 under the annulus 84, but to control the motion of the anchor 500 and guide the anchor 500 into position. If the anchor 500 becomes stuck while turning, the anchor 500 can be advanced and withdrawn with upward and downward motions on the grasping tool 540 to help free the anchor 500. In another embodiment, the grasping tool 540 can also be attached to the tip 506 of the helical anchor 500 so that it can turn with the anchor 500. If the tip 506 of the helical anchor 500 cannot move forward, the grasping tool 540 can be rotated with the anchor 500 and by pushing and pulling on the grasping tool 540, the tip 506 of the anchor 500 can be coaxed to make the complete turnaround the underside of the valve 44.

The distance of the coil guide catheter 504 along the U-shaped portion 504c from the stem 504b to the tip 506 of the coil guide catheter 504 can approximate the mitral annulus diameter or the distance between the commissures 80. When the distance from the end of the stem 504b to the end 506 of the coil guide catheter 504 are approximately the mitral valve diameter or the intercommissural distance, the grasping tool 540 and the stem 504b can be separated by the mitral valve diameter or the intercommissural distance such that the system is centered inside the mitral valve 44. The commissures 80 are easy to identify on echocardiography. By ensuring that the stem 504b and the grasping tool 540 are sitting in the commissures 80, the delivery of the coil 500 can be correctly oriented relative to the valve leaflets 38, 42. Most operators will likely wish to deliver the coil 500 starting at the commissures 80, so orienting the coil guide catheter 504 and the grasping tool 540 as shown will guarantee the correct starting position for the entry point of the helical anchor 500.

It should be restated that it is not necessary to deliver the helical anchor 500 at the commissures 80. The coil guide catheter 504 can be rotated so that any entry point is used. However, the commissures 80 may be useful starting points so that the positions of the stem 504b of the coil guide catheter 504 and the grasping tool 540 can be confirmed. The coil guide catheter 504 and grasping tool 540 can then be rotated to any desired entry point for the helical anchor 500.

Sometimes there is calcium under a mitral valve leaflet 38 and/or 42. The helical anchor 500 may not slide easily as it hits a deposit of calcium. The grasping tool 540 could be pulled downward and move the anchor 500 to a slightly lower position to navigate around the calcium. Similarly, the helical anchor 500 may go off course and rather than turn into position just below the valve 44 and in the plane of the valve 44, it may take a skewed course. The grasping tool 540 can be used to prevent or remedy this problem. By sliding the helical anchor 500 between the jaws 542 544, it is possible to keep the anchor 500 turning on a desirable course. The easy removal of the grasping tool 540 should be noted. The jaws 542, 544 can be opened and the tool 540 simply pulled out of the introducer sheath 2.

Figure 33:
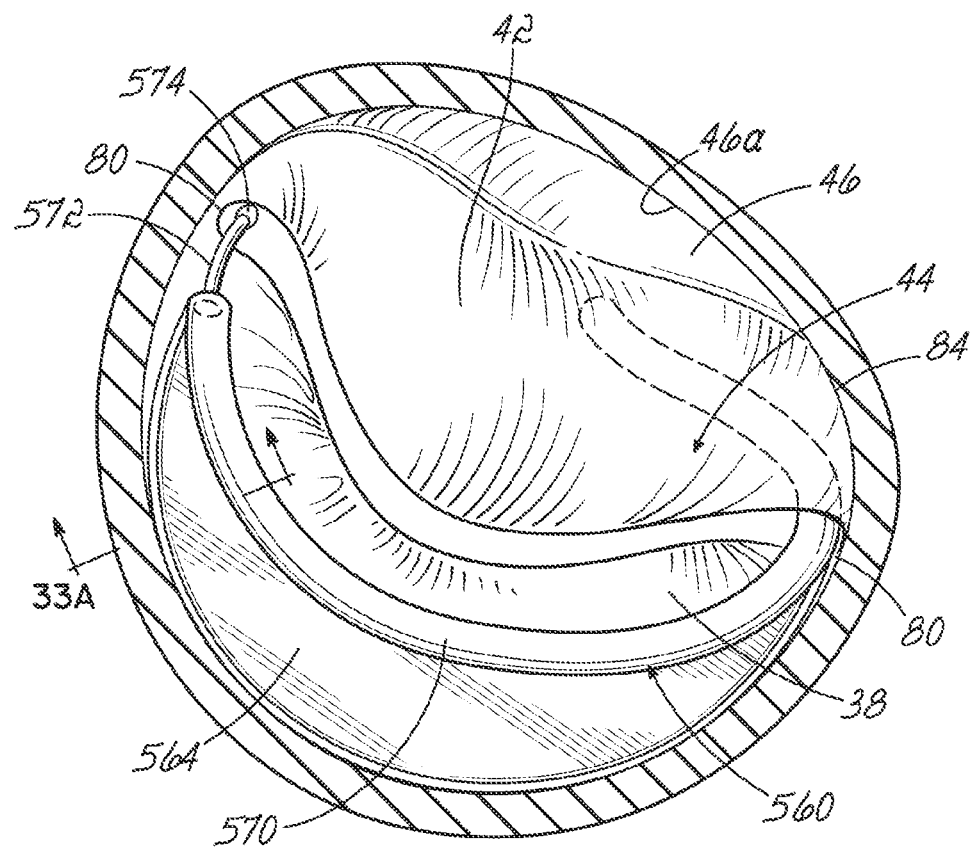
FIG. 33 is a perspective view of an alternative embodiment of a coil delivery catheter or coil guide catheter having a sail-like extension which sits on the wall of the left atrium, shown in cross section.
Figure 33A:
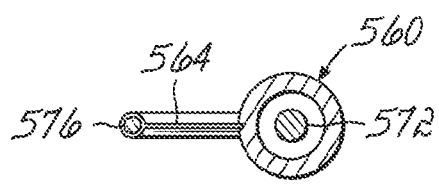
FIG. 33A shows the coil delivery catheter or coil guide catheter and sail-like extension of FIG. 33 in cross section.

Referring now to FIGS. 33 and 33A, a feature for positioning a coil guide catheter 560 within the left atrium 46 is illustrated. A coil guide catheter 560 having a membrane extension 564 is advanced into the left atrium 44 through a commissure 80 of the mitral valve 44. The extension 564 lies in the same plane as a U-shaped portion 570 of the coil guide catheter 560 and travels beyond the perimeter of the mitral annulus 84 so that it sits on the wall 46a of the left atrium 46. Alternatively, the extension 564 may have a downward turn forming an arched passage around the U-shaped portion 570 of the coil guide catheter 560. This downward turn would create a space for coils to sit above the annulus 84 should the operator wish to extrude coils of the helical anchor 572 before the tip 574 of the anchor 572 is placed under the mitral valve 44. Referring to FIG. 33, the extension 564 seats against the atrial wall 46a and provides tactile feedback to the operator by producing a clear stopping point when the operator pulls back on the coil guide catheter 560. This serves to keep the coil guide catheter 560 inside the left atrium 46 and in a plane parallel to the plane of the valve 44. In this manner the extension 564 provides assistance with correct depth positioning of the coil guide catheter 560 and helps to keep the helical anchor 572 delivery roughly parallel with the plane of the valve 44. In this embodiment the extension 564 runs the length of the U-shaped portion 570 of the coil guide catheter 560. However, in other embodiments the extension 564 may be shorter or longer, even such that the extension 564 may produce a full circle around the mitral annulus 84. Also, rather than comprising a continuous projection as shown, the extension 564 could comprise a number of smaller separate projections or extensions that perform similar functions.

The extension 564 may comprise a membrane of plastic material or biologic material. Any suitable biologically compatible material could be used such as nylon, polypropylene, polyester, PTFE, or ePTFE. Biologic materials such as animal or human pericardium or animal intestinal derived membranes could also be used. A wire-like structure 576 may give shape and integrity to the membrane 564. The wire could be moveable to activate the sail-like membrane 564. For example, pushing on the wire could move the sail-like membrane 564 from a collapsed position where the membrane 564 sits close to the coil guide catheter 560 to an active position where the membrane 564 is expanded and provides support for the coil guide catheter 560 on the atrial wall 46a. The wire material could be made from any suitable material such as stainless steel or Nitinol.

Figure 34A:
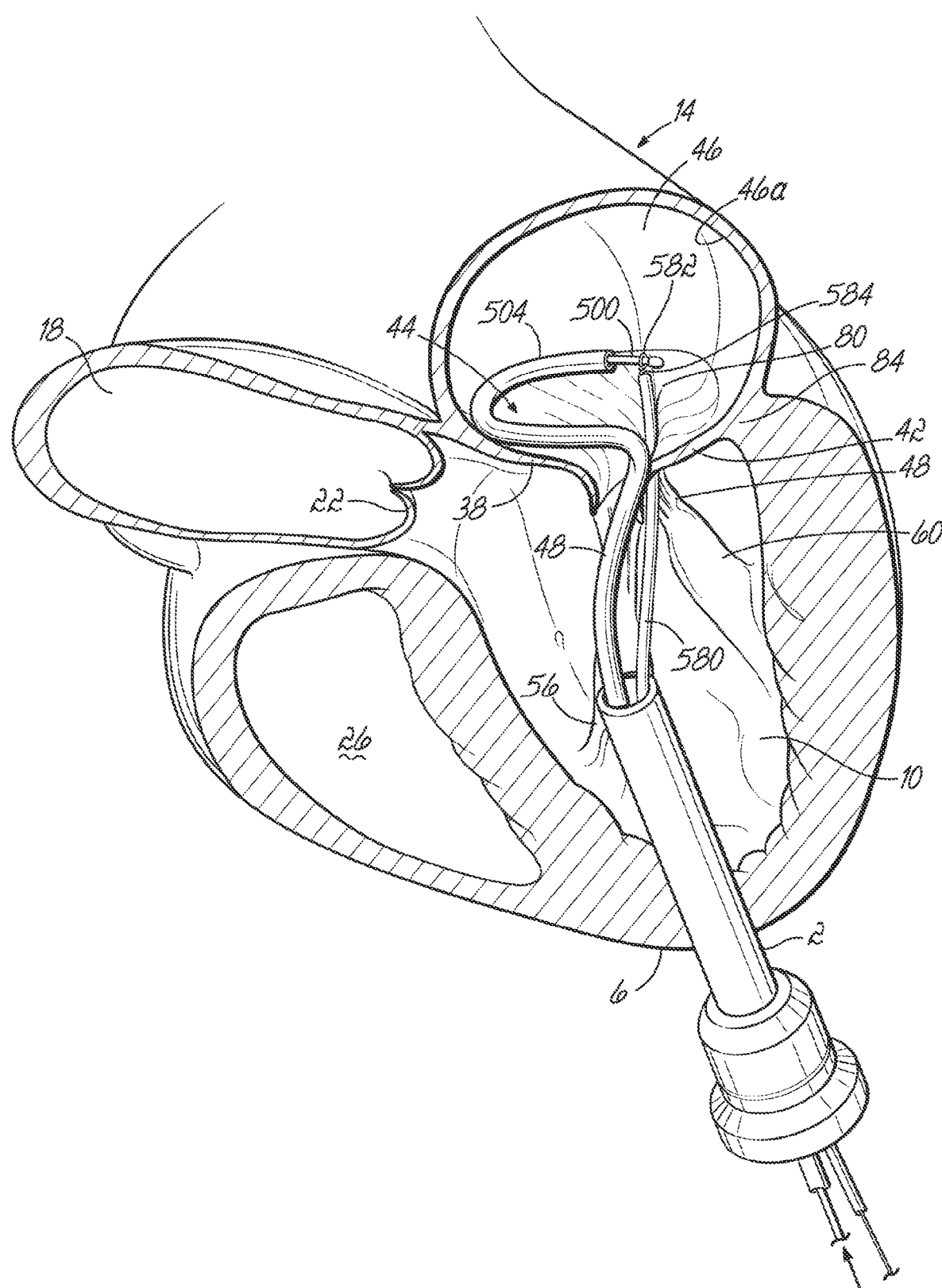
FIG. 34A illustrates in perspective a system in accordance with the present invention in which a snare catheter is attached near the end of a helical anchor extending from a coil delivery catheter or coil guide catheter into the atrium of a heart, shown in partial cross section.
Figure 34B:
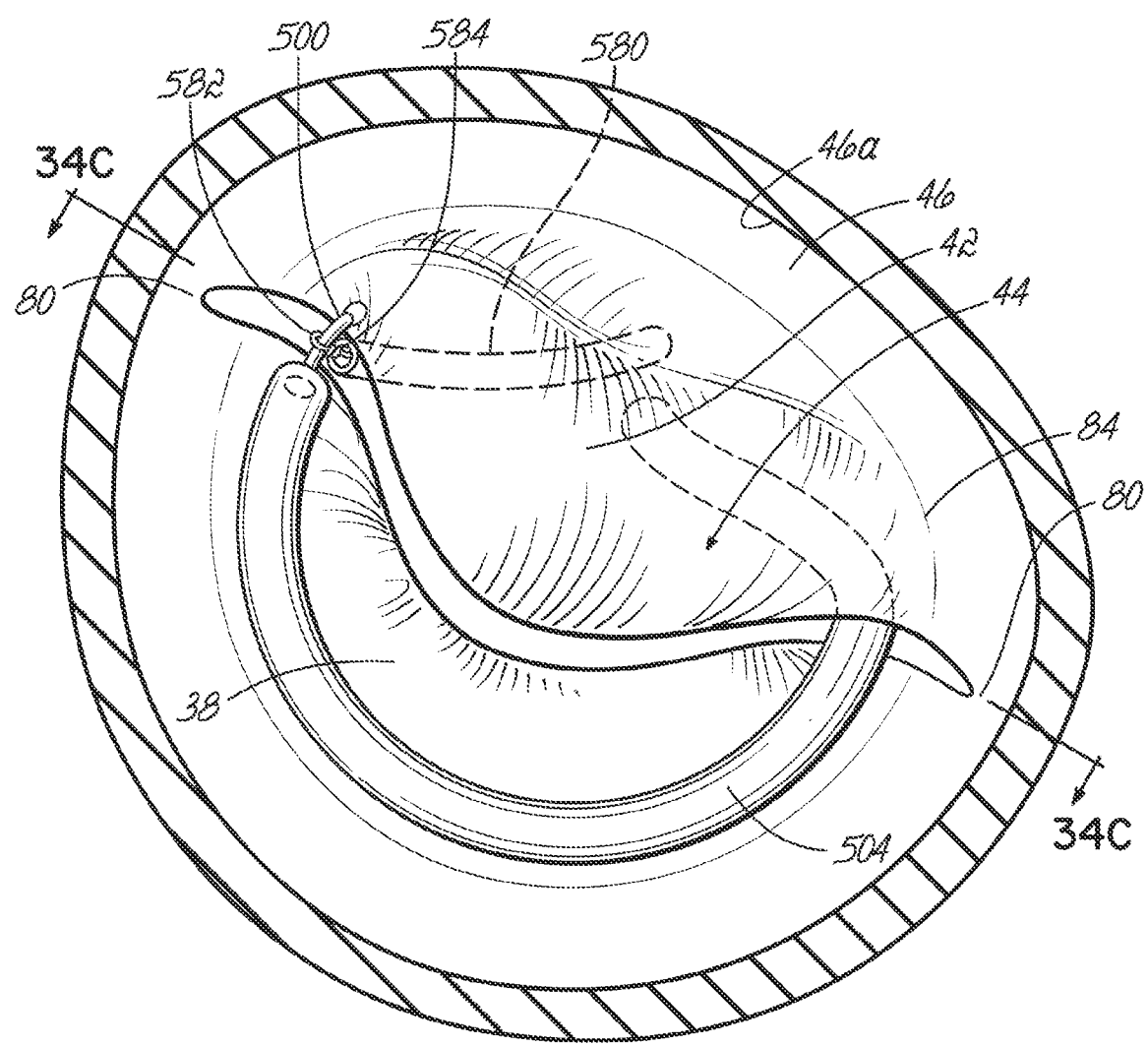
FIG. 34B is a top view of the system of FIG. 34A, showing that the mitral valve annulus is substantially larger than the U-shaped portion of the coil delivery catheter or coil guide catheter.

Referring now to FIGS. 34A-34G, a device, system, and method of closing the commissures 80 of a mitral valve 44 are illustrated. In FIG. 34A a snare catheter 580 is attached to the end of a helical anchor 500 which extends from the end of a coil guide catheter 504 within the left atrium 46 as has been previously described. A suture 582 is tied with a knot 584 to connect the snare catheter 580 to the end of the helical anchor 500. In other embodiments it may not be necessary to use a knot for this connection. For example, the suture 582 could pass through a loop in the tip of the anchor. Or the snare can be tightened around the end of the anchor. However, in this embodiment the knot 584 is useful when the snare catheter 580 is loosened to maintain attachment to and control of the helical anchor 500 to prevent disconnection. The suture 582 can be cut at the end of the procedure or any time during the procedure. There have been a number of devices described that can be used to cut a suture through a catheter. The snare catheter 580 passes between the leaflets 38, 42 of the mitral valve 44 near a commissure 80 and the coil guide catheter 504 passes between the leaflets 38, 42 of the mitral valve 44 near the opposing commissure 80 as shown in FIG. 34B. The mitral valve annulus 84 shown here is large, such that about 4 mm to 5 mm of gap between the leaflets 38, 42 is shown at each commissure 80. This could cause a serious leak after a helical anchor 500 and valve prosthesis 120 are installed. To prevent this leak, an operator may proceed to implant a mitral valve prosthesis 120 as described herein, and subsequently add progressively larger amounts of fabric cuff (FIG. 22) to plug the gap between the valve prosthesis 120 and the mitral valve annulus 84.

However, with a catheter-based implant it is difficult to add a sufficient amount of fabric cuff as the material is bulky. One alternative is to provide a valve prosthesis that is large enough to accommodate the large mitral valve annulus 84. However, a large valve prosthesis will also be difficult to implant via a catheter. Both large sized valve prostheses and prostheses with cuff material would require large delivery systems requiring large incisions and surgical cut down for entry into the heart or vascular system.

Alternatively, the mitral valve leaflets 38, 42 could be closed together or the space between the leaflets 38, 42 could be corked or plugged. A variety of devices are available to plug leaks at commissures 80. Devices like Amplatzer are composed of coils of metal such a Nitinol or stainless steel. They can have fabric covers or fabric in the interior to increase thrombogenicity and reduce leak. These plugging devices are used to close atrialseptal defects, patent foramina ovale, paravalve leaks etc. These could be used in this situation. Other devices and methods could be used to close the commissures 80. A pledget of fabric could be used to close the gap. A fabric structure with an hourglass shape is one variation that could be inserted so that the narrow part of the fabric is positioned in the commissure 80 and the larger part of the fabric is located above and below the valve leaflets 38, 42 would serve this purpose. The plugging material could wrap around the helical anchor 500. It does not have to sit on just the outside of the anchor 500. The anchor 500 could retain the plugging material so there is no risk of the material being dislodged. It is also possible to produce occluder devices, systems and methods that could be integrated or ride on the coil of the anchor 500. A pledget or amplatzer or other occluder device could be anchored to the coil and produce closure at the commissures. For example, two occluders could be pre-attached to the coil before its insertion. One occluder could be delivered to the first commissure 80. The coil 500 could be advance to the opposite commissure 80 and the second occluder could be delivered at this location. The occluders could travel along the coil 500 like a guiding rail and could be pushed around the helical anchor, for example, by using a catheter which is fed over the anchor 500. It is also possible to insert the helical anchor 500 and then deliver the plugging material along the track or rail of the helical anchor 500 later. Imaging systems could be used to confirm that there was no leak (for example, with echocardiography). Additional occluders could be added until no leak occurred. In another embodiment, an occluder that is free-standing could be used to close the commissures 80 and prevent leakage. It should be noted that the occluder could be delivered during or after the positioning of the helical anchor 500.

Figure 34C:
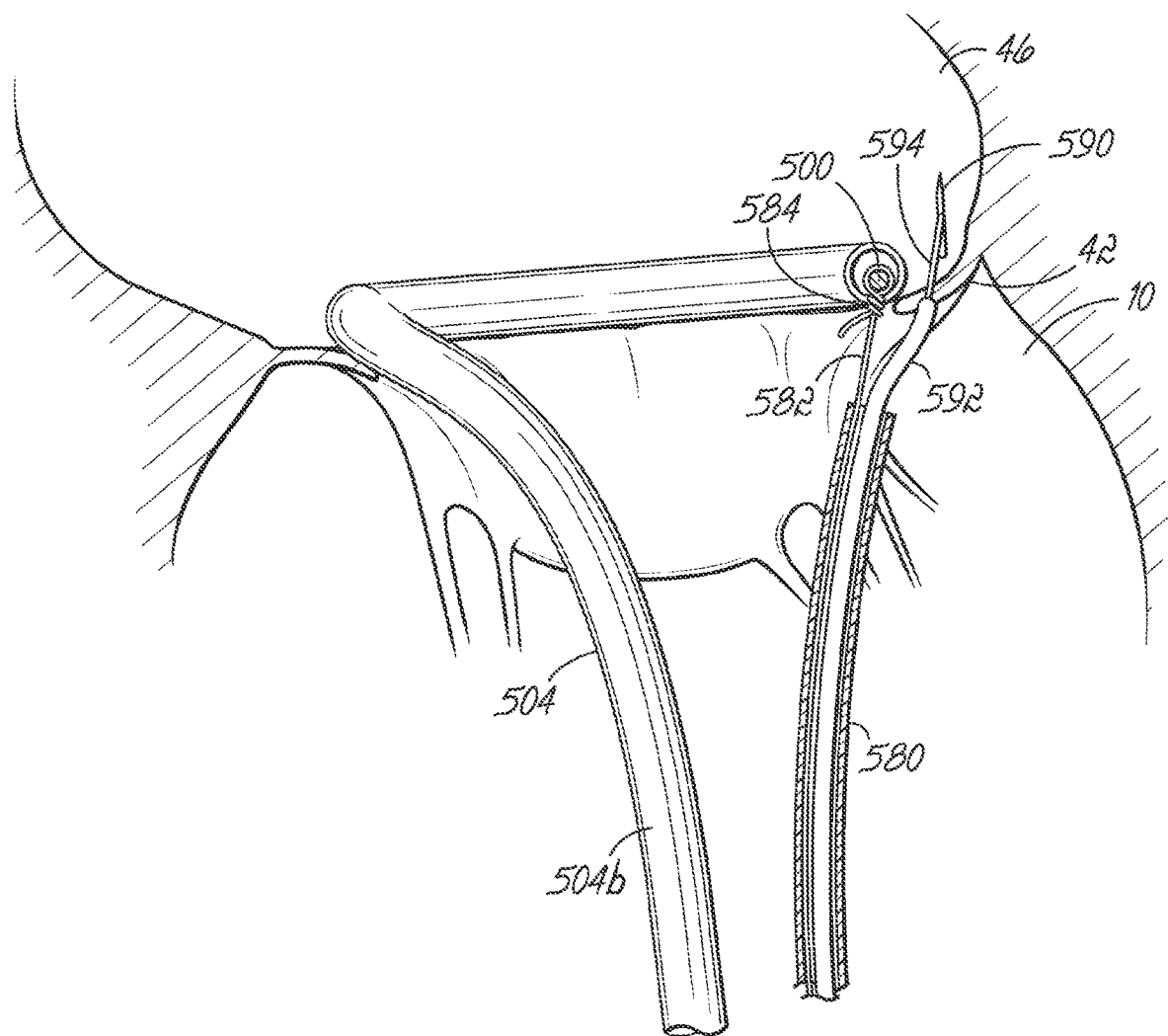
FIG. 34C is a perspective view of the system of FIG. 34A, showing the placement of an anchor between the mitral valve leaflets at a commissure via the snare catheter.

Another option to prevent a leak around the anchor is to approximate the anterior leaflet 38 and the posterior leaflet 42 together around the helical anchor 500. FIG. 34C shows a leaflet anchor 590 being placed through a mitral valve leaflet 42. When the helical anchor 500 is in the correct position, the snare catheter 580 is loosened and maneuvered to the outside of the helical anchor 500 to one of the leaflets 38, 42. Imaging with fluoroscopy and echocardiography or other techniques may assist this step. A stiffening rod or a catheter control steering system could be useful in manipulating the catheter. The snare catheter 580, or a catheter or lumen associated with it, also delivers leaflet anchors 590. The snare catheter 580 may be, for example, a simple double lumen catheter or a separate catheter for delivering the leaflet anchors 590 may be joined to the snare catheter 580 near their tips.

In one embodiment, the leaflet anchor 590 is T-shaped and is inserted like a fabric label anchor commonly used on clothing such that the long stem of the T and the short stem are parallel during insertion. The T anchor 590 has one sharpened end which is used to penetrate the tissue. The sharp end is fed through a catheter 592 and pushed through the leaflet 42. In another embodiment, the leaflet anchor 590 may be delivered through a cylindrical tube with a sharpened end to penetrate through the leaflet tissue. A needle-like distal tipped catheter can be used to deliver the anchor 590 through the leaflet tissue. In any event, the catheter 592 is withdrawn after the T-shaped anchor is pushed out. This leaves the T-shaped anchor on the atrial side of the leaflet 42 and the tail 594 of the anchor travels through the valve tissue into the catheter 592.

Figure 34D:
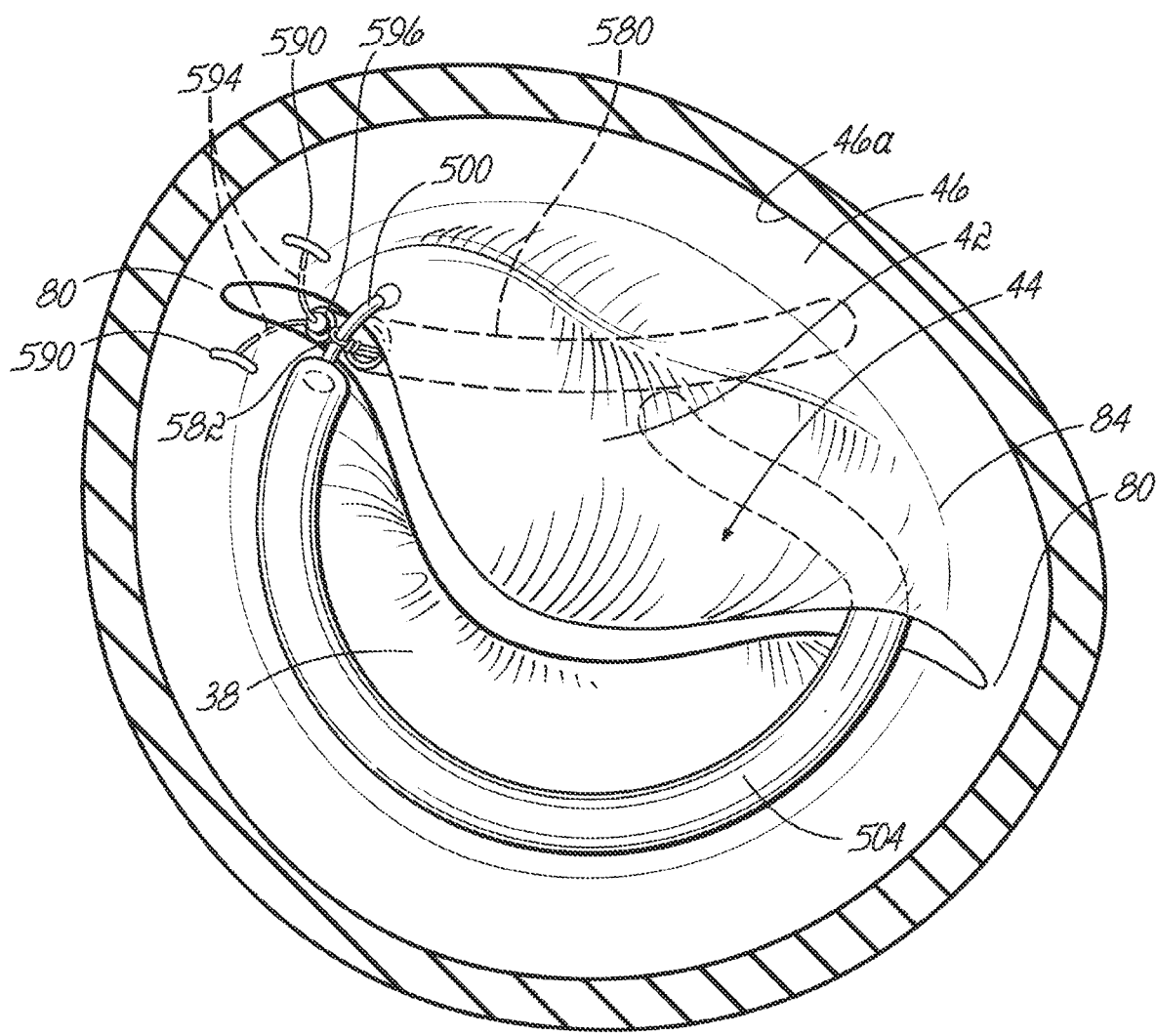
FIG. 34D is a top view of the system of FIG. 34A, showing the placement of anchors through both the anterior and posterior mitral valve leaflets via the snare catheter.

Once the leaflet anchor 590 has passed through the tissue, it returns to its initial T-shape. The leaflet anchor 590 is then pulled flush with the valve tissue. The same process is repeated for the other leaflet 38 with another anchor 590 as shown in FIG. 34D. Individual anchors 590 are then cinched tight by fastening their suture ends or tails 594 together as shown in FIG. 34G. A tissue suture locker 596 can be used to strengthen the connection. The locker 596 can be composed of one or more of a plastic and metal material. At the completion of the plication, the suture tails 594 are cut.

Figure 34E:
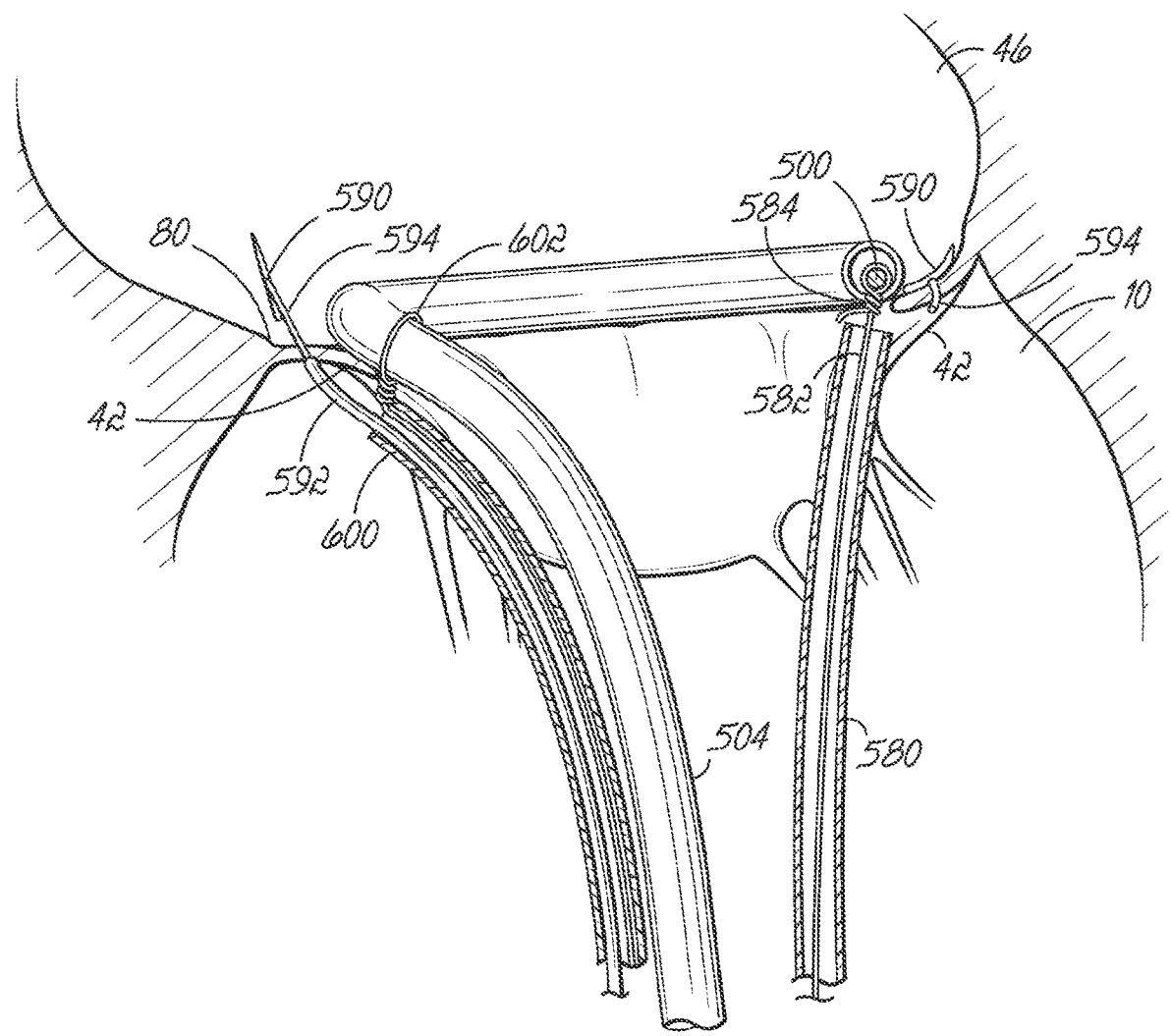
FIG. 34E illustrates in perspective the system of FIGS. 34A-34D showing the placement of a tissue anchor through tissue, such as the mitral valve leaflet at a second commissure via an tissue anchor delivery catheter after the first commissure has been plicated.
Figure 34F:
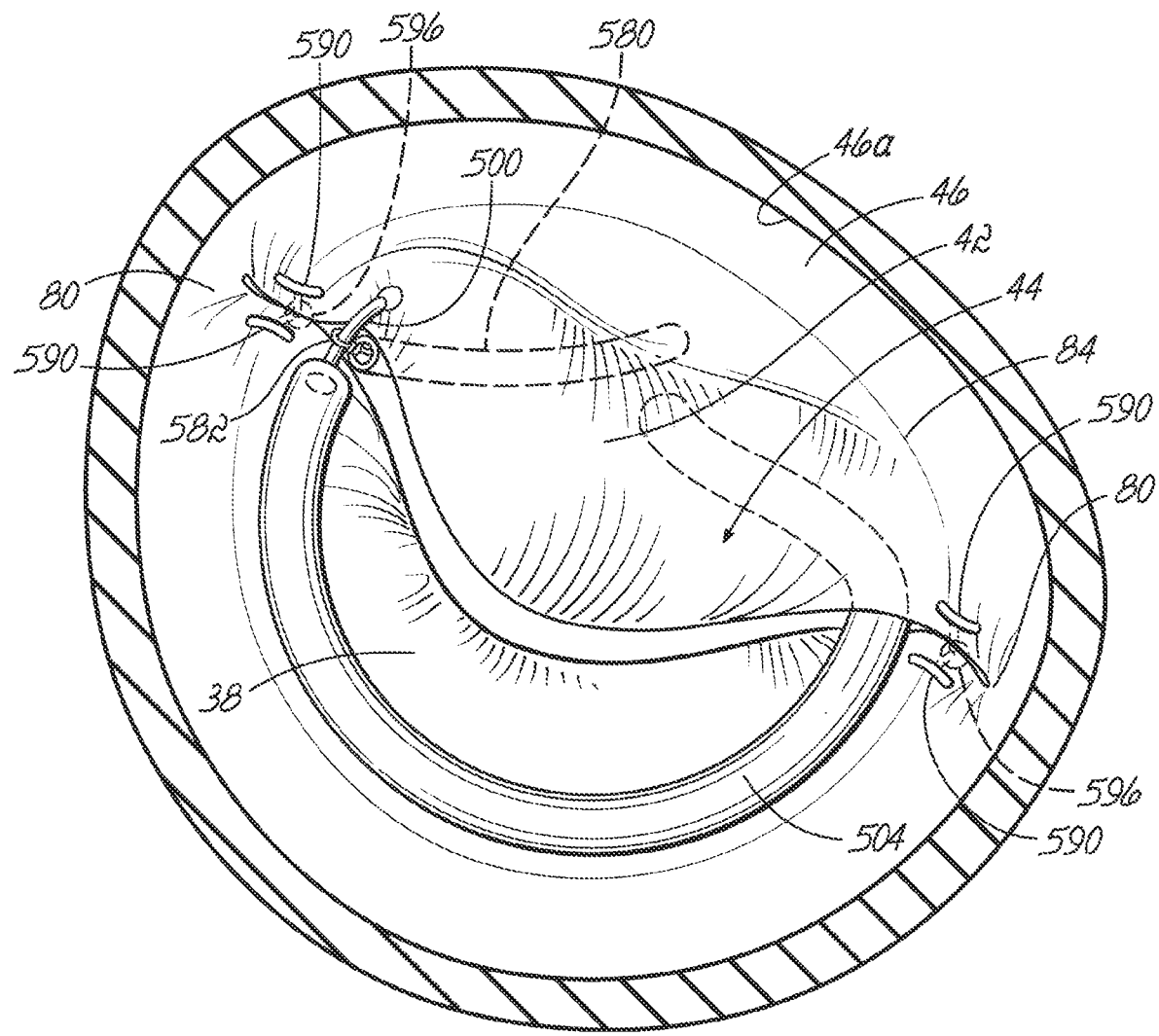
FIG. 34F is a top view of the system of FIGS. 34A-34E, showing the completed plications at both commissures.
Figure 34G:
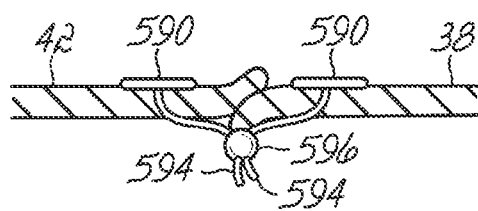
FIG. 34G is a cross sectional view of a plication as shown in FIG. 34F.

FIG. 34E shows a second snare catheter 600 advanced upon the coil guide catheter 504 using a suture connection 602 toward the second commissure 80 of the mitral valve. The T anchor plication process is repeated for the anterior and posterior leaflets 38, 42. FIG. 34F shows the completed plications at both commissures 80.

Alternatively, the helical anchor 500 can be used to enable the plication at the second commissure 80. The helical anchor 500 can be advanced to the second commissure 80 by pushing it forward. The correct position for the end of the helical anchor 500 and the anchor delivery system can be indicated by the location of the stem 504b and the use of imaging methods that can include fluoroscopy, echo, MR and CT. The helical anchor 500 both carries and positions the delivery of any anchor or system to plicate leaflets 38, 42 or annulus 84. Once the correct position has been reached on the commissure 80 shown on the left, fasteners or anchors 590 are again placed through the anterior leaflet 38, the posterior leaflet 42 or the annulus 84 as desired. The anchors 590 can then be locked together and the suture tails 594 cut to complete the procedure. It should be re-stated that the commissure plication does not have to be performed with these specific anchors 590. Any of the many described systems can be used in conjunction with the orienting and delivery methods and devices described in this disclosure.

In another embodiment, a single anchor could be created that delivers an anchor to each of the anterior and posterior leaflets 38, 42. The two anchors could be held together by a suture or an elastic material and spring shut after delivery so that the leaflets 38, 42 are approximated between the helical anchor and the annulus. This idea of joining anchors does not apply only to T-shaped anchors, but any anchor.

The helical anchor 500 and/or coil guide catheter 504 is used as a guide for the delivery of the leaflet and/or annulus anchor 590. Snare catheters 580, 600 can be used to deliver the anchors 590. The snare catheters can ride with the helical anchor 500 as it slides around the margin of the annulus 84. The operator can loosen the snare and then using imaging (such as fluoroscopy, echocardiographic, MR or CT), move the snare catheter 580, 600 relative to the helical anchor 500. This will bring the snare catheter 580, 600 toward a correct location such as the commissure 80. The amount of loosening of the snare 580, 600 can be adjusted to the required location to place an anchor 590. For example, if the gap between the helical anchor 500 and the commissure is 5 mm, the operator may decide to deliver an anchor 590 about half way between the helical anchor 500 and the commissure 80—about 2.5 mm from the outside of the helical anchor 500. This measure is visible by imaging systems. An anchor 590 could be delivered into one leaflet 38 or 42, then the other leaflet 38 or 42. The leaflets 38, 42 can then be approximated.

It may also be useful to plicate the leaflets 38, 42 together at more than one point if the gap at the commissures 80 is large or if implanting a first anchor pair 590 is not successful in closing the gap between the leaflets 38, 42. If leaflet closure is not successful on its own, plicating the annulus 84 toward the leaflets 38, 42 may be very useful to prevent leak. This could be simply accomplished by placing an anchor 590 into the annulus 84 near or at the commissure 80 and joining it with the anchors 590 to the leaflets 38, 42.

There are many ways devised to approximate leaflets 38, 42. Clips have been pioneered by Abbott's eValve. Anchors do not necessarily need to penetrate leaflet tissue. Non-penetrating anchors could also be used in the procedure described previously. A variety of anchors have been described by Edwards for their edge-to-edge leaflet repair which was pioneered by the Italian surgeon Ottavio Alfieri. Mitralign has published the use of anchors in the annulus. Any of these anchors or any suitable anchor could be used to accomplish the task of closing the commissures and preventing paravalvular leak.

These options are described to indicate that many systems devices and methods can be used to approximate leaflet and annulus tissue. Any of these devices and methods could be integrated with this delivery system. The anchors 590 can be carried on the helical anchor 500 or carried with the snare delivery catheter 580, 600.

It is also possible to plicate the annulus 84 to leaflets 38, 42. Anchors 590 could be placed in the annulus 84 and the leaflets 38, 42 to produce a "triangular" closure to the commissure 80 and prevent a leak.

Leaks can occur at locations other than commissures 80. For examples, there are often clefts, or gaps between the leaflets 38, 42. These clefts can cause leaks. The helical anchor 500 can be used to guide anchors 590 into any location that would benefit from approximation around the helical anchor 500.

It is also possible, that part of the leaflets 38, 42 is/are not completely positioned inside the helical anchor 500. The methods, systems and devices shown here can be used to prevent and eliminate leaks. A gap could be plicated for example by folding a segment of a leaflet 38, 42 together. A pledget of fabric material (Polyester, Dacron, PTFE) or an occluder device (as described previously) could be used.

Combinations of leaflet, annulus and plugging may also be useful. All of these could be integrated with the helical anchor 500 and the snare catheter 580, 600. The use of concentric coils at one plane under the leaflets 38, 42 or above the leaflets 38, 42 with the coils sitting in a single plan parallel to the mitral valve 44 may also assist in closing the mitral leaflets 38, 42 and preventing paravalve leaks.

FIG. 34E shows a plication being performed using a catheter 592 introduced from the ventricular side of the valve 44. It is clearly possible to plicate the leaflets 38, 42, commissures 80 or annulus 84 from an atrial approach also.

The anchor delivery is also shown using a relatively straight catheter 592. Catheter 592 could have other shapes such as a J. A J shape would allow delivery of an anchor 590 from the opposite side of the leaflet 38 or 42 from catheter entry. For example, a catheter with a J tip could be delivered from the apex of the left ventricle and directed into the left atrium 46. An anchor 590 could then be delivered into the leaflet 38 or 42 from the atrium 46 towards the ventricle 10.

A snare catheter does not have to deliver the anchor 590. A separate anchor delivery catheter could be used. This could be attached to the helical anchor 500 or to a snare catheter. A double-lumen catheter may suit this purpose. One lumen of the snare delivery catheter could provide attachment to the helical anchor. The other could serve to deliver the leaflet plication. There could be a gap between the ends of the two lumens of a double lumen catheter or a two catheter system. For example, a gap of 2.5 mm between the lumens could be useful in providing a plication that is 2.5 mm from the edge of the helical anchor. A number of fixed gaps could be available depending on the situation. For example, if the gap at the commissure might be 7 mm, a catheter with a gap of 3.5 mm could be produced. Alternatively, there could be an adjustable gap between the ends of the two lumens to allow for various anatomical situations. The gap could be adjusted by pulling on the tip of one of the ends of the catheter or a completely steerable tip could be produced. A steering system could allow the two lumens to remain at a fixed distance, but the entire catheter could be steered by the operator.

The stem 504b of the coil guide catheter 504 may be a useful marker for the location of the commissure 80. One anchor 612 could be delivered outside of the stem 504b of the coil guide catheter 504 between the helix and the commissure 80. The other anchor 612 can be delivered at the distal end of the coil guide catheter 504 between its end and the commissure 80.

Figure 34H:
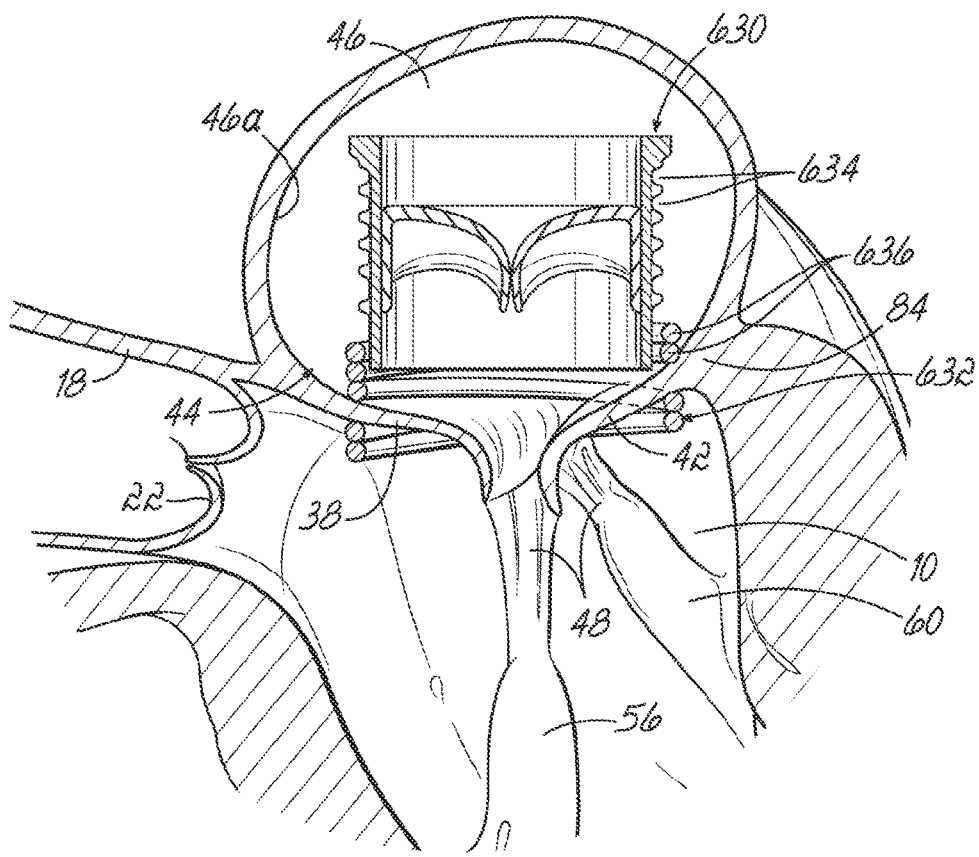
FIG. 34H is a cross sectional view of a prosthetic mitral valve with a helically grooved surface that is designed to engage with the coils of a helical anchor which has been placed in the mitral position of a heart.
Figure 34I:
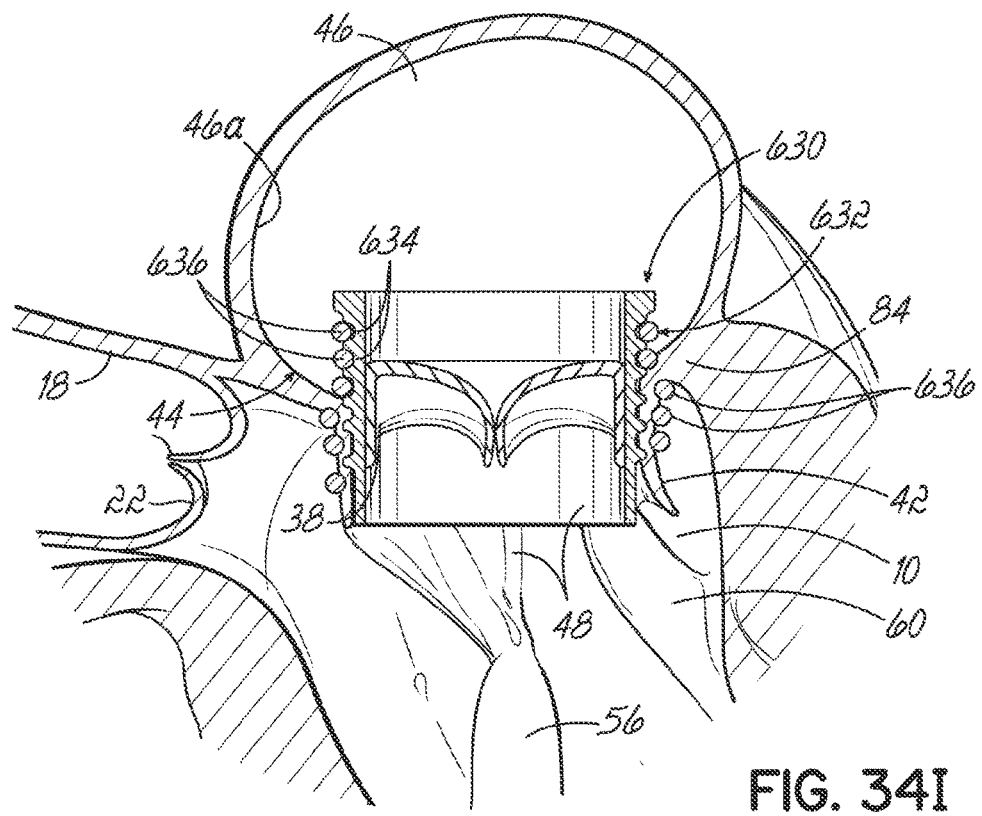
FIG. 34I is a cross sectional view of the grooves of the prosthetic mitral valve engaged with the coils of the helical anchor.

Referring now to FIGS. 34H and 34I, a device and method of retaining a valve prosthesis 630 in the mitral position of a heart 14 are shown. A valve prosthesis 630 is shown prior to placement within a helical anchor 632 which has been placed in the mitral position in FIG. 34H. The valve prosthesis 630 features threads or grooves 634 which correspond to the turns or coils 636 of the helical anchor 632. The valve prosthesis may otherwise be formed as desired, such as described herein. FIG. 34I shows the valve prosthesis 630 retained by the helical anchor 632 with the grooves 634 engaging the helical anchor 632. The fit of the coils 636 of the anchor 632 and the valve prosthesis 630 is quite precise above the mitral leaflets 38, 42, but where the leaflets 38, 42 are secured between the coils 636 and the prosthesis 630, the fit is not so precise. Thus, the grooves 634 located below the leaflets 38, 42 may be larger to allow for the tissue of the leaflet to fit in addition to the coils 636. The grooves 634 in the prosthesis 630 could precisely mirror the coils 636. This would optimally require the valve prosthesis 630, which is delivered on a catheter, to land precisely or slide precisely relative to the coils 636—upward or downward to lock. To increase the chance that a successful non-slipping mating occurs, the grooves 634 could be made larger in the prosthetic valve 630 to allow for imprecision in the delivery of the valve prosthesis 630 relative to the helical anchor 632. The grooves 634 could form a continuous thread or the grooves 634 could be intermittent. For example, one-third of the helical anchor 632 being engaged with the prosthesis 630 may be sufficient to prevent dislodgement. A pattern of grooves 634 coursing along segments at different levels along the prosthetic mitral valve 630 could accomplish the same effect. The coils 636 could engage more randomly and still effect a solid connection.

The grooves 634 in the prosthetic mitral valve 630 could be much wider than the coils 636 of the helical anchor 632. For example, two turns of the helical anchor 632 could sit in a single groove 634 in the valve prosthesis 630. This would allow more random interaction between the prosthetic valve 630 and the helical anchor 632 to produce a secure connection. For fabrication, the valve prosthesis 630 could have a grooved shape designed into it, or additional stents or other materials could be added to the prosthetic valve structure to produce grooves. For example, a stent or collapsible tube could be spiraled around the margin of a prosthetic mitral valve that when enlarged, produces a groove to engage the coils 636 of the helical anchor 632. The stent of the prosthetic valve 630 could be folded on itself (imbricated) to produce grooves. This could be accomplished by collapsing segments of the stent on one another. The grooves 634 or imbrications could be arranged in any pattern including a continuous groove or intermittent grooves. Fabric coatings on the exterior surface of the prosthetic valve stent could be used to create a mating structure to engage the helical anchor. For example, a groove could be created on the outside of the prosthetic valve with a fabric covering wrapped around to create a groove. A bumpy surface could be created by applying segments of fabric to engage the helical anchor at many locations. For example, rectangles of fabric could be added to the outer surface of the prosthetic valve stent to engage the coils.

In another embodiment, the prosthetic valve stent could have bumps that could collapse where it engages the coil. These features would adapt to the coil to help engage the prosthetic valve against the coil 632. Alternatively, segments of the prosthetic mitral valve stent could move outward. A valve made of Nitinol may have segments that slowly move outward to produce a gritty or bumpy surface that adapts to the helical anchor location. Alternatively, a Nitinol stent may slowly expand such that the expansion results in a grooved pattern around the stent that retains the prosthetic valve more securely inside the coils. A Nitinol stent can be designed to allow its margin to adapt to the grooves of the coils.

The helical anchor 632 could extend above or below the prosthetic valve 630 to engage the ends of the prosthetic valve 630. The helical anchor 632 could also be modified. Instead of being completely circular, the anchor 632 could have a generally circular design with segments that extend inward to engage the prosthetic valve stent 630. The inward turning segments could also have an upward or downward bias. Alternatively, the helical anchor 632 could be made of a chain of balls and chains, with the balls able to interact in the spaces of the stent of the prosthetic valve. Enlargements other than circles could be used also.

The surface of the helical anchor 632 or the prosthetic valve 630, and any of the implanted components of this invention, such as helical anchors, docks, or prosthesis may include outer coverings or coatings for various purposes, such as friction promoting purposes and tissue in growth purposes. For example, the outer surfaces can be roughened to make slipping or unintended movement of the implanted component less likely. The implanted component can be roughened by, for example, sand blasting its surface or chemically etching its surface. Coatings or coverings such as sleeves of biologically compatible materials could be added. These could include silicone, polyester, urethanes or any other desirable materials. The helical anchors of this invention could have other friction promoting and/or tissue in growth surfaces composed of fabric or even Nitinol or stainless steel to help engage with the prosthetic valve.

The prosthetic valve stent 630 can also be flared at one or both ends. This can be used to prevent dislodgement up or down. Many prosthetic valves are balloon inflated so the balloon that inflates the stent can have an hourglass shape or just one end flared to expand the valve.

The leaflet commissures of mitral valve leaflets close when they are pressurized. It is unusual to have a serious commissural leak after valve repair, because the pressure on the leaflets brings their edges together. Any of these helical anchor designs could be modified to encourage closure of the valve commissures by placing the leaflets in the same position they are when the ventricle is pressurized. The coils below the leaflets in most of the previous figures are "stacked" upon one another—that is each coil is at a different plane as the coils travel away from the mitral valve when taking the plane of the mitral valve into consideration.

It is also possible for the coils under the leaflets 38, 42 to be concentric and at the same time the coils could sit in relatively the same plane under the leaflet. The diameter of each turn can be slightly wider or narrower with the coils all sitting in approximately the same plane. This means the coils will sit right under the leaflets 38, 42 of the mitral valve 44. By creating a spring force against the annulus 84 or leaflets 38, 42, the leaflets 38, 42 will be pushed upward toward their closed position as they are when the ventricle 10 is pressurized in systole. The spring force can come from coils on the opposite side of the leaflets 38, 42 that sit against the atrial wall 46a. The coils can also be biased upward (to sit against the underside of the native mitral valve leaflets) in manufacturing to further encourage leaflet apposition at the commissure 80. Closure of the commissures 80 may be best accomplished with a series of concentric coils above the leaflets 38, 42 and below the leaflets 38, 42 that are arrange to create a compression force against the mitral valve leaflets 38, 42 and close the commissures 80. In this arrangement the smaller diameter turns of coils under the leaflets 38, 42 can retain the prosthetic mitral valve. The larger turns or coils can close off the commissures.

For fabrication, a helical anchor that consists of three concentric turns all sitting in one plane may work well. When the helical anchor is inserted with two turns below the leaflets and one turn sitting against the atrial wall 46a, the spring force will tend to pull the turns of the helical anchor below and above the commissures 80 together and close the commissure 80.

Furthermore, it is simple to add additional coils to the helical anchor and simple for the operator to push the coils in position. Combinations of coils that close the commissures 80 by exerting an upward spring force with coils that retain the prosthetic mitral valve 44 may provide an optimal structure. The coils under the helical anchor can consist of a series of coils that push the leaflets 38, 42 upward into a closed position (coils relatively parallel to the plant of the native valve) and coils that retain leaflets 38, 42 (more perpendicular to the native valve plane). The coils above the leaflets 38, 42 can abut the leaflets 38, 42 on their atrial side or the atrial wall itself.

The use of coils which close the commissure 80 can be combined with "plugging" devices and methods, systems and devices that approximate the leaflets 38, 42 and the annulus 84. For example, the coils that are located under the annulus 84 could be combined with a plugging or occluding device that is positioned on the coil in the region of the commissure 80.

Figure 34J:
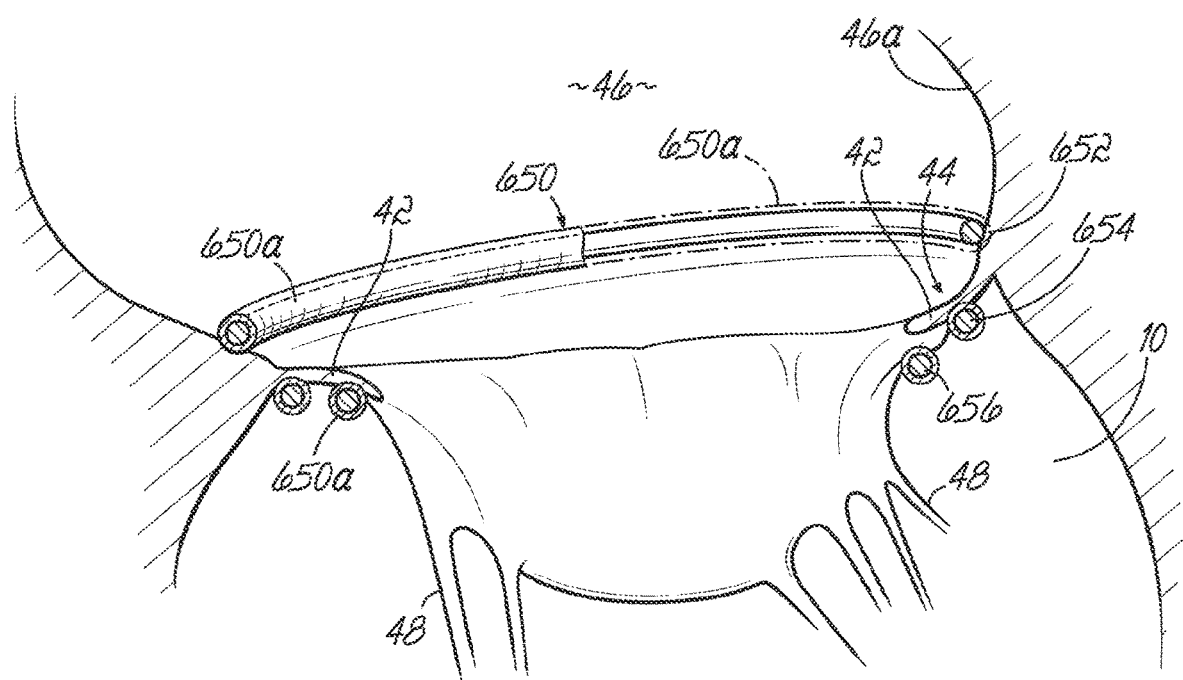
FIG. 34J is a cross sectional view of an alternative helical anchor placed in the mitral position of a heart such that the coils of the anchor placed below the mitral leaflets press or are biased upward against the leaflets.
Figure 34K:
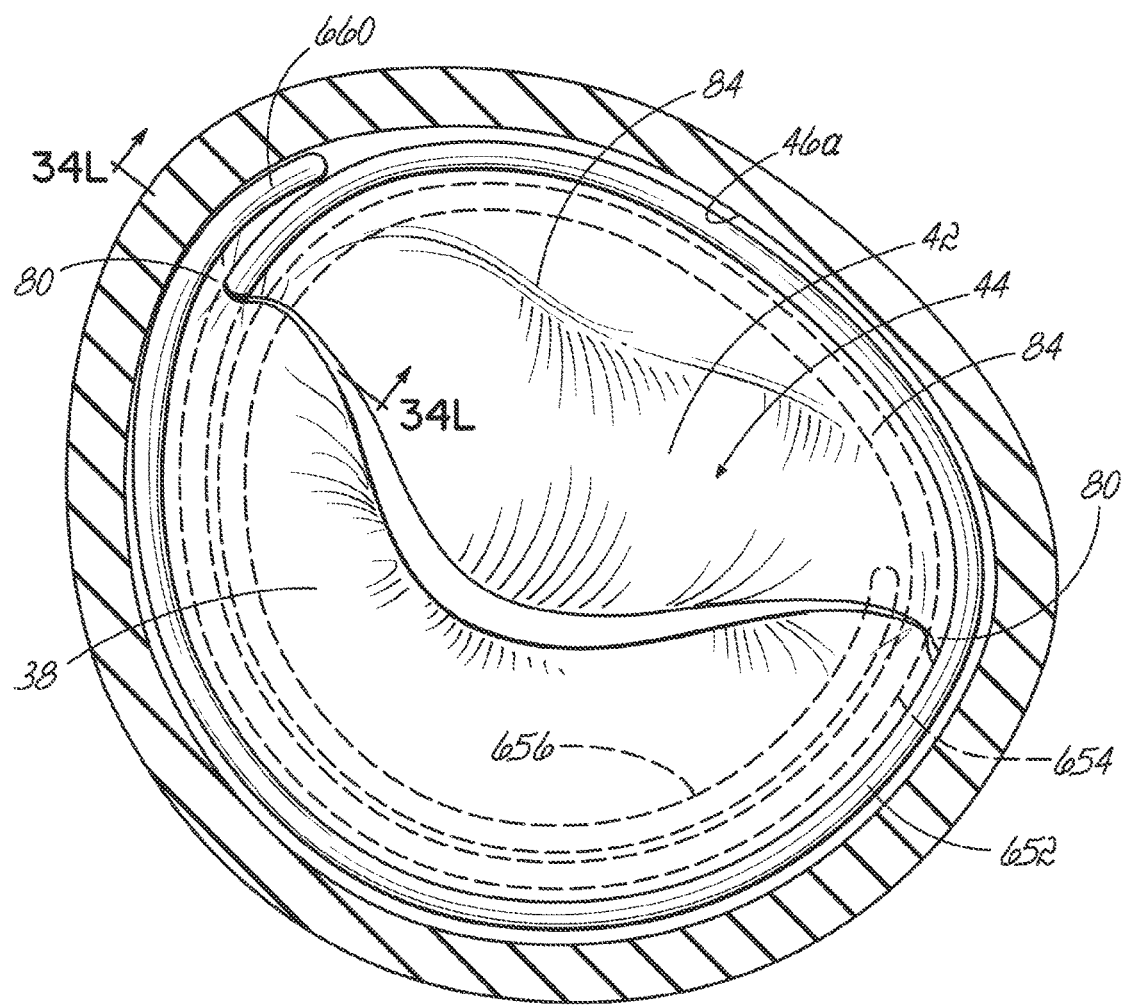
FIG. 34K is a top view of the helical anchor of FIG. 34J showing the coil of the anchor placed above the mitral leaflets compressing against the atrial wall while the coils of the anchor placed below the mitral leaflets press upward against the leaflets to close the commissures.
Figure 34L:
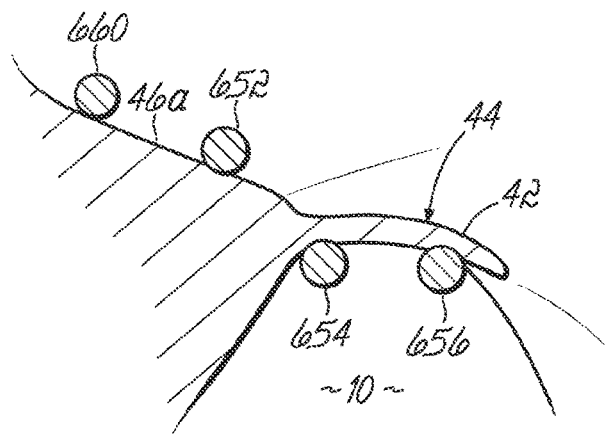
FIG. 34L is a cross section taken along line 34L-34L of FIG. 34K.

Referring now to FIGS. 34J-34L, an alternative embodiment of a helical anchor 650 in accordance with the present invention is shown. As generally noted above, helical anchor 650 includes a covering 650a, which may be a tissue in growth surface such as a covering (fabric, for example) or coating or sleeve, or simply a surface treatment. Any of the options discussed herein may be used for purposes of improving the implantation process and/or the quality of the implantation post-procedure. FIG. 34J shows a helical anchor 650 having one turn 652 above the mitral valve 44 in the left atrium 46, where it compresses against the atrial wall 46a close to the valve 44. Two turns 654, 656 sit under the leaflets 38, 42 and press upward against the leaflets to bring the margins of the anterior and posterior leaflets 38, 42 together to close the commissures 80 as shown in FIG. 34K. This prevents para-valve leaks once the prosthetic mitral valve is anchored. Additional coils around the perimeter of the helical anchor 650 ensure that a valve prosthesis will be positioned in the center of the anchor 650. It should be noted that this is particularly advantageous when a valve prosthesis is substantially smaller than a patient's native mitral valve annulus 84, since the valve prosthesis could otherwise slip from within the anchor and become dislodged. Before insertion into the mitral position, the helical anchor 650 can sit flat in one plane. Therefore, after it is implanted there is a spring force exerted by the anchor 650 pushing the mitral leaflets 38, 42 upward and together. In another embodiment even greater spring force can be applied if the anchor 650 is constructed so that before insertion into the mitral position, the two turns 654, 656 that sit under the annulus 84 are arranged to naturally position higher than the turn or coil 652 shown above the leaflets 38, 42. During insertion, the coils 654, 656 will be directed first to spiral into the ventricle 10 and around the chords 48, then the final coil or coils 652 will be delivered onto an upper side of the valve 44. Because the lower coils 654, 656 will move toward their normal position (which is above coil 652), there will be a compressive force applied by coils 654, 656 upwardly as viewed in FIG. 34J. FIG. 34L is a cross section taken along line 34L-34L of FIG. 34K showing the upward force exerted by the lower coils 654, 656 on the mitral leaflets 38, 42. A portion of a second coil 660 of the anchor above the annulus 84 is shown.

Appendix A is attached and forms a part of this specification. Appendix A is a catalogue of Prototypes 1 through 8 that illustrate examples of helical anchors constructed in accordance with embodiments of the invention and used for mitral valve prosthesis docking as described herein. Each prototype helical anchor is represented by respective top and side view photographs as well as a diagrammatic side cross-sectional view of the helical coil configuration relative to anterior and posterior mitral valve leaflets (represented by downwardly curved lines) after implantation.

In other embodiments involving a helical anchor, alternative configurations may be used in accordance with the invention. For example, some of the coils of the helical anchor above the leaflets 38, 42 may be placed in contact with the leaflets 38, 42 and some of the coils of the helical anchor above the leaflets 38, 42 may be placed in contact with the atrial wall 46a. The number of coils and the order of contact could vary. For example, coils may alternate between contacting the leaflets 38, 42 and contacting the atrial wall 46a. Alternatively, some of the coils of the helical anchor above the leaflets may retain a valve prosthesis without contacting the leaflets 38, 42 and some of the coils above the leaflets 38, 42 may be placed in contact with the atrial wall. The coils that contact the atrial wall 46a could pass either upward away from the mitral valve 44 or downward to contact the atrial wall 46a proximate the mitral valve 44. In one embodiment the coils may pass downward such that they contact the outside of the coils which retain the valve prosthesis, forming a double-coil. Advantages of a double coil include improved structural strength of the helical anchor and decreased risk of thrombogenicity or embolization of the coils.

In further embodiments involving a helical anchor, the coils of the anchor can be carriers for an occluder device. For example, a pledget of fabric or an Amplatzer devices could be threaded on the coils and moved to any position where a leak is possible. Occluding materials could also be positioned between coils. The previously described devices, systems and methods for approximating the anterior and posterior leaflets 38, 42 together may be used in conjunction with such occluding to provide improved leak resistance.

In other embodiments, devices and systems as described can be introduced using an open heart or puncture approach from the atrium 46, ventricle 10 or aorta 18 or from catheters delivered into the left atrium 46 or retrograde from the aortic valve 22 into the left ventricle 10. Likewise, the system could be introduced in an open chest into the atrium 46 or percutaneously via the apex 6 with an apical occluder. Alternatively, introduction may be by way of other means, for example, through a min-incision in the heart 14 and/or endoscope.

Additionally, devices and systems as described can be introduced using an approach in part or completely via the aorta 18. A coil guide catheter or delivery catheter can be fed from any peripheral location (such as the groin, the shoulder region or the arm/wrist) or a central aortic location to the aortic valve 22. All of these entry approaches are used commonly clinically for approaching the aortic valve 22 and coronary arteries. The coil guide catheter or delivery catheter can then be fed across the aortic valve 22 into the left ventricle 10. Any of the previously described devices, systems and methods may then be employed to implant a mitral valve prosthesis using an approach from the left ventricle 10. Assisting tools described herein (e.g. snare catheter, grasping tool, etc.) may also be introduced via the aorta 18. Any route of helical anchor or stent dock delivery (e.g. transseptal, transventricular, transaortic) can be used in conjunction with any route of valve prosthesis delivery (e.g. transseptal, transventricular, transaortic).

In one embodiment, the grasping tool may be connected by a suture or thread to the end of the helical anchor. The suture or thread may comprise a plastic material such as polypropylene which is commonly used in sutures, or another synthetic material like polyester which is frequently braided into sutures. The suture joins the grasping tool to the end of the helical anchor by sliding through an aperture in the grasping tool and leading it to the end of the anchor. At the end of the procedure, the suture may be cut. The grasping tool may have integrated scissors for this purpose or the suture may be sheared with a separate tool. In another embodiment, the suture could be wrapped over the end of the helical anchor and tugged for release. The end of the helical anchor, preferably characterized by an enlarged ball shape, may comprise an aperture for the suture to pass through, wherein the suture may be retained by crimping or gluing. After the procedure the suture could be cut or tugged out. A useful maneuver to remove the suture with a grasping tool is to slide the grasping tool over the suture so that it is sitting at the end of the ball. The grasping tool is then rotated to jerk the suture from the inside of the ball so that it can be removed. It may also be desirable to avoid a rigid connection or link between the grasping tool and the end of the helical anchor and avoid the use of a suture. Instead, a joint that pivots such as a universal joint may be desirable.

There are some important dimensions to consider for the coil guide catheter. The first dimension is the distance between the distal tip of the guide and the stem or straight part of the guide. This distance can be constructed to be approximately equal to the diameter of the mitral annulus or the distance between the commissures so that when the stem of the coil guide catheter is directed through one commissure, the distal tip of the coil guide catheter will rest at the other commissure. This means that the grasping tool will also pass through the mitral valve at the commissure opposite to the stem so that the system is centered inside the valve. It also provides a clear orientation for the starting point of the anchor delivery with respect to the mitral valve leaflets. The tip of the coil guide catheter is close to the commissure to ensure that the commissure receives the start of the helical anchor. The commissures of the mitral valve are relatively easy to identify on echocardiography so that the stem of the coil guide catheter and the grasping tool can thus be identified to be passing through the opposite commissures of the mitral valve. By using this anatomic landmark, the operator will be able to be sure that he or she is pushing the helical anchor under the mitral valve leaflet at the commissure. This simple relationship can make it relatively easy for the correct placement of the anchor. If the stem and the grasping tool do not pass through the commissure, the coil guide catheter can be rotated until they do. It is appreciated that the orientation does not have to be at the commissures. Any point along the valve can be chosen, but the commissures are particularly easy to identify with non-invasive imaging. If the operator desires to introduce the anchor at a point different from the commissure, the position of the stem and the grasping tool in relation to the mitral valve annulus can be compared to the valve to precisely position the entry point of the anchor.

Another important dimension for the coil guide catheter is the distance from the widest point of the curve to a line joining the tip of the coil guide catheter to the distal end of the stem of the coil guide catheter. This dimension can be adjusted so that the curved part of the coil guide (which generally or roughly follows the path of the mitral annulus, sits beyond the end of the native mitral valve on the base of the heart. An operator can then place the coil guide catheter in position inside the heart at the commissures with echocardiographic guidance and then pull back on the coil guide catheter until it sits flush against the left atrial wall. This provides tactile positioning to the operator and allows the depth of the coil guide catheter to be precisely adjusted. Visually, for example of fluoroscopy or echocardiography, the stopping can be recognized with a slight movement of the coil guide catheter as it hits against the atrial wall. As there is a slight upward curve of the left atrium as it passes away from the native mitral valve, a curve upward in the coil guide catheter over this curved part may be useful to track the shape of the heart.

While the present invention has been illustrated by a description of preferred embodiments and while these embodiments have been described in some detail, it is not the intention of the Applicants to restrict or in any way limit the scope of the appended claims to such detail. Additional advantages and modifications will readily appear to those skilled in the art. The various features and concepts of the invention may be used alone or in any combination depending on the needs and preferences of the operator. This has been a description of the present invention, along with the preferred methods of practicing the present invention as currently known. However, the invention itself should only be defined by the appended claims.

What is claimed is:

1. A helical anchor for docking a mitral valve prosthesis, the helical anchor adapted to be received in and delivered from a coil guide catheter and comprising:
    a plurality of coils having a preformed, coiled configuration after being delivered from the coil guide catheter and adapted to support the mitral valve prosthesis upon being fully delivered from the coil guide catheter and implanted with coil portions above and below a mitral valve annulus of a native mitral valve of a heart, wherein the plurality of coils comprises an upper coil, one or more middle coils, and a lower coil, wherein the upper coil has a larger diameter than the one or more middle coils and the lower coil, and wherein the upper coil is configured to engage a wall of an atrium of the heart at a position superior to and spaced axially from the mitral valve annulus after the plurality of coils have been fully delivered from the coil guide catheter.

2. The helical anchor of claim 1, wherein the helical anchor comprises a solid wire.

3. The helical anchor of claim 1, wherein the helical anchor comprises a hollow wire configured to be delivered over a guide wire.

4. The helical anchor of claim 1, wherein the one or more middle coils and the lower coil are configured to be positioned below the mitral valve annulus in a ventricle of the heart, after being delivered from the coil guide catheter.

5. A system comprising:
    a prosthetic heart valve that is radially expandable; and
    an anchor for docking the prosthetic heart valve, the anchor comprising a plurality of helical coils transitionable to a straightened configuration to be held in a coil guide catheter;
    wherein the plurality of helical coils is adapted to support the prosthetic heart valve upon being fully delivered from the coil guide catheter at a native heart valve of a heart and implanted with respective portions above and below a native heart valve annulus of the native heart valve, wherein the plurality of helical coils includes a lower portion comprising a plurality of lower coils and an upper portion comprising at least one upper coil, wherein the upper portion is adapted to be placed above the native heart valve annulus and wherein the plurality of lower coils is configured to encircle heart valve leaflets of the native heart valve; and
    wherein the at least one upper coil is configured to engage a wall of an atrium of the heart at a position spaced away from the native heart valve annulus after being delivered from the coil guide catheter, and wherein the at least one upper coil extends beyond an inflow end of a frame of the prosthetic heart valve when the prosthetic heart valve is docked within the anchor.

6. The system of claim 5, wherein the at least one upper coil has a diameter that is larger than a largest diameter of the plurality of lower coils when the prosthetic heart valve is docked within the anchor.

7. The system of claim 5, wherein the plurality of lower coils includes a plurality of middle coils and a lower coil.

8. The system of claim 7, wherein an outflow end of the frame of the prosthetic heart valve extends beyond the lower coil when the prosthetic heart valve is docked within the anchor.

9. The system of claim 5, wherein the prosthetic heart valve is balloon expandable.

10. The system of claim 5, wherein the plurality of lower coils is configured such that, when the prosthetic heart valve is docked within the anchor, the heart valve leaflets of the native heart valve are secured between the plurality of lower coils and the prosthetic heart valve, and such that the anchor and the prosthetic heart valve are locked in place relative to the heart valve leaflets.

11. A system comprising:
- a prosthetic heart valve comprising a frame that is radially expandable from a collapsed configuration to an expanded configuration, the frame having an inflow end and an outflow end; and
- an anchor for docking the prosthetic heart valve, the anchor adapted to be held in a delivery catheter in an elongated configuration and delivered from the delivery catheter, and the anchor comprising an upper coil and a plurality of lower coils after being delivered from the delivery catheter, the plurality of lower coils adapted to support the prosthetic heart valve upon being fully delivered from the delivery catheter and implanted at a native heart valve of a heart, and the upper coil adapted to engage a wall of an atrium of the heart;
- wherein the upper coil is adapted to be spaced axially from a native heart valve annulus of the native heart valve and, when the prosthetic heart valve is docked within the anchor, the upper coil extends axially beyond the inflow end of the frame of the prosthetic heart valve; and
- wherein the plurality of lower coils is adapted to be placed below the native heart valve annulus of the native heart valve such that the plurality of lower coils encircle native leaflets of the native heart valve and, when the prosthetic heart valve is docked within the anchor, the native leaflets are secured between the plurality of lower coils and the prosthetic heart valve.

12. The system of claim 11, wherein the outflow end of the frame of the prosthetic heart valve extends beyond a lower coil of the plurality of lower coils when the prosthetic heart valve is docked within the anchor.

13. The system of claim 11, wherein the native leaflets are native mitral valve leaflets of a native mitral valve and wherein the plurality of lower coils are configured to encircle the native mitral valve leaflets such that an anterior leaflet is prevented from obstructing a native aortic valve.

14. The system of claim 11, wherein multiple coils of the plurality of lower coils have a same diameter.

15. The system of claim 11, wherein a diameter of the upper coil is larger than a diameter of each coil of the plurality of lower coils.

16. The system of claim 11, wherein the upper coil is configured as a tail-like extension that is formed as an enlarged diameter coil relative to a next adjacent coil of the anchor.

17. The system of claim 11, wherein the plurality of lower coils includes two or more middle coils and a lower coil and wherein the upper coil has a first diameter and the lower coil has a second diameter, the first diameter larger than the second diameter.

18. The system of claim 11, wherein the anchor comprises a solid wire.

* * * * *